United States Patent
Lu et al.

(10) Patent No.: US 10,961,513 B2
(45) Date of Patent: Mar. 30, 2021

(54) METHODS AND COMPOSITIONS FOR RECOMBINASE-BASED GENETIC DIVERSIFICATION

(71) Applicant: Massachusetts Institute of Technology, Cambridge, MA (US)

(72) Inventors: Timothy Kuan-Ta Lu, Cambridge, MA (US); Sara da Luz Areosa Cleto, Quincy, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 43 days.

(21) Appl. No.: 15/757,530

(22) PCT Filed: Sep. 7, 2016

(86) PCT No.: PCT/US2016/050533
§ 371 (c)(1),
(2) Date: Mar. 5, 2018

(87) PCT Pub. No.: WO2017/044476
PCT Pub. Date: Mar. 16, 2017

(65) Prior Publication Data
US 2019/0024099 A1    Jan. 24, 2019

Related U.S. Application Data

(60) Provisional application No. 62/215,281, filed on Sep. 8, 2015.

(51) Int. Cl.
| | | |
|---|---|---|
| C12N 9/00 | (2006.01) | |
| C12N 15/00 | (2006.01) | |
| C12N 15/82 | (2006.01) | |
| C07H 21/04 | (2006.01) | |
| C12N 15/52 | (2006.01) | |
| C12N 9/24 | (2006.01) | |
| C12N 15/70 | (2006.01) | |
| C12N 15/74 | (2006.01) | |

(52) U.S. Cl.
CPC ............ *C12N 9/00* (2013.01); *C12N 9/2402* (2013.01); *C12N 15/52* (2013.01); *C12N 15/70* (2013.01); *C12N 15/74* (2013.01); *C12Y 302/01031* (2013.01)

(58) Field of Classification Search
None
See application file for complete search history.

(56) References Cited

U.S. PATENT DOCUMENTS

| | | |
|---|---|---|
| 2003/0073824 A1 | 4/2003 | Sherman et al. |
| 2012/0213764 A1 | 8/2012 | Naumer et al. |

OTHER PUBLICATIONS

Schmidt-Dannert. Molecular breeding of carotenoid biosynthetic pathways Nature Biotechnology vol. 18 Jul. 2000.*
Oliynyk. Analysis of the biosynthetic gene cluster for the polyether antibiotic monensin in Streptomyces cinnamonensis and evidence for the role of monB and monC genes in oxidative cyclization Mol Microbiol. Sep. 2003;49(5):1179-90.*

(Continued)

*Primary Examiner* — Yong D Pak
(74) *Attorney, Agent, or Firm* — Wolf, Greenfield & Sacks, P.C.

(57) ABSTRACT

Compositions and methods using shufflon recombinases are presented for use in generating genetic diversity in molecules of interest.

14 Claims, 32 Drawing Sheets
Specification includes a Sequence Listing.

(56) References Cited

OTHER PUBLICATIONS

Gyodha et al., Asymmetry of shufflon-specific recombination sites in plasmid R64 inhibits recombination between direct sfx sequences. J Biol Chem. Jul. 28, 2006;281(30):20772-9. Epub May 23, 2006.
Gyodha et al., Sequence-specific and non-specific binding of the Rci protein to the asymmetric recombination sites of the R64 shufflon. J Mol Biol. May 10, 2002;318(4):975-83.
Kittendorf et al., The methymycin/pikromycin pathway: a model for metabolic diversity in natural product biosynthesis. Bioorg Med Chem. Mar. 15, 2009;17(6):2137-46. doi: 10.1016/j.bmc.2008.10.082. Epub Nov. 5, 2008.
Komano et al., Shufflon: multi-inversion of four contiguous DNA segments of plasmid R64 creates seven different open reading frames. Nucleic Acids Res. Feb. 11, 1987;15(3):1165-72.
Gyohda et al., Purification and characterization of the R64 shufflon-specific recombinase. J Bacteriol. May 2000;182(10):2787-92.
Gyohda et al., Structure and function of the shufflon in plasmid R64. Adv Biophys. 2004;38:183-213.
Peikon et al., In vivo generation of DNA sequence diversity for cellular barcoding. Nucleic Acids Res. 2014;42(16):e127. doi:10.1093/nar/gku604. Epub Jul. 10, 2014.

\* cited by examiner

= Regions ligated PCRed to check for correct assembly

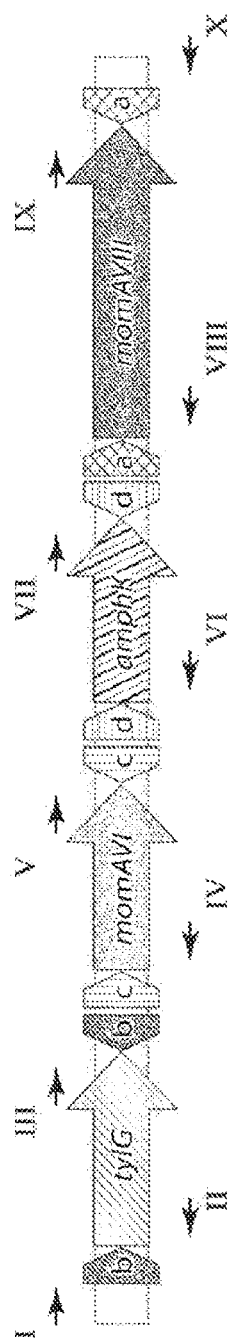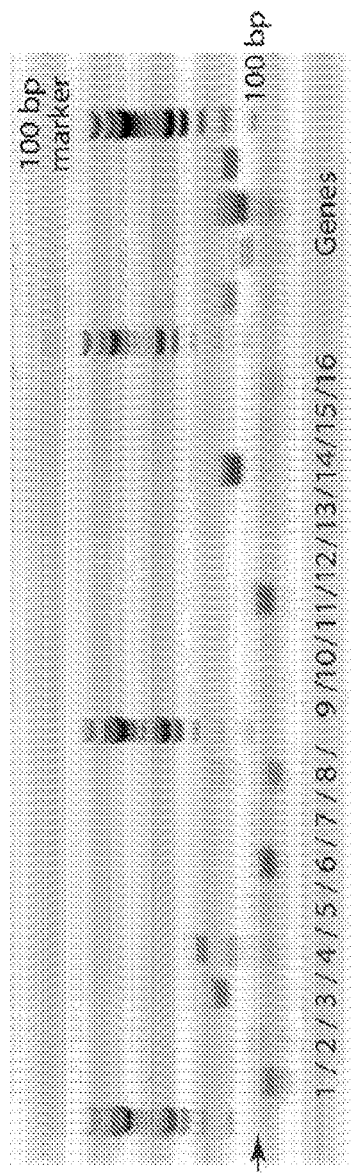
Fig. 23

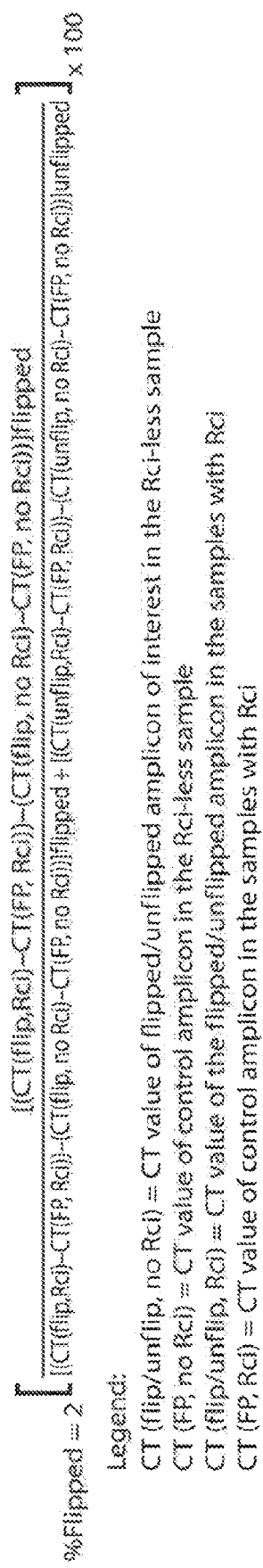

$$\%Flipped = 2\left[\frac{\{(CT(flip,Rci)-CT(FP,Rci))-(CT(flip,no\ Rci)-CT(FP,no\ Rci)\}flipped}{\{(CT(flip,Rci)-CT(FP,Rci))-(CT(flip,no\ Rci)-CT(FP,no\ Rci)\}flipped + \{(CT(unflip,Rci)-CT(FP,Rci))-(CT(unflip,no\ Rci)-CT(FP,no\ Rci))\}unflipped}\right] \times 100$$

Legend:
CT (flip/unflip, no Rci) = CT value of flipped/unflipped amplicon of interest in the Rci-less sample
CT (FP, no Rci) = CT value of control amplicon in the Rci-less sample
CT (flip/unflip, Rci) = CT value of the flipped/unflipped amplicon in the samples with Rci
CT (FP, Rci) = CT value of control amplicon in the samples with Rci

Fig. 31

METHODS AND COMPOSITIONS FOR RECOMBINASE-BASED GENETIC DIVERSIFICATION

RELATED APPLICATIONS

This application is a national stage filing under 35 U.S.C. § 371 of international application number PCT/US2016/050533, filed Sep. 7, 2016, which claims the benefit under 35 U.S.C. § 119(e) of U.S. provisional application No. 62/215,281, filed Sep. 8, 2015, each of which is incorporated by reference herein in its entirety.

BACKGROUND

There has been a steady increase in bacterial resistance to antibiotics, particularly in the clinic. Nonetheless, generating new antibiotics is challenging, in part because it is difficult to generate new molecules using existing technologies.

SUMMARY

One of the biggest challenges in engineering new molecules, such as antibiotics, is the large amount of manual labor required when using traditional cloning techniques. Provided herein are methods and compositions (e.g., nucleic acids, cells and cell-free compositions) that streamline and expedite biosynthetic pathway engineering and new molecule production. The technology provided herein integrates synthetic biology with natural gene shuffling systems to scale up and engineer genetically diverse pathways containing multiple genes that individually, or in combination, encode a variety of bioactivities of interest, which in turn function together to produce a variety of new molecules. In particular, the technology provided herein uses modified components of a recombinase-based bacterial shufflon system that enables flipping (inverting) the orientation of genes in a controlled and predictable manner to turn expression of genes "on" (expressed) or "off" (not expressed), thereby avoiding leaky gene expression, which often accompanies conventional inducible systems.

Thus, the present disclosure provides engineered nucleic acids that include a promoter operably linked to at least two heterologous genes of a biosynthetic pathway of interest, and at least two different pairs of shufflon recombinase recognition sequences (RRSs), wherein at least one of the genes is located between at least one of the pairs of shufflon RRSs.

In some embodiments, at least two heterologous genes encode enzymes, regulatory proteins, transport proteins, or combinations thereof.

In some embodiments, an engineered nucleic acid further includes a promoter operably linked to a gene encoding a shufflon recombinase.

The present disclosure also provides cells and cell-free compositions that include the engineered nucleic acids, as described herein.

The present disclosure further provides methods of producing new molecules using the nucleic acids, cells and compositions, as described herein.

BRIEF DESCRIPTION OF THE DRAWINGS

FIG. 2 also shows a map of an integrative pSET152 plasmid that includes a gusA reporter gene.

FIG. 23 shows a schematic of the shuffling system (top panel). Primers for verification of shuffling represented by black arrows and roman numerals. PCR results using Herculase II polymerase (middle panel) and the combinations of primers listed (bottom panel) in Arabic numerals. qPCR-estimates % of flipping depicted in the table (bottom panel, right).

FIG. 31 shows the equation for the calculation of the DNA inversion frequencies.

DETAILED DESCRIPTION

Provided herein is a system that uses modified components of a bacterial shufflon system to engineer genetically diverse pathways. Several rounds of shuffling (inversion) of a particular engineered pathway results in expression of different combinations genes (genetic diversity), each combination potentially producing a new molecule (molecular diversity).

Some bacteria, such as *Salmonella typhimurium*, have the capacity to 'shuffle' (vary) the type of conjugative pili they produced, as a function of their conjugative partner in liquid matings (Komano, T. *Annu Rev Genet.* 1999; 33:171-91; Gyohda, A. et al. *J. Bacteriol.* 1997; 179:1867-71; Gyohda, A. et al. *J. Mol. Biol.* 2002; 318:975-83; and Komano, T. et al. *Nucleic Acids Res.* 1987; 15(3):1165-72). The plasmid R64 shufflon contains seven recombination sites, which flank and separate four DNA segments. Site-specific recombinations mediated by the product of the rci gene between any two inverted recombination sites result in the inversion of four DNA segments independently or in groups. The shufflon functions as a biological switch to select one of seven C-terminal segments of the PilV proteins, which is a minor component of R64 thin pilus. The shufflon determines the recipient specificity in liquid matings of plasmid R64 (Komano, T. 1999).

The present disclosure describes (1) the assembly of a complete genetically engineered shufflon system encoding heterologous genes (e.g., enzymes), (2) integration of this system into a bacterial (e.g., *Streptomyces* spp.) target locus, (3) induction of rci gene/protein expression and subsequent shuffling events, and (4) production of new molecules.

Biosynthetic Pathways of Interest

Common approaches to new molecule discovery and production (e.g., antibiotic production), such as screening of new bacterial isolates, mix-and-match of genes through traditional cloning, chemical synthesis and medicinal chemistry, are slow to yield results. Provided herein is a pathway-based system that generates its own diversity and, in some embodiments, permits "hands-free" molecular engineering, maximizes the number of possible pathways without an increase in labor, can undergo several rounds of engineering with minimal labor, and permits an exponential increase of possible molecules.

The present disclosure provides a system that is able to generate molecular diversity, in some embodiments, by replacing a single gene of a biosynthetic pathway with a new biosynthetic pathway (multiple heterologous genes) and shuffling genes of the new biosynthetic pathway to produce new molecules (e.g., new antibiotics).

Figure 10:
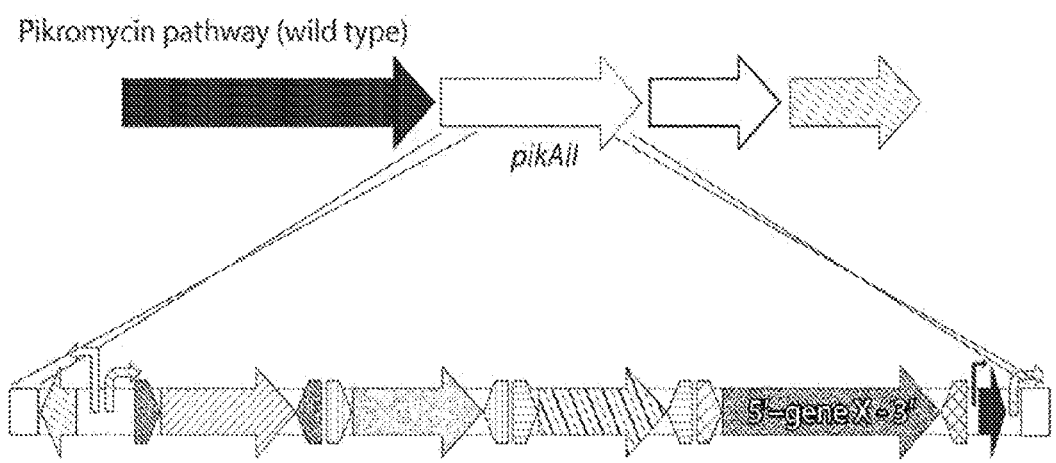
FIG. 10 shows a representation of the double crossover event and integration of the synthetic shufflon system, which originates a new semi-synthetic pikromycin pathway.
Figure 11:
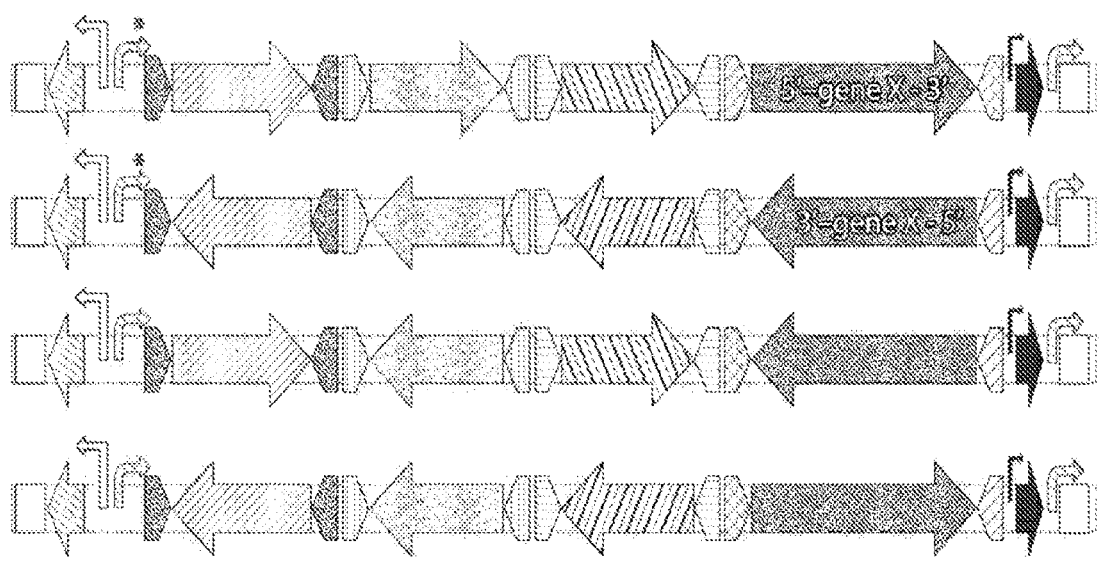
FIG. 11 shows examples of gene combinations as a result of selective inversion.

The methods as provided herein are not limited by any particular biosynthetic pathway. Polyketide biosynthetic pathways (e.g., pikromycin, erythromycin, lovastatin, discodermolide, aflatoxin B 1, avermectins, nystatin and rifamycin) are used as examples throughout the disclosure, as shown in FIG. 10 and FIG. 11. A (one or more) gene of a biosynthetic pathway of interest may be replaced with at least two heterologous genes that encode particular bioactivities. As shown, for example, in FIG. 10, the pikAII gene of the pikromycin pathway is replaced with tylG, momAVI, amphK and momAVIII, each of which encodes an enzyme having a particular bioactivity. Each of tylG, momAVI, amphK and momAVIII is flanked by a different pair of shufflon recombinase recognition sequences (RRSs), and each RRS recombines at a different rate in the presence of shufflon recombinase activity. FIG. 11 shows the different combinations of gene expression following selective inversion (shuffling). Each combination can potentially produce a new molecule (e.g., when expressed in combination with other genes of the particular biosynthetic pathway of interest).

The expression of these one or more genes is shuffled to produce new molecules.

For example, as shown in FIG. 10 and FIG. 11, the pikAII gene of the pikromycin pathway may be replaced with one or more genes encoding selected enzymatic activities.

Examples of other biosynthetic pathways of interest include other small molecule biosynthetic pathways, such as, but not limited to, alkaloid biosynthetic pathways (e.g., hyoscyamine, atropine, cocaine, scopolamine, codeine, morphine, tetrodotoxin, vincristine and vinblastine), terpenoid biosynthetic pathways (e.g., azadirachtin, artemisinin, tetrahydrocannabinol, steroids and saponins), glycoside biosynthetic pathways (e.g., nojirimycin and glucosinolates), phenazine biosynthetic pathways (e.g., pyocyanin and phenazine-1-carboxylic acid (and derivatives)), biphenyl biosynthetic pathways, dibenxofuran biosynthetic pathways, fatty acid biosynthetic pathways (e.g., FR-900848, U-106305 and phloroglucinols), nonribosomal peptide biosynthetic pathways (e.g., vancomycin, ramoplanin, teicoplanin, gramicidin, bacitracin and ciclosporin), and ribosomal peptide biosynthetic pathways (e.g., microcin-J25).

A "heterologous gene of a biosynthetic pathway of interest" refers to a gene that is not normally a component of a naturally-occurring biosynthetic pathway. For example, the wild-type pikromycin biosynthetic pathway includes the following genes: the pikRa and pikR1 genes, the pikAI-V genes, the pikBI-VIII genes, the pikBR gene, the pikC gene and the pikD gene. The pikAIII gene, as discussed below, may be replaced with other genes, such as tylG, momAVI, amphK and momAVIII, that encode bioactivities of interest. The genes that replace the pikAIII gene are considered to be heterologous genes because they do not normally/naturally participate in the pikromycin biosynthetic pathway.

In some embodiments, the pikAII gene is replaced with at least one, at least two, at least three or at least four genes selected from S. fradiae tylG, S. cinnamonensis momVI, S. cinnamonensis momVIII and S. nodosus amphK.

At least one gene (wild-type gene) of a biosynthetic pathway of interest may be replaced with at least one heterologous gene (shuffling gene). The selection of heterologous genes (to be shuffled) may be based on a number of factors, including phylogenetic distance between the wild type gene and the heterologous gene (increased relatedness is preferred, in some embodiments), the size of the gene (e.g., between 5-15 kilobases) and the predicted bioactivity score (e.g., using an algorithm-based prediction of molecule structure based on genetic information (NP.searcher), used in combination with a bioactivity prediction algorithm (Molinspiration)). In some embodiments, an engineered nucleic acid comprises at least two heterologous genes of a biosynthetic pathway of interest. For example, an engineered nucleic acid may comprise (a promoter operably linked to) at least 2, at least 3, at least 4, or at least 5 heterologous genes of a biosynthetic pathway of interest. In some embodiments, an engineered nucleic acid may comprise (a promoter operably linked to) 1-5, 2-5, 1-10 or 2-10 heterologous genes of a biosynthetic pathway of interest. In some embodiments, an engineered nucleic acid may comprise (a promoter operably linked to) 1, 2, 3, 4, 5, 6, 7, 8, 9, 10 or more heterologous genes of a biosynthetic pathway of interest.

Heterologous genes of a biosynthetic pathway of interest generally encode proteins, such as enzymes, regulatory proteins (proteins that regulate gene/protein expression) and transport proteins (proteins that move materials within an organism, e.g., carrier proteins, membrane proteins). In some embodiments, genes of a biosynthetic pathway of interest encode receptors, ligands, lytic proteins, or antimicrobial proteins/peptides.

Examples of enzymes include, but are not limited to, oxidoreductases (EC 1) (e.g., dehydrogenase, oxidase), transferases (EC 2) (e.g., transaminase, kinase), hydrolases (EC 3) (e.g., lipase, amylase, peptidase), lyases (EC 4) (e.g., decarboxylase), isomerases (EC 5) (e.g., isomerase, mutase) and ligases (EC 6) (e.g., synthetase). The International Union of Biochemistry and Molecular Biology developed a nomenclature for enzymes, the EC numbers; each enzyme is described by a sequence of four numbers preceded by "EC". Specific enzymes encompassed by the present disclosure may be selected from and identified based on their EC number retrieved from the website of the Nomenclature Committee of the International Union of Biochemistry and Molecular Biology (Moss G P. "Recommendations of the Nomenclature Committee". International Union of Biochemistry and Molecular Biology on the Nomenclature and Classification of Enzymes by the Reactions they Catalyse).

Examples of regulatory proteins include, but are not limited to, transcriptional activators and transcriptional repressors. Transcriptional activators typically bind nearby to transcriptional promoters and recruit RNA polymerase to directly initiate transcription. Transcriptional repressors typically bind to transcriptional promoters and sterically hinder transcriptional initiation by RNA polymerase.

Examples of transport proteins include, but are not limited to, transporters, channels and pumps. Transporters are membrane proteins responsible for transport of substances across the cell membrane. Channels are made up of proteins that form transmembrane pores through which selected ions can diffuse. Pumps are membrane proteins that can move substances against their gradients in an energy-dependent process known as active transport. In some embodiments, nucleic acid sequences encoding proteins and protein domains whose primary purpose is to bind other proteins, ions, small molecules, and other ligands may be used in accordance with the present disclosure.

Receptors, ligands and lytic proteins encoded by at least one heterologous gene include any receptor, ligand and lytic protein, described herein or known to one of ordinary skill in the art. Receptors tend to have three domains: an extracellular domain for binding ligands such as proteins, peptides or small molecules, a transmembrane domain and an intracellular or cytoplasmic domain, which frequently can participate in some sort of signal transduction event such as phosphorylation.

Examples of antimicrobial proteins and/or peptides include, but are not limited to, genes that encode instructions for cell death, or genes that encode bactericidal proteins. Examples of such gene modules include pemI-pemK genes of plasmid R100, the phd-doc genes of phage P1, the ccdA-ccdB genes of plasmid F, mazE-mazF (or chpAI-chpAK), sof-gef kicA-kicB, relB-relE, chpBI-chpBK and gef. Other examples of antimicrobial proteins and/or peptides include, but are not limited to, bacteriocins, hydramacin-1, cecropins, moricins, papiliocins, poneratoxins, mastoparans, melittins, spinigerins, cupiennins, oxyopinins, magainins, dermaseptins, cathelicidins, defensins and protegrins. Other antimicrobial proteins and/or peptides are encompassed by the present disclosure.

Shufflon Recombinase and Recombinase Recognition Sites

A "shufflon recombinase" is the product of a site-specific recombinase gene, rci. The Tel gene encodes a basic protein belonging to the integrase (Int) family of site-specific recombinases (Kubo A., et al. *Mol. Gen. Genet.* 213:30-35, 1988). A shufflon recombinase (also referred to as a shufflon-specific DNA recombinase) catalyzes site-specific recombination between a pair of inverted repeat sequences of the multiple DNA inversion system in plasmid R64. There are several pairs of inverted repeat sequences that recombine in the presence of shufflon recombinase activity, any of which may be used as provided herein. Table 3 provides examples of shufflon recombinase recognition sequences (RRSs), including RRS a GTGCCAATCCGGTACGTGG (SEQ ID NO: 5), RRS b GTGCCAATCCGGTACCTGG (SEQ ID NO: 6), RRS c GTGCCAATCCGGTCGGTGG (SEQ ID NO: 7), and RRS d GTGCCAATCCGGTACTTGG (SEQ ID NO: 8). Thus, a "pair" of shufflon RRSs may include (a) GTGCCAATCCGGTACGTGG (SEQ ID NO: 5) and CCACGTACCGGATTGGCAC (SEQ ID NO: 66), (b) GTGCCAATCCGGTACCTGG (SEQ ID NO: 6) and CCAGGTACCGGATTGGCAC (SEQ ID NO: 67), (c) GTGCCAATCCGGTCGGTGG (SEQ ID NO: 7) and CCACCGACCGGATTGGCAC (SEQ ID NO: 68), or (d) GTGCCAATCCGGTACTTGG (SEQ ID NO: 8) and CCAAGTACCGGATTGGCAC (SEQ ID NO: 69). Other shufflon RRSs are encompassed by the present disclosure.

In some embodiments, different shufflon recombinase restriction sites (e.g., RRSs a-d) recombine (are inverted) at different rates relative to one another. Thus, in some embodiments, an engineered nucleic acid of the present disclosure comprises at least two (e.g., at least 2, at least 3, or at least 4) pairs of shufflon recombinase recognitions sites that recombine, in the presence of shufflon recombinase activity, at different rates relative to each other. For example, RRS a may recombined in 29% of the molecules, while RRS b may recombine in only 0.025% of the molecules. In some embodiments, RRS c recombines in 0.02% of the molecules and, in some embodiments, RRS d recombines in 0.1% of the molecules.

A shufflon recombinase (and/or shufflon recombination recognition sites), in some embodiments, is obtained from a *Salmonella* spp. (e.g., *Salmonella enterica*), however, shufflon recombinase may be obtained from other bacterial species. For example, a shufflon recombinase may be obtained from an *Escherichia* spp. (e.g., *Escherichia coli*), a *Yersinia* spp. (e.g., *Yersinia enterocolitica*), a *Klebsiella* spp. (e.g., *Klebsiella pneumoniae*), a *Acinetobacter* spp. (e.g., *Acinetobacter baumannii*), a *Bordetella* spp. (e.g., *Bordetella pertussis*), a *Neisseria* spp. (e.g., *Neisseria meningitidis*), an *Aeromonas* spp., a *Franciesella* spp., a *Corynebacterium* spp., a *Citrobacter* spp., a *Chlamydia* spp., a *Hemophilus* spp., a *Brucella* spp., a *Mycobacterium* spp., a *Legionella* spp., a *Rhodococcus* spp., a *Pseudomonas* spp., a *Helicobacter* spp., a *Salmonella* spp., a *Vibrio* spp., a *Bacillus* spp., a *Erysipelothrix* spp., a *Salmonella* spp., a *Streptomyces* spp., a *Bacteroides* spp., a *Prevotella* spp., a *Clostridium* spp., a *Bifidobacterium* spp., or a *Lactobacillus* spp.

In some embodiments, a shufflon recombinase is a *Salmonella enterica* shufflon recombinase.

The gene encoding a shufflon recombinase as provided herein may be located on the same nucleic acid comprising heterologous genes of a biosynthetic pathway of interest. Alternatively, the gene encoding a shufflon recombinase may be located on nucleic acid that is separate from a nucleic acid comprising heterologous genes of a biosynthetic pathway of interest. For example, a gene encoding a shufflon recombinase may be located in a chromosome of a cell that includes a plasmid containing an engineered nucleic acid comprising a promoter operably linked to at least two heterologous genes of a biosynthetic pathway of interest. In other instances, a gene encoding a shufflon recombinase may be located on one plasmid (or other vector), while an engineered nucleic acid comprising a promoter operably linked to at least two heterologous genes of a biosynthetic pathway of interest may be located on another plasmid (or other vector).

Typically, a single gene is located between a pair of shufflon recombinase recognition sites (e.g., RRS a-gene X-RRS a). In some embodiments, however, more than one gene is located between a pair of shufflon recombinase recognition sites (e.g., RRS a-gene X, gene Y-RRS a). In some embodiments, an engineered nucleic acid comprises a single gene located between a pair of shufflon recombinase recognition sites (e.g., RRS a-gene X-RRS a) and at least two genes located between a different pair of shufflon recombinase recognition sites (e.g., RRS b-gene Y, gene Z-RRS b).

A gene encoding a shufflon recombinase, in some embodiments, is codon-optimized for expression in a host cell of interest (e.g., a bacterial host cell). Thus, a gene encoding a shufflon recombinase may be obtained from one species of bacterial cell (e.g., *Escherichia* spp.) and then expressed in another species of bacterial cell (e.g., *Streptomyces* spp.). There are several online tools available for codon optimization of a gene (see, e.g., Chin, J. X. et al. *Bioinformatics, Codon Optimization OnLine (COOL): a web-based multi-objective optimization platform for synthetic gene design,* 2014; idtdna.com/CodonOpt; jcat.de; dna20.com/services/genegps; and genscript.com/gsfiles/techfiles/Webinar_Codon_Optimization_Rachel_Speer_GenScript.pdf.

In some embodiments, a gene encoding the shufflon recombinase comprise a nucleotide sequence as set forth in SEQ ID NO: 35 or SEQ ID NO: 36 (codon optimized for expression in *Streptomyces* spp.

Figure 4:
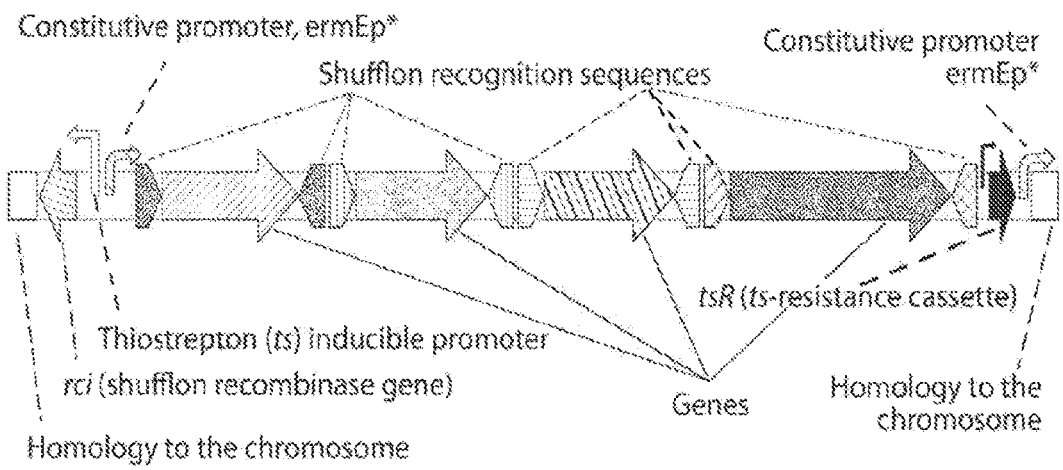
FIG. 4 shows the organization and description of a biosynthetic pathway assembled.

A gene encoding a shufflon recombinase, in some embodiments, is located on the same engineered nucleic acid that contains heterologous genes of a biosynthetic pathway of interest. In such embodiments, the gene encoding a shufflon recombinase (operably linked to a promoter) may be oriented in the forward 5' to 3' direction, or in the reverse 3' to 5' direction, as shown, for example, in FIG. 4. In FIG. 4, the rci gene and its promoter are oriented in the 3' to 5' direction, while the heterologous genes and their promoter are oriented in the 5' to 3' direction.

Engineered Nucleic Acids

The engineered nucleic acids of the present disclosure contain genetic elements that can regulate gene/protein expression. A "genetic element," as used herein, refers to a nucleotide sequence that has a role in gene expression. For example, nucleic acids (e.g., recombinant nucleic acids) encoding proteins, promoters, enhancers and terminators are genetic elements. The nucleic acids of the present disclosure may be engineered using, for example, standard molecular cloning methods (see, e.g., *Current Protocols in Molecular Biology*, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., *Nature Methods* 6(5):343-345 (2009), the teachings of which relating to molecular cloning are herein incorporated by reference).

The term "nucleic acid" refers to at least two nucleotides covalently linked together, and in some instances, may contain phosphodiester bonds (e.g., a phosphodiester "backbone"). In some embodiments, a nucleic acid of the present disclosure may be considered to be a nucleic acid analog, which may contain other backbones comprising, for example, phosphoramide, phosphorothioate, phosphorodithioate, O-methylphophoroamidite linkages, and/or peptide nucleic acids. Nucleic acids (e.g., components, or portions, of the nucleic acids) of the present disclosure may be naturally occurring or engineered. Engineered nucleic acids include recombinant nucleic acids and synthetic nucleic acids. "Recombinant nucleic acids" may refer to molecules that are constructed by joining nucleic acid molecules and, in some embodiments, can replicate in a living cell. "Synthetic nucleic acids" may refer to molecules that are chemically or by other means synthesized or amplified, including those that are chemically or otherwise modified but can base pair with naturally occurring nucleic acid molecules. Recombinant and synthetic nucleic acids also include those molecules that result from the replication of either of the foregoing.

The nucleic acids may be single-stranded (ss) or double-stranded (ds), as specified, or may contain portions of both single-stranded and double-stranded sequence. The nucleic acid may be DNA, both genomic and cDNA, RNA or a hybrid/chimeric, where the nucleic acid contains any combination of deoxyribonucleotides and ribonucleotides, and any combination of bases, including uracil, adenine, thymine, cytosine, guanine, inosine, xanthine, hypoxanthine, isocytosine, and isoguanine.

Some aspects of the present disclosure provide methods and systems that use multiple components, such as a gene encoding shufflon recombinase and gene(s) encoding proteins or other molecules of a biosynthetic pathway. It should be understood that components may be encoded by a single nucleic acid (e.g., on the same plasmid or other vector) or by multiple different (e.g., independently-replicating) nucleic acids.

Engineered nucleic acids of the present disclosure may contain promoter sequences (promoters) operably linked to a heterologous gene of a biosynthetic pathway of interest. As used herein, a "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof.

A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence. In some embodiments, a promoter is operably linked to a gene that is in the "on position" (e.g., forward, 5' to 3') or "off position" (e.g., reverse, 3' to 5'). A gene is in the "on position" if the gene and the promoter to which it is operably linked are oriented in the same direction along a nucleic acid (e.g., both oriented 5' to 3', or both oriented 3' to 5'). By contrast, a gene is in the "off position" if the gene and the promoter to which it is operably linked are oriented in opposition directions along a nucleic acid (e.g., the promoter oriented 5' to 3' and the gene oriented 3' to 5'). In such embodiments, the gene (located between (flanked by) a pair of recombinase recognition sites) may be turned "on" following an inversion event. In FIGS. 10 and 11, for example, a block arrow is representative of a gene of a pathway of interest. Gene X, flanked by a pair of shufflon recombinase recognition sites (short inverted arrows) is operably linked to the promoter represented by a starred arrow. In FIG. 10, gene X is in the "on position." Gene X is also in the "on position" in FIG. 11, top and bottom panels. Following recombination of the recombinase recognition sites that flank Gene X, gene X is flipped (inverted) and turned "off." Thus, in the middle panels of FIG. 11, gene X is in the "off position."

In some embodiments, a promoter operably linked to at least two heterologous genes of a synthetic pathway of interest is oriented in the 5' to 3' direction, and each gene operably linked to the promoter is oriented in a 5' to 3' direction. Thus, each gene is in the "on position" when the promoter is active.

In some embodiments, a promoter operably linked to at least two heterologous genes of a synthetic pathway of interest is oriented in the 5' to 3' direction, and each gene operably linked to the promoter is oriented in a 3' to 5' direction. Thus, each gene is in the "off position" when the promoter is active.

In some embodiments, a promoter operably linked to at least two heterologous genes of a synthetic pathway of interest is oriented in the 5' to 3' direction, and at least one gene operably linked to the promoter is oriented in a 5' to 3' direction and at least one gene operably linked to the promoter is oriented in a 3' to 5'.

A promoter may be classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used herein.

A promoter may be one naturally associated with a gene or sequence, as may be obtained by isolating the 5' non-coding sequences located upstream of the coding segment of a given gene or sequence.

A promoter is "recombinant" or "heterologous" if it is not naturally/normally associated with (does not naturally/normally control transcription of) a gene to which is it operably linked. In some embodiments, a gene (or other nucleotide sequence) may be positioned under the control of a recombinant or heterologous promoter. Such promoters may include promoters of other genes; promoters isolated from any prokaryotic cell; and synthetic promoters that are not "naturally occurring" such as, for example, those that contain different elements of different transcriptional regulatory regions and/or mutations that alter expression through methods of genetic engineering. In addition to producing nucleic acid sequences of promoters synthetically, sequences may be produced using recombinant cloning and/or nucleic acid amplification technology, including polymerase chain reaction (PCR) (see U.S. Pat. Nos. 4,683,202 and 5,928,906).

As used herein, an "inducible promoter" is one that is characterized by initiating or enhancing transcriptional activity when in the presence of, influenced by or contacted by an inducer or inducing agent. An "inducer" or "inducing agent" may be endogenous or a normally exogenous condition, compound or protein that contacts a programmable nuclease circuit in such a way as to be active in inducing transcriptional activity from the inducible promoter.

Inducible promoters for use in accordance with the present disclosure, in some embodiments, function in a bacterial cell. Examples of inducible promoters for use herein include, without limitation, bacteriophage promoters (e.g. Pls1con, T3, T7, SP6, PL) and bacterial promoters (e.g. Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated *E. coli* promoters such as positively regulated $\sigma^{70}$ promoters (e.g., inducible pBad/araC promoter, Lux cassette right promoter, modified lamdba Prm promote, placa Or2-62 (positive), pBad/AraC with extra REN sites, pBad, P(Las) TetO, P(Las) CIO, P(Rhl), Pu, FecA, pRE, cadC, hns, pLas, pLux), $\sigma^S$ promoters (e.g., Pdps), $\sigma^{32}$ promoters (e.g., heat shock) and $\sigma^{54}$ promoters (e.g., glnAp2); negatively regulated *E. coli* promoters such as negatively regulated $\sigma^{70}$ promoters (e.g., Promoter (PRM+), modified lamdba Prm promoter, TetR-TetR-4C P(Las) TetO, P(Las) CIO, P(Lac) IQ, RecA_Dlex-O_DLacO1, dapAp, FecA, Pspac-hy, pcI, plux-cI, plux-lac, CinR, CinL, glucose controlled, modifed Pr, modifed Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), $\sigma^S$ promoters (e.g., Lutz-Bujard LacO with alternative sigma factor $\sigma^{38}$), $\sigma^{32}$ promoters (e.g., Lutz-Bujard LacO with alternative sigma factor $\sigma^{32}$), and $\sigma^{54}$ promoters (e.g., glnAp2); negatively regulated *B. subtilis* promoters such as repressible *B. subtilis* $\sigma^A$ promoters (e.g., Gram-positive IPTG-inducible, Xyl, hyper-spank) and $\sigma^B$ promoters. Other inducible promoters may be used in accordance with the present disclosure.

The administration or removal of an inducer results in a switch between activation and inactivation of the transcription of the operably linked gene or other nucleic acid sequence (e.g., heterologous gene). Thus, as used herein, the active state of a promoter operably linked to a gene refers to the state when the promoter is actively driving transcription of the gene (i.e., the linked gene is expressed). Conversely, the inactive state of a promoter operably linked to a gene refers to the state when the promoter is not actively driving transcription of the gene (i.e., the linked gene is not expressed).

An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, the inducer used in accordance with the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters. In some embodiments, the inducer used in accordance with the present disclosure is anhydrotetracycline (aTc), which is a derivative of tetracycline that exhibits no antibiotic activity and is designed for use with tetracycline-controlled gene expression systems, for example, in bacteria.

Other inducible promoter systems are known in the art and may be used in accordance with the present disclosure.

Some engineered nucleic acids may include nucleotide sequences homologous to a chromosomal locus of a host cell of interest. Such sequences facilitate integration of an engineered nucleic acid into a chromosomal locus of a host cell. It should be understood, however, than chromosomal integration of an engineered nucleic acid encoding heterologous genes of a biosynthetic pathway is optional.

In some embodiments, an engineered nucleic acid also comprises an antibiotic resistance gene (see, e.g., online database: card.mcmaster.ca) to facilitate cloning and selection of the nucleic acid. Thus, in some embodiments, an engineered nucleic acid comprises a kanamycin resistance gene, spectinomycin resistance gene, streptomycin resistance gene, ampicillin resistance gene, carbenicillin resistance gene, bleomycin resistance gene, erythromycin resistance gene, polymyxin B resistance gene, tetracycline resistance gene, chloramphenicol resistance gene, hygromycin resistance gene and/or a ts-resistance gene resistance gene.

Cells

Engineered nucleic acids of the present disclosure may be introduced into a host cell of interest, and in some embodiments, are optimized (e.g., codon-optimized) for expression in a host cell of interest. In some embodiments, the host cell is a bacterial cell. In some embodiments, the host cell is a mammalian cell, a yeast cell or an insect cell.

Bacteria are small (typical linear dimensions of around 1 micron), non-compartmentalized organisms, with at least one circular DNA chromosomes and ribosomes of 70S. As used herein, the term "bacteria" encompasses all variants of bacteria (e.g., endogenous bacteria, which naturally reside in a closed system, environmental bacteria or bacteria released for bioremediation or other efforts). Bacterial cells of the present disclosure include bacterial subdivisions of Eubacteria and Archaebacteria. Eubacteria can be further subdivided into Gram-positive and Gram-negative Eubacteria, which depend upon a difference in cell wall structure. Also included herein are those classified based on gross morphology alone (e.g., cocci, bacilli). In some embodiments, bacterial cells are Gram-negative cells, and in some embodiments, the bacterial cells are Gram-positive cells. Examples of bacterial cells of the present disclosure include, without limitation, cells classified as *Yersinia* spp., *Escherichia* spp., *Klebsiella* spp., *Acinetobacter* spp., *Bordetella* spp., *Neisseria* spp., *Aeromonas* spp., Franciesella spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are classified as *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Streptococcus* spp., *Enterococcus faecalis, Bacillus coagulans, Bacillus ceretus, Bacillus popillae, Synechocystis* strain *PCC6803, Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes*, or *Streptomyces ghanaenis*. Thus, the engineered nucleic acids of the present disclosure may be introduced into a bacterial cell from any one or more of the foregoing genus and/or species of bacteria. Other bacterial cells and microbes may also be used. As used herein, "endogenous" bacterial cells may refer to non-pathogenic bacteria that are part of a normal internal ecosystem such as bacterial flora.

In some embodiments, a host cell is a *Streptomyces* spp. cell, such as a *Streptomyces venezuelae* cell or a *Streptomyces coelicolor* cell.

In some embodiments, bacterial cells of the present disclosure are anaerobic bacterial cells (e.g., cells that do not require oxygen for growth). Anaerobic bacterial cells include facultative anaerobic cells such as, for example, *Escherichia coli, Shewanella oneidensis* and *Listeria monocytogenes*. Anaerobic bacterial cells also include obligate anaerobic cells such as, for example, *Bacteroides* and *Clostridium* species. In humans, for example, anaerobic bacterial cells are most commonly found in the gastrointestinal tract. Thus, engineered nucleic acids of the present disclosure may be introduced into anaerobic bacterial cells.

Cells of the present disclosure are generally considered to be modified. A modified cell is a cell that contains an exogenous nucleic acid or a nucleic acid that does not occur in nature (e.g., an engineered nucleic acid of the present disclosure). In some embodiments, a cell contains a deletion or a modification (e.g., mutation) in a genomic/chromosomal nucleic acid. For example, a cell may comprise a deletion or modification in a (at least one) gene of a biosynthetic pathway of interest, such as a deletion or a modification in the pikromycin biosynthetic pathway (e.g., in a pikAI-V, pikBI-VIII, pikBR gene, pikC gene or pikD gene). In some embodiments, a host cell comprises a deletion in the pikAII or pikAIII gene.

In some embodiments, a cell contains an exogenous independently replicating nucleic acid (e.g., an engineered nucleic acid located on an episomal vector). In some embodiments, a cell is produced by introducing a foreign or exogenous nucleic acid (e.g., engineered nucleic acid) into a cell. Thus, provided herein are methods of introducing engineered nucleic acid into a cell. A nucleic acid may be introduced into a cell by conventional methods, such as, for example, electroporation (see, e.g., Heiser W. C. *Transcription Factor Protocols: Methods in Molecular Biology*™ 2000; 130: 117-134), chemical (e.g., calcium phosphate or lipid) transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W. *Proc Natl Acad Sci USA.* 1980 April; 77(4): 2163-7), transduction, conjugation, or microinjection of purified DNA directly into the nucleus of the cell (see, e.g., Capecchi M. R. *Cell.* 1980 November; 22(2 Pt 2): 479-88).

Engineered nucleic acids of the present disclosure may be transiently expressed or stably expressed. "Transient cell expression" refers to expression by a cell of a nucleic acid that is not integrated into the nuclear genome of the cell. By comparison, "stable cell expression" refers to expression by a cell of a nucleic acid that remains in the nuclear genome of the cell and its daughter cells. Typically, to achieve stable cell expression, a cell is co-transfected with a marker gene and an exogenous nucleic acid that is intended for stable expression in the cell. The marker gene gives the cell some selectable advantage (e.g., resistance to a toxin, antibiotic, or other factor). Few transfected cells will, by chance, have integrated the exogenous nucleic acid into their genome. If a toxin, for example, is then added to the cell culture, only those few cells with a toxin-resistant marker gene integrated into their genomes will be able to proliferate, while other cells will die. After applying this selective pressure for a period of time, only the cells with a stable transfection remain and can be cultured further. Expression of nucleic acids in transiently-transfected and/or stably-transfected cells may be constitutive or inducible. Inducible promoters for use as provided herein are described above.

Cell Free Compositions

Also provided herein are cell-free compositions (e.g., in vitro transcription and/or translation reactions) that may be used, for example, to generate/produce new molecules. In some embodiments, a cell-free composition comprises an engineered nucleic acid comprising (i) a promoter operably linked to at least two heterologous genes of a synthetic pathway of interest, and (ii) at least two different pairs of shufflon recombinase recognition sequences (RRSs), wherein at least one of the genes is located between at least one of the pairs of shufflon RRSs. A cell-free composition typically further comprises an engineered nucleic acid comprising a promoter operably linked to a gene encoding a shufflon recombinase, a cell extract and a polymerase.

A "cell extract" (cell lysate) refers to the contents of a cell without the intact cell wall. In some embodiments, a cell extract contains portions of the cell wall, for example, in the form of inverted membrane vesicles. A typical bacterial cell extract may include, for example, at least one component selected from the group consisting of: ribosomes, amino acids, NTPs, phosphoenolpyruvate, pyruvate kinase, polyethylene glycol, ammonium acetate, potassium acetate and folinic acid. In some embodiments, a cell extract comprises a S30 cell fraction obtained from a bacterial cell. In some embodiments, a cell-free composition comprises ribosomes, amino acids, NTPs, phosphoenolpyruvate, pyruvate kinase, polyethylene glycol, ammonium acetate, potassium acetate and folinic acid.

A cell-free composition may further comprise an engineered nucleic acid encoding additional proteins of the biosynthetic pathway of interest, or may further comprise additional proteins of the biosynthetic pathway of interest. For example, if the pikromycin biosynthetic pathway is the pathway of interest, a cell may have a deletion in the pikAII gene (replaced with an engineered nucleic acid encoding heterologous (shuffling) genes) and may express some or all of the remaining genes of the pikromycin biosynthetic pathway (e.g., in a pikAI-V, pikBI-VIII, pikBR gene, pikC gene or pikD gene). Thus, a cell-free composition may also comprises the remaining genes of the pikromycin biosynthetic pathway (e.g., in a pikAI-V, pikBI-VIII, pikBR gene, pikC gene or pikD gene).

Cell-free compositions may also contain polymerase, such as RNA polymerase (e.g., RNA T7, T3 or SP6 polymerase). Other RNA polymerases may be used.

Methods

Provided herein are methods of producing molecules (e.g., new molecules, such as new antibiotic molecules). The methods may comprise incubating a cell-free composition under conditions that result in expression of a shufflon recombinase, recombination of RSSs, expression of at least two heterologous genes, and production of molecules produced by the synthetic pathway of interest.

In some embodiments, the methods comprise culturing cells that comprise a gene encoding a shufflon recombinase and an engineered nucleic acid that includes (a) a promoter operably linked to at least two heterologous genes of a biosynthetic pathway of interest, and (b) at least two different pairs of shufflon recombinase recognition sequences (RRSs), wherein at least one of the genes is located between at least one of the pairs of shufflon RRSs, under conditions that result in expression of a shufflon recombinase, recombination of RSSs, expression of at least two heterologous genes, and production of molecules produced by the synthetic pathway of interest.

In some embodiments, the methods comprise culturing cells that comprise (a) an engineered nucleic acid that includes a promoter operably linked to a gene encoding a shufflon recombinase, and (b) an engineered nucleic acid comprising (i) a promoter operably linked to at least two heterologous genes of a synthetic pathway of interest, and (ii) at least two different pairs of shufflon recombinase recognition sequences (RRSs), wherein at least one of the genes is located between at least one of the pairs of shufflon RRSs, under conditions that result in expression of a shufflon recombinase, recombination of RSSs, expression of at least two heterologous genes, and production of molecules produced by the synthetic pathway of interest. In some embodiments, the methods further comprise isolating the molecules. In some embodiments, the molecules comprise (or are) antibiotics.

The present disclosure provide methods that include delivering to cells at least one of the engineered nucleic acid constructs as provided herein. Constructs may be delivered by any suitable means, which may depend on the residence and type of cell. For example, if cells are located in vivo within a host organism (e.g., an animal such as a human), engineered nucleic acid constructs may be delivered by injection into the host organism of a composition containing engineered nucleic acid constructs. Constructs may be delivered by a vector, such as a viral vector (e.g., bacteriophage or phagemid). For cells that are not located within a host organism, for example, for cells located ex vivo/in vitro or in an environmental (e.g., outside) setting, engineered nucleic acid constructs may be delivered to cells by electroporation, chemical transfection, fusion with bacterial protoplasts containing recombinant, transduction, conjugation, or microinjection of purified DNA directly into the nucleus of the cells.

The present disclosure further provides embodiments encompassed by the following numbered paragraphs:

1. An engineered nucleic acid, comprising: (a) a promoter operably linked to at least two heterologous genes of a biosynthetic pathway of interest; and (b) at least two different pairs of shufflon recombinase recognition sequences (RRSs), wherein at least one of the genes is located between at least one of the pairs of shufflon RRSs.

2. The engineered nucleic acid of paragraph 1, wherein the at least two heterologous genes encode proteins selected from the group consisting of: enzymes, regulatory proteins and transport proteins.

3. The engineered nucleic acid of paragraph 1 or 2 further comprising (c) a promoter operably linked to a gene encoding a shufflon recombinase.

4. The engineered nucleic acid of paragraph 3, wherein the shufflon recombinase is a *Salmonella enterica* shufflon recombinase.

5. The engineered nucleic acid of paragraph 3 or 4, wherein the gene encoding the shufflon recombinase is codon-optimized for expression in a host cell of interest.

6. The engineered nucleic acid construct of any one of paragraphs 1-5, wherein the gene encoding the shufflon recombinase comprise a nucleotide sequence as set forth in SEQ ID NO: 35 or SEQ ID NO: 36.

7. The engineered nucleic acid of any one of paragraphs 1-7 further comprising (d) nucleotide sequences homologous to a chromosomal locus of a host cell of interest.

8. The engineered nucleic acid of any one of paragraphs 5-7, wherein the host cell of interest is a bacterial cell.

9. The engineered nucleic acid of paragraph 8, wherein the bacterial cell belongs to a genus selected from the group consisting of: *Yersinia* spp., *Escherichia* spp., *Klebsiella* spp., *Bordetella* spp., *Neisseria* spp., *Aeromonas* spp., Franciesella spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp. and *Lactobacillus* spp.

10. The engineered nucleic acid of paragraph 9, wherein the bacterial cell is a *Streptomyces* spp. cell.

11. The engineered nucleic acid of paragraph 10, wherein the *Streptomyces* spp. cell is a *Streptomyces venezuelae* cell or a *Streptomyces coelicolor* cell.

12. The engineered nucleic acid of any one of paragraphs 3-11, wherein the gene encoding the shufflon recombinase is oriented in a 3' to 5' direction.

13. The engineered nucleic acid of any one of paragraphs 3-12, wherein the promoter of (a) and/or (c) is an inducible promoter.

14. The engineered nucleic acid of any one of paragraphs 1-13, wherein the engineered nucleic acid construct further comprises an antibiotic resistance gene.

15. The engineered nucleic acid of any one of paragraphs 1-14, wherein the RRSs recombine, in the presence of shufflon recombinase activity, at different rates relative to each other.

16. The engineered nucleic acid of paragraph 15, wherein the RRSs comprises a nucleotide sequence selected from sequences set forth as SEQ ID NO: 5-8.

17. The engineered nucleic acid of any one of paragraphs 1-16, wherein at least two of the heterologous genes are selected from *S. fradiae* tylG, *S. cinnamonensis* momVI, *S. cinnamonensis* momVIII and *S. nodosus* amphK.

18. The engineered nucleic acid of any one of paragraphs 1-17, wherein the promoter of (a) is operably linked to at least three heterologous genes of a biosynthetic pathway of interest.

19. The engineered nucleic acid of paragraph 18, wherein at least three of the heterologous genes are selected from *S. fradiae* tylG, *S. cinnamonensis* momVI, *S. cinnamonensis* momVIII and *S. nodosus* amphK.

20. The engineered nucleic acid of paragraph 18 or 19, wherein the promoter of (a) is operably linked to at least four heterologous genes of a biosynthetic pathway of interest.

21. The engineered nucleic acid of paragraph 20, wherein at least four of the heterologous genes are selected from *S. fradiae* tylG, *S. cinnamonensis* momVI, *S. cinnamonensis* momVIII and *S. nodosus* amphK.

22. The engineered nucleic acid of any one of paragraphs 1-21, wherein the promoter of (a) is oriented in the 5' to 3' direction, and wherein each gene operably linked to the promoter of (a) is oriented in a 5' to 3' direction.

23. The engineered nucleic acid of any one of paragraphs 1-21, wherein the promoter of (a) is oriented in the 5' to 3' direction, and wherein each gene operably linked to the promoter of (a) is oriented in a 3' to 5' direction.

24. A cell comprising the engineered construct of any one of paragraphs 1-23.

25. The cell of paragraph 24, wherein the cell is bacterial cell.

26. The cell of paragraph 25, wherein the bacterial cell belongs to a genus selected from the group consisting of: *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp. and *Lactobacillus* spp.

27. The cell of paragraph 26, wherein the bacterial cell is a *Streptomyces* spp. cell.

28. The cell of paragraph 27, wherein the *Streptomyces* spp. cell is a *Streptomyces venezuelae* cell or a *Streptomyces coelicolor* cell.

29. The cell of any one of paragraphs 24-28, wherein the cell comprises a deletion or modification in a gene of a biosynthetic pathway of interest.

30. The cell of paragraph 29, wherein the biosynthetic pathway of interest is a pikromycin biosynthetic pathway.

31. The cell of paragraph 30, wherein the cell comprises a deletion or modification in a pikAI-V, pikBI-VIII, pikBR gene, pikC gene or pikD gene.

32. The cell of paragraph 31, wherein the cell comprises a deletion in a pikAII gene.

33. The cell of any one of paragraphs 24-32, wherein the engineered nucleic acid is present on an episomal vector or integrated into a chromosome of the cell.

34. A cell comprising: (a) an engineered nucleic acid comprising a promoter operably linked to a gene encoding a shufflon recombinase; and (b) an engineered nucleic acid comprising (i) a promoter operably linked to at least two heterologous genes of a biosynthetic pathway of interest, and (ii) at least two different pairs of shufflon recombinase recognition sequences (RRSs), wherein at least one of the genes is located between at least one of the pairs of shufflon RRSs.

35. The cell of paragraph 34, wherein the at least two heterologous genes encode proteins selected from the group consisting of: enzymes, regulatory proteins and transport proteins.

36. The cell of paragraph 34 or 35, wherein the shufflon recombinase is a *Salmonella enterica* shufflon recombinase.

37. The cell of any one of paragraph 34-36, wherein the gene encoding the shufflon recombinase is codon-optimized for expression in the cell.

38. The cell of any one of paragraphs 34-37, wherein the gene encoding the shufflon recombinase comprise a nucleotide sequence as set forth in SEQ ID NO: 35 or SEQ ID NO: 36.

39. The cell of any one of paragraphs 34-38, wherein the promoter of (a) and/or (b) is an inducible promoter.

40. The cell of any one of paragraphs 34-39, wherein the engineered nucleic acid construct of (a) and/or (b) further comprises an antibiotic resistance gene.

41. The cell of any one of paragraphs 34-40, wherein the RRSs recombine, in the presence of shufflon recombinase activity, at different rates relative to each other.

42. The cell of paragraph 41, wherein the RRSs comprises a nucleotide sequence selected from sequences set forth as SEQ ID NO: 5-8.

43. The cell of any one of paragraphs 34-42, wherein at least two of the heterologous genes are selected from *S. fradiae* tylG, *S. cinnamonensis* momVI, *S. cinnamonensis* momVIII and *S. nodosus* amphK.

44. The cell of any one of paragraphs 34-43, wherein the promoter of (b) is operably linked to at least three heterologous genes of a biosynthetic pathway of interest.

45. The cell of paragraph 44, wherein at least three of the heterologous genes are selected from *S. fradiae* tylG, *S. cinnamonensis* momVI, *S. cinnamonensis* momVIII and *S. nodosus* amphK.

46. The cell of paragraph 44 or 45, wherein the promoter of (b) is operably linked to at least four heterologous genes of a biosynthetic pathway of interest.

47. The cell of paragraph 46, wherein at least four of the heterologous genes are selected from *S. fradiae* tylG, *S. cinnamonensis* momVI, *S. cinnamonensis* momVIII and *S. nodosus* amphK.

48. The cell of any one of paragraphs 34-47, wherein the promoter of (a) is oriented in the 5' to 3' direction, and wherein each gene operably linked to the promoter of (a) is oriented in a 5' to 3' direction.

49. The engineered nucleic acid of any one of paragraphs 34-47, wherein the promoter of (a) is oriented in the 5' to 3' direction, and wherein each gene operably linked to the promoter of (a) is oriented in a 3' to 5' direction.

50. The cell of paragraph any one of paragraphs 34-49, wherein the cell is bacterial cell.

51. The cell of paragraph 50, wherein the bacterial cell belongs to a genus selected from the group consisting of: *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp. and *Lactobacillus* spp.

52. The cell of paragraph 51, wherein the bacterial cell is a *Streptomyces* spp. cell.

53. The cell of paragraph 52, wherein the *Streptomyces* spp. cell is a *Streptomyces venezuelae* cell or a *Streptomyces coelicolor* cell.

54. The cell of any one of paragraphs 34-53, wherein the cell comprises a deletion or modification in a gene of a biosynthetic pathway of interest.

55. The cell of paragraph 54, wherein the biosynthetic pathway of interest is a pikromycin biosynthetic pathway.

56. The cell of paragraph 55, wherein the cell comprises a deletion or modification in a pikAI-V, pikBI-VIII, pikBR gene, pikC gene or pikD gene.

57. The cell of paragraph 56, wherein the cell comprises a deletion in a pikAII gene.

58. The cell of any one of paragraphs 34-57, wherein the engineered nucleic acid of (a) and/or (b) is present on an episomal vector or integrated into a chromosome of the cell.

59. A cell-free composition, comprising
(a) an engineered nucleic acid comprising a promoter operably linked to a gene encoding a shufflon recombinase;
(b) an engineered nucleic acid comprising (i) a promoter operably linked to at least two heterologous genes of a biosynthetic pathway of interest, and (ii) at least two different pairs of shufflon recombinase recognition sequences (RRSs), wherein at least one of the genes is located between at least one of the pairs of shufflon RRSs;
(c) a cell extract; and
(d) a polymerase.

60. The cell-free composition of paragraph 59, wherein the cell extract comprises at least one component selected from the group consisting of: ribosomes, amino acids, NTPs, phosphoenolpyruvate, pyruvate kinase, polyethylene glycol, ammonium acetate, potassium acetate and folinic acid.

61. The cell-free composition of paragraph 59 or 60 further comprising an engineered nucleic acid encoding additional proteins of the biosynthetic pathway of interest, or further comprising additional proteins of the biosynthetic pathway of interest.

62. The cell-free composition of any one of paragraphs 59-61, wherein the cell extract comprises a S30 cell fraction obtained from a bacterial cell.

63. The cell-free composition of paragraph 62, wherein the bacterial cell belongs to a genus selected from the group consisting of: *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp. and *Lactobacillus* spp.

64. The cell-free composition of paragraph 63, wherein the bacterial cell is a *Escherichia* spp. cell or a *Streptomyces* spp. cell.

65. The cell-free composition of any one of paragraphs 59-64, wherein the polymerase is a RNA polymerase.

66. The cell-free composition of any one of paragraphs 59-64, wherein the RNA polymerase is a RNA T7 polymerase.

67. A method of producing molecules, comprising incubating the cell-free composition under conditions that result in expression of a shufflon recombinase, recombination of RSSs, expression of at least two heterologous genes, and production of molecules produced by the biosynthetic pathway of interest.

68. A method of producing molecules, comprising:
culturing the cells of any one of paragraphs 24-58 under conditions that result in expression of a shufflon recombinase, recombination of RSSs, expression of at least two heterologous genes, and production of molecules produced by the biosynthetic pathway of interest.

69. The method of paragraph 68 further comprising isolating the molecules.

70. The method of paragraph 69 or 70, wherein the molecules comprise antibiotics.

71. A cell, comprising (a) an engineered nucleic acid, comprising a promoter operably linked to at least one heterologous gene encoding an antimicrobial peptide or an antimicrobial protein located between a pair of shufflon recombinase recognition sites (RRSs), and (b) a nucleic acid comprising a gene encoding a shufflon recombinase.

72. The cell of paragraph 71, wherein the promoter of (a) is oriented in the 5' to 3' direction, and wherein at least one heterologous gene encoding an antimicrobial peptide or an antimicrobial protein is oriented in a 3' to 5' direction.

73. The cell of paragraph 71 or 72, wherein the cell is a bacterial cell.

74. The cell of paragraph 73, wherein the bacterial cell is an *Escherichia* spp. cell.

75. The cell of paragraph 73, wherein the bacterial cell is an *Salmonella* spp. cell.

EXAMPLES

Example 1

Selection of a Base Pathway

Figure 3:
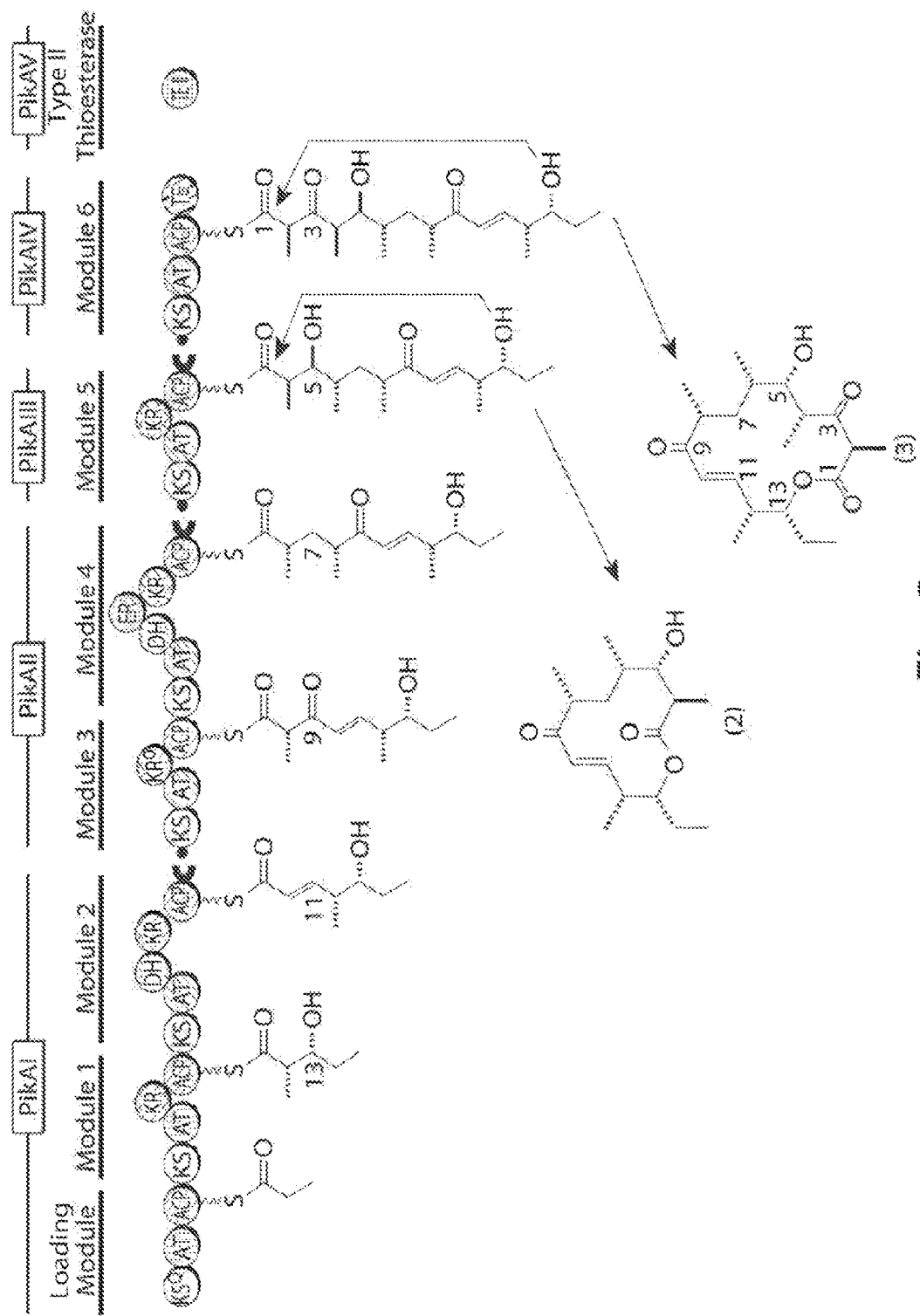
FIG. 3 shows the pikromycin pathway (tailoring enzymes are not displayed). Molecules 10-deoxy-methynolide (2) and narbonolide (3) are converted to methymycin and pikromycin, respectively (Kittendorf, J. et al. *Bioorg. Med. Chem.* 17:2137-46).

Upon a thorough bibliographic search, the biosynthetic pathway assembling Pikromycin (FIG. 3) was selected for shuffling. In the basis of such decision were the following facts: it is a very well characterized pathway (39-42), the promiscuity of its enzymes has been studied and enables the generation of pikromycin-derived molecules (39-41), the pathway naturally assembles two different but related molecules (39, 42), and dedicated glycosyltransferases further transfer sugar moieties to the pikromycin aglycon (narbonolide) (39-42).

Selection of Genes to Shuffle

The final choice of genes to shuffle was made based on several considerations. First, the phylogenetic distance was analyzed. An increased relatedness can potentially result in an increased probability of enzymes from different pathways recognizing each other, thus participating in the assembly of the molecules instead of stopping the assembly line (43-46). Both more distantly and closer related species were used as gene donors. Gene size was also taken into account. The extremely repetitive and high GC polyketide biosynthetic genes can be a major barrier to gene synthesis and even PCR. To obtain such amplicons, to manipulate the resulting very large constructs in vitro, and to promote inversion of the sequences, genes of conservative size (6-12 kbp) were selected. The predicted bioactivity score was also examined. Looking to increase the likelihood of generating bioactive molecules, an algorithm-based prediction of molecule structure based on genetic information (NP.searcher) was used in combination with a bioactivity prediction algorithm (Molinspiration) for a more educated selection of genes to incorporate into the synthetic shufflon pathway (Table 1). Once a decision had been made regarding the best pathway to manipulate and potential genes to use, the question was which of the pathway's elongation Pik enzymes should be replaced. Strain availability was also considered. Biosynthetic genes from organisms of unascertainable ID were discarded, having the attention been placed on genes from well-characterized pathways and organisms, available from any of the major organisms collection. The strains used in this project were obtained from the German collection, DSMZ (Deutsche Sammlung von Mikroorganismen and Zellkulturen).

Four genes were selected for shuffling. Using the aforementioned algorithms piKAII was selected over piKAIII.

TABLE 1

List of strains providing the genes to be shuffled

| Species | Strain | Gene Name (ID) | Pathway | Web link |
|---|---|---|---|---|
| S. venezuelae | DSM 41110 | — | Pikromycin | biocyc.org/META/NEW-IMAGE?type=PATHWAY&object=PWY-7421 |
| S. fradiae | DSM 41456 | tylG (AAB66508) | Tylactone | uniprot.org/uniprot/O33958 |
| S. cinnamonensis | DSM 1042 | momAVI (AAO65801) | Monensis | uniprot.org/uniprot/Q846X1 |
| | | momAVIII (AAO65807) | | uniprot.org/uniprot/Q846W5 |
| S. nodosus | DSM 40109 | amphK (AAK75303) | Amphotericin | Uniprot.org/uniprot/Q93NX7 |

In Silico Design of Full Construct

The full shufflon system (FIG. 4) used an array of parts, obtained following different strategies as described below.

Genes to be Shuffled

Based on the predicted bioactivity it was concluded that the best gene to be replaced, within the pikromycin pathway, would be piKAII. It was decided as well to use tylG, momVI, momVIII and amphK as replacements for pikAII and as genes to be shuffled, as they have all the aforementioned properties. Furthermore, these genes, when considered individually as additions to the pikAII defective pathway, should display high values of bioactivity (FIG. 5).

Figure 5:
FIG. 5 shows the organization of genes to be shuffled, respective recognition sequences assigned, and bioactivity score predicted for pathway complementation with each individual gene (not combinations). Higher scores are preferred.
Figure 6:
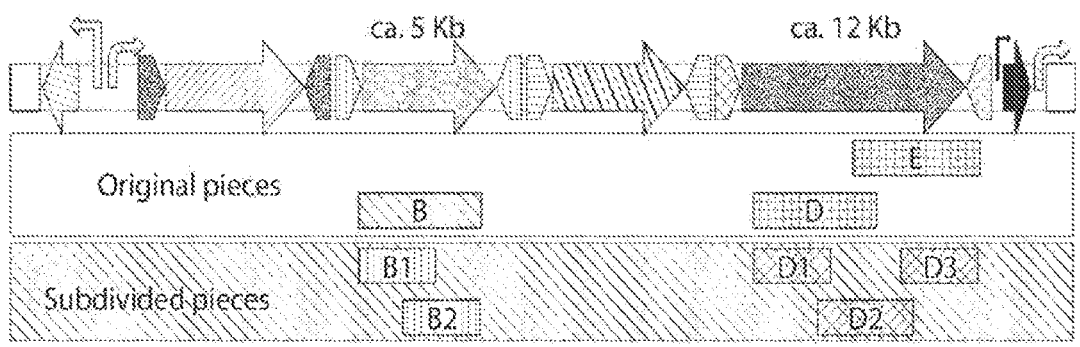
FIG. 6 shows a subdivision of sequences designated B, D, and E for use in obtaining respective PCR products.

Given the previous report regarding the shuffling frequency per recognition sequence (23), the recognition sequence "a" was assigned to momAVIII, "b" to tylG, "c" to momAVI and "d" to amphK (FIG. 5). It was expected to find a higher number of inversion events for momAVIII>amphK>tylG>momAVIII.

As ribosomal bidding sites (RBSs) for transcription of these genes it was decided to use their native sequences (Table 2). Therefore, the DNA sequence between the upstream stop codon and the genes start codon was cloned in together with the gene sequence. As the genes utilized in this assembly are organized in operons, the resulting mRNAs are polycistronic. In addition, not being the first gene of the respective operons, these upstream sequences should not contain promoters, only RBSs. To further attest this, the typical Streptomyces spp.-10 (TAGGAT) and -35 (GGCT) promoter sequences were found not to be present.

TABLE 2

DNA sequences upstream initiation codon, which includes the respective RBSs (putative sequences underlined)

| Gene | RBS-inclusive sequence upstream the gene | SEQ ID NO: |
|---|---|---|
| tylG | CCGGCCGGCGGAGCACACCCGGCCGT CTCCGGCCCGGCCGCGGCCGGGCCGG AAGCCATCCGCCGCCCACCCGGTACC GACCCCTCAAGCCCTTCAAGCCCTTC GACCCGTCCGATCAGTCAGTCCGGCG GTCCTCCACGACCGGTCCGGAATCGC CCCCACACGAGTCAGGAAGCACACC | 1 |
| momAVI | TCAGGAGTGGAGAAGAC | 2 |
| momAVIII | GCAGCGATCAGTCCTGAGCGCGATGA GCCCCGGCCACACCGGCCCCCTTGCC CTCCCCCAACCTCATACGCCCCGATC ACCACGTAGCGCCAAGGAGCCTGGGT CAG | 3 |
| amphK | TGACCCGGGCCCACCCCAACTACGTG CGAAACATCTGAGGAAGGTTCAACGG ACG | 4 |

Rci Gene, Coding for the Shufflon Recombinase

The 1155 bp gene rci (NC_019104.1), coding for the shufflon recombinase and described for Salmonella enterica subsp. enterica serovar Kentucky, can be found in the organisms episomal DNA, pR64 (pCS0010A).

Given the disparity between Salmonella spp. and Streptomyces spp. in terms of GC content and codon usage, the rci gene was codon optimized for use in Streptomyces spp. by GenScript Corp using their proprietary algorithm. This company then synthesized the gene. The optimized sequence had a GC content of 67.79%, versus the 48.83% original one, a Streptomyces-friendly codon-usage. This gene was cloned upstream of the genes to be shuffled and to avoid any risk of polymerase read-through, it was cloned in the 3'-5' direction.

Inducible Promoter Driving Rci

The best-studied inducible promoter system in Streptomyces spp. is tipAp, which is induced by thiostrepton. As the inducer is itself an antibiotic, the use of tipAp implies cloning a thiostrepton-resistance cassette, tsr.

As this promoter is driving the expression of rci, it was cloned upstream of it and also in the 3'-5' direction, to prevent any read-through towards the genes to be shuffled.

Recognition Sequences Placed Between the Genes to be Shuffled

After the discovery of shufflons in 1987 by Komano et al. (25), some work was carried out by a few different groups in order to better understand the logic behind the recognition and inversion of sequences (23, 24, 27).

It has been previously determined (26, 27) that different recognition sites are inverted at different rates, higher for sequence "a", then "d", "b" and lower for sequence "c" (Table 3).

TABLE 3

List of shufflon recognition sequences and gene each will be shuffling

| Recognition sequence name | Recognition sequence (5'-3') | SEQ ID NO: | Gene to shuffle | Fraction of rearranged molecules (%) |
|---|---|---|---|---|
| a | GTGCCAATCCG GTACGTGG | 5 | momAVIII | 29 |
| b | GTGCCAATCCG GTACCTGG | 6 | tylG | 0.025 |
| c | GTGCCAATCCG GTCGGTGG | 7 | momAVI | 0.02 |
| d | GTGCCAATCCG GTACTTGG | 8 | amphK | 0.1 |

Regions of Homology to the Chromosomal Loci for Integration

The complete shufflon system could either be maintained as episomal DNA or integrated into the organism's chromosome. Due to the size of the full construct and vector backbone, of ca. 45 kbp, and to maintain enzyme stoichiometry, it was decided to integrate the shufflon pathway into the pikII gene of the pikromycin pathway. This way, the gene to be replaced would also be knocked out the same time that alternative genes are provided in the pathway.

Integration is to be achieved by a Campbell-like double crossover event. The regions of homology incorporated in the construct correspond to the first and last ca. 500 bp of the gene pikAII, which is the gene to be replaced with those in the shufflon system. Homology towards those regions will guarantee that the pikAII gene will be disrupted and that the shufflon system will take its place.

Constitutive Promoter at the End of the Shufflon System, for the Prevention of Polar Effects Gene disruption, such as the pikAII disruption by integration of the shufflon system, can cause polar effects, in which the transcription of the whole operon is affected. In order to prevent this, the constitutive ermEp* promoter was cloned in the shufflon system, upstream of the 3' region of homology. By cloning the promoter at the 3' end of the shufflon system, one expects to prevent possible polar effects.

Gene synthesis (GenScript Corp)

The expression of the rci gene was improved due to the high discrepancy in terms of codon usage between *Streptomyces* spp. and *Salmonella* spp. GenScript's proprietary algorithm was used to improve protein expression of the gene.

As in any method for DNA parts assembly, higher numbers of fragments lead to lower probabilities obtaining the right construct. Therefore, it was sought to compress the number of parts as much as possible.

With this in mind, and given the 5' location of the rci gene and promoter, it was decided to synthesize the 5' region of homology towards pikAII together with the rci system and the small region of homology towards the backbone of the vector (YAC, pYes-1L) and to the DNA part downstream of rci as well.

The *Streptomyces* spp.-inducible promoter tipAp was cloned in the gene tsr to confer the organism with resistance to the inducer molecule thiostrepton, which is an antibiotic. This gene was directly synthesized by GenScript Corp., as it already originated from a *Streptomyces* sp. Similarly to what is traditionally done, the region cloned exceeded that of the tsR ORF to ensure successful transcription. Similar to the approach taken for the 5' extremity of this construct, the 3' region of homology towards pikAII and pYES-1L, and homology to the DNA fragment upstream was also synthesized with the tsR operon.

The backbone carrying the synthesized parts was pUC57, containing the parts released by plasmid digestion with NsiI and PstI (the rci-inclusive part) or Bsu36I and BglII (the tsR-inclusive part).

The digestions were run in 1% agarose gels at 120 v, and the parts were purified from the gels.

gBlock Synthesis (IDT DNA)

Short linear synthetic DNA sequences were synthesized by Integrated DNA Technologies, Inc. (IDT DNA). These sequences were designed to be stitching double-stranded DNA blocks, homologous to both an upstream and downstream amplicon. These stitching blocks are crucial for the yeast-based assembly of fragments that do not share homology with the neighboring DNA fragments, as they provide homology for correct assembly.

The gBlocks designed and used were the following: gBlock1 (links tylG and momAVI, while adding the shufflon recognition sequences to momAVI), gBlock 2 (links momAVI and the YAC backbone), and gBlock 3 (links amphK and momAVIII, while adding the shufflon recognition sequences to momAVIII).

PCR

Genes amphK, tylG, momAVI and momAVIII were obtained by PCR from the genomic DNA preps of *S. nodosus*, *S. fradiae* and *S. cinnamonensis* (mon genes), respectively.

A vast array of PCR conditions was tested in order to find the amplification conditions that allowed for gene amplification. The conditions that eventually led to the successful amplification of all parts are listed in Table 4.

Figure 8:
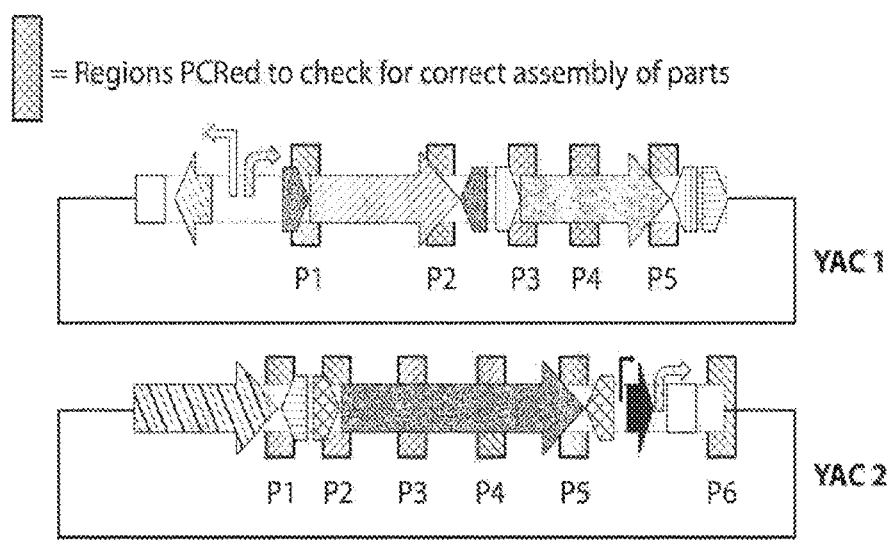
FIG. 8 shows a schematic of two YACs containing the assemblies of interest and the regions amplified by PCR to determine proper assembly. P1-5 represent the primer sets used for the amplifications.

Initially, attempts were made to amplify momAVI in its entirety (single amplicon) and momAVIII in two amplicons. Yet, extensive processing did not allow for successful amplification of fragments with the expected size. A different approach was then undertaken. Following this approach, momAVI was subdivided into two amplicons (instead of one) and momAVIII into three (instead of two) (FIG. 8), resulting in successful amplification.

Figure 7:
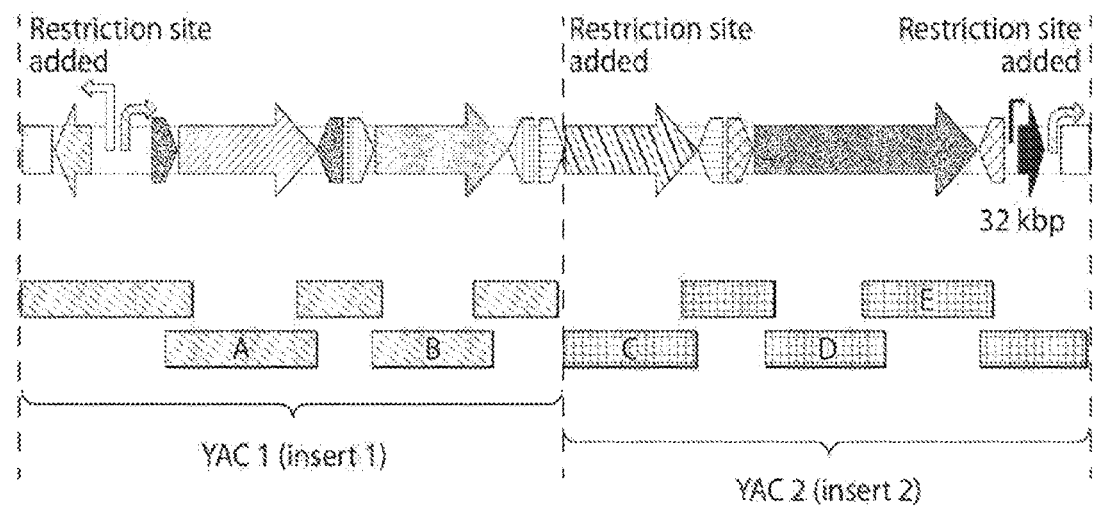
FIG. 7 shows a schematic of a complete engineered nucleic acid of the present disclosure. Blocks represent DNA fragments and the letters indicate pieces to be obtained by PCR.

Upon experimentation, several conditions were found to result in highly specific and efficient amplification (Table 4). From the array of available options, the conditions used for PCR scale-up of all amplicons (FIG. 7) are described in Table 4.

TABLE 4

PCR conditions that allowed for successful amplification of genes and gene parts

| Gene | Amplicons | Polymerase | Additives | Primer annealing T (C.) | Primer extension T (C.) |
|---|---|---|---|---|---|
| tylG | — | Herculase II | — | 58 | 72 |
| momAVI | 1 | Herculase II | D2 + M2 | 58 | 72 |
| | 2 | Herculase II | D2 + M2 | 58 | 72 |
| momAVIII | 1 | Herculase II | D1 | 58 | 72 |
| | 2 | Herculase II | D2 + M2 | 60 | 72 |
| | 3 | Herculase II | D1.5 + M1.5 | 58 | 72 |
| amphK | — | KOD | D2.5 | 56 | 68 |

Figure 9:
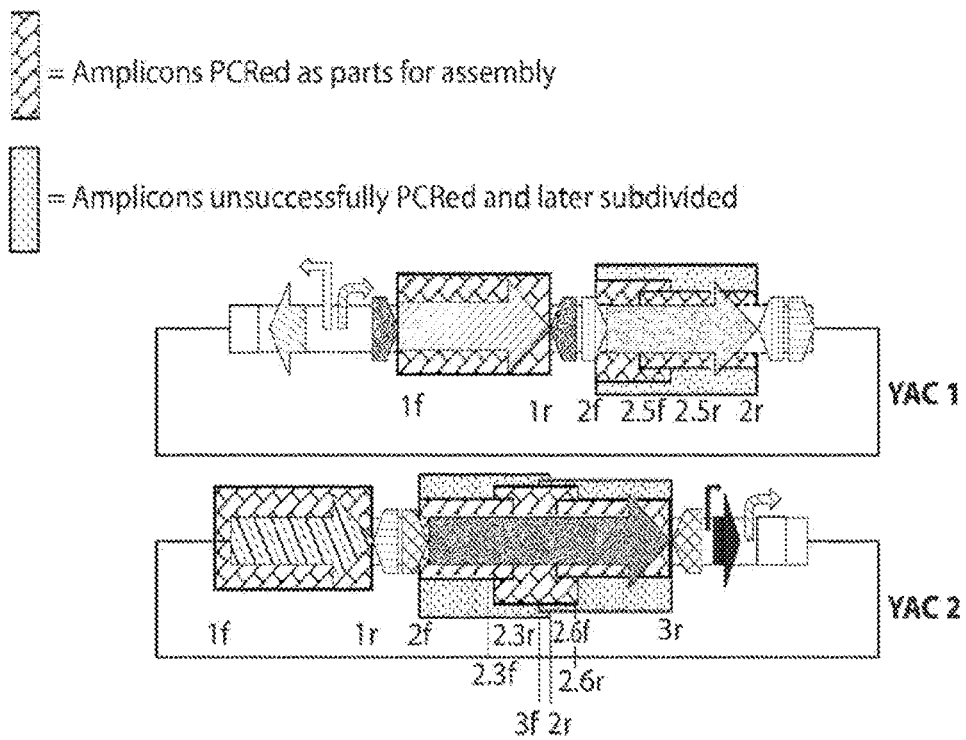
FIG. 9 shows a schematic of an initial PCR approach and the amplicons effectively obtained upon experimentation. Alphanumeric nomenclature corresponds to the primers used (see Table 5).

In order to obtain by PCR the several amplicons used for the shufflon system, PCR experimentation was performed. Information about the annealing loci (FIG. 9) and sequences of the primers (Table 5) used is provided.

TABLE 5

Primers used for the amplifications of DNA pieces.

| PCR Primers | Sequence (5'-3') | SEQ ID NO: |
|---|---|---|
| YAC1 | | |
| 1f | CCTGGCCGGCCGGCGGAGCACACCCGG | 51 |
| 1r | TCACGGCCTCTCCTCTCTCC | 52 |
| 2f | GGAGAAGACATGCCGGGTACG | 53 |
| 2r | TCACCGCGTGCCCCACTC | 54 |
| 2.5f | CGACGGTGATTTCAGGTCCG | 55 |
| YAC2 | | |
| 1f | CCGAGCGCAGCGGCGGCCGCGCTGATACCG CCGCcaattgTGACCCGGGCCCACCCCAAC | 56 |
| 1r | GGCCTCGGCGGTCAGATCC | 57 |
| 2f | CCACGTAGCGCCAAGGAGCC | 58 |
| 2r | CGTACAGCGTCTCCAGGTCC | 59 |
| 3f | CCGACGACGAGCCGATCGCG | 60 |
| 3r | CGTTGCCGTGTCCGTTGCCCTGC | 61 |
| 2.3f | GTGCGACGCCTCATCGACG | 62 |
| 2.3r | CCGACACGTCGCCGAGACC | 63 |
| 2.6f | GCGAGCAGGATCCGTACGG | 64 |
| 2.6r | GCTCACCAGTCCCTGTGAGC | 65 |

Assembling of parts (synthesized and PCRed) using an yeast-based recombination method Several methods for the assembly of multiple DNA parts are available. Some of the most commonly used include the following: Golden Gate (47), which relies on the use of restriction enzymes whose recognition sequence and cut site differ; isothermal assembly (48), aka Gibson assembly, which is a one-pot 50 C reaction of exonuclease and ligase activity, allowing for the generation sticky homologous ends and its ligation; and yeast-based assembly (49), which relies on the organism's extraordinary ability to recombine homologous DNA at high efficiency.

Yet, the nature of the gene sequences that code natural product biosynthetic enzymes greatly limit the methods one can use. Experience shows that the few enzymes used for Golden-Gate based assembly cannot usually be selected in such assemblies, as they would also cut within the parts. This problem does not exist with Gibson-based assembly, but the high part number, and the repetitive and high-GC nature of the genes results in incorrect assembly more often. Yet, these are issues are not experienced when using yeast-based assembly.

Thus, for the assembly of the many, very large and high GC shufflon system parts, it was decided to use the yeast-based system. More precisely, the GeneArt® High-Order seamless Genetic Assembly (Life Technologies, Inc).

As already described, once the colonies of yeast carrying the assemblies were grown, PCRs for confirmation (FIG. 8) of the correct assembly of parts was carried out. Though not a great deal of information was provided, due to their dirtiness and lack of some expected PCR products, there was enough data to select a few transformants for additional studies.

Three seemingly correctly assembled yeast colonies were selected per construct. The *E. coli* transformants carrying YAC1 and YAC2 were mini-prepped using the BAC Zymo Research kit. The YAC preps were then used as template for confirmation PCRs with Herculase II, KOD and Kapa Hifi polymerases. A selection of three polymerases was used as a way to guarantee that all fragments would be successfully amplified. It was previously seen that different DNA polymerases amplified different DNA fragments with different success rates. Also in this case, by combining the results obtained from the different PCRs, a nearly 100% success in PCR was reached. The single PCR that did not work was not due to missing DNA fragments, but to troublesome PCR, since both the up and downstream PCRs did work, which proves that the fragment is indeed there.

TABLE 6

List of primers used for screening of correct assemblies and sequencing

| Confirmation and sequencing primers | Primer sequences Forward/Reverse (5'-3') | SEQ ID NO: |
|---|---|---|
| YAC 1 | | |
| P1 | GGTAGCGTGCATCCTGTTAGCC/ GTCATGGACGGTCCTTCGAGACC | 9 10 |
| P2 | CCGATCTGCTCTTCGACCGG/ TCACGGCCTCTCCTCTCTCC | 11 12 |
| P3 | CGTTTGATGAGGTGTGCGGC/ GATGTCCGCCAGCCAGAAGC | 13 14 |
| P4 | GGAGAAGACATGCCGGGTACG/ CGTACGTCGCGAGGAGTGCG | 15 16 |
| P5 | GGACCTGGGCTTCGACTCGC/ GCACTTGCCGATCTATGCGG | 17 18 |
| YAC 2 | | |
| P1 | CTCGCTGGTCTCGGTCAGCC/ GGCCTCGGCGGTCAGATCC | 19 20 |
| P2 | GCGATCAGTCCTGAGCGCG/ CGTATCACCGCAAGGACCTTGTGG | 21 22 |
| P3 | GTGCGACGCCTCATCGACG/ CGTACAGCGTCTCCAGGTCC | 23 24 |
| P4 | CGACGTACGCCTTCCAGCG/ CGCACCGAACGTGTCCCA | 25 26 |
| P5 | GGTCGAGGAGGTGATGCGCG/ CGTTGCCGTGTCCGTTGCCCTGC | 27 28 |
| P6 | GCACTTGCCGATCTATGCGG/ GCACTTGCCGATCTATGCGG | 29 30 |

Construction a reporting suicide vector; for shufflon integration and double crossover selection and confirmation of gusA reporting capabilities One of the challenging aspects of this project consists on the successful integration of the shufflon system into the chromosome of *S. venezuelae*. The goal is to achieve a clean integration, with loss of YAC backbone.

Failed attempts to obtain in a timely manner the reporter vector pKGLP2 led to the in house construction of a similar but ideal system—pSETSC3—described below.

Very few reporter systems have been successfully used in *Streptomyces* spp. The widely used lacZ system cannot be used as a reporter in these organisms, due to their production of ß-galactosidases. Most commonly, the neo and cat genes (neomycin and chloramphenicol resistance-conferring genes) are preferred, but many *Streptomyces* spp. are also naturally resistant to these compounds. The spore pigment-conferring gene whiE, is an easy and visual reporter, but useless for strains that produce already pigmented spores. Furthermore, problems have been found when trying to express gfp in *Streptomyces* spp., given the difference in codon usage (28). A more recently described reporter system, using the gusA reporter gene, was preferred. gusA, which codes for ß-glucuronidase can be used as an efficient and visible reporter, by overlaying the bacterial colonies with the enzymatic substrate X-Gluc (5-bromo-4-chloro-3-indolyl-beta-D-glucuronic acid, cyclohexylammonium salt) (50).

*Streptomyces* spp. have a potent native DNA restriction machinery, which cleaves foreign methylated DNA being transformed into this organism. Spores and mycelia transformation yield, for many species, a very low number—if any—of transformants. The most efficient way of introducing DNA into *Streptomyces* spp. is by means of conjugation using methylation-deficient *E. coli* ET12567 (CamR) either with or without plasmid pUZ8002 (KanR), a conjugative plasmid that provides the tra machinery for the initiation of DNA transfer, without being itself transmitted to the recipient strain. pSet152-gusA does not contain the tra machinery, therefore it was electroporated into *E. coli* ET12567 pUZ8002.

Bioactivity and SMILES of Predicted Novel Structures

Possible Gene Combinations and Predicted Molecule Bioactivity Scores

Upon integration of the shufflon system and induction of shuffling events, the semi-synthetic novel Pikromycin pathway (FIG. 10) consists of genes pikAI, pikAIII, pikAIV and the heterologous genes: (1) momAVI, amphK, tylG, momAVIII, (3) momAVI, (4) momAVI, amphK, (5) momAVI, amphK, tylG, (6) amphK, tylG, momAVIII, (7) tylG, (8) momAVIII, (9) amphK, (10) tylG, momAVIII, (11) momAVI, momAVIII, (12) tylG, amphK, (13) momAVI, tylG, (14) amphK, momAVIII, (15) momAVI, tylG, momAVIII, or (16) momAVI, amphK, momAVIII.

The different combination of genes (FIG. 11), and thus enzymes, are expected to result in novel molecules. Initially, the bioactivity of novel pathways was only determined for those where PikAII would be replaced by a single new enzyme (FIG. 5). This was due to the goal being gene selection from a pool of available options (Table 7). In Table 8 the bioactivity score is shown for all possible pathway combinations.

Bioactivity score is estimated using a web-based predictor (www.molinspiration.com/cgi-bin/properties). Briefly, it compares the properties of the submitted molecules to a large database of molecules of known activity. The score varies between −2 and 2, being the most frequent value for bioactivity 0.50, according to information provided on the website. Yet, these values are merely indicative, as they rely on the prediction of a structure that might not be indeed assembled by the pathway.

TABLE 7

List of genes preselected as potential DNA to be shuffled

| Species | Molecule | Gene |
|---|---|---|
| S. halstedii | Halstoctacosanolide | hlsE |
| S. halstedii | Vicenistatin | vinP2 |
| S. avermitilis | Oligomycin | olmA5 |
| S. avermitilis | Oligomycin | olmA6 |
| S. avermitilis | Oligomycin | olmA3 |
| S. cinnamonensis | Monensin | momAVIII |
| S. hygroscopicus | Rapamycin | rapC |
| S. hygroscopicus | Geldanamycin | gdmAI |
| S. hygroscopicus | Herbamycin | hbmaII |
| S. halstedii | Vicenistatin | vinP3 |
| S. avermitilis | Avermectin | aveA2 |
| S. nodosus | Amphotericin | amphK |
| S. avermitilis | Oligomycin | olmA4 |
| S. violaceusniger | Nigericin | nigAIX |
| S. violaceusniger | Nigericin | nigAII |
| S. violaceusniger | Nigericin | nigAVIII |
| S. coelicolor | Rifampicin | rifC |
| S. pristinaespiralis | Pristinamycin | snbC |
| S. cinnamonensis | Monensin | momAI |
| S. coelicolor | Rifampicin | rifE |
| S. hygroscopicus | Geldanamycin | gdmAII |
| S. cinnamonensis | Monensin | momAVI |
| S. nodosus | Amphotericin | amphB |
| S. fradiae | Tylactone | tylG |

TABLE 8

Predicted bioactivity scores of predicted molecules

| Bioactivity | Original | 1 | 2 | 3 | 4 |
|---|---|---|---|---|---|
| GPCR ligand | −0.66 | ND | 0.15 | 0.09 | −0.13 |
| Ion channel modulator | −1.57 | ND | 0.02 | −0.34 | −0.81 |
| Kinase inhibitor | −1.45 | ND | −0.31 | −0.44 | −0.81 |
| Nuclear receptor ligand | −1.03 | ND | 33 | 0.11 | −0.32 |
| Protease inhibitor | −0.32 | ND | 0.18 | 0.22 | 0.03 |
| Enzyme inhibitor | −0.92 | ND | 0.2 | 0.06 | −0.32 |

| | 5 | 6 | 7 | 8 | 9 |
|---|---|---|---|---|---|
| GPCR ligand | −0.87 | −1.32 | 0.09 | 0.15 | 0.14 |
| Ion channel modulator | −1.87 | −2.36 | −0.34 | 0.02 | −0.2 |
| Kinase inhibitor | −1.71 | −2.14 | −0.44 | −0.31 | −0.36 |
| Nuclear receptor ligand | −1.32 | −1.73 | 0.11 | 0.33 | 0.22 |
| Protease inhibitor | −0.46 | −0.75 | 0.22 | 0.18 | 0.17 |
| Enzyme inhibitor | −1.16 | −1.52 | 0.06 | 0.2 | 0.09 |

| | 10 | 11 | 12 | 13 | 14 |
|---|---|---|---|---|---|
| GPCR ligand | −0.62 | −0.62 | −0.17 | −0.38 | −0.4 |
| Ion channel modulator | −1.54 | −1.54 | −0.82 | −1.15 | −1.22 |
| Kinase inhibitor | −1.39 | −1.39 | −0.8 | −1.06 | −1.1 |
| Nuclear receptor ligand | −0.91 | −0.91 | −0.31 | −0.61 | −0.6 |
| Protease inhibitor | −0.27 | −0.27 | 0.06 | −0.08 | −0.15 |
| Enzyme inhibitor | −0.82 | −0.82 | −0.31 | −0.55 | −0.61 |

| | 15 | 16 |
|---|---|---|
| GPCR ligand | ND | −1.19 |
| Ion channel modulator | ND | −2.35 |
| Kinase inhibitor | ND | −2.15 |
| Nuclear receptor ligand | ND | −1.74 |
| Protease inhibitor | ND | −0.78 |
| Enzyme inhibitor | ND | −1.53 |

TABLE 9

Predicted pathway SMILES

| Number | Predicted SMILES |
|---|---|
| 1 | C(C)C(O0)C(C)C=CC(O)CC=CC(O)CC(O)C(C)C(O)C(C)C(=O)C(C)C0(=O)•C(C)C(O)C(C)C=C C(O0)CC=CC(O)CC(O)C(C)C(O)C(C)C(=O)C(C)C0(=O)•C(C)C(O)C(C)C=CC(O)CC=CC(O0)C C(O)C(C)C(O)C(C)C(=O)C(C)C0(=O)•C(C)C(O)C(C)C=CC(O)CC=CC(O)CC(O0)C(C)C(O)C(C) C(=O)C(C)C0(=O)•C(C)C(O)C(C)C=CC(O)CC=CC(O)C(C)C(O)C(C)C(=O)C(C)C(=O)O•C (C)C(O(C(=O)C(C)C(=O)C(C)C(O)C(C)C(O)CC(O)C=CCC(O)C=CC(C)C(O0)C(C)))C(C)C=C C(O)CC=CC(O)CC(O)C(C)C(O)C(C)C(=O)C(C)C0(=O)•C(C)C(O(C(=O)C(C)C(=O)C(C)C(O)C (C)C(O)CC(O)C=CCC(O)C=CC(C)C(O)C(C)))C(C)C=CC(O)CC=CC(O)CC(O)C(C)C(O)C(C)C(=O) C(C)C(=O)O |
| 2 | C(C)C(O0)C(C)C=CC(O)C(C)C(=O)C(C)C0(=O)•C(C)C(O)C(C)C=CC(O)C(C)C(=O)C(C)C(=O) O•C(C)C(O(C(=O)C(C)C(=O)C(C)C(O)C=CC(C)C(O0)C(C)))C(C)C=CC(O)C(C)C(=O)C(C)C0 (=O)•C(C)C(O(C(=O)C(C)C(=O)C(C)C(O)C=CC(C)C(O)C(C)))C(C)C=CC(O)C(C)C(=O)C(C)C (=O)O |
| 3 | C(C)C(O0)C(C)C=CC(O)C(O)C(C)C(=O)C(C)C0(=O)•C(C)C(O)C(C)C=CC(O)C(O)C(C)C(=O) C(C)C(=O)O•C(C)C(O(C(=O)C(C)C(=O)C(C)C(O)CC(O)C=CC(C)C(O0)C(C)))C(C)C=CC(O) CC(O)C(C)C(=O)C(C)C0(=O)•C(C)C(O(C(=O)C(C)C(=O)C(C)C(O)CC(O)C=CC(C)C(O)C(C)))C (C)C=CC(O)CC(O)C(C)C(=O)C(C)C(=O)O |
| 4 | C(C)C(O0)C(C)C=CC(O)CC=CC(O)C(C)C(=O)C(C)C0(=O)•C(C)C(O)C(C)C=CC(O0)CC=CC(O) C(C)C(=O)C(C)C0(=O)•C(C)C(O)C(C)C=CC(O)CC=CC(O)C(C)C(=O)C(C)C(=O)O•C(C)C(O(C (=O)C(C)C(=O)C(C)C(O)C=CCC(O)C=CC(C)C(O0)C(C)))C(C)C=CC(O)CC=CC(O)C(C)C(=O) C(C)C0(=O)•C(C)C(O(C(=O)C(C)C(=O)C(C)C(O)C=CCC(O)C=CC(C)C(O)C(C)))C(C)C=CC(O) CC=CC(O)C(C)C(=O)O |
| 5 | C(C)C(O0)C(C)C=CC(O)CC=CC(O)CC(O)C(C)C(=O)C(C)C0(=O)•C(C)C(O)C(C)C=CC(O0)CC=CC (O)CC(O)C(C)C(=O)C(C)C0(=O)•C(C)C(O)C(C)C=CC(O)CC=CC(O)CC(O)C(C)C(=O)C(C) C(=O)O•C(C)C(O(C(=O)C(C)C(=O)C(C)C(O)CC(O)C=CCC(O)C=CC(C)C(O0)C(C)))C(C)C=CC (O)CC=CC(O)CC(O)C(C)C(=O)C(C)C0(=O)•C(C)C(O(C(=O)C(C)C(=O)C(C)C(O)CC(O)CC=CCC (O)C=CC(C)C(O)C(C)))C(C)C=CC(O)CC=CC(O)CC(O)C(C)C(=O)C(C)C(=O)O |
| 6 | C(C)C(O0)C(C)C=CC=CC(O)CC(O)C(C)C(O)C(C)C(=O)C(C)C0(=O)•C(C)C(O)C(C)C=CC=CC (O0)CC(O)C(C)C(O)C(C)C(=O)C(C)C0(=O)•C(C)C(O)C(C)C=CC=CC(O)CC(O0)C(C)C(O)C(C) C(=O)C(C)C0(=O)•C(C)C(O)C(C)C=CC=CC(O)CC(O)C(C)C(O)C(C)C(=O)C(C)C(=O)O•C(C)C (O(C(=O)C(C)C=O)C(C)C(O)C(C)C(O)CC(O)C=CC=CC(C)C(O0)C(C)))C(C)C=CC=CC(O)CC (O)C(C)C(O)C(C)C(=O)C(C)C0(=O)•C(C)C(O(C(=O)C(C)C(=O)C(C)C(O)C(C)C(O)CC(O)C=CC=CC (C)C(O)C(C)))C(C)C=CC=CC(O)CC(O)C(C)C(O)C(C)C(=O)C(C)C(=O)O |
| 7 | C(C)C(O0)C(C)C=CC(O)C(O)C(C)C(=O)C(C)C0(=O)•C(C)C(O)C(C)C=CC(O)C(O)C(C)C(=O) C(C)C(=O)O•C(C)C(O(C(=O)C(C)C(=O)C(C)C(O)CC(O)C=CC(C)C(O0)C(C)))C(C)C=CC(O) CC(O)C(C)C(=O)C(C)C0(=O)•C(C)C(O(C(=O)C(C)C(=O)C(C)C(O)CC(O)C=CC(C)C(O)C(C)))C (C)C=CC(O)CC(O)C(C)C(=O)C(C)C(=O)O |
| 8 | C(C)C(O0)C(C)C=CC(O)C(C)C(O)C(C)C(=O)C(C)C0(=O)•C(C)C(O)C(C)C=CC(O0)C(C)C(O)C (C)C(=O)C(C)C0(=O)•C(C)C(O)C(C)C=CC(O)C(C)C(O)C(C)C(=O)C(C)C(=O)O•C(C)C(O(C(=O) C(C)C(=O)C(C)C(O)C(C)C(O)C=CC(C)C(O0)C(C)))C(C)C=CC(O)C(C)C(O)C(C)C(=O)C(C)C0 (=O)•C(C)C(O(C(=O)C(C)C(=O)C(C)C(O)C(C)C(O)C=CC(C)C(O)C(C)))C(C)C=CC(O)C(C)C(O) C(C)C(=O)C(C)C(=O)O |
| 9 | C(C)C(O0)C(C)C=CC=CC(O)C(C)C(=O)C(C)C0(=O)•C(C)C(O)C(C)C=CC=CC(O)C(C)C(=O)C (C)C(=O)O•C(C)C(O(C(=O)C(C)C(=O)C(C)C(O)C=CC=CC(C)C(O0)C(C)))C(C)C=CC=CC(O)C (C)C(=O)C(C)C0(=O)•C(C)C(O(C(=O)C(C)C(=O)C(C)C(O)C=CC=CC(C)C(O)C(C)))C(C)C=CC=CC (O)C(C)C(=O)C(C)C(=O)O |
| 10 | C(C)C(O0)C(C)C=CC(O)CC(O)C(C)C(O)C(C)C(=O)C(C)C0(=O)•C(C)C(O)C(C)C=CC(O0)CC (O)C(C)C(O)C(C)C(=O)C(C)C0(=O)•C(C)C(O)C(C)C=CC(O)CC(O0)C(C)C(O)C(C)C(=O)C(C)C 0(=O)•C(C)C(O)C(C)C=CC(O)CC(O)C(C)C(O)C(C)C(=O)C(C)C(=O)O•C(C)C(O(C(=O)C(C)C(=O) C(C)C(O)C(C)C(O)CC(O)C=CC(C)C(O0)C(C)))C(C)C=CC(O)CC(O)C(C)C(O)C(C)C(=O)C(C) C0(=O)•C(C)C(O(C(=O)C(C)C(=O)C(C)C(O)C(C)C(O)CC(O)C=CC(C)C(O)C(C)))C(C)C=CC(O) CC(O)C(C)C(O)C(C)C(=O)C(C)C(=O)O |
| 11 | C(C)C(O0)C(C)C=CC(O)CC(O)C(C)C(O)C(C)C(=O)C(C)C0(=O)•C(C)C(O)C(C)C=CC(O0)CC (O)C(C)C(O)C(C)C(=O)C(C)C0(=O)•C(C)C(O)C(C)C=CC(O)CC(O0)C(C)C(O)C(C)C(=O)C(C)C 0(=O)•C(C)C(O)C(C)C=CC(O)CC(O)C(C)C(O)C(C)C(=O)C(C)C(=O)O•C(C)C(O(C(=O)C(C)C(=O) C(C)C(O)C(C)C(O)CC(O)C=CC(C)C(O0)C(C)))C(C)C=CC(O)CC(O)C(C)C(O)C(C)C(=O)C(C) C0(=O)•C(C)C(O(C(=O)C(C)C(=O)C(C)C(O)C(C)C(O)CC(O)C=CC(C)C(O)C(C)))C(C)C=CC(O) CC(O)C(C)C(O)C(C)C(=O)C(C)C(=O)O |
| 12 | C(C)C(O0)C(C)C=CC=CC(O)C(O)C(C)C(=O)C(C)C0(=O)•C(C)C(O)C(C)C=CC=CC(O)CC(O) C(C)C(=O)C(C)C(=O)O•C(C)C(O(C(=O)C(C)C(=O)C(C)C(O)C(C)C(O)C=CC=CC(C)C(O0)C(C)))C (C)C=CC=CC(O)C(O)C(C)C(=O)C(C)C0(=O)•C(C)C(O(C(=O)C(C)C(=O)C(C)C(O)CC(O)C=C C=CC(C)C(O)C(C)))C(C)C=CC=CC(O)CC(O)C(C)C(=O)C(C)C(=O)O |
| 13 | C(C)C(O0)C(C)C=CC(O)CC(O)CC(O)C(C)C(=O)C(C)C0(=O)•C(C)C(O)C(C)C=CC(O0)CC(O)C C(O)C(C)C(=O)C(C)C0(=O)•C(C)C(O)C(C)C=CC(O)CC(O0)CC(O)C(C)C(=O)C(C)C(=O)O•C(C) C(O(C(=O)C(C)C(=O)C(C)C(O)CC(O)CC(O)C=CC(C)C(O0)C(C)))C(C)C=CC(O)CC(O)C(O) C(C)C(=O)C(C)C0(=O)•C(C)C(O(C(=O)C(C)C(=O)C(C)C(O)CC(O)CC(O)C=CC(C)C(O)C(C)))C (C)C=CC(O)CC(O)CC(O)C(C)C(=O)C(C)C(=O)O |
| 14 | C(C)C(O0)C(C)C=CC=CC(O)C(C)C(C)C(=O)C(C)C0(=O)•C(C)C(O)C(C)C=CC=CC(O0)C (C)C(O)C(C)C(=O)C(C)C0(=O)•C(C)C(O)C(C)C=CC=CC(O)C(C)C(O)C(C)C(=O)C(C)C(=O)O•C (C)C(O(C(=O)C(C)C(=O)C(C)C(O)C(C)C(O)C=CC=CC(C)C(O0)C(C)))C(C)C=CC=CC(O)C(C) C(O)C(C)C(=O)C(C)C0(=O)•C(C)C(O(C(=O)C(C)C(=O)C(C)C(O)C(C)C(O)C=CC=CC(C)C(O)C (C)))C(C)C=CC=CC(O)C(C)C(O)C(C)C(=O)C(C)C(=O)O |
| 15 | C(C)C(O0)C(C)C=CC(O)C(C)C(O)CC(O)C(C)C(O)C(C)C(=O)C(C)C0(=O)•C(C)C(O)C(C)C=CC(O 0)CC(O)CC(O)C(C)C(O)C(C)C(=O)C(C)C0(=O)•C(C)C(O)C(C)C=CC(O)CC(O0)CC(O)C(C)C(O) C(C)C(=O)C(C)C0(=O)•C(C)C(O)C(C)C=CC(O)CC(O)CC(O0)C(C)C(O)C(C)C0(=O)•C (C)C(O)C(C)C=CC(O)CC(O)CC(O)C(C)C(O)C(C)C(=O)C(C)C(=O)O•C(C)C(O(C(=O)C(C)C (=O)C(C)C(O)C(C)C(O)CC(O)CC(O)C=CC(C)C(O0)C(C)))C(C)C=CC(O)CC(O)CC(O)C(C)C(O) |

TABLE 9-continued

Predicted pathway SMILES

| Number | Predicted SMILES |
|---|---|
|  | C(C)C(=O)C(C)C0(=O)•C(C)C(O(C(=O)C(C)C(=O)C(C)C(O)C(C)C(O)CC(O)CC(O)C=CC(C)C(O)C(C)))C(C)C=CC(O)CC(O)CC(O)C(C)C(O)C(C)C(=O)C(C)C(=O)O |
| 16 | C(C)C(O0)C(C)C=CC(O)CC=CC(O)C(C)C(O)C(C)C(=O)C(C)C0(=O)•C(C)C(O)C(C)C=CC(O0)CC=CC(O)C(C)C(O)C(C)C(=O)C(C)C0(=O)•C(C)C(O)C(C)C=CC(O0)CC=CC(O0)C(C)C(O)C(C)C(=O)C(C)C0(=O)•C(C)C(O)C(C)C=CC(O)CC=CC(O)C(C)C(O)C(C)C(=O)C(C)C(=O)O•C(C)C(O(C(=O)C(C)C(=O)C(C)C(O)C(C)C(O)C=CCC(O)C=CC(C)C(O0)C(C)))C(C)C=CC(O)CC=CC(O)C(C)C(O)C(C)C(=O)C(C)C0(=O)•C(C)C(O(C(=O)C(C)C(=O)C(C)C(O)C(C)C(O)C=CCC(O)C=CC(C)C(O)C(C)))C(C)C=CC(O)CC=CC(O)C(C)C(O)C(C)C(=O)C(C)C(=O)O |

Materials and Methods

Microorganisms and Growth Conditions

All organisms used in this Example are listed on Table 10, where information about growth conditions is also provided. Table 11 lists the plasmids and yeast artificial chromosomes (YACs) used and built for this project.

Medium ISP2 (International *Streptomyces* Project, formulae #2) consisted of 4.0 g/L of yeast extract, 10.0 g/L of malt extract and 4.0 g/L of dextrose. ISP2 plates for general purposes were made by adding 15 g/L of agar (Apex), while ISP2 plates for spore production were made with 18 g/L of yeast-grade agar (Sunrise). When growing *Streptomyces* spp. in liquid, sterile coils were added to the culture flasks, to avoid clumping. Organisms were stored at −80 C in 30% glycerol in water (yeast or spores) or LB (bacteria).

LB medium (Luria Bertani, Miller) consisted of 10.0 g/L of tryptone, 5.0 g/L of yeast extract, 10.0 g/L of sodium chloride and 15.0 g/L of agar (Apex).

The yeast medium CSM-Trp (Complete Supplement Mixture minus tryptophan) consisted of 1.7 g/L of yeast nitrogen base (MPBio), 5.0 g/L of ammonium sulfate, 20.0 g/L of dextrose and 20 g/L yeast-grade agar (Sunrise).

TABLE 10

List of microorganisms and growth conditions

| Species | Strain | Temperature (C.) | Medium |
|---|---|---|---|
| S. venezuelae | DSM 41110 | 30 | ISP2 |
| S. fradiae | DSM 41456 | 30 | ISP2 |
| S. cinnamonensis | DSM 1042 | 30 | ISP2 |
| S. nodosus | DSM 40109 | 30 | ISP2 |
| E. coli | MG1655 | 37 | LB |
| E. coli | Top10 | 37 | LB |
| S. cerevisiae | MaV203 | 30 | CSM-Trp |
| E. coli | ET12567 | 37 | LB + Chloramphenicol 34 µg/Ml |

TABLE 11

List of plasmids

| Plasmid | Features | Resistance | Strain | Source |
|---|---|---|---|---|
| pUZ8002 | DNA transfer machinery | Kanamycin | Replicative in E. coli | (28) |
| pYes1L | YAC | Spectinomycin Tryptophan | Replicative in S. cerevisiae and E. coli | GENEART ® kit (Life Technologies) |
| pSET152 | *Streptomyces* integrative plasmid (attB) | Apramycin | Integrative in *Streptomyces* spp., replicative in E. coli | (29) |
| pSET-gusA | pSET152 carrying gusA | Apramycin | Replicative in E. coli; suicide vector in *Streptomyces* spp. | This study |
| pSETSC1 | pSET152 without integration machinery | Apramycin | Replicative in E. coli; suicide vector in *Streptomyces* spp. | This study |
| pSETSC2 | pSETSC1 carrying a cos site | Apramycin | Replicative in E. coli; suicide vector in *Streptomyces* spp. | This study |
| pSETSC3 | pSETSC2 carrying the gusA reporter | Apramycin | Replicative in E. coli; suicide vector in *Streptomyces* spp. | This study |
| pSETSC-Shuf | pSETSC3 carrying insert 1 and 2 | Apramycin | Replicative in E. coli; suicide vector in *Streptomyces* spp. | This study |
| pYES1L-insert1 | pYES1L carrying insert 1 | Apramycin | Replicative in S. cerevisiae and E. coli | This study |

TABLE 11-continued

List of plasmids

| Plasmid | Features | Resistance | Strain | Source |
|---|---|---|---|---|
| pYES1L-insert2 | pYES1L carrying insert 2 | Spectinomycin Tryptophan | Replicative in *S. cerevisiae* and *E. coli* | This study |
| pUC57-tsR | pUC57 carrying the tsR-inclusive synthetic DNA | Ampicillin | Replicative in *E. coli* | This study |
| pUC57-rci | pUC57 carrying the rci-inclusive synthetic DNA | Ampicillin | Replicative in *E. coli* | This study |

Selection of a Base Pathway

In order to select a pathway onto which add gene diversity and enzyme variation by shufflon-based conditional expression, the following aspects were taken into account. The available pathway characterization, as a (deep knowledge of the pathway will facilitate the selection of genes to shuffle and help predict molecule outcome. Known enzyme promiscuity was also considered, as it has been previously determined that some enzymes are more prone to accept substrates other than their usual, than other enzymes. Given the fact that the shufflon system will be made of genes from different pathways and organisms, higher enzyme promiscuity will increase the odds of successful novel molecule assembly (30, 31). The molecule(s) assembled by the pathway were also examined because if a single pathway is capable of assembling several related molecules, there is an increase probability of the shufflon system resulting in several novel molecules also being assembled (32). Additional molecule diversity can be generated by tailoring enzymes, which adds post-assembly modifications to the assembled molecules. Sugar or lipid moieties can be added (33, 34).

Selection of Genes to Shuffle

A preselection of genes to shuffle, listed in Table 7, was made from the pathway information available online (gate.smallsoft.co.kr:8008/pks/mapsidb/, www.bio.nite.go.jp/pks/top, and smart.embl-heidelberg.de/), taking into account the factors described below.

Phylogenetic distance was examined through evolutionary relatedness (carried out by performing protein homology searches using BLAST and against the entire NCBI database). The top 100 hits, corresponding to the 100 sequences in the database with the highest homology to the query sequence, were used for phylogenetic comparisons. Unrooted trees displaying phylogenetic distance between the sequences were generated using NCBI's BLAST Tree View Neighbor Joining algorithm. The Maximum Sequence Difference allowed was 0.85 using the evolutionary distance model according to Grishin.

Due to the technical limitations associated with very large genes (natural product genes can be as large as 25,000 bp), gene size was restricted.

Bioactivity was determined using the freely available algorithms that predict molecule structure from the genetic information (NP.searcher (35)) and molecule function (Molinspiration (36)). The selection of a pathway and its gene to be replaced influenced the choice of heterologous genes selected to be incorporated into the biosynthetic pathway and shuffled.

Reliable access to the strains was a factor in determining the genes to be used or replaced. Only strains from reputable collections were used.

In Silico Design of Full Construct

The full shufflon system construct uses the following parts: heterologous genes, which will be shuffled, rci gene, which codes for the recombinase (shufflon) that inverts DNA sequences, inducible promoter driving rci, recognition sequences, which are placed between the genes to be shuffled, regions of homology to the chromosomal loci, which will allow for integration of the shufflon system into a desired locus, constitutive promoter at the end of the shufflon system, which will prevent the occurrence of polar effects, and unique restriction sites are also used, in order to recover the shufflon system from the carrier YAC and subsequently clone it in the target vector.

The several parts used for the system were obtained using three strategies: gene synthesis (GenScript Corp), gBlock synthesis (IDTDNA), and PCR.

The amplification of high GC and long templates can be challenging (37, 38), using specialized polymerases and conditions. A set of different DNA polymerases, specifically engineered for the amplification of long and/or high GC templates, were used for successful amplification of the parts, including: Phusion® Polymerase NEB®, Kapa Hifi Biosystems®, KOD Xtreme High GC Long Template EMD Milipore®, KOD XL EMD Milipore®, Herculase II Hot Start Agilent®, AccuTaq LA DNA Polymerase Sigma Aldrich®, and TaKaRa LA Taq Clonetech®.

A vast array of conditions was tested, where different buffers, and additives at different concentrations and combinations were used (Tables 12 and 13). This was done in order to find the amplification conditions that allowed for gene amplification.

TABLE 12

PCR mix protocols (25 μL reactions)

| Reagent | Phusion | Kapa | Herculase II | Robust |
|---|---|---|---|---|
| Buffer* (μL) | 5 | 5 | 5 | 5 |
| Additive A** (μL) | 0-3 | 0-3 | 0-3 | 0-3 |
| Additive B** (μL) | 0-3 | 0-3 | 0-3 | 0-3 |
| dNTP* (μL) | 1 | 1 | 1 | 0.5 |
| Primer (forward) (μL) | 0.5 | 0.5 | 0.5 | 0.5 |
| Primer (reverse) (μL) | 0.5 | 0.5 | 0.5 | 0.5 |
| DNA (template) (μL) | 0.5 | 0.5 | 0.5 | 0.5 |
| Enzyme (μL) | 0.2 | 1 | 0.5 | 0.2 |
| H$_2$O (μL) | 13.3-17.3 | 12.5-16.5 | 13-17 | 13.8-17.8 |
| Reagent | KOD | XL KOD | AccuTaq | TaKaRa |
| Buffer* (μL) | 12.5 | 2.5 | 2.5 | 12.5 |
| Additive A** (μL) | 0-3 | 0-3 | 0 | 0 |
| Additive B** (μL) | 0-3 | 0-3 | 0 | 0 |
| dNTP* (μL) | 5 | 2.5 | 2.5 | 4 |
| Primer (forward) (μL) | 0.5 | 0.5 | 0.5 | 0.5 |
| Primer (reverse) (μL) | 0.5 | 0.5 | 0.5 | 0.5 |

TABLE 12-continued

PCR mix protocols (25 μL reactions)

| DNA (template) (μL) | 0.5 | 0.5 | 0.5 | 0.5 |
|---|---|---|---|---|
| Enzyme (μL) | 0.5 | 0.5 | 0.25 | 0.25 |
| H₂O (μL) | 1.5-5.5 | 14-18 | 18.25 | 6.75 |

*The buffer and dNTPs volume varies according to the stock provided with the individual kits. The final concentrations are always 1x for the buffers, 0.3 mM for each dNTP, 0.3 μM per primer and 100 ng DNA/reaction.
**The additive was added, per reaction, in the following fashion:

TABLE 13

List of type and volume of additives used for PCR

| Volume/25 (μL) | Additive Combination |
|---|---|
| 0 | b, d or m |
| 1 | b, d or m |
| 1.5 | b, d, m, b + m or d + m |
| 2 | b, d or m |
| 2.5 | b, d, m, b + m or d + m |
| 3 | b, d or m | b = 5M Betaine
d = 100% DMSO
m = 2 mM MgCl₂

For the DNA polymerases used, the PCR cycling protocols used are indicated in Table 14.

TABLE 14

PCR Cycling Protocols

| | Phusion | | | Kapa | | |
|---|---|---|---|---|---|---|
| Step | Cycles (#) | T (C.) | t (mm:ss) | Cycles (#) | T (C.) | t (mm:ss) |
| Initial denaturation | 1 | 98 | 0:30 | 1 | 98 | 3:00 |
| Denaturation | 28 | 98 | 0:10 | 28 | 98 | 0:20 |
| Annealing | | 58 | 0:30 | | 60 | 0:20 |
| Extension | | 70 | 4:00 | | 72 | 4:00 |
| Final extension | 1 | 70 | 10:00 | 1 | 72 | 5:00 |

| | KOD | | | XL KOD | | |
|---|---|---|---|---|---|---|
| Step | Cycles (#) | T (C.) | t (mm:ss) | Cycles (#) | T (C.) | t (mm:ss) |
| Initial denaturation | 1 | 94 | 2:00 | 1 | 94 | 2:00 |
| Denaturation | 28 | 98 | 0:10 | 28 | 94 | 0:30 |
| Annealing | | 58 | 0:30 | | 56 | 0:05 |
| Extension | | 70 | 3:00 | | 72 | 3:00 |
| Final extension | | — | | 1 | 72 | 10:00 |

| | Herculase II | | | Robust | | |
|---|---|---|---|---|---|---|
| Step | Cycles (#) | T (C.) | t (mm:ss) | Cycles (#) | T (C.) | t (mm:ss) |
| Initial denaturation | 1 | 95 | 2:00 | 1 | 95 | 5:00 |
| Denaturation | 28 | 95 | 0:20 | 28 | 95 | 0:15 |
| Annealing | | 56 | 0:20 | | 58 | 0:15 |
| Extension | | 72 | 4:00 | | 72 | 1:00 |
| Final extension | 1 | 72 | 3:00 | | — | |

The PCR reaction volume was 25 μL. Scaled-up reaction were 4 of 50 μL. Reactions were run in 1% agarose gels, at 120 V for 1-1.5 h and the 1 kb NEB DNA ladder was used has size marker.

Assembling of Parts (Synthesized and PCRed) Using an Yeast-Based Recombination Method The PCRed and synthesized gene fragments were assembled using the GeneArt® High-Order Genetic Assembly kit (Life Technologies, Inc.).

This assembly kit has been devised to assemble up to 10 DNA fragments of up to 110 kb. The higher the number of fragments, the lower the probability of the yeast assembling the correct construct. Taking this into account, the final 13-fragment construct (12+backbone) was subdivided in two fragments, for a total of 7+7 fragments (twice 6+backbone) (FIG. 1):

YAC 1—Linearized pYes1L; rci-containing fragment (contains XbaI site); gBlock 1; gBlock 2; tylG and momAVI (gene split in 2 pieces; contains MfeI site); and YAC 2—Linearized pYes1L; gBlock 3 (contains MfeI site); amphK; momAVIII (gene split in 3 pieces) and tsr-containing fragment (contains the Bsu36I site).

In brief, 100 ng of each linearized fragment was mixed together in a total volume of <10 μL. One hundred microliters of competent yeast cells were then added to this DNA mixture, to which a PEG/Lithium Acetate solution was added afterwards.

After a 30 min incubation at 30° C., ß-mercaptoetanol was added to the cell-DNA mixture, which was then heat-shocked at 42° C.

After replacement of the transformation solution with NaCl, the cells were plated on yeast medium (CSM-Trp) for selection of yeast cells carrying the tryptophan-producing vector (and insert) and incubated at 30° C.

Upon 3 days of incubation at 30 C, PCR was performed on the yeast colonies to identify transformants with the correct assembly. Several pairs of primers were used, each targeting a recombination locus (junctions).

A first screening of the transformants was performed by lysing 8 yeast colonies per construct and performing PCR using the lysate as template DNA.

The lysing was performed by resuspending the yeast colonies in 20 mM NaOH and boiling the suspensions for 10 minutes at 99° C. in a thermocycler.

One microliter of each lysate was used as template in the 25 μL PCR reactions, with Kapa Robust as DNA polymerase and no additives.

Three yeast colonies per assembly were selected to be moved to *E. coli*, based on the PCR screening. They were lysed using a proprietary lysis buffer and beads included with the GeneArt® kit. Briefly, one microliter of the lysate was electroporated into *E. coli* Top10 competent cells provided with the kit, and plated on Luria Bertani (LB) medium supplemented with spectinomycin (50 μg/mL) for selection of transformants.

Construction Reporting Suicide Vector, for Shufflon Integration and Double Crossover Selection A reporter vector was designed to carry the shufflon system and to allow for its integration into the host organism, while reporting on its efficiency.

Thus, the vector was designed to include an apramycin resistance cassette, an origin of replication that replicates in *E. coli* but not in *Streptomyces* spp. (ColE1), a codon-optimized reporter gene gusA and a cos site for vector stability with large inserts.

The desired plasmid was derived from pSET152, an integrative vector. Prior to cloning in the parts of interest, the C31 and integrase-coding regions were removed, as the goal was to integrate the vector's insert in a specific locus, which is not the attB site of the organism. The resulting plasmid was named pSETSC1.

Figure 2:
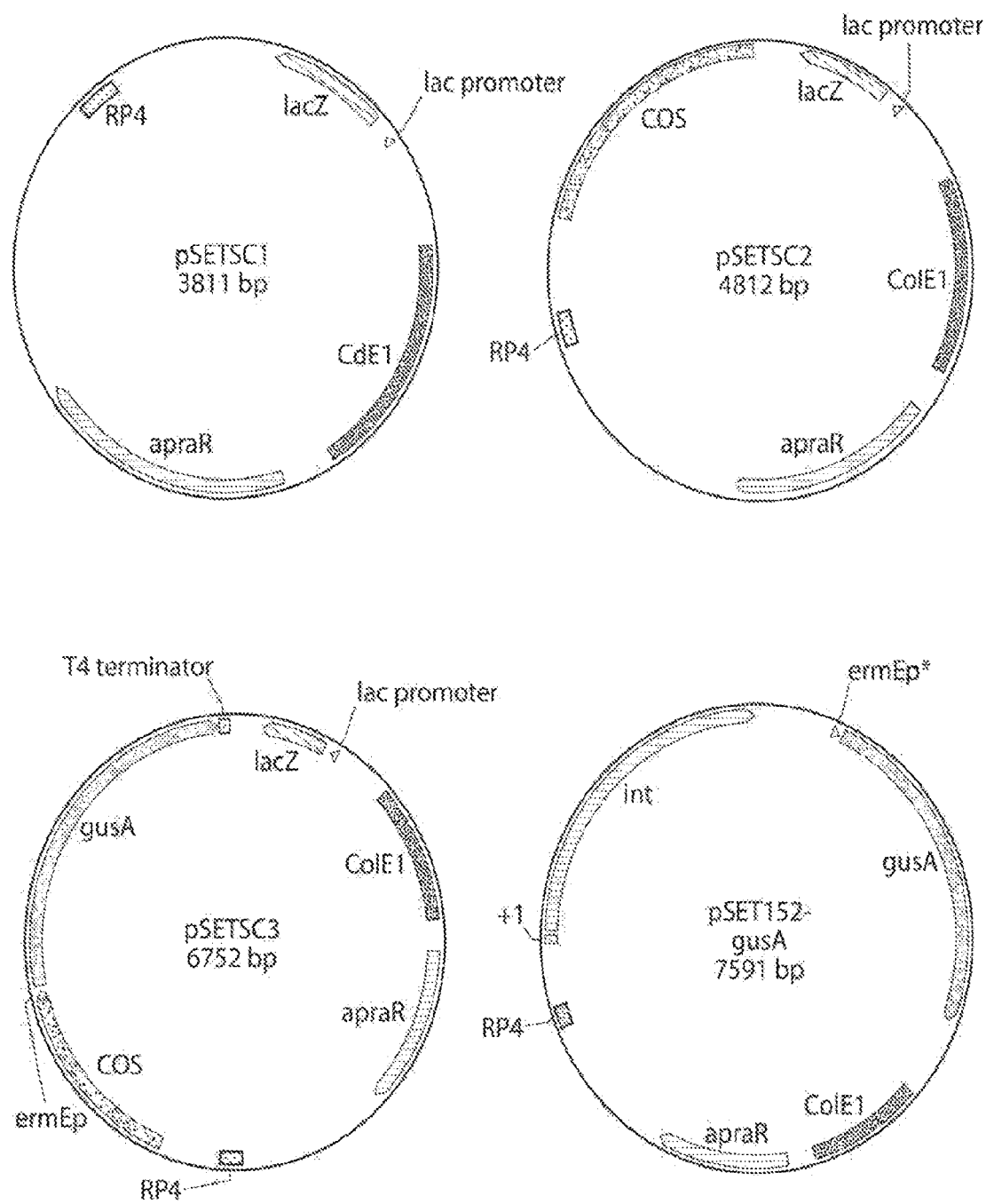
FIG. 2 shows maps of a pSETSC1 plasmid used to generate pSETSC2 and a final pSETSC3 plasmid.

The integration machinery was removed from pSET152 by PCRing out the backbone parts of interest by PCRing around it. This PCR product, which contained the resistance cassette, the origin of replication, and the lacZ counter selection machinery, was ligated into the cos site fragment (PCRed from pYES1L) by isothermal assembly. In order for this to be achieved, the primers used in the amplification of both pieces contained regions of homology to each other, with an annealing temperature of 50 C. Furthermore, the cos site amplicon also contained a NcoI cloning site, (pSETSC2) into which the codon-optimized gusA was subsequently cloned (pSETSC3, FIG. 2).

At the same time that the reporter suicide vector was being built, another vector was designed to contain the reporter gene alone (pSET152-gusA), which was used to determine whether gusA is expressed in the target organism and reports in a visual manner and to assess whether it reports even if integrated into the chromosome (in single copy).

All restriction enzyme-based DNA digestion was done in 50 µL reactions at 37 C, following the product protocol. DNA dephosphorylation, when used, was performed using Alkaline Phosphatase Calf Intestinal (CIP).

Construction of a gusA-Based Reporter System in *Streptomyces* Spp.

In order to test this, a DNA amplicon carrying the ermEp* promoter and gusA, from pSETSC3 (FIG. 2), was PCRed using primers that added XbaI restriction sites at both extremities of the amplicon. Upon digestion of the fragment and the pSET152 recipient vector, these pieces were ligated together and transformed into *E. coli*. The gene gusA and the promoter ermEp* driving it were PCRed from the suicide reporter vector. The restriction site XbaI was added to both terminus of the amplicon by PCR, which upon digestion was cloned into the digested and dephosphorylated backbone of pSET152 by CIP, by overnight ligation at 16 C (NEB T4 DNA Ligase), resulting in plasmid pSET-gusA.

All enzymes (restriction and ligation) used were purchased from NEB Inc. The isothermal assembly mix was prepared in house.

Confirmation of the correct ligation was performed by sequencing the construct (Genewiz Inc.).

Moving PSET152-gusA into *S. venezuelae*

Briefly, 10 mL of an exponentially growing culture of the methylation-deficient *E. coli* ET12567, carrying the non-transmissible plasmid pUZ8002 and the transmissible plasmid pSet152-gusA was pelleted and resuspended in 1 mL of LB and mixed 1:1 with 500 µL of synchronally-germinating spores (50 C, 10 min) in Yeast Tryptone (YT) medium.

References for Example 1

1. Nikaido H. 2009. Multidrug resistance in bacteria. Annu. Rev. Biochem. 78:119.
2. Bronzwaer S. 2003. European antimicrobial resistance surveillance as part of a Community strategy. Groningen Rijksuniv.
3. Knothe H, Shah P, Krcmery V, Antal M, Mitsuhashi S. 1983. Transferable resistance to cefotaxime, cefoxitin, cefamandole and cefuroxime in clinical isolates of *Klebsiella pneumoniae* and Serratia marcescens. Infection 11:315-317.
4. Alanis A J. 2005. Resistance to antibiotics: are we in the post-antibiotic era? Arch. Med. Res. 36:697-705.
5. McGowan J E. 1983. Antimicrobial Resistance in Hospital Organisms and Its Relation to Antibiotic Use. Clin. Infect. Dis. 5:1033-1048.
6. Levy S B, Marshall B. 2004. Antibacterial resistance worldwide: causes, challenges and responses. Nat. Med. 10:S122-9.
7. Centers for Disease Control and Prevention. 2013. Antibiotic resistance threats.
8. Cantón R, Morosini M-I. 2011. Emergence and spread of antibiotic resistance following exposure to antibiotics. FEMS Microbiol. Rev. 35:977-91.
9. U.S. Food and Drug Administration. 2014. Antibacterial Drug Development Task Force.
10. The White House. 2014. National Strategy for Combating Antibiotic Resistant Bacteria.
11. The White House, Office of the Press Secretary. 2014. Executive Order—Combating Antibiotic-Resistant Bacteria.
12. Executive Office of the President, President's Council of Advisors on Science and Technology. 2014. Report to the President on Combating Antibiotic Resistance.
13. Bérdy J. 2012. Thoughts and facts about antibiotics: where we are now and where we are heading. J. Antibiot. (Tokyo). 65:385-95.
14. Bergmann S, Schümann J, Scherlach K, Lange C, Brakhage A a, Hertweck C. 2007. Genomics-driven discovery of PKS-NRPS hybrid metabolites from Aspergillus nidulans. Nat. Chem. Biol. 3:213-7.
15. Allsop a E. 1998. New antibiotic discovery, novel screens, novel targets and impact of microbial genomics. Curr. Opin. Microbiol. 1:530-4.
16. Payne D J, Gwynn M N, Holmes D J, Pompliano D L. 2007. Drugs for bad bugs: confronting the challenges of antibacterial discovery. Nat. Rev. Drug Discov. 6:29-40.
17. Silver L L. 2011. Challenges of antibacterial discovery. Clin. Microbiol. Rev. 24:71-109.
18. Donadio S, Maffioli S, Monciardini P, Sosio M, Jabes D. 2010. Antibiotic discovery in the twenty-first century: current trends and future perspectives. J. Antibiot. (Tokyo). 63:423-30.
19. Fischbach M A, Walsh C T. 2009. Antibiotics for Emerging Pathogens. Science (80-.). 325:1089.
20. Komano T. 1999. Multiple Inversion Systems and Integrons.
21. Esposito D, Scocca J J. 1997. The integrase family of tyrosine recombinases: evolution of a conserved active site domain. Nucleic Acids Res. 25:3605-3614.
22. Siuti P, Yazbek J, Lu T K. 2013. Synthetic circuits integrating logic and memory in living cells. Nat. Biotechnol. 31:448-52.
23. Gyohda A, Funayama N, Komano T. 1997. Analysis of DNA inversions in the shufflon of plasmid R64. J. Bacteriol. 179:1867-1871.
24. Gyohda A, Furuya N, Kogure N, Komano T. 2002. Sequence-specific and nonspecific binding of the Rci protein to the asymmetric recombination sites of the R64 shufflon. J. Mol. Biol. 318:975-83.
25. Komano T, Kubo A, Nisioka T. 1987. shufflon: multi-inversion of four contiguous DNA segments of plasmid R64 crestes seven different open reading frames. Nucleic Acids Res. 15.
26. Gyohda A, Zhu S, Furuya N, Komano T. 2006. Asymmetry of shufflon-specific recombination sites in plasmid R64 inhibits recombination between direct sfx sequences. J. Biol. Chem. 281:20772-9.
27. Gyohda A, Komano T. 2000. Purification and Characterization of the R64 Purification and Characterization of the R64 shufflon-Specific Recombinase 182.

28. Kieser T, Bibb M J, Buttner M J, Chater K F, Hopwood D A. 2000. Practical *Streptomyces* genetics. John Innes Foundation.
29. Bierman M, Logan R, O'Brien K, Seno E T, Rao R N, Schoner B E. 1992. Plasmid cloning vectors for the conjugal transfer of DNA from *Escherichia coli* to *Streptomyces* spp. Gene 116:43-49.
30. Zimmermann M, Fischbach M a. 2010. A family of pyrazinone natural products from a conserved nonribosomal peptide synthetase in *Staphylococcus aureus*. Chem. Biol. 17:925-30.
31. Meier J L, Burkart M D. 2009. The chemical biology of modular biosynthetic enzymes. Chem. Soc. Rev. 38:2012-45.
32. Mootz H D, Schwarzer D, Marahiel M a. 2002. Ways of assembling complex natural products on modular nonribosomal peptide synthetases. Chembiochem 3:490-504.
33. Khosla C, Keasling J. 2003. Metabolic engineering for drug discovery and development. Nat. Rev. Drug Discov. 2.
34. Staunton J, Wilkinson B. 1997. Biosynthesis of Erythromycin and Rapamycin. Chem. Rev. 97:2611-2630.
35. Röttig M, Medema M H, Blin K, Weber T, Rausch C, Kohlbacher O. 2011. NRPSpredictor2—a web server for predicting NRPS adenylation domain specificity. Nucleic Acids Res. 39:W362-W367.
36. Molinspiration.
37. Jensen M a, Fukushima M, Davis R W. 2010. DMSO and betaine greatly improve amplification of G C-rich constructs in de novo synthesis. PLoS One 5:e11024.
38. Mamedov T, Pienaar E. 2008. A fundamental study of the PCR amplification of G C-rich DNA templates . . . . Biol. Chem. 32:452-457.
39. Kittendorf J, Sherman D. 2009. The methymycin/pikromycin pathway: a model for metabolic diversity in natural product biosynthesis. Bioorg. Med. Chem. 17:2137-2146.
40. Hansen D a, Rath C M, Eisman E B, Narayan A R H, Kittendorf J D, Mortison J D, Yoon Y J, Sherman D H. 2013. Biocatalytic synthesis of pikromycin, methymycin, neomethymycin, novamethymycin, and ketomethymycin. J. Am. Chem. Soc. 135:11232-8.
41. Xue Y, Sherman D H. 2001. Biosynthesis and combinatorial biosynthesis of pikromycin-related macrolides in *Streptomyces venezuelae*. Metab. Eng. 3:15-26.
42. Xue Y, Zhao L. 1998. A gene cluster for macrolide antibiotic biosynthesis in *Streptomyces venezuelae*: architecture of metabolic diversity. Proc . . . . 95:12111-12116.
43. Christiansen G, Philmus B, Hemscheidt T, Kurmayer R. 2011. Genetic variation of adenylation domains of the anabaenopeptin synthesis operon and evolution of substrate promiscuity. J. Bacteriol. 193:3822-31.
44. Jenke-Kodama H, Dittmann E. 2009. Bioinformatic perspectives on NRPS/PKS megasynthases: advances and challenges. Nat. Prod. Rep. 26:874-83.
45. Rausch C, Hoof I, Weber T, Wohlleben W, Huson D H. 2007. Phylogenetic analysis of condensation domains in NRPS sheds light on their functional evolution. BMC Evol. Biol. 7:78.
46. Villiers B, Hollfelder F. 2011. Directed evolution of a gatekeeper domain in nonribosomal peptide synthesis. Chem. Biol. 18:1290-9.
47. Engler C, Gruetzner R, Kandzia R, Marillonnet S. 2009. Golden Gate Shuffling: A One-Pot DNA Shuffling Method Based on Type IIs Restriction Enzymes. PLoS One 4:e5553.
48. Gibson D G, Young L, Chuang R-Y, Venter J C, Hutchison C A, Smith H O. 2009. Enzymatic assembly of DNA molecules up to several hundred kilobases. Nat Meth 6:343-345.
49. Struhl K, Stinchcomb D T, Scherer S, Davis R W. 1979. High-frequency transformation of yeast: autonomous replication of hybrid DNA molecules. Proc. Natl. Acad. Sci. 76:1035-1039.
50. Myronovskyi M, Welle E, Fedorenko V, Luzhetskyy A. 2011. Beta-glucuronidase as a sensitive and versatile reporter in actinomycetes. Appl. Environ. Microbiol. 77:5370-83.

Example 2

The experiments described below were conducted to develop and test the tools used in Example 1.

Testing the Reporter gusA in *S. venezuelae*

The reporting capability of gusA in *Streptomyces* spp. was tested in *S. venezuelae*. The sequence of gusA (ID 946149) was obtained from NCBI. Since the original host is *E. coli*, it was codon optimized and synthesized by Genscript Corp. In order to test its activity in *S. venezuelae*, the optimized gusA was cloned into the integrative plasmid pSET152 via Isothermal Assembly[2]. The purified DNA was then electroporated into *E. coli* MG1655 and plated on apramycin-supplemented LB (50 µg/mL). The colonies were screened for proper assembly and the selected clones were tested for β-glucuronidase activity. This testing was not used as a method for colony selection because the overlaying process leads to cell mixing.

Positive clones were re-streaked onto LB-Apramycin, incubated for 24 hours and overlaid with 1 mL of 0.5 mg/mL of 5-bromo-4-chloro-3-indolyl-beta-D-glucuronic acid, cyclohexylammonium sal (X-Gluc). The plates were checked for substrate breakdown into a blue pigment after 3 hours of incubation at room temperature. A strong blue/green color developed within this time frame. The hydrophobicity of the spore layer hinders the absorption of the solution, having the phenotype been stronger around individual colonies than the busiest sections of the plate.

It was thus confirmed that in *S. venezuelae* the codon-optimized gusA is an efficient reporter.

Recovery of Inserts from YAC-1 and YAC-2, and Assembly of Full Construct

In order to assemble the complete shufflon construct and move it to its dedicated integrative vector, 2 inserts were recovered from the YAC backbone. The recovery of the two inserts was performed by restriction digest of the two YACs. YAC 1 was digested with the restriction enzymes PmeI and XbaI, and YAC2 with PmeI and Bsu36I. The digestion step was allowed to occur for 10 hours at 37 C,
and following the product protocol. The digestions were gel-purified (0.7% agarose).

Figure 12:
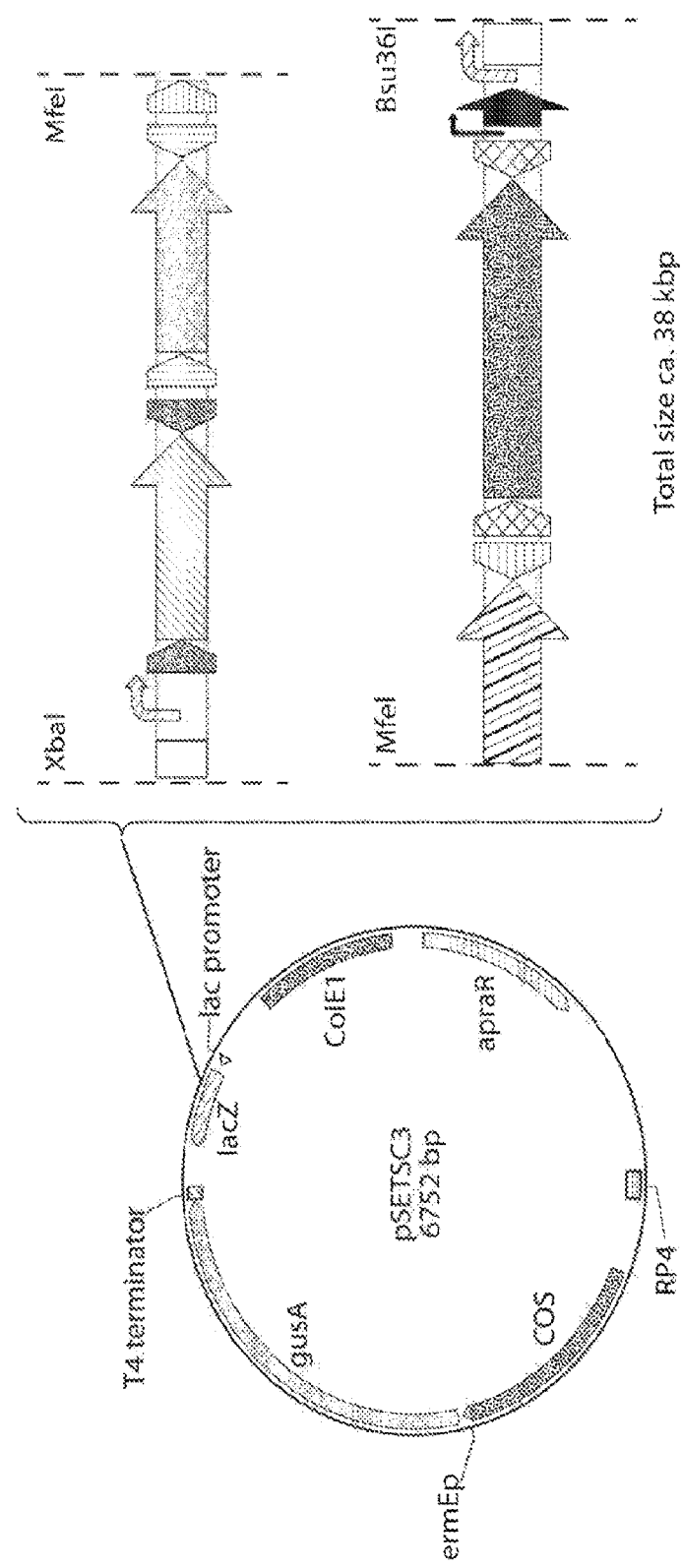
FIG. 12 shows a map of plasmid pSETSC3 and the approach to the cloning of the two shufflon parts.

The pSETSC3 vector digested with Bsu36I and XbaI, and the two inserts, digested as aforementioned (FIG. 12), were ligated overnight at 16 C using NEB T4 DNA Ligase and according to the product specifications. The ligation reaction was subsequently purified and electroporated into *E. coli* MG1655.

Figure 13:
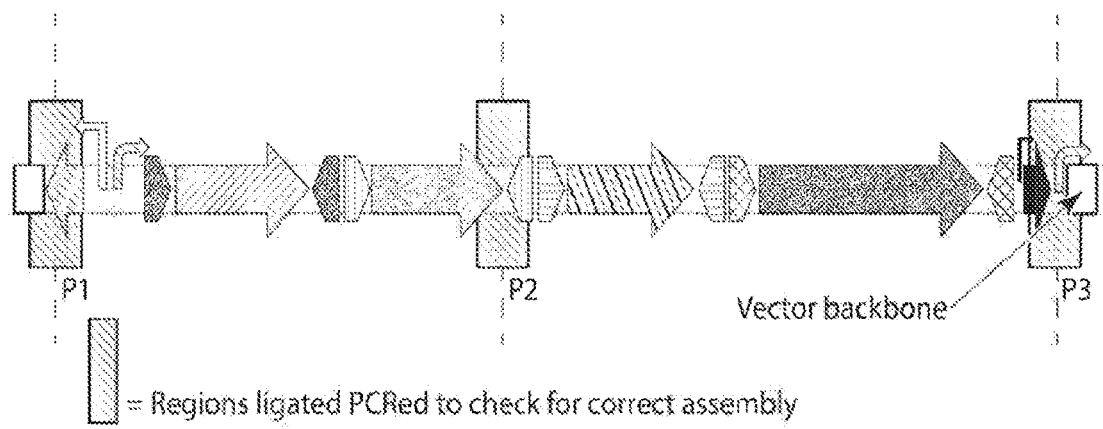
FIG. 13 shows the two shufflon parts (of FIG. 12) ligated into the dedicated backbone pSETSC3.
Figure 14:
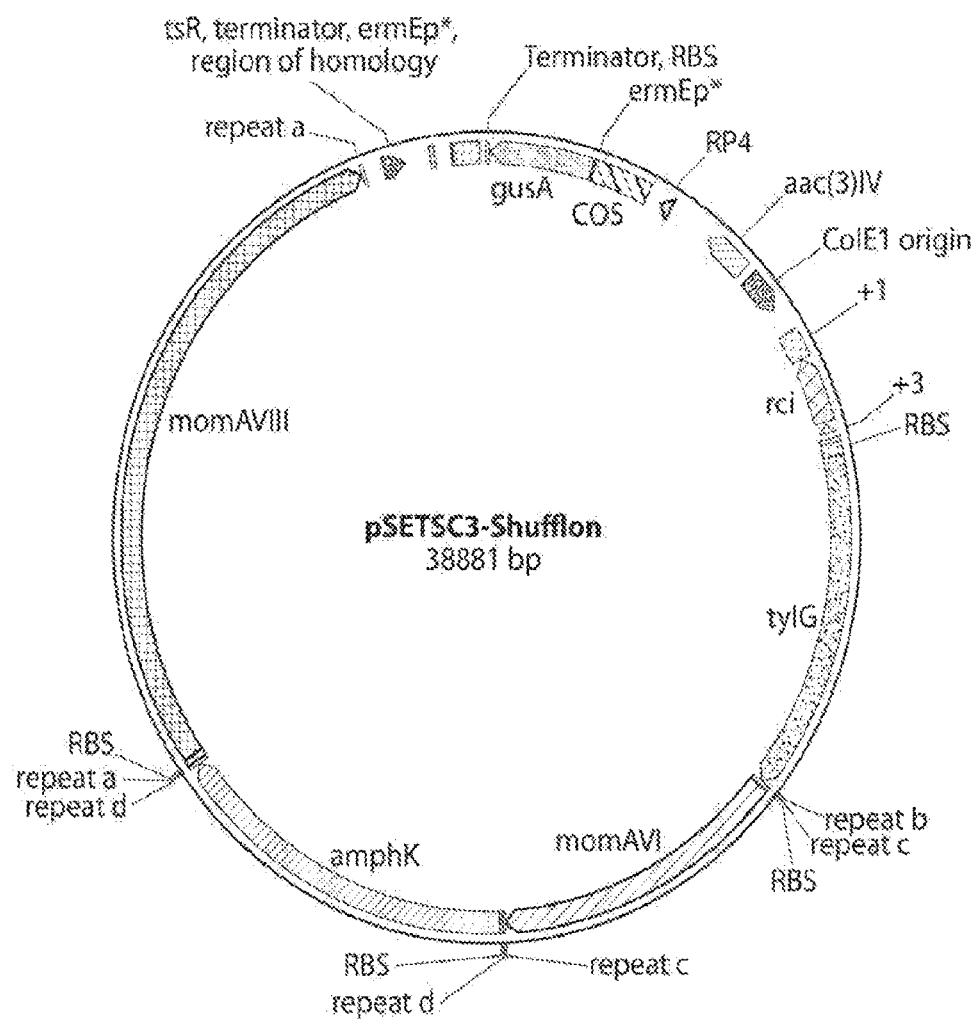
FIG. 14 shows a map of pSETSC3-shufflon.

A subset of the transformants obtained was midiprepped and PCRed using set of primers for the ligated loci (FIG. 13). Initial attempts at performing colony-PCR for confirmation of proper assembly were unsuccessful.

Upon confirmation of correct assembly using the midiprepped DNA, two constructs were selected and cryopreserved.

The 2-part shufflon system was initially made up of several smaller parts that were assembled in yeast. The two parts were designed to include restriction sites that enable an easy recovery of the insert and removal of the Yeast Artificial Chromosome (YAC) backbone. Furthermore, they were designed to share a restriction site for assembling the 2-part shufflon into a complete one.

By digestion, gel purification, and 3-way ligation of the parts to the pSETSC3 backbone, it was possible to fully construct, in vitro, the pathway designed in silico.

Three-way ligations, particularly of very large inserts, are not particularly efficient. By using the information obtained from PCRs aimed at amplifying the ligated loci, it was possible to select isolates with the proper assembly (FIG. 13). As previously experienced, only the combined use of information from PCRs using a variety of polymerases allowed for such selection. Again, this was due to the very high GC content of the construct and the high repetitiveness of the coding DNA.

Rebuilding the Shufflon System

Removing rci from the shufflon system implied, nonetheless, rebuilding it. Given that the assembly in yeast was performed in two independent YACs (1 and 2; see Example 1), only one was altered: the one containing rci.

Figure 15:
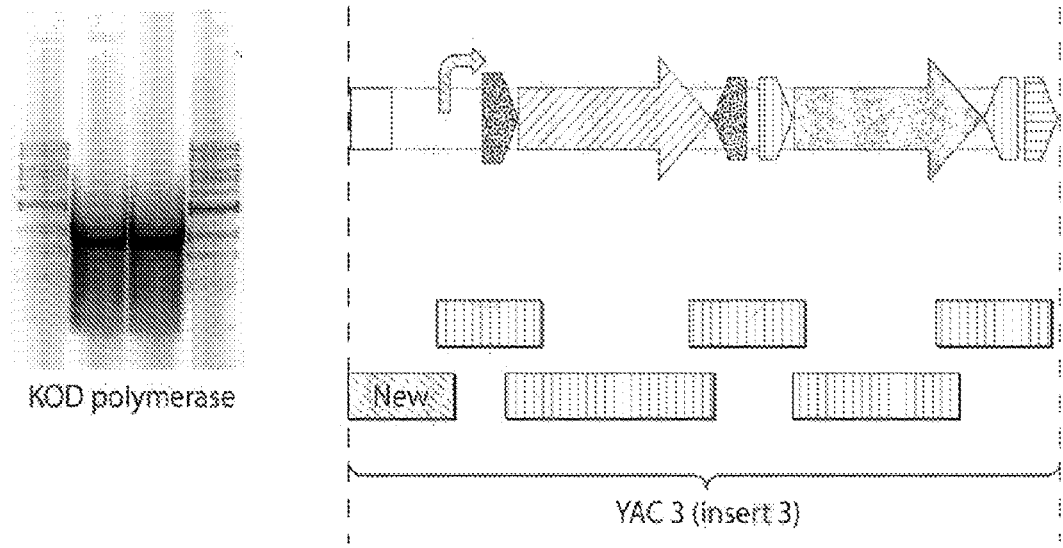
FIG. 15 shows amplicon (PCR-amplified by KOD polymerase) and schematic of the shufflon part without the rci gene.

Furthermore, given that all pieces of YAC1 would remain the same except for one, only one new piece was obtained (FIG. 15). This piece would connect the regions up and downstream of the rci locus (which previously connected them).

A new step of yeast-based assembly was performed and several yeast colonies were checked for successful assembly. Upon confirmation of a correct construct, named YAC3, it was moved to *E. coli* Top10, extracted, digested and ligated into pSETSC3 as already explained for the original pathway, resulting in pSETSC3-shufflon b. As before, the colonies were checked for proper assembly, and correct 3-way ligations were obtained and stored at −80 C.

Moving Rci to a Temperature-Sensitive Replicative Plasmid

To address the concern that the tipAp promoter would be leaky in *S. venezuelae*, which would not allow for complete stop or control of Rci-mediated shuffling, it was decided to move this gene out of pSETSC3 and onto an independent plasmid.

Figure 16:
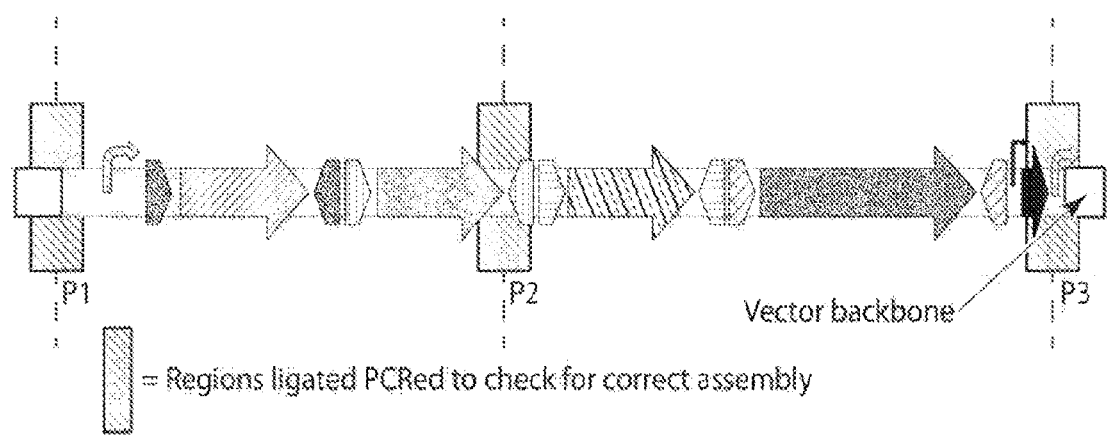
FIG. 16 shows a schematic of the shuffling system without the rci gene.
Figure 17:
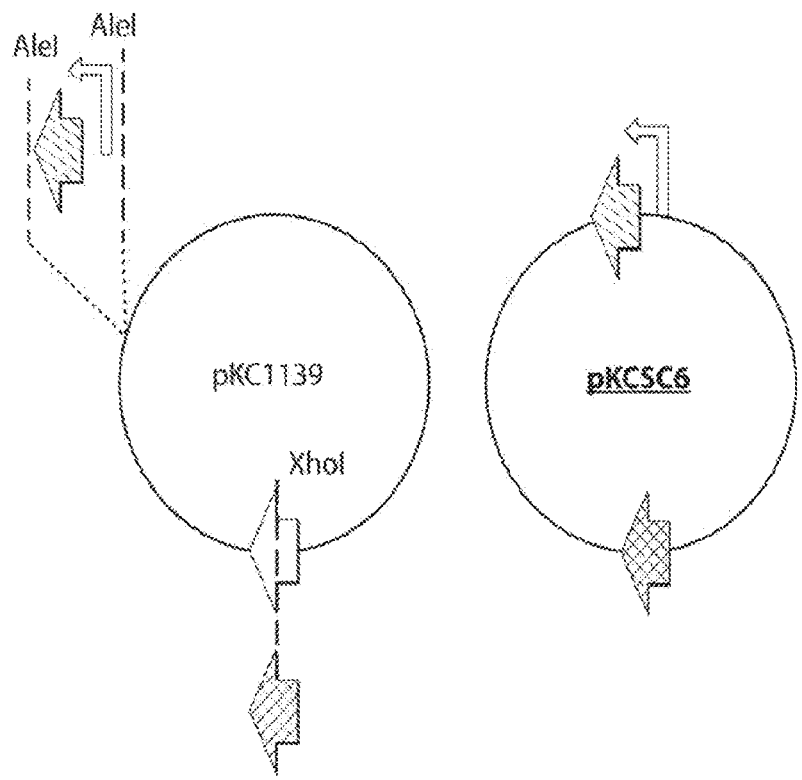
FIG. 17 shows a cloning approach for moving the rci gene to a temperature-sensitive plasmid and a final hygromycin resistant construct.

This plasmid was derived from pKC1139 3, a replicative temperature-sensitive plasmid. The rci gene driven by the tipAp promoter was cloned in the restriction sites HindIII and BamHI, which were added to the insert by means of PCR (FIG. 16). Given that the selection marker for this plasmid was apramycin, which is also present in plasmid carrying the shufflon system and will only be removed if a double crossover event will be achieved, it was also decided to replace it with a hygromycin resistance cassette.

The hygromycin resistance cassette was amplified from plasmid pIJ10700 by PCR and cloned into restriction site xhoI, located in the middle of the gene coding for the apramycin resistance.

Testing Rci-Based Shuffling

To address concerns that rci might not work in *S. venezuelae*, it was decided to pause the incursion into the use of rci as a tool to generate chemotype diversity. A new approach to test rci-mediated shuffling was then devised.

In this approach, four different genes coding for fluorescent proteins were chosen for the screening of the shuffling events and their frequency, in *S. venezuelae*. Given that the shufflon pathway of interest—the one carrying genes coding for polyketide synthases—is made of very large genes of very high GC content, the same type and length of DNA was used in between recognition sites.

Therefore, four different constructs were designed, with different inter-recognition sites distances: 1, 5, 10 and 15 kbp of high GC DNA. This inter-site DNA was PCR-amplified from *Streptomyces coelicolor* A3(2), a species of *Streptomyces* close enough to share many of the cumbersome aspects of the species from this genus (the very high GC content results in very tight DNA and potential inaccessibility of enzymes to the nucleotides). Yet, this strain is also not close enough to share high homology that could result in the integration of the construct through the DNA amplicons.

Using the NCBI Genome Graphic View, the genome of *S. coelicolor* A3(2) was scanned and 5, 10 and 15 kbp of regions not coding for antibiotics of genes that could potential affect the host phenotype were selected (Table 15). These regions were then blasted against the whole chromosome of *S. venezuelae*, to assess the degree of similarity (Table 15), which was lower than 82% in up to 47% coverage of the sequences (i.e., very low).

TABLE 15

Length, coordinates and similarity of *S. coelicolor* DNA fragments to be flipped by Rci with the 4-color system

| Piece | Length (kbp) | Locus (chromosome coordinates) | Coverage % | Similarity % |
|---|---|---|---|---|
| A | 5 | 566133 ... 571711 | 31 | 80 |
|   | 10 | 565091 ... 575044 | 24 | 80 |
|   | 15 | 77298 ... 93961 | 3 | 73 |
| B | 5 | 682108 ... 687070 | NA | NA |
|   | 10 | 676426 ... 686815 | 5 | 73 |
|   | 15 | 581427 ... 598131 | 14 | 76 |
| C | 5 | 8319286 ... 8324450 | 26 | 82 |
|   | 10 | 8318514 ... 8329225 | 40 | 82 |
|   | 15 | 8317786 ... 8333304 | 25 | 82 |
| D | 5 | 1295599 ... 1300243 | 29 | 82 |
|   | 10 | 1289613 ... 1300079 | 28 | 82 |
|   | 15 | 1284740 ... 1299845 | 47 | 82 |

Coverage % - Stretch of DNA with some degree of similarity;
Similarity % - How similar the covered stretches of DNA are;
NA - No significant similarity found Selection of Fluorescent Proteins To this date, only green and red fluorescent proteins (FPs) have been developed or shown to be functional in *Streptomyces* spp[4,5]. Four genes coding for fluorescent proteins used in other prokaryotes were codon optimized and synthesized by Genscript Corp. The selection of these four FPs took into account their excitation and emission spectra, so that minimal overlap occurs (Table 16).

TABLE 16

Excitation and emission wavelengths for the selected FPs

| Protein | Excitation (nm) | Emission (nm) |
|---|---|---|
| dsRed2 | 563 | 582 |
| nirFP | 605 | 670 |
| ebfp2 | 380 | 448 |
| mKate2 | 588 | 633 |

Testing the FPs in *S. venezuelae*

Upon codon optimization and synthesis of the four genes coding for the FPs, it was taken into account that optimization alone might not be the single barrier to the expression of these genes by *S. venezuelae*.

Therefore, it was decided to test these independently, before testing the 4-FP shufflon systems.

Figure 18:
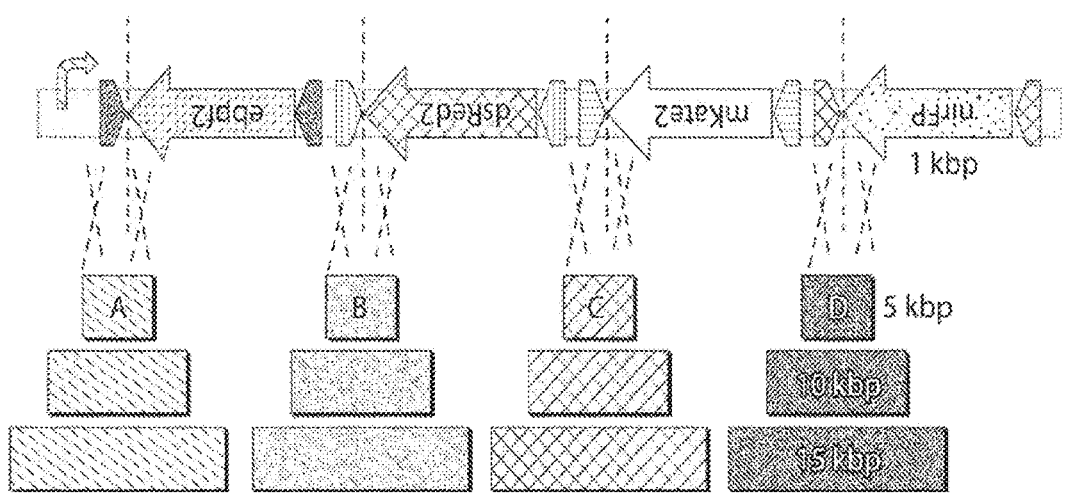
FIG. 18 shows four-FP shuffling system with different distances between recognition sites.

A constitutive expression vector, based on pSET152, was then designed and built (FIG. 18). The constitutive promoter ermEp* was cloned by Isothermal Assembly, having the plasmid backbone been amplified by PCR so as to remove the lacZ system. Thinking of maximizing its usefulness to the Streptomyces community of researchers, a multiple cloning site (MCS) was cloned downstream of ermEp*. This MCS was designed to include 12 restriction sites with lower GC content, so as to increase their usefulness with high GC sequences by increasing the probability of uniqueness of restriction sites.

The terminator sequence from phage T4 was cloned downstream of the MCS and the final expression vector was designated pSETSCexp.

Figure 19:
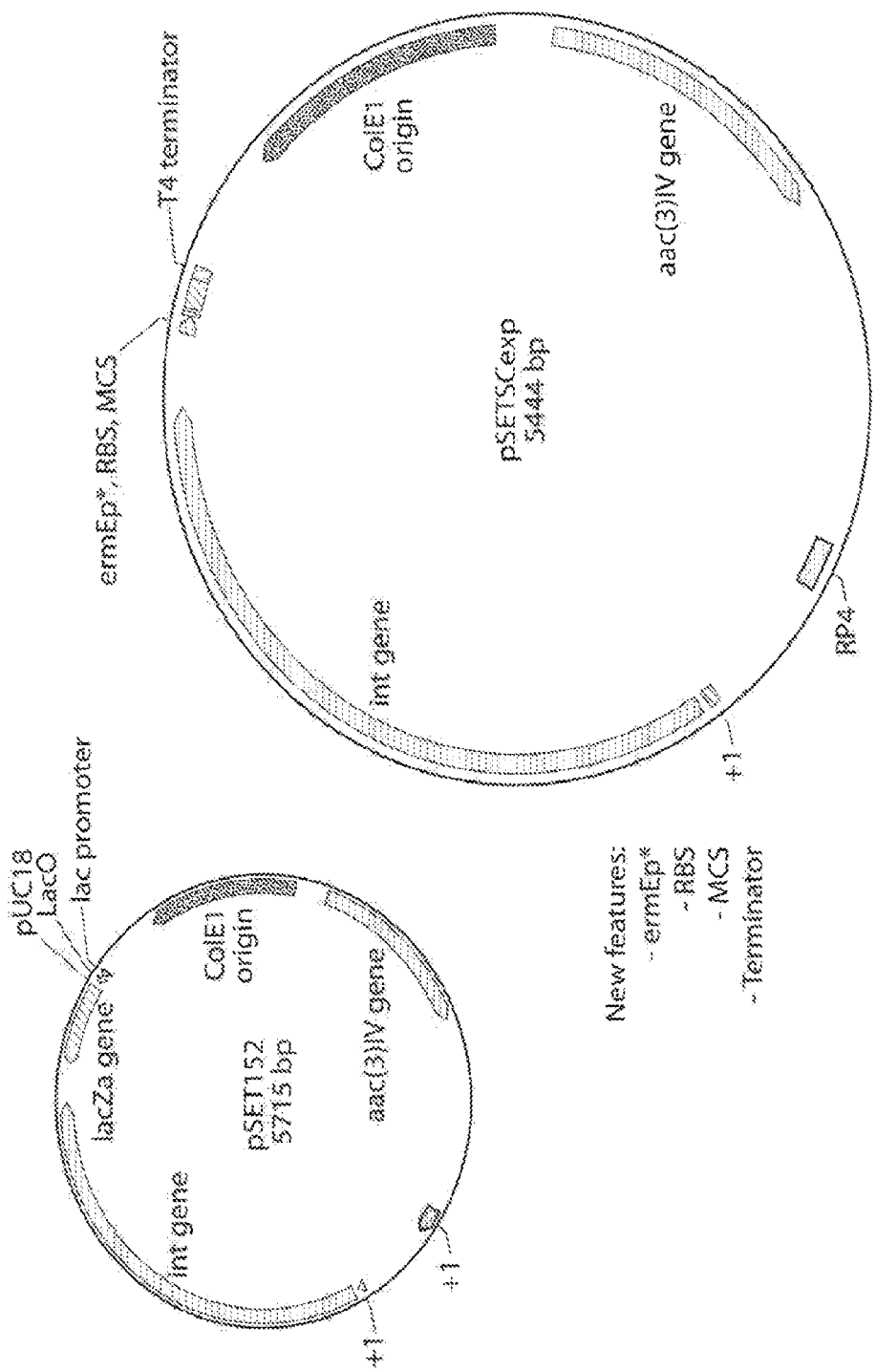
FIG. 19 shows an integrative expression plasmid pSETSCexp, based on pSET152.
Figure 20:
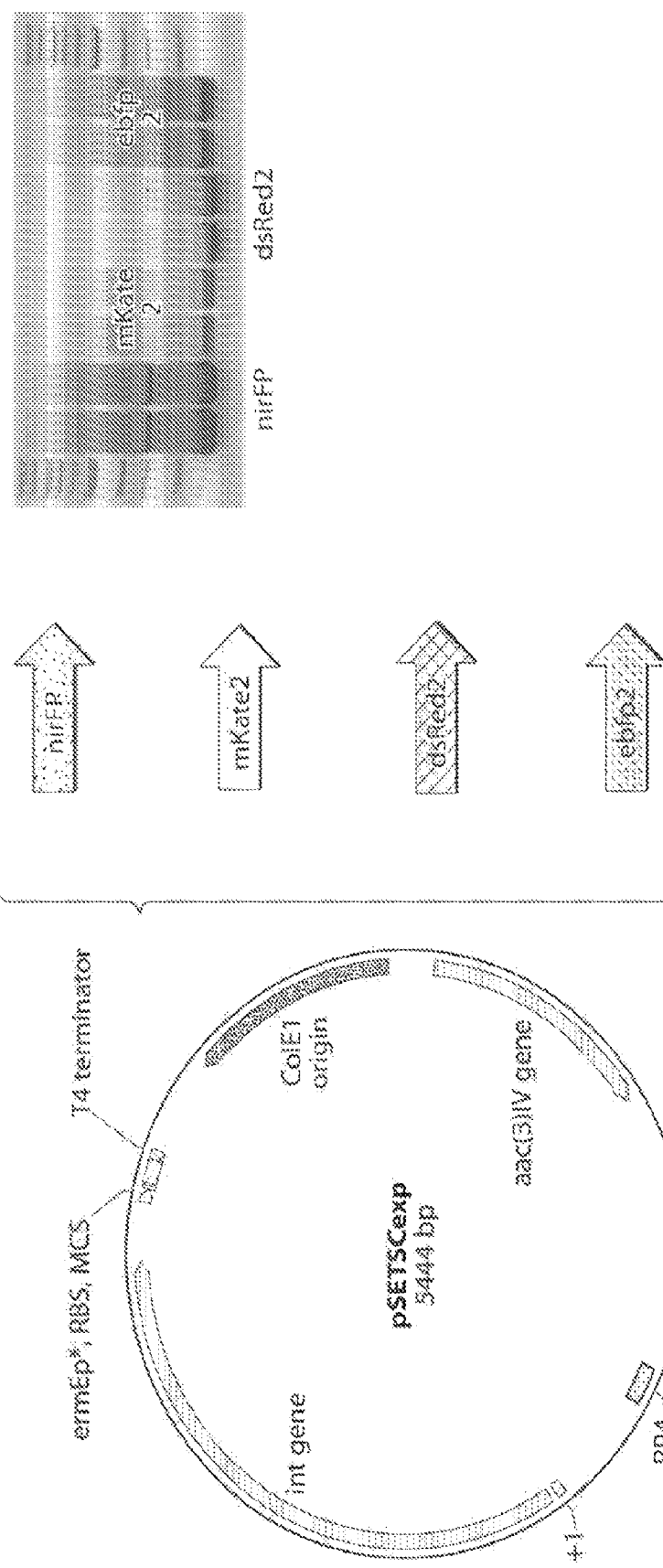
FIG. 20 shows a schematic of the cloning scheme of each of the gene encoding the FPs and respective PCR confirmation.

All for genes coding for the FPs have been successfully cloned into the MCS of pSETSCexp, in the sites BglII and SpeI, as confirmed by PCR (FIG. 19).

These constructs were subsequently moved to E. coli ET12456 pUZ8002 and conjugated into S. venezuelae, as described below.

Nonetheless, upon multiples attempt, no ex-conjugants were obtained. In order to troubleshoot this, different lots of mannitol-soya medium were used. The plates were prepared with soya flour or powder, and 10 or 20 mM of $MgCl_2$ was used. The E. coli cells carrying the constructs were also grown to initial, mid or late exponential phase, for conjugation.

Figure 30:
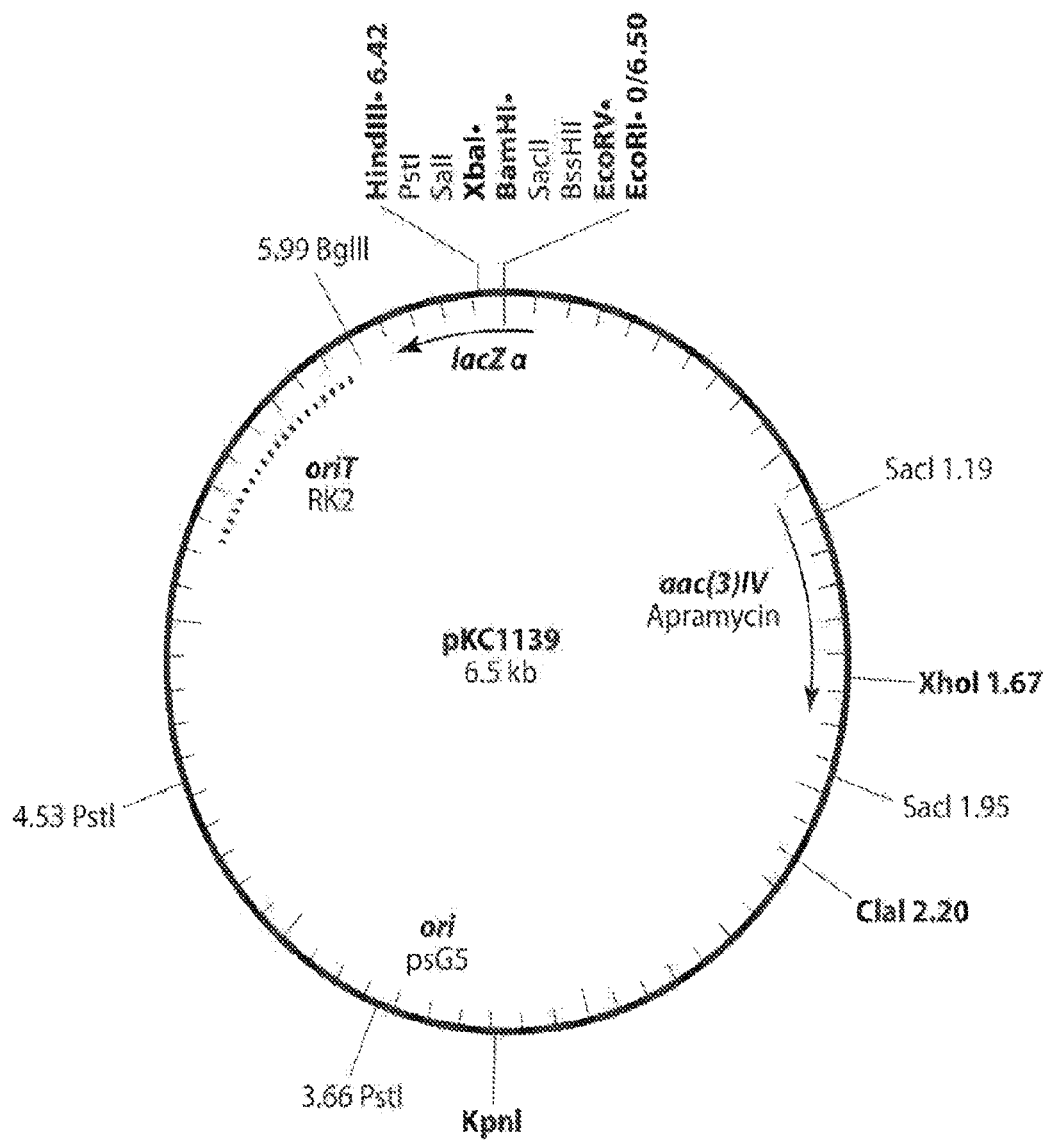
FIG. 30 shows a map of the pKC1139 plasmid. New versions of this plasmid, with a hygromycin and then with a gentamycin cassette were built to deliver rci and tsr to the *Streptomyces* spp.

Upon 8 attempts, no ex-conjugants were obtained, whereas the plasmid pSET-GusA used as control was very successfully integrated. It is believed that the levels of expression of the FPs, driven by ermEp*, were too high and thus toxic to S. venezuelae (FIG. 30).

Therefore, it was decided to rebuild these plasmids where the promoter driving expression is weaker. Promoter C4 6 was selected and ordered as a gBlock (IDTDNA) exactly as done for the pSETSCexp vector. The approach to cloning of this gBlock and genes coding for the several FPs was the exact same as for pSETSCexp. This new low-expression vector was designated pSETSCexp-low and or pSETSCexp-lowX, depending on the gene cloned in.

Obtaining the 5, 10, and 15 kb Amplicons

Upon selection of S. coelicolor and the loci for amplification, PCR was performed. Given the knowledge gathered from the previous high GC PCR experiments, the first polymerase used was KOD Hot Start Polymerase, without any additives. This allowed for the amplification of three of the four 5 kbp amplicons, and one of the 10 kbp. None of the 15 kbps amplicons were obtained.

Following this, Herculase II with and without additives, KOD with 8% DMSO and $MgCl_2$, as well as Kapa Hifi were tested. None of the PCR reactions were successful. The PCR reactions were then further modified, as 8% betaine or DMSO, and/or 8% $MgCl_2$, were used as additives for KOD-based PCRs. The remaining 5 kbp amplicon was obtained when using 8% DMSO, but no other amplicons were obtained.

Next, the same protocol was used for Herculase II, which resulted in the successful amplification of an additional 10 kbp amplicon, but no additional amplicons.

At this point, it was decided to follow a different strategy. Given that there were no real requirements in terms of amplicon boundaries, new primers were designed to the same overall locus, but with primers annealing slightly further up or downstream of the initial sites.

Following this approach the remaining 5 and 10 kb amplicons were successfully obtained. Nonetheless, only a single 15 kb piece was amplified.

Another new approach is in the process of being implemented, where the 15 kb pieces of S. coelicolor DNA are obtained by digestion of cosmids carrying its complete genome. The pieces will then be obtained by restriction digest of the cosmids. The homology required for yeast assembly will be provided by overhangs added by PCR to the 4 genes coding for the FPs.

Construction of a YAC-E. coli-Streptomyces Integrative Shuttle Vector

Figure 21:
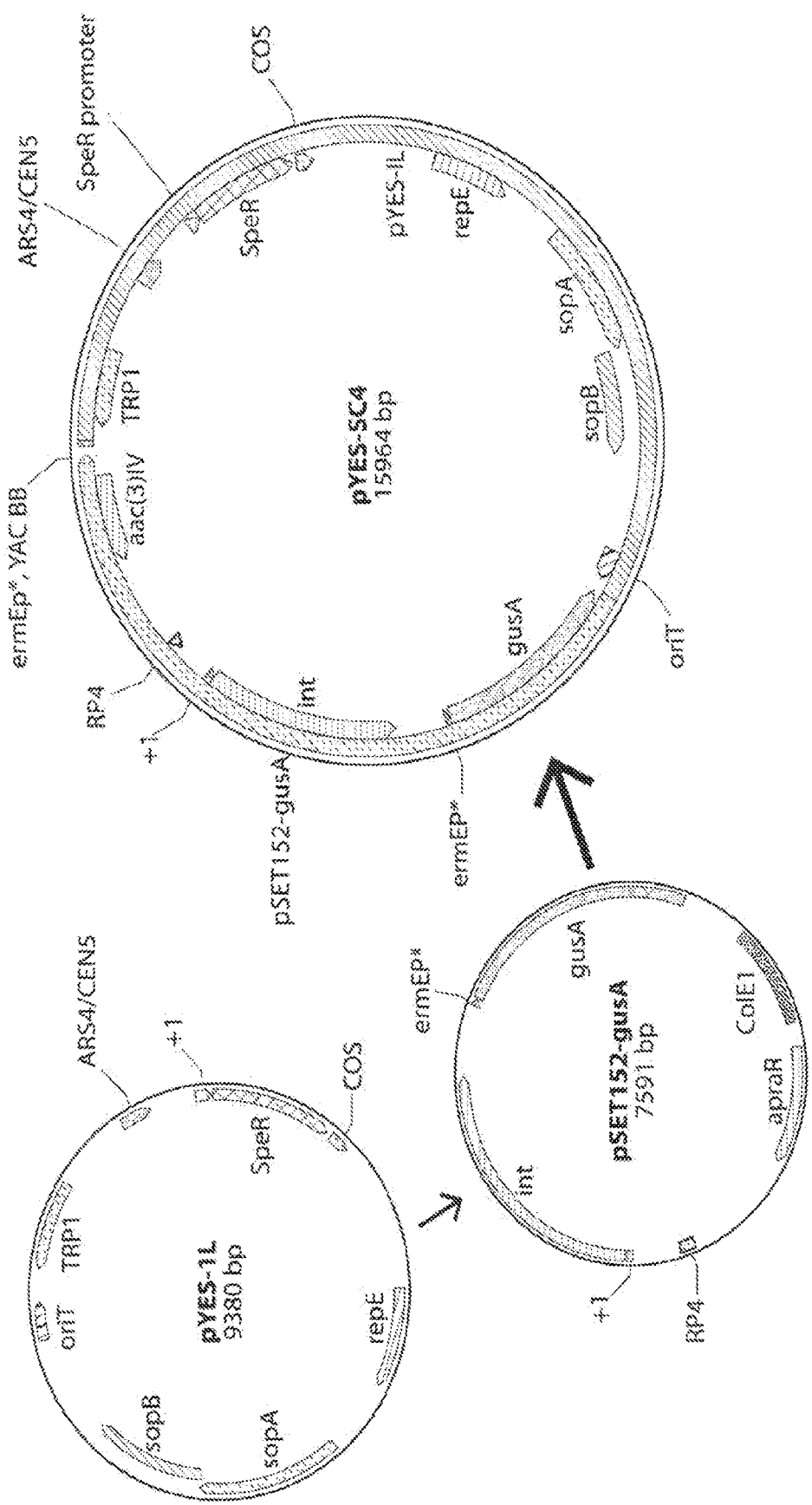
FIG. 21 shows construction of a YAC-*E. coli-Streptomyces* integrative vector.

For the 4-FPs shufflon pathway, the ultimate goal was to integrate it into the chromosome of S. venezuelae. This would enable a comparable circumstance to when integrating the antimicrobial shufflon pathway. Given that the 4-FPs pathway was to be assembled in yeast, it made sense to build a YAC that would also enable the integration of the pathway into S. venezuelae. As such, the near totality of pSET152-gusA plasmid was PCR-amplified. Its E. coli oriR was its only portion not amplified, as it pYES-1L already contained one. The primers also added overhangs to the amplicon, for recombination with pYES-1L in yeast. A gBlock containing ermEp* and further linking the two vectors were also used (FIG. 21).

Upon assembly in yeast the construct was colony-PCRed, for confirming proper assembly, and moved to E. coli, as previously described. This vector can be linearized by digestion with the restriction enzyme PmeI.

Building a Vector Carrying Rci and tsR

Previously, a temperature sensitive vector carrying rci—pKCSC6—was assembled. tsR was not cloned in this same vector. Nonetheless, the new shufflon 4-FPs systems did not carry either of these genes. As such, a new version of pKC1139 was designed to include both rci and tsR. The selection marker was switched from apramycin to hygromycin. In the case of pKCSC5 this was mandatory, as pYes-SC4 is a C31/attP integrative plasmid carrying that same marker.

rci and tsR were cloned in the HindIII and XbaI unique restriction sites of pKC1139, in a three-way ligation where both inserts shared the KpnI restriction site. The hygromycin selection marker was cloned into the XhoI site, disrupting the Apramycin resistance cassette.

Assessing the Presence of Rci Recognition Sites in the Chromosome of S. venezuelae Another concern was that, given the small size of the Rci recognition sites (20 bp), the S. venezuelae chromosome might contain regions that Rci could interpret as being recognition sites.

Figure 22:
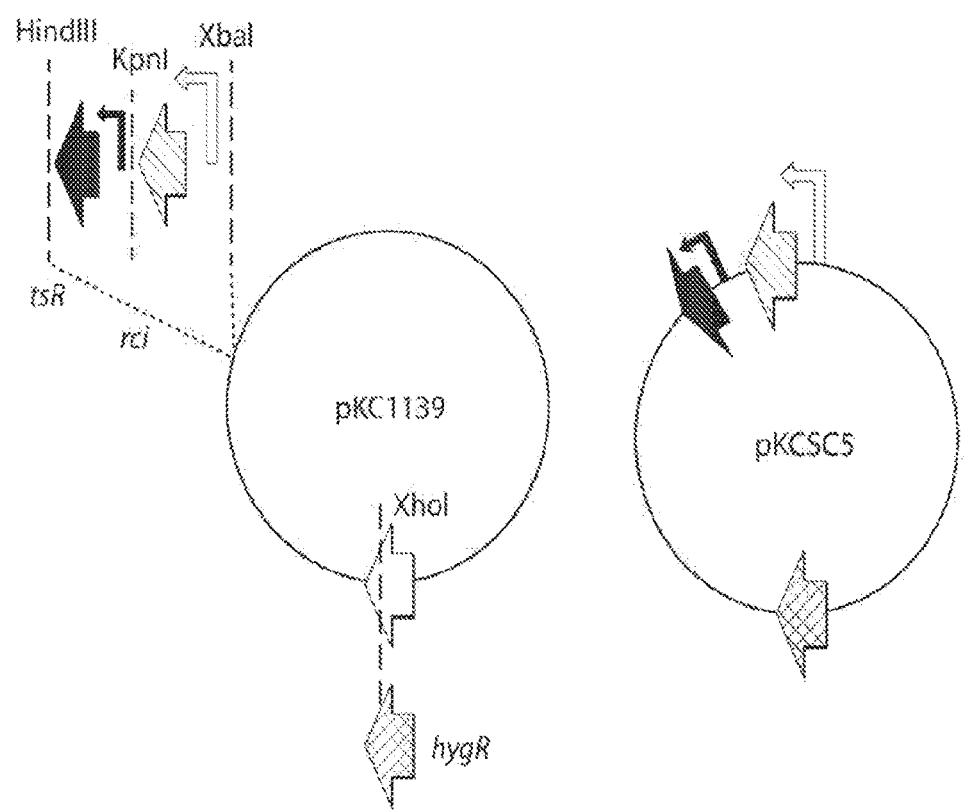
FIG. 22 shows construction of a temperature sensitive plasmid carrying tsR, rci and an hygromycin-resistance cassette.

Using NCBI Blast, its whole genome was scanned for such sequences. No full homology was found The closest homology was 12 bp without any mismatches, and there was a single case of 18 bp with one mismatch, which corresponded to a siderophore biosynthetic gene (FIG. 22).

Nonetheless, this was performed for *S. venezuelae* ATCC 10712, not ATCC 15439 (DSM 41110)—the target organism. Only ATCC 10712 has been fully sequenced.

Testing the DNA Flipping Abilities or Rci, in *E. coli*

Two independent constructs were inoculated overnight without thiostrepton (50 μg/mL), the inducer. The cultures were then reinoculated with and without thiostrepton until the exponential phase was reached. At this point they were reinoculated with and without thiostrepton once again, and grown overnight. Twenty-five milliliters of culture were then midiprepped and the DNA was used as template for qPCR (Kapa SYBR Fast qPCR Master Mix) and regular PCR (Herculase II).

Primers were designed to anneal to the 3' or 5' of each gene, having all possible combinations of primer sets been used (FIG. 23). Primers were also designed to the middle of each gene to be flipped, to serve as reference for gene abundance. The amplicons were 100-150 bp long.

The flipping observed is listed in FIG. 23. It was particularly high for the recognition sequence b, which flipped ca. 6 kbp, and lowest for the recognition sequence c, which flipped ca. 5.5 kbp (FIG. 23). This differed from that reported previously[7], tested in the original shufflon system (plasmid R64) with ca. 250 bp between recognition sequences. Reports of flipping frequencies vary among studies[7-10].

Materials and Methods

TABLE 17

List of strains used in this study

| Species | Strain | Temperature (C.) | Medium | Source |
|---|---|---|---|---|
| S. venezuelae | DSM 41110 | 30 | ISP2 | DSMZ |
| S. coelicolor | A3(2) | 30 | ISP2 | USDA |
| E. coli | MG1655 | 37 | LB | Lab collection |
| E. coli | ET12567 | 37 | LB + Chloramphenicol 34 μg/mL | Lab collection |
| E. coli | Top10 | 37 | LB | Geneart ™ |

TABLE 18

List of plasmids sourced from other labs, used in this study

| Plasmid | Features | Selection | Strain | Source |
|---|---|---|---|---|
| pUZ8002 | DNA transfer machinery | Kanamycin | Replicative in *E. coli* | 14 |
| pSET152 | *Streptomyces* integrative plasmid (attB) | Apramycin | Integrative in *Streptomyces* spp., replicative in *E. coli* | 3 |
| pKC1139 | Shuttle vector with temperature-sensitive *Streptomyces* oriR | Apramycin | Replicative in *E. coli* and *Streptomyces* spp. | 3 |
| pIJ10700 | | Hygromycin | Replicative in *E. coli* | S. O'Rourke (unpublished) |

TABLE 19

List of plasmids built for this study

| Plasmid | Features | Selection | Strain | Source |
|---|---|---|---|---|
| pSET-gusA | pSET152 carrying gusA | Apramycin | Replicative in *E. coli*; integrative in *Streptomyces* spp. | This study |
| pSETSC3 | pSETSC2 carrying the gusA reporter | Apramycin | Replicative in *E. coli*; integrative in *Streptomyces* spp. | This study |
| pSETSC3-Shufflon | pSETSC3 carrying insert 1 and 2 | Apramycin | Replicative in *E. coli*; integrative in *Streptomyces* spp. | This study |
| pYES1L-insert1 | pYES1L carrying insert 1 | Spectinomycin Tryptophan | Replicative in *S. cerevisiae* and *E. coli* | This study |
| pYES1L-insert2 | pYES1L carrying insert 2 | Spectinomycin Tryptophan | Replicative in *S. cerevisiae* and *E. coli* | This study |
| pYES1L-insert3 | pYES1L carrying insert 3 | Spectinomycin Tryptophan | Replicative in *S. cerevisiae* and *E. coli* | This study |
| pYES-SC4 | pYES1L carrying part of pSET-gusA | Apramycin Spectinomycin Tryptophan | Replicative in *S. cerevisiae* and *E. coli*, integrative in *Streptomyces* spp. | This study |
| pKC1139-rci | pKC1139 carrying rci | Apramycin | Replicative in *E. coli* and *Streptomyces* spp. | This study |
| pKC1139-rci-tsr | pKC1139 carrying rci and tsR | Apramycin | Replicative in *E. coli* and *Streptomyces* spp. | This study |

TABLE 19-continued

List of plasmids built for this study

| Plasmid | Features | Selection | Strain | Source |
|---|---|---|---|---|
| pKC-SC5 | pKC1139 carrying rci and tsr | Hygromycin | Replicative in E. coli and Streptomyces spp. | This study |
| pKC-SC6 | pKC1139 carrying rci | Hygromycin | Replicative in E. coli and Streptomyces spp. | This study |
| pSETSCexp | pSET152 carrying the ermEp* promoter, a MCS and terminator | Apramycin | Replicative in E. coli; integrative in Streptomyces spp | This study |
| pSETSCexp-mKate2 | Expresses mKate2 | Apramycin | Replicative in E. coli; integrative in Streptomyces spp | This study |
| pSETSCexp-nirFP | Expresses nirFP | Apramycin | Replicative in E. coli; integrative in Streptomyces spp | This study |
| pSETSCexp-dsRed2 | Expresses dsRed2 | Apramycin | Replicative in E. coli; integrative in Streptomyces spp | This study |
| pSETSCexp-ebfp2 | Expresses ebfp2 | Apramycin | Replicative in E. coli; integrative in Streptomyces spp | This study |
| pYES-SC4-1 | 1 kbp - 4 FP system | Apramycin Spectinomycin Tryptophan | Replicative in E. coli and yeast; integrative in Streptomyces spp. | This study |
| pYES-SC4-5 | 5 kbp - 4 FP system | Apramycin Spectinomycin Tryptophan | Replicative in E. coli and yeast; integrative in Streptomyces spp. | This study |
| pYES-SC4-10 | 10 kbp - 4 FP system | Apramycin Spectinomycin Tryptophan | Replicative in E. coli and yeast; integrative in Streptomyces spp. | This study |

Media Recipes

MS agar was created from 20 g/L agar, 20 g/L mannitol, 20 g/L soya flour, and 1 L tap water. It was then autoclaved twice for 15 minutes at 115 C.

2×YT broth was created from 16 g/L tryptone, 1-g/L yeast extract, 5 g/L NaCl, and 1 L deionized water, followed by autoclaving for 20 minutes at 121 C.

References for Example 2

1. Myronovskyi, M., Welle, E., Fedorenko, V. & Luzhetskyy, A. Beta-glucuronidase as a sensitive and versatile reporter in actinomycetes. Appl. Environ. Microbiol. 77, 5370-83 (2011).
2. Gibson, D. G. et al. Enzymatic assembly of DNA molecules up to several hundred kilobases. Nat Meth 6, 343-345 (2009).
3. Bierman, M. et al. Plasmid cloning vectors for the conjugal transfer of DNA from Escherichia coli to Streptomyces spp. Gene 116, 43-49 (1992).
4. Sun, J., Kelemen, G. H., Fernández-Abalos, J. M. & Bibb, M. J. Green fluorescent protein as a reporter for spatial and temporal gene expression in Streptomyces coelicolor A3(2). Microbiology 145 (Pt 9, 2221-7 (1999).
5. Nguyen, K. D., Au-Young, S. H. & Nodwell, J. R. Monomeric red fluorescent protein as a reporter for macromolecular localization in Streptomyces coelicolor. Plasmid 58, 167-173 (2007).
6. Siegl, T., Tokovenko, B., Myronovskyi, M. & Luzhetskyy, A. Design, construction and characterisation of a synthetic promoter library for fine-tuned gene expression in actinomycetes. Metab. Eng. 19, 98-106 (2013).
7. Gyohda, A., Funayama, N. & Komano, T. Analysis of DNA inversions in the shufflon of plasmid R64. J. Bacteriol. 179, 1867-1871 (1997).
8. Gyohda, A., Zhu, S., Furuya, N. & Komano, T. Asymmetry of shufflon-specific recombination sites in plasmid R64 inhibits recombination between direct sfx sequences. J. Biol. Chem. 281, 20772-9 (2006).
9. Gyohda, A. & Komano, T. Purification and Characterization of the R64 Purification and Characterization of the R64 shufflon-Specific Recombinase. 182, (2000).
10. Gyohda, A., Furuya, N., Kogure, N. & Komano, T. Sequence-specific and non-specific binding of the Rci protein to the asymmetric recombination sites of the R64 shufflon. J. Mol. Biol. 318, 975-83 (2002).
11. Warth, L., Haug, I. & Altenbuchner, J. Characterization of the tyrosine recombinase MrpA encoded by the Streptomyces coelicolor A3(2) plasmid SCP2*. Arch. Microbiol. 193, 187-200 (2011).
12. Fedoryshyn, M., Welle, E., Bechthold, A. & Luzhetskyy, A. Functional expression of the Cre recombinase in actinomycetes. Appl. Microbiol. Biotechnol. 78, 1065-1070 (2008).
13. Herrmann, S. et al. Site-specific recombination strategies for engineering actinomycete. Appl. Environ. Microbiol. 78, 1804-1812 (2012).
14. Kieser, T., Bibb, M. J., Buttner, M. J., Chater, K. F. & Hopwood, D. A. Practical streptomyces genetics. (John Innes Foundation, 2000).

Example 3

Testing the PFs in *S. venezuelae*

The selection and cloning of the new, codon-optimized genes encoding fluorescent proteins (FPs) was explained in Example 2. It was also explained that no exconjugants were obtained after over 8 attempts of conjugating the pSETSC-exp plasmids carrying each of the FPs into *S. venezuelae*.

Possible causes for this phenotype include: toxicity associated with the overexpression of the FPs, mutation in the resistance cassette, which impedes selection, and mutation in the int gene, resulting in nonfunctional recombinase for integration of pSETSCexp into the attB site.

Initially, it was decided to build a lower-expression vector, but upon further Discussion, the pSETSCexp plasmids were rebuilt. Each FP, preceded by the ermEp* promoter and an RBS and followed by a terminator, was PCR-amplified. The plasmid backbone was obtained by PCR, for assembly with each FP amplicon by Isothermal Assembly[1]. Upon assembly, the mixture was transformed into *E. coli* DHSα.

Upon confirmation of proper assembly, transformation into *E. coli* ET12456 pUZ8002 and conjugation into *S. venezuelae*, exconjugants were successfully obtained. It was thus concluded that the previous failure to obtain exconjugants resided on the integration machinery within the plasmid.

Each of the strains carrying individual FPs was grown in Tryptic Soy Broth supplemented with apramycin and incubated at 30 C and for a period of up to 96 hours. To prevent clumping, a sterile stainless steel spring (Ace Glass Incorporated, USA) was added to each culture.

Aliquots of all cultures were taken after overnight growth and at 24, 72 and 96 hours, for analysis by Fluorescence Assisted Cell Sorting (FACS). The aliquots were diluted 1:10 (overnight and 24 hours) or 1:100 (72 and 96 hours) in Phosphate Buffered Saline (pH=7) and ran in a BDFACS LSR Fortessa cell analyzer (BO Biosciences, CA). For each sample, 50,000 cells were analyzed and gated using a forward scatter and side scatter.

After overnight and 24 hours of growth, no fluorescence was observed. The cultures were allowed to grow for a total period of 4 days. Aliquots were taken daily and analyzed through FACS. New and daily re-inoculated cultures were also ran, and a slight part of the population started fluorescing after the third day of incubation. Nonetheless, this represented less than 0.5% of the total population, which for this purpose does not suffice.

*E. coli*'s transcriptional machinery recognizes the ermEp* promoter used to drive the expression of the genes encoding the fluorescent proteins. As no fluorescence was observed when the genes were expressed in *S. venezuelae*, it was decided to check whether they were in *E. coli*. Again, no any fluorescence was detected by FACS. This suggests that the problem might reside in the genes themselves, codon-optimized for *S. venezuelae* but also expressible in *E. coli*. The issue could potentially be misfolding.

To assess the flipping abilities of Rci, it is imperative that, upon flipping, the transcribed fluorescent proteins glow, otherwise the flipping events will not be registered or recognized. As such, it was decided to determine the flipping events by qPCR.

Figure 24:
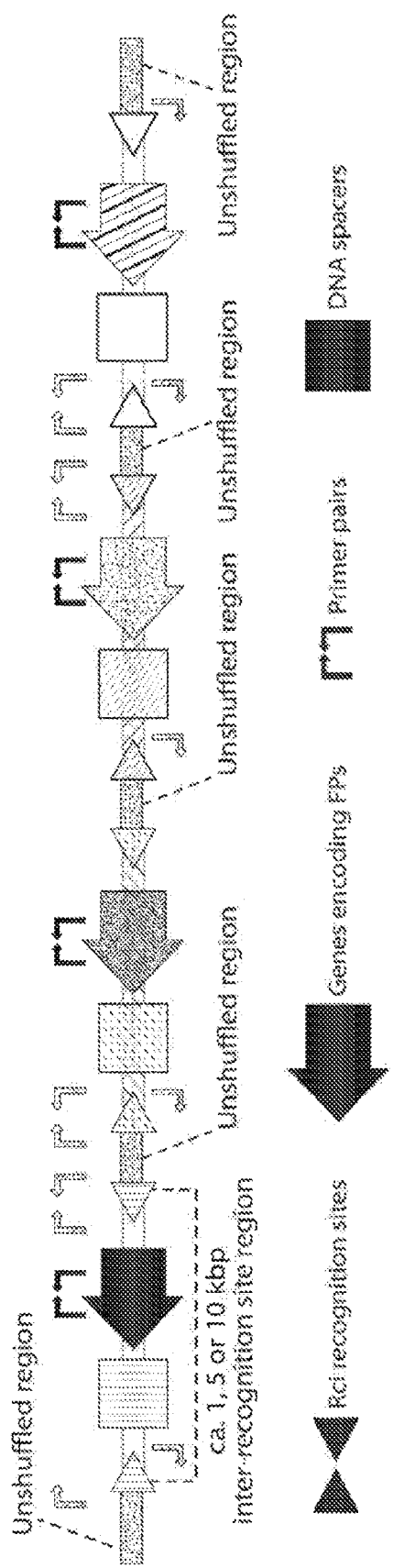
FIG. 24 is a schematic of the primer design for determination of flipping events by qPCR.

In order to detect the flipping events by qPCR, several primers were designed, as illustrated (FIG. 24). The design of the primers enabled the use of a single set of primers for each of the shuffling regions, independent of the size of the sequence to be shuffled (1, 5 or 10 kbp). Nonetheless, several sets of primers were designed and used to properly calculate the inversion events by qPCR. These sets included primers to standardize for DNA amount and DNA replication efficiency.

Assembly of the 5 and the 10 Kbp Amplicons

Figure 25:
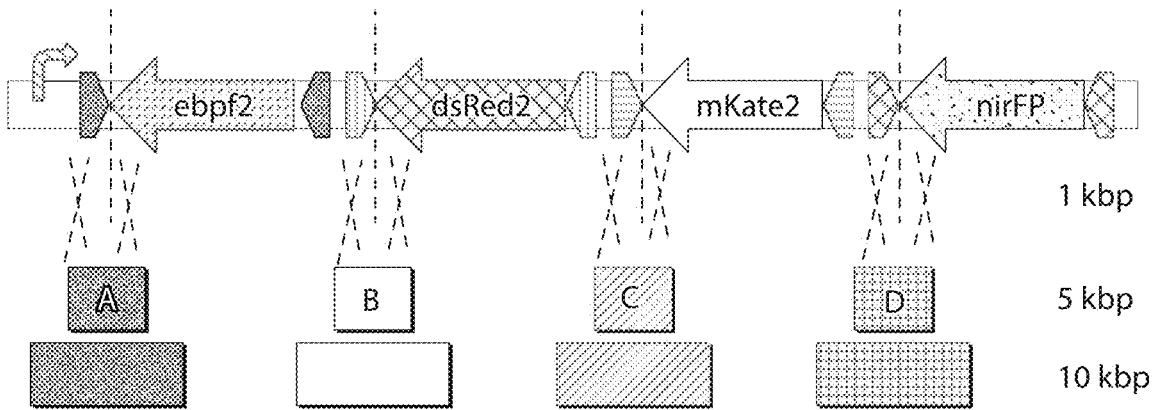
FIG. 25 shows shuffling systems to test the RCI flipping efficiency with increased inter-recognition sites distance. Systems with 1, 5 and 10 kbp between each pair of recognition sites.

For the purpose of testing the flipping efficiency of Rci, it was decided to proceed only with the 1, 5 and 10 kbp inter-recognition sites assemblies (FIG. 25). On the basis of this decision lies the fact that, in the antibiotic-shufflon system, only one gene is over 6 kbp, and the technical impracticability of manipulating such large constructs—the total size would be above 75 kbp—and the conjugation issues arising thereof.

Initially, the 5 and 10 kbp 4-FP constructs—of 9 pieces each—were tentatively assembled in yeast. Upon two failed attempts, it was decided to subdivide the process into 2 steps, which would reduce the number of pieces to assemble per reaction to 5 from 9.

Facing failed attempts again, the suspicion of the failed assembly fell on the YAC-*E. coli*-*Streptomyces* integrative shuttle vector built for this purpose. A possible explanation is its low stability in yeast due to the great capacity of this organism to recombine DNA.

Thus, it was decided to assemble these pathways in the traditional pYES-1L YAC, in one step and in two steps. Three new amplicons were obtained due to homology to the YAC backbone at the 5' and 3': 5 kbp amplicon A, 10 kbp amplicon A, dsRed2 amplicon (now the 3' of the 2-step insert).

These amplicons were obtained via PCR with KOD (5 and 10 kbp pieces) or Hifi (dsRed2) polymerase without additives. These pieces were then combined in the following mixtures: pYes-1L, 5 or 10 kbp A amplicon, 5 or 10 kbp B amplicon, ebfp2, and dsRed2 (with homology to pYes-1L).

Figure 26:
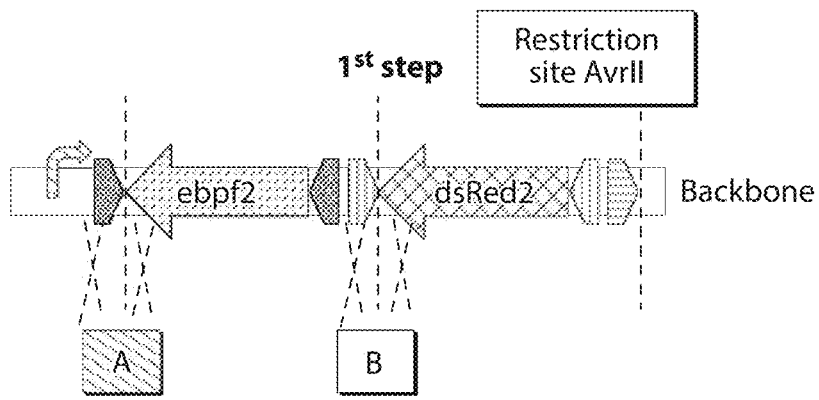
FIG. 26 shows the first step of the 2-step approach to assembling the shuffling systems.

Transformants were recovered and the YACs were moved into *E. coli*. Upon confirmation of proper assembly, they were digested with PmeI following the insert directions. This constituted the first step in the assembly process (FIG. 26). Once digested, this YAC constituted the backbone for the second step in the assembly.

Figure 27:
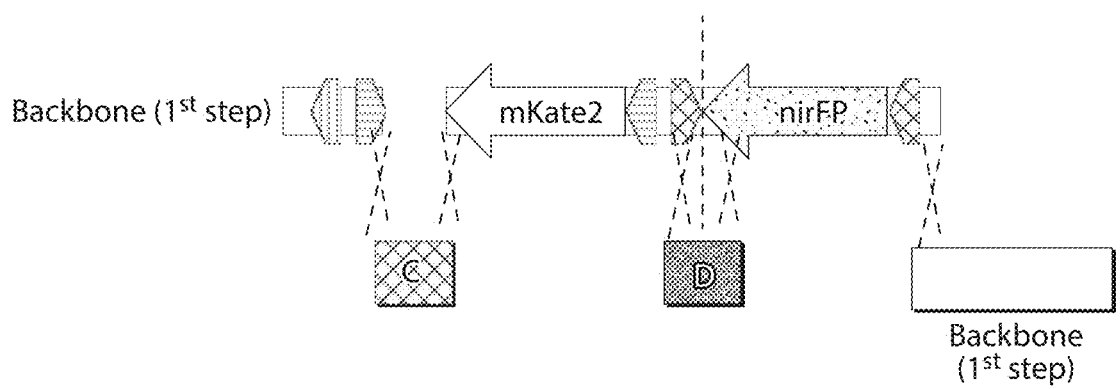
FIG. 27 is a schematic of the first step of the 2-step assembly of the 4-FP shuffling system.

The second step combined the following parts (FIG. 27): pYes-lst_step, 5 or 10 kbp C amplicon, 5 or 10 kbp D amplicon, mKate, and nirFP (with homology to pYes-1 L).

Colonies was checked for proper assembly of the whole construct. The yeast-based assembly was explained above.

The YACs obtained after this second step were move into *E. coli* and the culture was miniprepped using a kit specific for the purification of large-sized plasmids (ZRBAC DNA Miniprep Kit, Zymo Research).

The insert was designed to be popped out with the restriction enzymes Eco RV and Bsu361, both predicted to be unique cutters. Nonetheless, it was found that there were errors/differences in the *S. coelicolor* A3(2) sequence deposited in the NCBI database, which resulted in the insert being cut into additional fragments. This is known to happen with sequences obtained from NCBI, as they correspond to the sequencing of a specific organism that might have accumulated differences from the one in use. Another issue is potential sequencing errors when elucidating the genomic makeup of this organism.

Upon digestion with each of the enzymes, it was found that the additional restriction sites corresponded to the recognition sites of Eco RV. This blunt end cutter was then replaced with Bsu361, which cuts in the YAC backbone and originated a sticky end.

In order to clone the insert into the blunt-end site of PmeI, in the recipient backbone, the sticky-ends of the 5 and 10 kbp inserts were first blunted using Quick Blunt Enzyme Mix (NEB). The total size of the final vectors was ca. 30 kbp for the 5-kbp 4-FP shufflon system and 50 kbp for the 10 kbp one.

Figure 28:
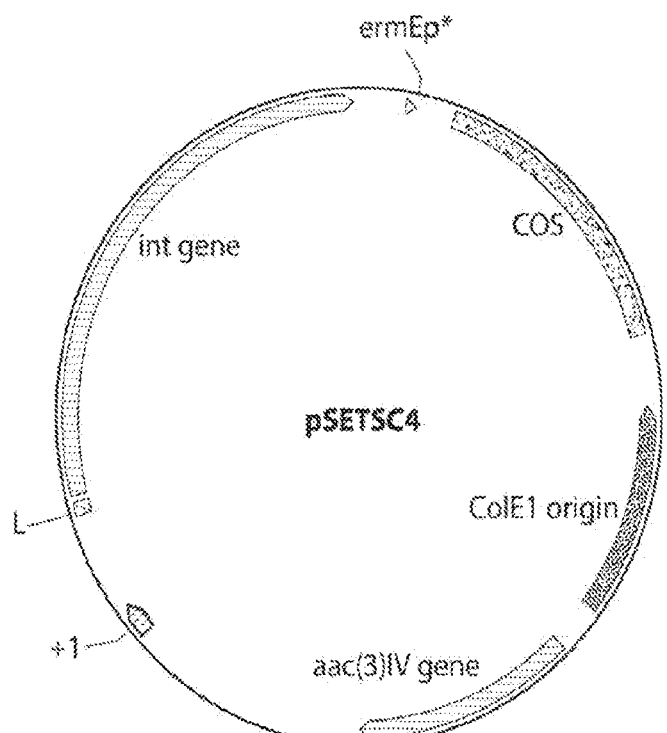
FIG. 28 shows a plasmid for the integration of the large-size FP shuffling systems in *Streptomyces* spp.

Construction of an *E coli-Streptomyces* Integrative Shuttle Vector, pSET-SC4, for the 4-FP Assemblies This vector was designed to replace the YAC-*E. coli-Streptomyces* integrative shuttle vector. It consisted of the pSET152 backbone (FIG. 28) to which a cos site, and the ermEp* promoter followed by recognition sequence a and the PmeI restriction site were added.

The promoter, recognition sequence, and restriction site were ordered as a gBlock from IDTDNA Corp and the cos site was obtained via PCR from pWEB-TNC using KAPA Hifi polymerase (no additives).

The 4-FP pathways were then cloned into this plasmid in the PmeI site and checked clones for the correct orientation.

Successful cloning in the proper orientation was achieved for the 10-kbp shuffling, but not for the 5-kbp one. It was then decided to assemble the insert into the backbone by Isothermal Assembly. For this, the backbone was PCR-amplified with primers with an overhang that matched the 5' (reverse primer) or 3' (forward primer) of the insert. Upon transformation into *E. coli* 10B and PCR screening, colonies carrying the right construct were found.

The 1, 5 and 10 kbp shuffling constructs were transformed into *E. coli* ET12456 pUZ8002 and conjugated into *S. venezuelae*. Exconjugants were successfully obtained and restreaked for purity.

Transforming Rci and tsR into the *S. venezuelae* Strains

Now that the integration of the multiple pathways in *S. venezuelae* was successful, the genes encoding the recombinase and the thiostrepton resistance had to be conjugated into the several strains.

Spores of *S. venezuelae* attB::pSET-SC4-1 kbp, −5 kbp and −10 kbp were used for conjugation with *E. coli* ET12456 pUZ8002 carrying pKC-SC5 (HygR). Upon several attempts, no exconjugants were obtained. It was determined that the hygromycin cassette was not a good selection marker in this strain of *S. venezuelae*, with this plasmid backbone. This conclusion was based on the fact that when using a version of pKC-SC5 with apramycin resistance (instead of hygromycin) and selecting for thiostrepton resistance (versus hygromycin resistance), exconjugants were indeed obtained. The selection was performed using thiostrepton (an antibiotic and the inducer of rci expression) and not apramycin because the integrated pSET-SC4-1/5/10 kbp plasmids contained already the apramycin resistance cassette.

Nonetheless, two different plasmids were built concomitantly (FIGS. 29-30), as new tsr and rci expression vectors, with a gentamycin selection marker. One plasmid was pKC1139-rci+tsr (ApraR) where the gentamycin cassette (FIG. 30) was introduced in the single blunt-end cutter NcoI site in the apramycin cassette by T4 DNA-ligase mediated ligation. The ligation was transformed into *E. coli* DH5 α and plated onto LB with 10 μg/mL of gentamycin. Positive clones (pKC-SC7) were moved into the conjugation strain *E. coli* ET12456 pUZ8002.

Figure 29:
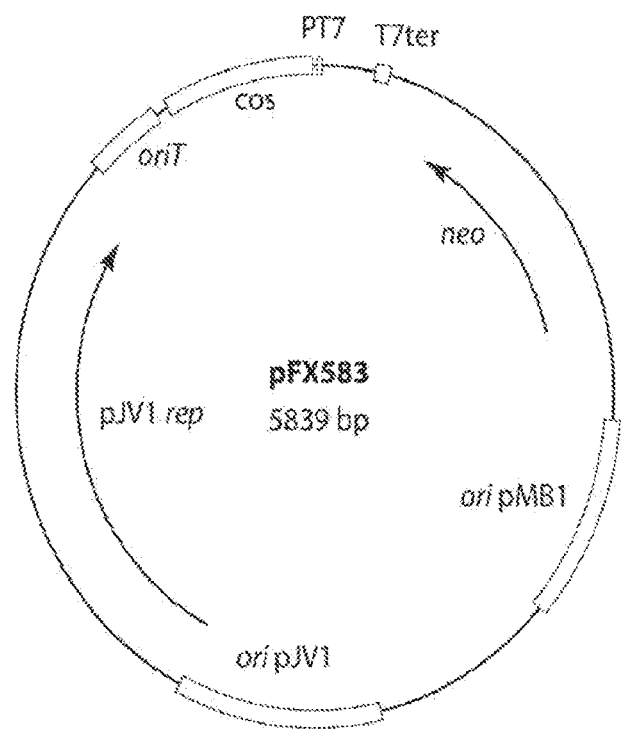
FIG. 29 shows a map of the pFX583 plasmid, a version of which (with a gentamycin cassette instead of neo) was used to deliver the rci and tsr to the *Streptomyces* spp.

Another plasmid also with a replicative origin of replication (but not temperature sensitive) was built (FIG. 29). This plasmid was based on pFX5832 and was generated using a version with gentamycin as selective marker, previously generated for unrelated purposes. An amplicon carrying the tsr and rci genes was PC Red from pKC1139-rci+tsr and the backbone of pFX583-GentR was amplified using primers that added overhangs homologous to the 5' and 3' of the tsr and rci amplicon. The two parts were joined by means of the Isothermal Assembly and transformed into *E. coli* DH5 α. Positive clones (pFX-SC6) were moved into the conjugation strain *E. coli* ET12456 pUZ8002.

The rci and tsr, carried by the appropriate plasmids, were conjugated into the *S. venezuelae* strains carrying the 1, 5 and 10 kbp 4-color shuffling pathways.

Calculation of Rci-Mediated Flipping Frequencies

Given that the expression of the fluorescent proteins in *S. venezuelae* was not successful, as already explained, it was not possible to use them as a method to discriminate and quantify the DNA flipping frequencies, mediated by Rci. Instead, qPCR (KAPA SYBR® FAST Universal 2× qPCR Master Mix) was used in a LightCycler® 96 System (Roche, USA), with the downside that it is not possible to individualize flipping per sequence, ie, in a given sequence (cell) what flipping occurred. Instead, a general picture of the population is obtained.

In order to quantify the DNA inversion frequencies of each recognition site (a, b, c and d) in the whole population, several sets of primers were designed, as explained below. The melting temperature was ca. 60 C and the length 18-20 bp. The amplicon was ca. 100 bp in length.

Primers that amplify the middle region of each FP were used as reference for the relative amount of template, and sets of primers were designed to amplify DNA in the eventuality of an inversion, or lack thereof.

Cultures of *S. venezuelae* attB::pSET-SC4-1 kbp and 10 kbp, with and without Rci were incubated for a period of 3 days, with 2 mL aliquots being taken on a daily basis, for qPCR measurements. A total of 25-50 ng of genomic DNA was used per reaction. The DNA was extracted using the ZR Fungal/Bacterial DNA MiniPrep Kit (Zymo Research) and the flipping rates were calculated as described elsewhere[3] and followed the Livak method[4]. The equations for calculation are shown below and in FIG. 31:

$$\% \text{ Flipped} = 2^{\left(\frac{flipped}{flipped+unflipped}\right)} \times 100$$

This equation incorporates the results obtained when no Rci is present, so that the values shown correspond solely to measurement of interest. There was no flipping when Rci was absent, but there was non-specific binding, which can introduce error in the measurements—thus the values have to be incorporated into the equation.

The values were adjusted for the different DNA replication rates and primer annealing efficiency.

The original publication that describes the recombination ability determined the inversion frequencies as being 29, 0.025, 0.02 and 0.1 for the recognition sequences a, b, c, and d respectively (a>d>b>c). The DNA shuffled in the original context is ca. 400 bp long, representing the 3' end of the pi IV gene in some strains of *E. coli* and *Salmonella* thyphimurium[7].

For the shortest inter-recognition site, of ca. 1 kbp, the highest flipping frequency was found for sequences a, followed by d, c and b (a>d>c>b). This is similar to the relative frequencies observed in the native organisms (a>d>b>c). Nonetheless, opposites results were obtained for the larger, 10 kbp, DNA pieces to be flipped by each pair of sites (Table 20), with b being the sequence that that resulted in the highest inversion rate, followed by c, d and a. These frequencies represent the average percentage of inverted sequences over the 4-day period.

TABLE 20

Percentage of inverted DNA, per pair of recognition sites and intersite distance during the duration of the screening.

| Recognition sequence | Estimated % of flipping |
|---|---|
| a | 1 |
| b | 32 |
| c | 0.09 |
| d | 9.6 |

Looking at each time point specifically, the recognition site a stands out as the overall best performer. The two recognition sites displaying the highest inversion rate were a (1 kbp) and c (10 kbp). The prevalence of a as the most efficient sequences was found also at 90 hours. The sites d were the best performers at 42 hours, while at 66 hours, both a and d performed well (Table 21).

The recognition sites that performed the best at inverting large DNA sequences (10 kpb) varied over the course of the analysis (Table 21), with c being the most efficient one at 18 hours, a at 42, b at 66, and c and d at 90 hours.

TABLE 21

Most efficient recognition sites in terms of percentage of inverted sequences, for each time point.

| | Recognition sequence | | |
|---|---|---|---|
| Sampling time (h) | 1 kbp | 5 kbp | 10 kbp |
| 18 | a | a, d | c |
| 42 | d | a, b | a |
| 66 | a, d | a | b |
| 90 | a | a, b | c, d |

Figure 32:
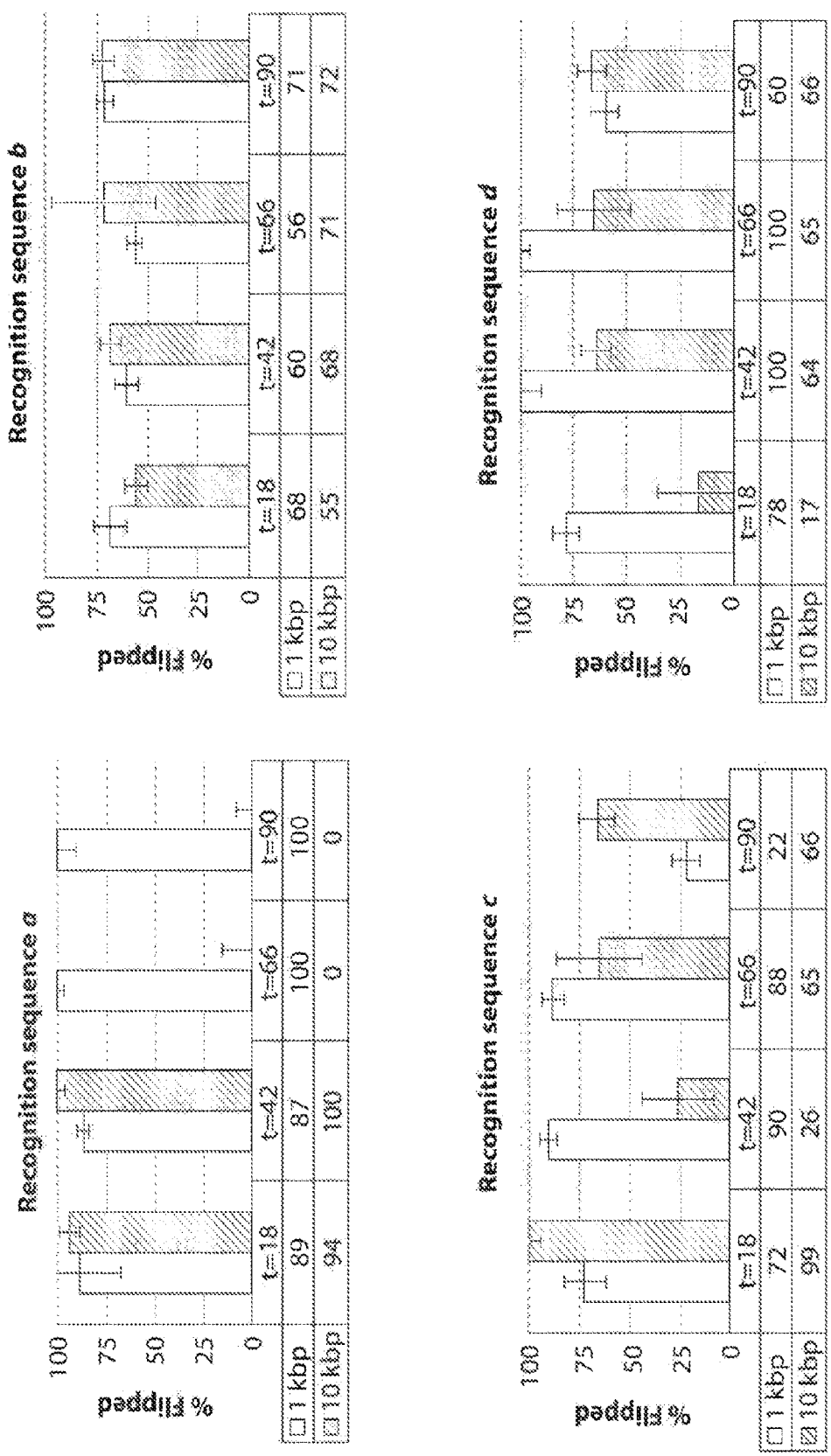
FIG. 32 shows the DNA-inversion efficiency of each pair of recognition sites over time.

In the case of sequence a, the percentage of inverted sequences displayed an opposite trend when comparing the short and the long flipping. The inversion of short, 1 kbp DNA sequences, increased over time, whereas it dramatically decreased for the 10 kbp sequences after 42 hours (FIG. 32).

For recognition sequence b, the 1 kbp inversion events were more frequent in the being and at the end of the experiments, with an inflexion point situated between the 66 and 71 hours.

For both recognition sequences c and d, the same pattern of increased inversion frequency, with a maximum between the 42 and 66 hours, was observed for the short 1 kb sequences. In the particular case of the 10 kbp sequences, the highest inversion frequency of c was detected in the first time point, whereas the performance of Rci on c remained stable at higher values after the first time point (FIG. 32).

As already explained, these values were calculated for the whole population and do not give information on the inversion of a given segment in regards to other, in the same cell.

The possibility of performing digital PCR or qPCR using sequence-specific probes (instead of SYBR-based qPCR), is being considered. In the case of digital PCR, upon multiplexing, the flipping of each sequence in each DNA molecule could be determined. Thus, it would provide the same results as the FACS, with the additional benefit of being independent of the FP expression (required for recognizing the flipping when measure by FACS). The use of probes to perform qPCR would enable a more exact quantification of the flipping events, as in this case it would be independent of the length of the amplicon (which varies by only a few base pairs, but can lead to higher fluorescence levels due to the longer amplicon size).

Integration of the PKS-shufflon system in *S. venezuelae*

The PKS-shufflon system was designed to be integrated into the pikAII gene of the pikromycin pathway in *S. venezuelae*, to delete the vast majority of this gene. For this purpose, the pathway to integration was designed and built to be surrounded by regions of homology towards the chromosomal pikAII. By means of a double crossover event, the synthetic shufflon pathway should be integrated and the plasmid backbone lost. A single crossover event results in the integration of the whole plasmid and the backbone is not lost.

Thus far, seven attempts to conjugate the plasmid into *S. venezuelae* were made but no exconjugants were obtained.

Figure 33:
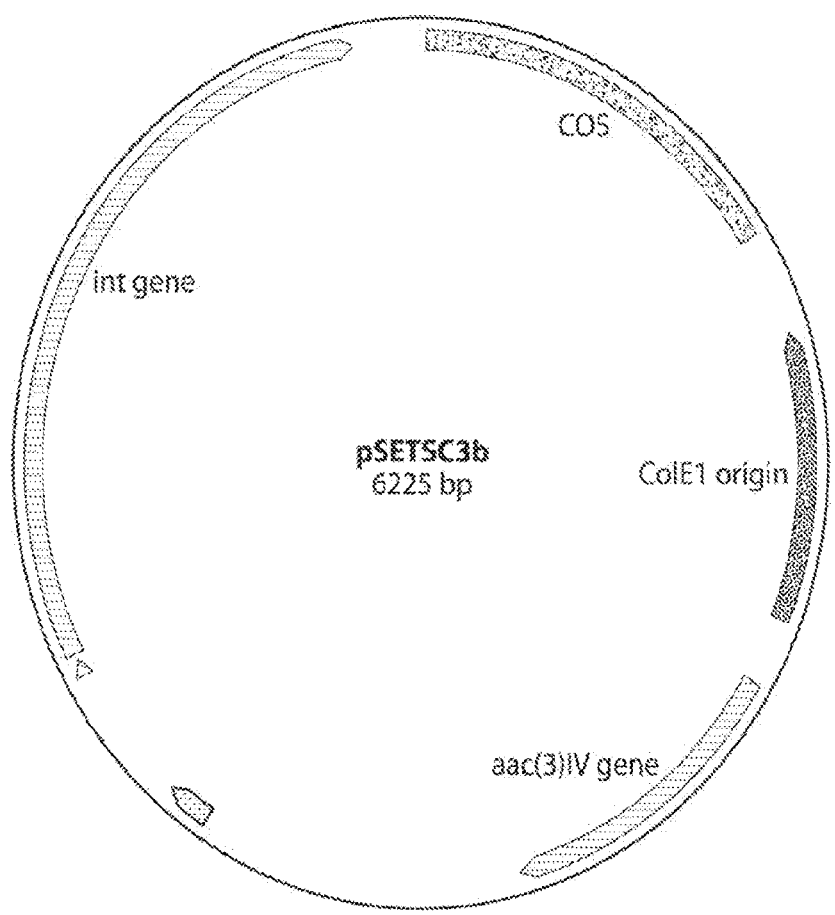
FIG. 33 shows a map of a plasmid built for integration of the PKS-shufflon system in *Streptomyces* spp.

It was suspected that the integration, by single crossover, was very inefficient and thus no exconjugants were being obtained. This led to another backbone being built, for integration in the attB site of *S. venezuelae*. The basis of this vector was pSET152, to which XbaI and Bsu36I restriction sites and a cos site obtained by PCR from pWEB-TNC (FIG. 33) were added by Isothermal Assembly.

Upon PCR-confirmation of the correct three-way assembly (FIG. 33), the new plasmid was obtained in large quantity and linearized using PmeI. To prevent recircularization without insert any insert, the phosphate groups were removed by incubation with the phosphatase CIP (NEB Biolabs).

Figure 34:
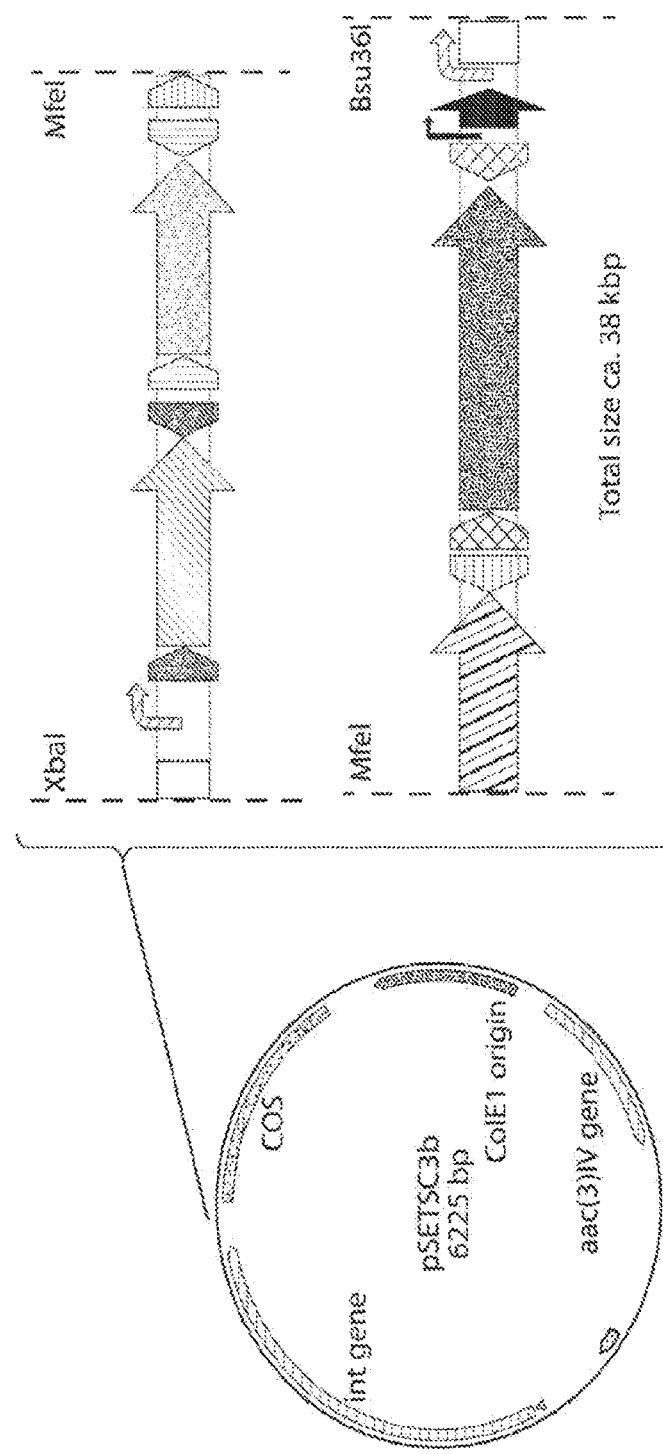
FIG. 34 is a schematic of PKS-shufflon cloning into a backbone.

The 2 parts of the synthetic PKS-shufflon previously obtained (Examples 1-2) were ligated into this vector by means of T4 DNA Polymerase (Example 1). Upon confirmation of proper 3-way assembly (FIG. 34), the plasmid was electroporated into *E. coli* ET12456 pUZ8002 and conjugated into *S. venezuelae*. Nonetheless, upon 4 attempts, no exconjugants were obtained. This indicates that the pathway with multiple heterologous pks genes is indeed functional in *S. venezuelae* and is leading to the assembly of molecules that are toxic for the host organism. It was also briefly considered that the issue might be the size of the plasmid (ca. 43 kbp), but since the integration of the 10 kbp 4-FP shufflon system of ca. 50 kbp was successful, the issue should indeed be the toxicity of the new molecules. This assumption is further supported by the predictive algorithm results for the possible molecules being assembled by the 4 genes cloned in an on position in the PKS-shufflon (Table 22).

TABLE 22

SMILES, structures and activity prediction for molecules being assembled by the genes incorporated in the PKS-shufflon pathway, to be integrated

| Gene combination* | SMILES | Structure | Activity prediction** | |
|---|---|---|---|---|
| 1, 2, 3, 4<br>1, 2, 4<br>1, 3, 4<br>1, 4 | CC=CC(O)CC(O)C(C)C(O)C(C)C(=O)O | (structure shown) | GPCR ligand | 0.28 |
| | | | Ion channel modulator | 0.38 |
| | | | Kinase inhibitor | −0.55 |
| | | | Nuclear receptor ligand | 0.69 |
| | | | Protease inhibitor | 0.18 |
| | | | Enzyme inhibitor | 0.87 |
| 2, 3, 4<br>2, 4 | CC(O)CC(O)C(C)C(O)C(C)C(=O)O | (structure shown) | GPCR ligand | −0.09 |
| | | | Ion channel modulator | 0.13 |
| | | | Kinase inhibitor | −0.76 |
| | | | Nuclear receptor ligand | 0.28 |
| | | | Protease inhibitor | −0.04 |
| | | | Enzyme inhibitor | 0.56 |

*When no molecule is predicted to be assembled, no data is provided
1—momAVI
2—amphK
3—tyl/G
4—momAVIII
**Higher values correspond to higher probabilities of activity (−3 < x~3; x > 0.10 is considered good)

Materials

TABLE 23

List of bacterial strains used and/or developed during this study

| Species | Strain | Temperature (C.) | Medium | Source |
|---|---|---|---|---|
| S. venezuelae | DSM 41110 | 30 | ISP2 | DSMZ |
| E. coli | MG1655 | 37 | LB | Lab collection |
| E. coli | ET12567 | 37 | LB + Chloramphenicol 34 μg/mL | Lab collection |
| E. coli | Top10 | 37 | LB | Geneart ™ |
| E. coli | DH5α | 37 | LB | Lab collection |
| E. coli | 10B | 37 | LB | Lab collection |
| S. venezuelae attB::pSET-SC4-1 kb | DSM 41110 | 30 | ISP2, Apramycin | This study |
| S. venezuelae attB::pSET-SC4-5 kb | DSM 41110 | 30 | ISP2, Apramycin | This study |
| S. venezuelae attB::pSET-SC4-10 kb | DSM 41110 | 30 | ISP2, Apramycin | This study |
| S. venezuelae attB::pSET-SC4-1 kb, pKC1139-rci-tsr | DSM 41110 | 30 | ISP2, Apramycin, Thiostrepton | This study |
| S. venezuelae attB::pSET-SC4-10 kb, pKC1139-rci-tsr | DSM 41110 | 30 | ISP2, Apramycin, Thiostrepton | This study |
| S. venezuelae attB::pSET-SC4-1 kb, pKC-SC7 | DSM 41110 | 30 | ISP2, Apramycin, Thiostrepton, Gentamycin | This study |

TABLE 23-continued

List of bacterial strains used and/or developed during this study

| Species | Strain | Temperature (C.) | Medium | Source |
| --- | --- | --- | --- | --- |
| S. venezuelae attB::pSET-SC4-5 kb, pKC-SC7 | DSM 41110 | 30 | ISP2, Apramycin, Thiostrepton, Gentamycin | This study |
| S. venezuelae attB::pSET-SC4-10 kb, pKC-SC7 | DSM 41110 | 30 | ISP2, Apramycin, Thiostrepton, Gentamycin | This study |
| S. venezuelae attB::pSET-SC4-1 kb, pFX-SC6 | DSM 41110 | 30 | ISP2, Apramycin, Thiostrepton, Gentamycin | This study |
| S. venezuelae attB::pSET-SC4-5 kb, pFX-SC6 | DSM 41110 | 30 | ISP2, Apramycin, Thiostrepton, Gentamycin | This study |
| S. venezuelae attB::pSET-SC4-10 kb, pFX-SC6 | DSM 41110 | 30 | ISP2, Apramycin, Thiostrepton, Gentamycin | This study |

TABLE 24

List of plasmids created for the purpose of this research project

| Plasmid | Features | Selection | Strain | Source |
| --- | --- | --- | --- | --- |
| pSET-SC4 | pSET152 carrying a cos site, the ErmEp* promoter and a PmeI site | Apramycin | Replicative in E. coli; integrative in Streptomyces spp. | This study |
| pSETSC3b | pSET152 carrying a cos site, the ErmEp* promoter and a XbaI and Bsu36I sites | Apramycin | Replicative in E. coli; integrative in Streptomyces spp. | This study |
| pSETSC3b-Shufflon | pSETSC3b carrying inserts 1 and 2 | Apramycin | Replicative in E. coli; integrative in Streptomyces spp. | This study |
| pYES1L-5 kb | pYES1L carrying insert 1 | Spectinomycin Tryptophan | Replicative in S. cerevisiae and E. coli | This study |
| pYES1L-10 kb | pYES1L carrying insert 2 | Spectinomycin Tryptophan | Replicative in S. cerevisiae and E. coli | This study |
| pYES1L-5.1 kb | pYES1L carrying part 1 of the 5 kb shuffling system | Spectinomycin Tryptophan | Replicative in S. cerevisiae and E. coli | This study |
| pYES1L-10.1 kb | pYES1L carrying part 1 of the 10 kb shuffling system | Spectinomycin Tryptophan | Replicative in S. cerevisiae and E. coli | This study |
| pYES1L-5.2 kb | pYES1L carrying the full 5 kb shuffling system | Spectinomycin Tryptophan | Replicative in S. cerevisiae and E. coli | This study |
| pYES1L-10.2 kb | pYES1L carrying the full 10 kb shuffling system | Spectinomycin Tryptophan | Replicative in S. cerevisiae and E. coli | This study |
| pKC1139-rci | pKC1139 carrying rci | Apramycin | Replicative in E. coli and Streptomyces spp. | This study |
| pKC1139-rci-tsr | pKC1139 carrying rci and tsR | Apramycin | Replicative in E. coli and Streptomyces spp. | This study |
| pKC-SC5 | pKC1139 carrying rci | Hygromycin | Replicative in E. coli and Streptomyces spp. | This study |
| pKC-SC7 | pKC1139 carrying rci and tsR | Gentamycin | Replicative in E. coli and Streptomyces spp. | This study |
| pFX-SC6 | pFX583-GentR carrying rci and tsR | Gentamycin | Replicative in E. coli and Streptomyces spp. | This study |
| pSETSCexp-mKate2 (repeat) | Expresses mKate2 | Apramycin | Replicative in E. coli; integrative in Streptomyces spp | This study |
| pSETSCexp-nirFP (repeat) | Expresses nirFP | Apramycin | Replicative in E. coli; integrative in Streptomyces spp | This study |

TABLE 24-continued

List of plasmids created for the purpose of this research project

| Plasmid | Features | Selection | Strain | Source |
|---|---|---|---|---|
| pSETSCexp-dsRed2 (repeat) | Expresses dsRed2 | Apramycin | Replicative in *E. coli*; integrative in *Streptomyces* spp | This study |
| pSETSCexp-ebfp2 (repeat) | Expresses ebfp2 | Apramycin | Replicative in *E. coli*; integrative in *Streptomyces* spp | This study |
| pSET-SC4-1 kb | pSET-SC4 carrying the 1 kb-shuffling system | Apramycin | Replicative in *E. coli*; integrative in *Streptomyces* spp | This study |
| pSET-SC4-5 kb | pSET-SC4 carrying the 5 kb-shuffling system | Apramycin | Replicative in *E. coli*; integrative in *Streptomyces* spp | This study |
| pSET-SC4-10 kb | pSET-SC4 carrying the 10 kb-shuffling system | Apramycin | Replicative in *E. coli*; integrative in *Streptomyces* spp | This study |

TABLE 25

List of independently developed published plasmids used during this study

| Plasmid | Features | Selection | Strain | Source |
|---|---|---|---|---|
| pUZ8002 | DNA transfer machinery | Kanamycin | Replicative in *E. coli* | 14 |
| pSET152 | *Streptomyces* integrative plasmid (attB) | Apramycin | Integrative in *Streptomyces* spp., replicative in *E. coli* | 3 |
| pKC1139 | Shuttle vector with temperature-sensitive *Streptomyces* oriR | Apramycin | Replicative in *E. coli* and *Streptomyces* spp. | 3 |
| pIJ10700 | | Hygromycin | Replicative in *E. coli* | S. O'Rourke (unpublished) |

References for Example 3

1. Gibson, D. G. et al. Enzymatic assembly of DNA molecules up to several hundred kilobases. Nat Meth 6, 343-345 (2009).
2. Lussier, F. X., Denis, F. & Shareck, F. Adaptation of the highly productive T7 expression system to *Streptomyces lividans*. Appl. Environ. Microbiol. 76, 967-970 (2010).
3. Mimee, M., Tucker, A. C., Voigt, C. A. & Lu, T. K. Programming a Human Commensal Bacterium, *Bacteroides thetaiotaomicron*, to Sense and Respond to Stimuli in the Murine Gut Microbiota. Cell Syst. 1, 62-71 (2015).
4. Livak, K. J. & Schmittgen, T. D. Analysis of relative gene expression data using real-time quantitative PCR and the 2(-Delta Delta C(T)) Method. Methods 25, 402-408 (2001).
5. Kieser, T., Bibb, M. J., Buttner, M. J., Chater, K. F. & Hopwood, D. A. Practical *streptomyces* genetics. (John Innes Foundation, 2000).
6. Bierman, M. et al. Plasmid cloning vectors for the conjugal transfer of DNA from *Escherichia coli* to *Streptomyces* spp. Gene 116, 43-49 (1992).
7. Gyohda, A., Funayama, N. & Komano, T. Analysis of DNA inversions in the shufflon of plasmid R64. J. Bacteriol. 179, 1867-1871 (1997).

Example 4

Preparation of a Cell-Free Translation and Transcription System

Given the inability to integrate the PKS-shufflon pathway in *S. venezuelae*, it was decided to test whether a cell-free transcription and translation system could be used for flipping DNA. The parts used for the cell-free transcription and translation system include: DNA, which serves as template for transcription; S30-based reaction, which is the basis of the system and contains the S30 cell fraction of the cell extract (ribosomes and soluble proteins); and a control gene, gusA was selected as the gene to test if the system was indeed transcribing and translating genes.

Given that the system used to transcribe and translate genes uses exogenously-supplemented RNA polymerase, this was an opportunity to use the most convenient promoter-polymerase pair. The T7 promoter was used, given that the RNA T7 polymerase can be purchased.

Also, since all genomic DNA is removed from S30, any chromosomal genes of interest were added back to the system: pikAI, III, IV and V had to be PCR amplified from the chromosome of *S. venezuelae* DSM 41110.

Figure 35:
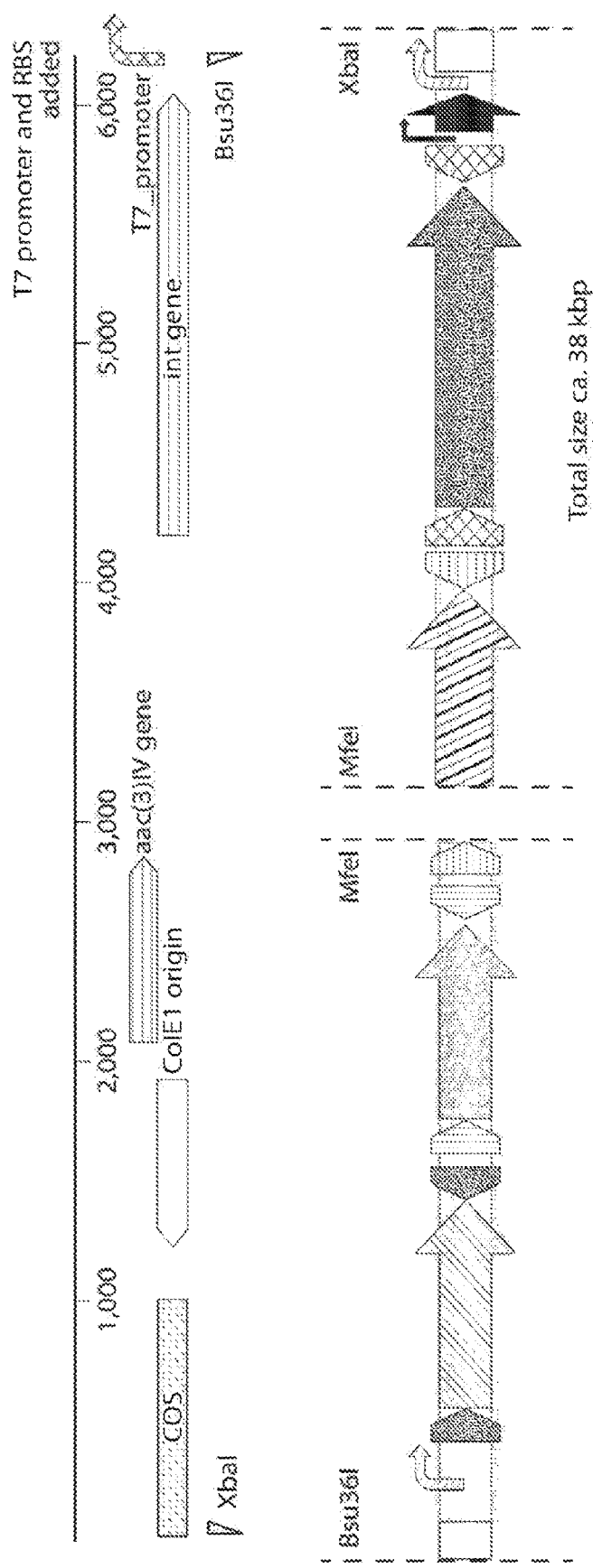
FIG. 35 shows a schematic of the process of adding the T7 promoter to the cosmid backbone, for cloning the PKS-shufflon system.

The T7 promoter and a ribosomal binding site were added upstream of the initiation codon of each gene in one of 2 different ways: by amplifying the gene of interesting using forward primers carrying overhangs with the T7 promoter and an RBS, or by amplifying cosmid backbones with a reverse primer carrying overhangs with the T7 promoter and an RBS (FIG. 35).

Figure 36:
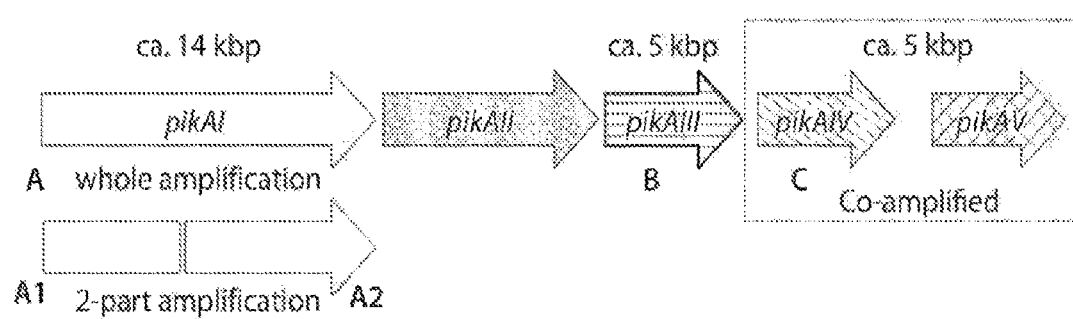
FIG. 36 shows a schematic of the pikromycin operon: gene pikAII was not amplified, as the goal was to replace it with a synthetic operon.

The first option was used for genes rci, pikAI, III, IV and V (FIG. 36), as they were amplified from the chromosome of *S. venezuelae*. Given the size of pikAI, it was PCRed in 1 or 2 pieces (if 1 piece failed). The second option was used for the PKS-shufflon pathway, as its genes were organized in an operon and it was used to replace the ermEp* promoter with T7.

The PCR conditions initially used were Herculase II Polymerase without additives and 58 C as annealing temperature. As this method was not successful, the PCR protocol had to be modified for the amplification of these genes. The rci was successfully amplified and a T7 promoter and an RBS were added upstream of its initiation codon.

It was decided to perform a full-range analysis, where magnesium and/or DMSO were added to the reaction with KOD polymerase, in varying concentrations. Utilizing this approach, it was possible to find functional amplification conditions for each gene.

After learning that PCR-based transcription did not perform in a satisfactory way, it was decided to clone these genes/amplicons into vectors.

This was achieved by blunting the amplicons previously obtained by PCR: this step also provided the phosphate groups to the amplicons and allowed the dephosphorylation of the blunt-end digested cosmid backbone. Cosmids were used instead of plasmids due to the size of the amplicons.

The template DNA for testing the efficiency of the system—gusA driven by T7—had been previously constructed for another purpose.

All plasmids were maxiprepped from 400 mL of culture using ZymoPure® MaxiPrep kit. The DNA extraction process was followed by ethanol precipitation for concentrating and further cleaning the DNA, which was then resuspended in sterile water and stored at −20° C.

Testing the Cell-Free System

Two 5 μL aliquots were taken at 15 and 60 min. One aliquot was mixed with X-Gluc to assess color formation while the other was ran in a Bis-Tris 4-12% protein gel (NuPage) and stained with Coomassie Blue. No color development was observed for the aliquot mixed with X-Gluc and the only band found in the gel, with the expected weight of gusA, was also present in the control, both for the ermEp*- and T7-driven expressions. The Coomassie Blue staining will not allow proteins in small amount to be seen on a gel. Furthermore, the system's proteins could potentially be obscuring GusA, as they run at ca. the same height. The lack of color development with X-Gluc could be due to the enzymatic action inhibition cause by the S30 system.

New Approaches to Calculate the Rci-Based DNA Inversion

It is well known in the field that amplifying high GC DNA is troublesome. This is also well documented in Examples 1-3.

The qPCR reaction is a DNA amplification reaction. In the case of the Sybr® Green assay, the amount of DNA being accumulated as the amplification process takes place is quantified based on the amount of dye binding double-stranded DNA. This is a problem because it is extraordinarily difficult to obtain a single, specific amplicon, when amplifying high GC DNA. When performing PCR, there is more flexibility in terms of buffer content and amplification conditions, which is not the case with qPCR.

The approach initially taken to quantify the flipping efficiency, and given that an all-flipped version of the system was not available, was to use a gene of reference to estimate the Rci-mediated flipping efficiency (Example 3).

Standards DNA-Ct and qPCR

Figure 37A:
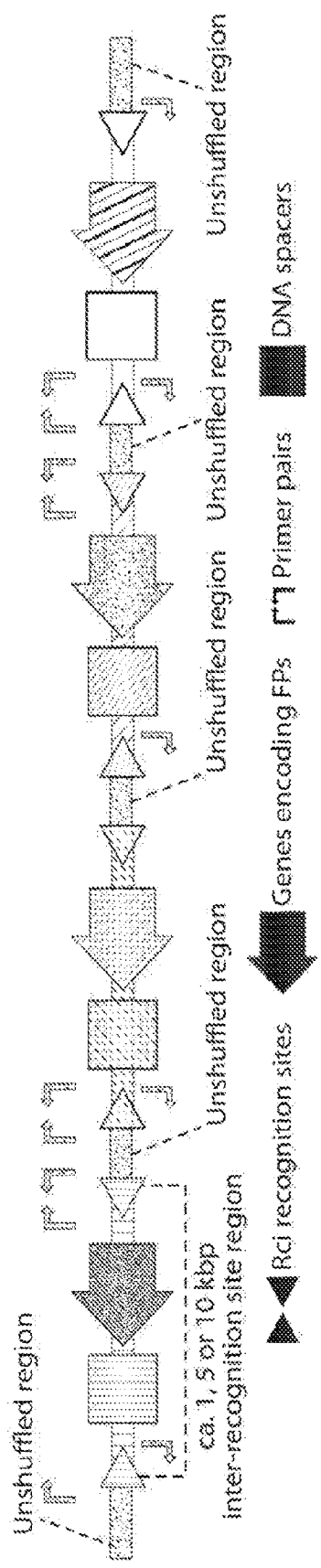
FIGS. 37A-37C show schematics of the 4-color shuffling constructs for assessing flipping efficiencies: unflipped (FIG. 37A), flipped (FIG. 37B), and schematic of the gBlock (all flipped amplicons) cloned into pSET152 (FIG. 37C).
Figure 37B:
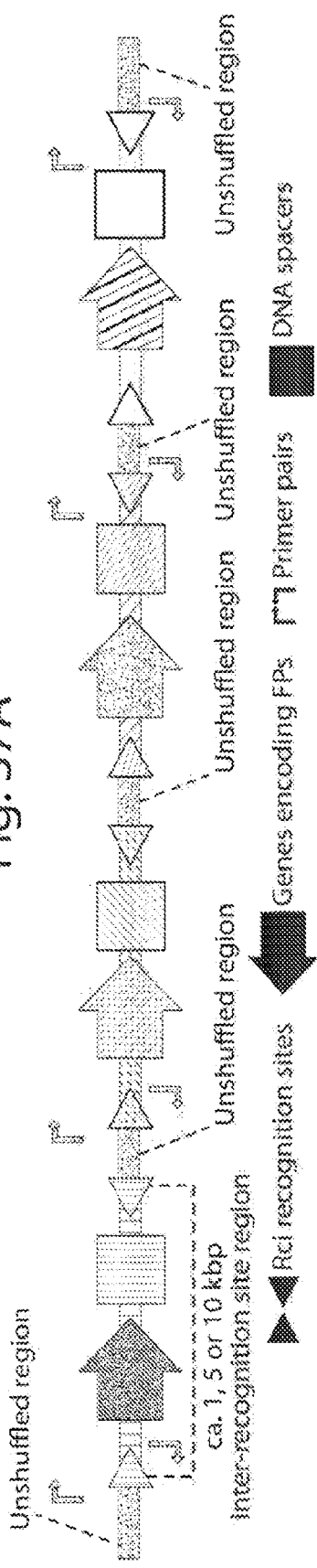
Figure 37C:
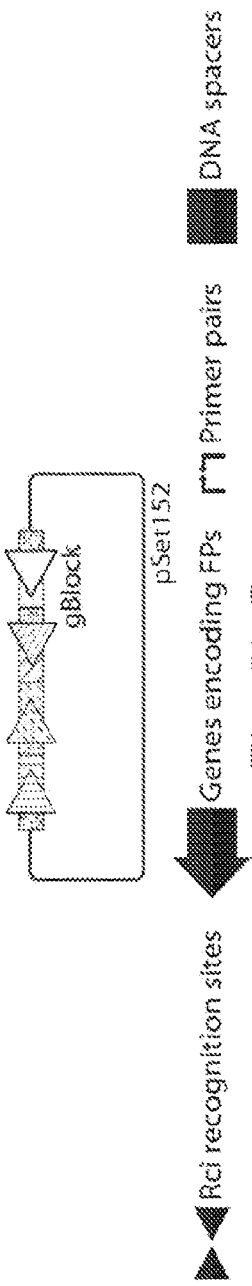

In this alternative approach to measure the Rci flipping efficiency, instead of relying on the internal standard and discount error, an "all-flipped" control was built. It was impractical to build versions of all 3 large pathways that contained the genes in a flipped (5'-3') orientation. Yet, the original (unflipped) pathways were built so that the same sets of primers could be used independently of the size of the DNA sequence to be flipped. Given that it is possible to predict the DNA sequence of the flipped version, it was possible to build a synthetic DNA sequence that contained the expected amplicons amplified, if the flipping indeed occurred (FIGS. 37A-37C). These amplicons, and additional DNA up and downstream of each of them, were synthesized as a gBlock and cloned into pSET152. Upon integration into the attB locus, the culture was grown and the genomic DNA extracted. The mere gBlock was not used directly as control DNA, but instead was placed in the context of the host organism, to mimic the other constructs and the background associated with amplifying DNA from a genomic prep of high GC DNA.

Now that a positive control was available, it was possible to estimate the number of molecules of DNA that had in fact flipped. For this, a standard curve relating the Ct values of the qPCR reaction with the number of molecules flipped. The Ct value (Cycle threshold) represents the number of cycles for the fluorescence measured to rise above the baseline value. The higher this value is, the more cycles are required and thus the less abundant the template is.

For calculating the standard curve, the flipped and unflipped templates were added to the qPCR reaction in different concentrations, ranging from 102 to 107 molecules of DNA per well. The number of molecules of DNA was estimated using Thermo Scientific's DNA Copy Number Calculator. The fluorescence (Ct value) measured per DNA concentration (copies/well) was plotted (FIG. 67).

Figure 40:
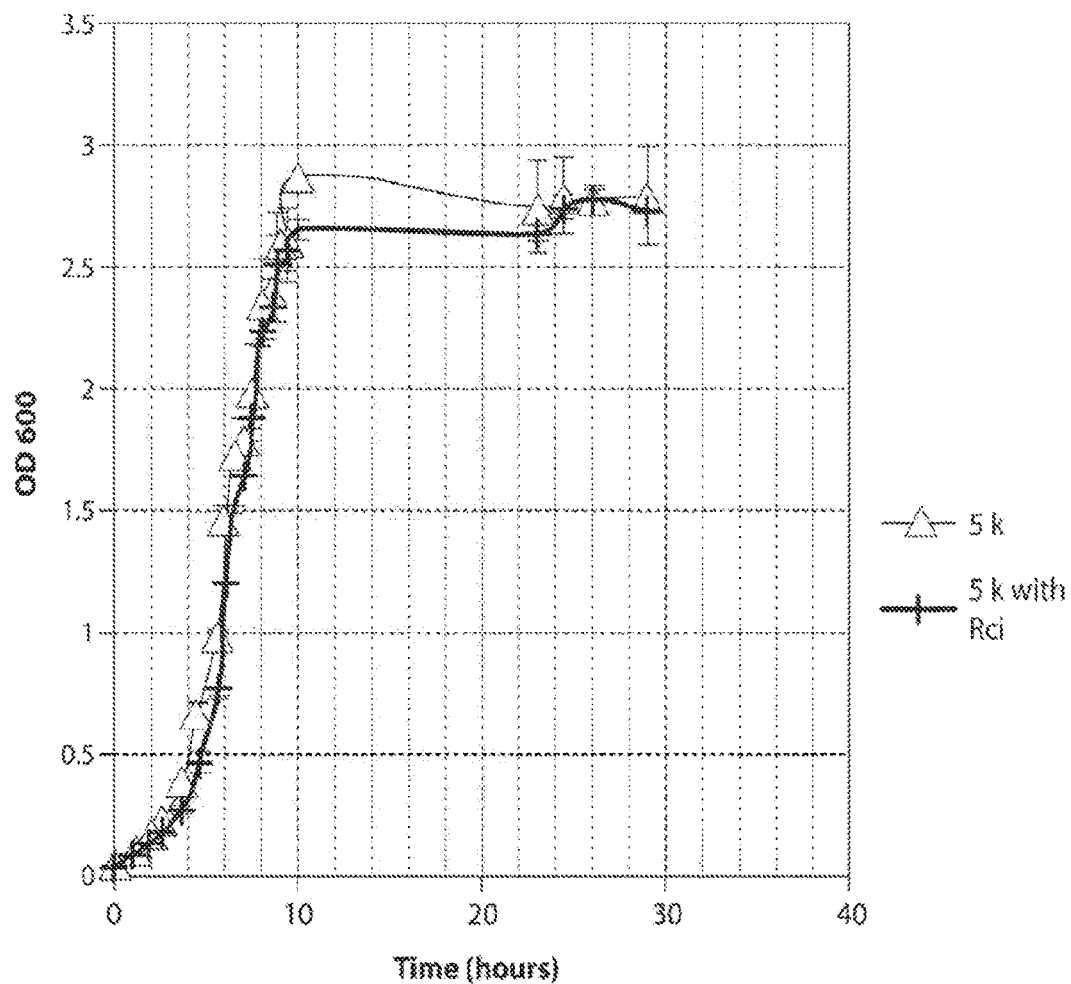
FIG. 40 shows a *S. venezuelae* growth curve with and without Rci recombinase.

For determining the flipping efficiency of Rci, 3 independent experiments with replicates were performed. In each experiment, the 1, 5, and 10 kb flipping strains of *S. venezuelae*, carrying Rci or not were grown overnight in tryptic soy broth, 30 C, 250 rpm. Upon overnight growth, the cultures were reinoculated into TSB to an optical density of 0.04 at 600 nm. Samples (2 mL aliquots) were taken in early exponential phase (4 hours), mid exponential phase (7 hours) and 20 hours of incubation, according to the growth curve previously determined (FIG. 40).

The DNA was purified using a Promega Maxwell 16 System Plant DNA Extraction Kit.

The qPCR reaction was performed using a Roche Light Cycler 480 II and 384-well plates. The reactions were prepared using a Kapa qPCR Universal Sybr® Green Kit (Kapa Biosystems) and following the manufacturer's instructions. The extension temperature used was 63 C, in order to decrease the probability of non-specific amplification.

TABLE 26

Averaged percentage of flipped DNA molecules per sampling time and recognition sequence, using Sybr® Green-based qPCR.

| Sampling phase | 1 kb | 5 kb | 10 kb |
|---|---|---|---|
| | Recognition sequence A (% of flipped sequences) | | |
| Early exponential | 2.18 ± 1.54 | 4.72 ± 1.54 | 6.43 ± 4.44 |
| Mid exponential | 2.44 ± 1.4 | 8.55 ± 8.7 | 19.46 ± 27.66 |
| Stationary | 4.27 ± 1.27 | 4.48 ± 2.74 | 2.46 ± 1.53 |

TABLE 26-continued

Averaged percentage of flipped DNA molecules per sampling time and recognition sequence, using Sybr ® Green-based qPCR.

| Sampling phase | 1 kb | 5 kb | 10 kb |
|---|---|---|---|
| Recognition sequence B (% of flipped sequences) | | | |
| Early exponential | 2.21 ± 1.93 | 2.95 ± 1.11 | 5.96 ± 1.48 |
| Mid exponential | 2.58 ± 1.01 | 3.15 ± 0.23 | 4.33 ± 3.81 |
| Stationary | 3.21 ± 1.4 | 3.88 ± 2.51 | 2.74 ± 0.52 |
| Recognition sequence C (% of flipped sequences) | | | |
| Early exponential | 33 ± 26 | 48 ± 39 | 44 ± 9 |
| Mid exponential | 40 ± 20 | 25 ± 24 | 62 ± 32 |
| Stationary | 38 ± 13 | 63 ± 32 | 36 ± 16 |
| Recognition sequence D (% of flipped sequences) | | | |
| Early exponential | 0.01 ± 0.02 | 0.001 ± 0.0006 | 0.001 ± 0.001 |
| Mid exponential | 0.02 ± 0.03 | 0.03 ± 0.05 | 19 ± 34 |
| Stationary | 0.001 ± 0.0006 | 0.003 ± 0.002 | 0.007 ± 0.01 |

TABLE 27

Flipping efficiency per recognition site, for each independent experiment and inter-site distance, using Sybr ® Green-based qPCR.

| Sampling phase | Independent experiment | 1 kb | 5 kb | 10 kb |
|---|---|---|---|---|
| Recognition sequence A (% of flipped sequences) | | | | |
| Early exponential | 1 | 0.63 | 6.47 | 11.54 |
|  | 2 | 4.06 | 18.39 | 51.40 |
|  | 3 | 5.58 | 7.58 | 4.20 |
| Mid exponential | 1 | 3.70 | 3.68 | 3.53 |
|  | 2 | 1.67 | 1.88 | 3.12 |
|  | 3 | 3.04 | 3.45 | 1.81 |
| Stationary | 1 | 2.21 | 4.01 | 4.22 |
|  | 2 | 1.60 | 5.38 | 3.87 |
|  | 3 | 4.20 | 2.40 | 1.37 |
| Recognition sequence B (% of flipped sequences) | | | | |
| Early exponential | 1 | 0.003 | 4.20 | 4.72 |
|  | 2 | 3.57 | 3.34 | 8.55 |
|  | 3 | 4.75 | 5.94 | 2.33 |
| Mid exponential | 1 | 3.55 | 2.11 | 7.59 |
|  | 2 | 2.62 | 2.90 | 3.26 |
|  | 3 | 2.02 | 4.61 | 2.57 |
| Stationary | 1 | 3.08 | 2.55 | 5.53 |
|  | 2 | 1.56 | 3.21 | 1.17 |
|  | 3 | 2.87 | 1.09 | 3.33 |
| Recognition sequence C (% of flipped sequences) | | | | |
| Early exponential | 1 | 3.45 | 27.94 | 36.47 |
|  | 2 | 62.13 | 49.25 | 98.34 |
|  | 3 | 51.82 | 43.90 | 48.54 |
| Mid exponential | 1 | 44.28 | 92.75 | 53.90 |
|  | 2 | 36.16 | 2.06 | 37.51 |
|  | 3 | 34.38 | 20.13 | 18.23 |
| Stationary | 1 | 51.29 | 21.79 | 43.18 |
|  | 2 | 21.38 | 23.37 | 49.75 |
|  | 3 | 27.20 | 42.74 | 39.88 |
| Recognition sequence D (% of flipped sequences) | | | | |
| Early exponential | 1 | 0.03 | $1.44 \times 10^{-03}$ | $2.16 \times 10^{-03}$ |
|  | 2 | 0.06 | 0.08 | 59.59 |
|  | 3 | 0.001 | $9.99 \times 10^{-04}$ | 0.02 |
| Mid exponential | 1 | $3.59 \times 10^{-04}$ | $2.93 \times 10^{-04}$ | $3.96 \times 10^{-04}$ |
|  | 2 | $2.39 \times 10^{-03}$ | 0.001 | $2.53 \times 10^{-03}$ |
|  | 3 | $5.32 \times 10^{-04}$ | 0.003 | $2.08 \times 10^{-03}$ |
| Stationary | 1 | $7.05 \times 10^{-04}$ | $5.60 \times 10^{-04}$ | $3.00 \times 10^{-04}$ |
|  | 2 | $8.82 \times 10^{-04}$ | $4.18 \times 10^{-04}$ | $2.38 \times 10^{-03}$ |
|  | 3 | $1.77 \times 10^{-03}$ | 0.005 | $9.47 \times 10^{-05}$ |

Figure 38:
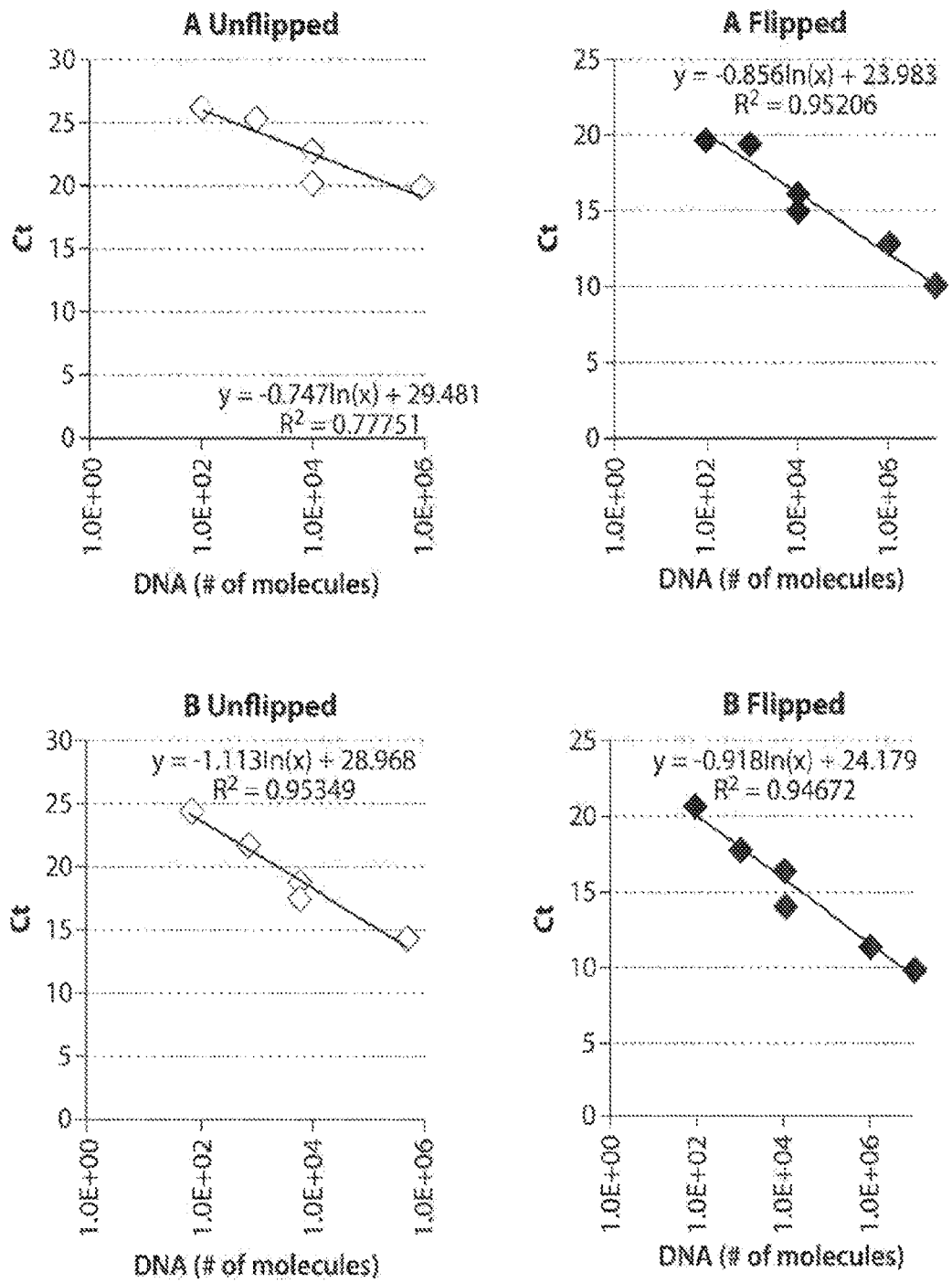
FIGS. 38-39 shows standards correlating Ct values and number of DNA molecules.
Figure 39:
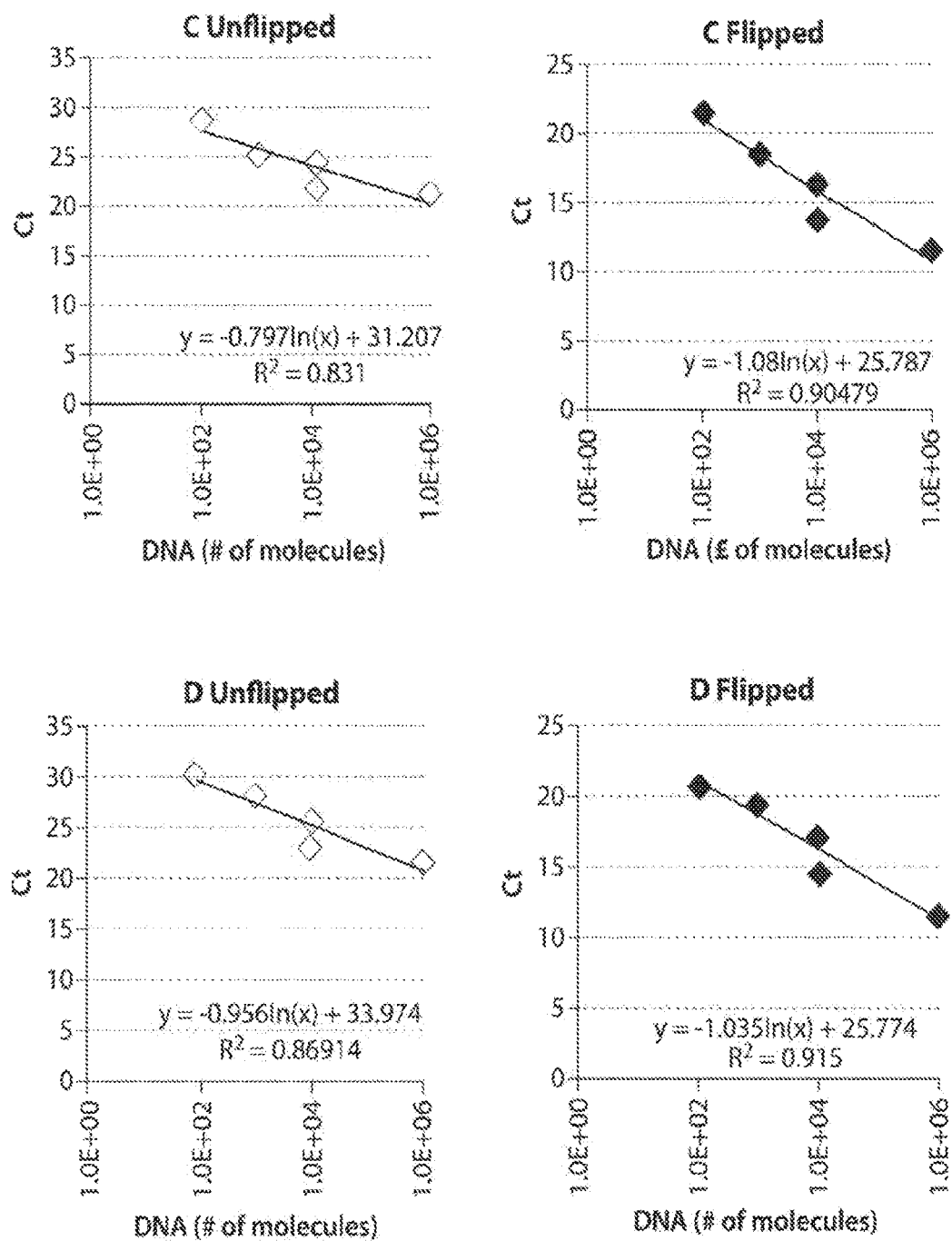

The results were averaged and the number of molecules of DNA were calculated using the control logarithmic regression lines, which were calculated by plotting the number of molecules, in logarithmic scale, against the Ct values (FIGS. 38-39). The percentages of flipping were calculated using the following fraction:

% Flipped sequences=#ON Amplicons/(#ON Amplicons+#OFF Amplicons)×100

Despite the attempts to reduce non-specific amplification, there was still a considerable amount of non-specificity in the qPCR amplification. Furthermore, the use of a higher extension temperature worked well with the primers for the flipped amplicons, but was detrimental to the amplification of unflipped sequences.

This impaired the calculation of precise flipping efficiencies. The initial approach (Example 3) seemed to overestimate the flipping efficiency of Rci. This new approach seemed to underestimate such efficiencies. Three independent experiments were also performed, which led to higher standard deviations (Table 26).

PrimeTime Probes and qPCR

Figure 41:
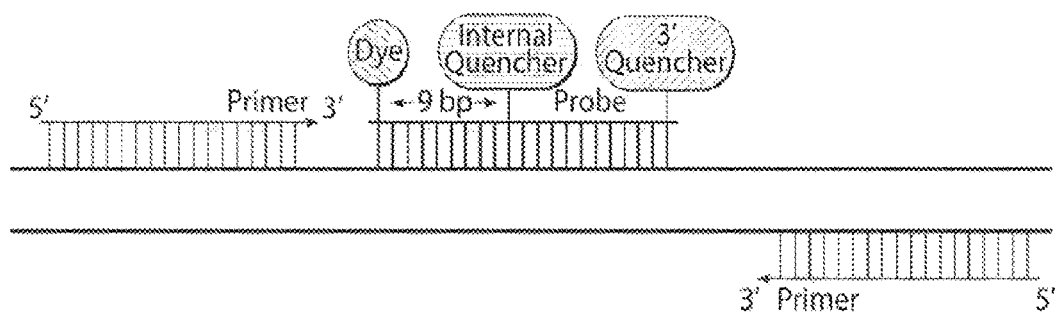
FIG. 41 shows a schematic of the PrimeTime probes and primers annealing, for probe-based qPCR (IDT DNA Technologies).
Figure 42:
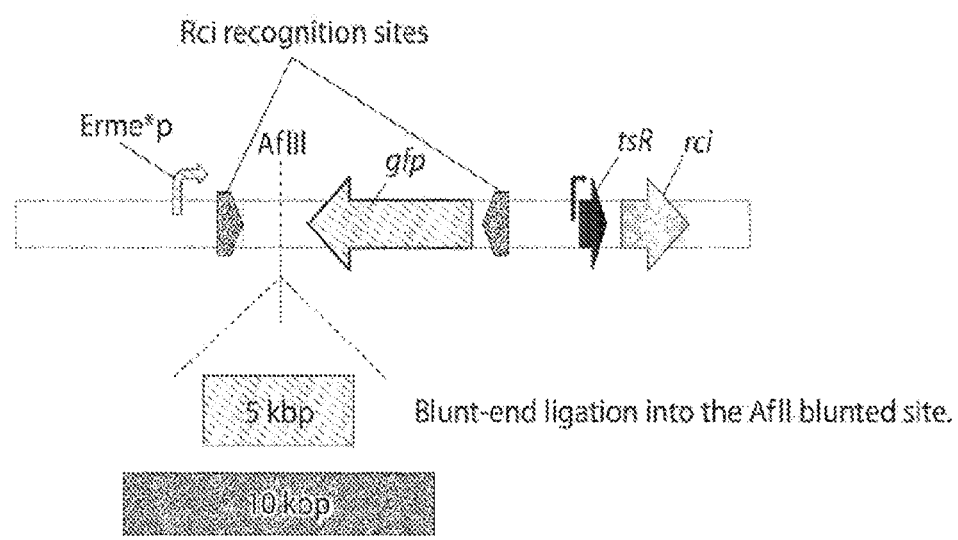
FIG. 42 shows a schematic of the construct to be built for using GFP to determine Rci's flipping efficiencies.
Figure 43:
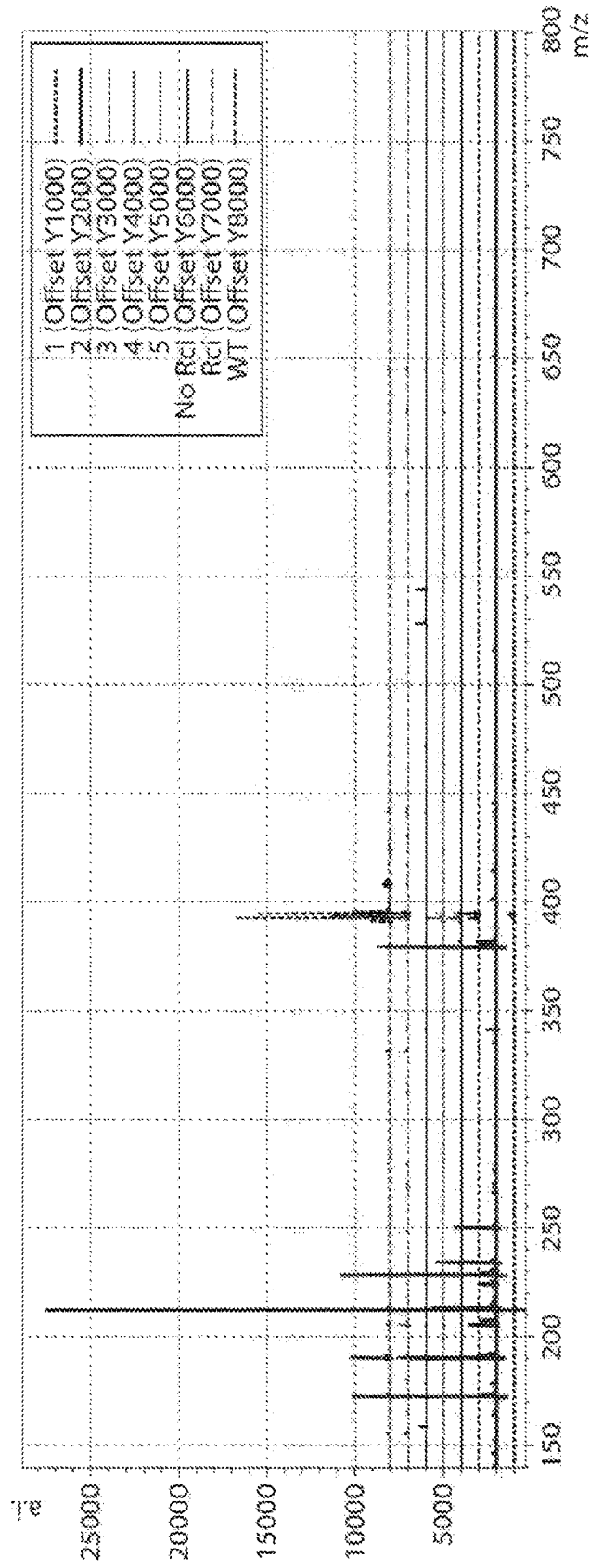
FIG. 43 shows MALDI-ToF trace of the samples analyzed. The test samples are labeled 1 through 5, corresponding to the number of the colony displaying a different phenotype that was picked. "No Rci" strain carries only the pathway only (without Rci), "Rci" strains carries only the Rci (no pathway) and "WY" is the wild type strain of *S. coelicolor*. WT is the top trace, Rci is the second from top trace, No Rci is the third from top trace. Test sample 1 is the bottom trace, test sample 2 is the second from bottom trace, test sample 3 is the third from bottom trace, test sample 4 is the fourth from bottom trace, and test sample 5 is the fifth from bottom trace.

Aiming to increase the specificity of the qPCR-based flipping quantification, it was decided to use sequence-specific labeled probes instead of Sybr® Green-based quantification (FIG. 41).

These synthetic probes—PrimeTime ZEN™ double-quenched probes for qPCR (IDT DNA Technologies)—hybridize onto the complementary DNA sequence. Once that region is amplified, the DNA polymerase hydrolyzes the FAM fluorophore located in the 5' end of the probe, releasing it. This causes a physical separation between the fluorophore and the internal ZEN™ and 3' Iowa Black® quenchers, which results in fluorescence between emitted (FIG. 41).

New sets of primers were also ordered along with the probes, for the flipped and unflipped amplicons. The PrimeTime qPCR Master Mix (IDT DNA Technologies) was also used, according to the manufacturer instructions. The 384 plates were run in a Roche LightCycler 480 II.

The measurements obtained for each sample were averaged and using the standard curves the number of molecules were extrapolated. They were then converted into percentage of flipped molecules over the number of flipped and unflipped molecules.

The flipping efficiencies obtained for each individual experiment varied, likely due to the fact that tipAp, the promoter driving the expression of rci, is very leaky. This results in an inability to start the assay with fully unflipped constructs.

Similarly to the previous results, the flipping efficiencies varied with the distance between recognition sites as well as with the recognition site used. The ranking of sites in terms of flipping efficiency, throughout the sampling times, was D>A>C>B, for the 1 kbp distance, C>D>A>B for 5 kb and D/A/C>B. Looking at the results per sampling time, C>D>A>B for the first time point, A>D>B>C for the second point and D>C>A>B for the last one (Table 28). As pervasively observed, there was a great inter-independent experiment variation (Table 29), possibly due to the leakiness of tipAp, as explained above.

TABLE 28

Averaged percentage of flipped DNA molecules per sampling time and recognition sequence, using PrimeTime qPCR probes.

| Sampling phase | 1 kb | 5 kb | 10 kb |
|---|---|---|---|
| Recognition sequence A (% of flipped sequences) | | | |
| Early exponential | 33 ± 58 | 50 ± 71 | 33 ± 58 |
| Mid exponential | 50 ± 71 | 0.03 ± 0.04 | 99 ± 2 |
| Stationary | 67 ± 58 | 33 ± 58 | 33 ± 58 |
| Recognition sequence B (% of flipped sequences) | | | |
| Early exponential | 33 ± 58 | 1.04 ± 1.44 | 0.92 ± 1.18 |
| Mid exponential | 2.5 ± 3.8 | 36 ± 55 | 65 ± 56 |
| Stationary | 1.15 ± 1.04 | 34 ± 57 | 11 ± 19 |
| Recognition sequence C (% of flipped sequences) | | | |
| Early exponential | 33 ± 58 | 67 ± 58 | 67 ± 58 |
| Mid exponential | 33 ± 58 | 0 | 33 ± 58 |
| Statonary | 33 ± 58 | 67 ± 58 | 67 ± 58 |
| Recognition sequence D (% of flipped sequences) | | | |
| Early exponential | 67 ± 58 | 33 ± 58 | 33 ± 58 |
| Mid exponential | 67 ± 58 | 33 ± 58 | 33 ± 58 |
| Stationary | 100 ± 0 | 33 ± 58 | 100 ± 0 |

TABLE 29

Flipping efficiency per recognition site, for each independent experiment and inter-site distance, using PrimeTime probes

| Sampling phase | Independent experiment | 1 kb | 5 kb | 10 kb |
|---|---|---|---|---|
| Recognition sequence A (% of flipped sequences) | | | | |
| Early exponential | 1 | 0.15 | $5.50 \times 10^{-10}$ | $2.52 \times 10^{-03}$ |
| | 2 | $3.70 \times 10^{-04}$ | $3.23 \times 10^{-15}$ | 96.13 |
| | 3 | 100.00 | 100.00 | 100.00 |
| Mid exponential | 1 | 100.00 | — | 0.00 |
| | 2 | — | $9.23 \times 10^{-11}$ | 100.00 |
| | 3 | $1.13 \times 10^{-05}$ | $9.44 \times 10^{-07}$ | 0.00 |
| Stationary | 1 | 0.00 | 100.00 | 100.00 |
| | 2 | 100.00 | 0.08 | 100.00 |
| | 3 | 100.00 | 0.01 | $6.10 \times 10^{-10}$ |
| Recognition sequence B (% of flipped sequences) | | | | |
| Early exponential | 1 | $1.78 \times 10^{-03}$ | 0.38 | 2.26 |
| | 2 | 6.94 | 8.07 | 98.94 |
| | 3 | 1.45 | 0.92 | 32.56 |
| Mid exponential | 1 | 100.00 | 0.01 | $5.50 \times 10^{-04}$ |
| | 2 | 0.22 | $2.13 \times 10^{-03}$ | 0.02 |
| | 3 | 2.03 | 0.06 | 0.05 |
| Stationary | 1 | 0.32 | 2.66 | 0.51 |
| | 2 | 0.36 | 100.00 | 95.95 |
| | 3 | $6.45 \times 10^{-07}$ | 100.00 | 0.16 |

TABLE 29-continued

Flipping efficiency per recognition site, for each independent experiment and inter-site distance, using PrimeTime probes

| Sampling phase | Independent experiment | 1 kb | 5 kb | 10 kb |
|---|---|---|---|---|
| Recognition sequence C (% of flipped sequences) | | | | |
| Early exponential | 1 | $2.79 \times 10^{-09}$ | $1.82 \times 10^{-07}$ | $2.17 \times 10^{-09}$ |
| | 2 | $1.71 \times 10^{-06}$ | $6.11 \times 10^{-06}$ | 0.09 |
| | 3 | $5.83 \times 10^{-15}$ | $3.60 \times 10^{-07}$ | 100.00 |
| Mid exponential | 1 | 100.00 | 100.00 | 100.00 |
| | 2 | $5.70 \times 10^{-23}$ | — | 100.00 |
| | 3 | 100.00 | 100.00 | 100.00 |
| Stationary | 1 | $3.69 \times 10^{-15}$ | 100.00 | 100.00 |
| | 2 | 100.00 | $1.65 \times 10^{-11}$ | $5.20 \times 10^{-10}$ |
| | 3 | $4.38 \times 10^{-12}$ | 100.00 | $2.83 \times 10^{-07}$ |
| Recognition sequence D (% of flipped sequences) | | | | |
| Early exponential | 1 | $5.43 \times 10^{-10}$ | $6.79 \times 10^{-05}$ | $6.37 \times 10^{-09}$ |
| | 2 | 100.00 | $4.15 \times 10^{-05}$ | $8.37 \times 10^{-04}$ |
| | 3 | 100.00 | $7.98 \times 10^{-06}$ | 100.00 |
| Mid exponential | 1 | 100.00 | $6.59 \times 10^{-09}$ | 100.00 |
| | 2 | 100.00 | $4.75 \times 10^{-22}$ | 0.00 |
| | 3 | 100.00 | 100.00 | — |
| Stationary | 1 | 100.00 | 100.00 | $5.10 \times 10^{-23}$ |
| | 2 | $3.15 \times 10^{-06}$ | 100.00 | 100.00 |
| | 3 | 100.00 | $7.17 \times 10^{-22}$ | 100.00 |

When comparing the three approaches undertaken thus far (Table 30), with the published characterization of Rci's flipping efficiency in Enterobacteriaceae, the second approach (Sybr® Green with DNA standards) led to results more similar to those published, in relative terms.

The third approach is the most reliable one, as probes—especially those used in this study—are the most precise method of quantification. For the smaller inter-recognition site distance, the relative results were similar to those of the native system (with distance smaller than 500 bp).

TABLE 30

Rci flipping efficiencies using three different methods: (2) Sybr ® Green and a DNA standard, (3) qPCR double-quenched probes and a DNA standard
Described % of rearranged molecules, in the original Enterobacteriaceae native system.
Recognition sequence a > d > b > c
29 > 0.1 > 0.025 > 0.02
Approaches 2 and 3, with efficiencies per time point averaged together:

| | 1 kbp | 5 kbp | 10 kbp |
|---|---|---|---|
| 2 | c > a/b > d | c > a > b > d | c > a/b > d |
| | 33 > 2/2 > 0.01 | 48 > 5 > 3 > 0.001 | 44 > 6/6 > 0.001 |
| 3 | d > a > c > b | c > d > a > b | c/d > a > b |
| | 78 > 50 > 33 > 12 | 44 > 33 > 28 > 24 | 56/56 > 55 > 26 |

Testing the expression of *Streptomyces*-gfp in *S. venezuelae*

Given the GC-content associated difficulties in the both exact and precise measurement of Rci-mediated DNA flipping efficiencies, it was decided to test the expression of gfp in the target organism.

This gfp was modified for *S. coelicolor* A3(2) in 1999[1]. This process involved codon-optimization, given the codon usage bias of the high GC *streptomycetes*. Since then it has been successfully used in multiple *Streptomyces* spp, such as *S. lividans*[2] and *S. hygroscopicus*[3]. Nonetheless, the level of performance were never has high as found in other organisms such as *E. coli*.

If this fluorescent protein works in S. venezuelae, it will be possible to build plasmids carrying this gfp surrounded by Rci recognition sites and a downstream copy of rci. Yet, this will also depend on whether 100% of the population fluoresces or not, as if it does not, the flipping efficiencies will be underestimated. An option would be to extensively determine the percentage of the population that does not fluoresce, and include such percentage in the calculation of the flipping efficiencies (i.e., if on average only 90% of the population fluoresces, and if it is determined that 90% of the population flipped, the efficiency is in fact 100%).

Nonetheless, before embarking on the construction of these vectors, the gfp carried by pSET152 and driven by the promoter rpsLp(XC) a plasmid was integrated into the attB site of S. venezuelae. The strain carrying gfp was incubated in TSB supplemented with apramycin, whereas the wild-type, used as negative control, in TSB alone. Growth was promoted at 30 C and 250 rpm. E. coli pZ8-gfp was used as a positive control and incubated in TSB supplemented with kanamycin, at 30 C and 250 rpm. Aliquots were taken at 18 hours for S. venezuelae and 6 hours for E. coli. The cultures were diluted 1:100 and 1:1000 in PBS and analyzed in a BD-FACS LSR Fortessa cell analyzer (BD Biosciences, CA). The fluorescence was measured using a FITC filter with a 490 nm excitation laser and a 520 emission filter.

Except for the positive control, none of the samples displayed fluorescence: gfp did not seem to work in S. venezuelae DSM 41110. Yet, it was decided to test this again, over a longer course of time and with multiple reinoculation steps: an overnight culture of S. venezuelae carrying gpf (and the respective controls) and reinoculated and grown overnight again. This second culture was then used to inoculate TSB (with the appropriate antibiotic, when needed). The reinoculation step was repeated 3 times (once a day, the last time point was 6 hours before analysis). Six hours after the third reinoculation step, 100 µL of each culture were mixed with 900 µL of PBS and tested for fluorescence by FACS. Interestingly, this time, fluorescence was observed, along with minimal background.

The fluorescence intensity varied with the incubation time and so did the percentage of the population that fluoresced. Six hours post-reinoculation, three populations of S. venzuelae were observed, two of which fluoresced with high intensity. A third population did not fluoresce. The oldest population (ca. 54 hours old) presented the highest percentage of non-fluorescent cells, possibly related with the aging population and sporulation. The positive control—E. coli expressing gfp—was not included in the S. venezuelae histograms as the cell morphology and the growth rate are very different, having served as an independent control of fluorescence. Interestingly this strain did not fluoresce at the last time point, in early stationary phase.

When fully characterizing the Rci-mediated DNA inversion independently of the previously built PKS-shufflon pathway and its characteristics, it is more straightforward to test each pair of recognition sites independently (instead of using the 4-color system).

Integration of the PKS-shufflon pathway in S. coelicolor A3(2)

As previously explained (Example 3), it was not possible to integrate the PKS-shufflon pathway in S. venezuelae, despite innumerable attempts.

This pathway was designed to interact with the S. venezuelae pikromycin pathway to generate new polyketides. As the PKS genes in the biosynthetic pathway were cloned in the 5'-3' orientation, it is suspected that new molecules are being made, which results in cell death. Given the death phenotype, it is impossible to test this in vivo. As such, it is hoped that the cell-free transcription and expression system will provide insight on this.

Nonetheless, it was decided to try to integrate the two version of this pathway—with or without rci—in S. coelicolor A3(2). This strain of Streptomyces does not carry the pikromycin pathway, despite carrying other natural product pathways. In order to be able to integrate it in this organism, the plasmid pSET-SC4 was used (Example 3), as it integrated into the attB site of the organism.

Shuffling in S. coelicolor A3(2) Following the usual conjugation protocol (please see report #2), both pathways were successfully integrated into S. coelicolor. Interestingly, the strain containing the rci-less pathway (all genes on) did not produce prodigiosin (red pigment) or actinorhodin (blue pigment). On the other hand, the pathway carrying rci produced none, both or either molecules.

The pigment production phenotype was particularly interesting in the case of the white colonies, as it was possible to see red spots developing with a single colony and over time, in some of them.

It is thought that expression of the additional PKSs interferes with the proper assembly of actinorhodin and prodigiosin. When the recombinase was integrated together with the PKS-pathway, the resulting colonies displayed different phenotypes, in terms of pigment production. This further supports that Rci will be turning some of the genes off.

Materials and Methods

Preparation of Reagents and S30 Fraction for the Cell-Free System

The following reagents were prepared for this system: 0.1 M Tris-HCl pH 7.6, 10 mM $MgCl_2$, 10% Glycerol, 1 mM PMSF, 50 mM $CaCl_2$, 5 mM $CaCl_2$, 25 mM EGTA-KOH pH 7.0, 0.1 M Magnesium acetate, 5% TCA, 10% TCA, 1 M HEPES-KOH pH 7.5, 1 $MgCl_2$, 4 M $NH_4Cl$, 14.3 M B-mercaptoethanol, 0.55 M Dithiothreitol, 38 mM ATP pH 7.0, 50 mM Glycine-KOH, 88 mM CTP pH 7.0, 88 mM ATP pH 7.0, 88 mM UTP pH 7.0, 88 mM GTP pH 7.0, 0.42 M PEP pH 7.0, 55 mM Alanine, 55 mM Cysteine, 55 mM Aspartic acid, 55 mM Glutamic acid, 55 mM Phenylalanine, 55 mM Glycine, 55 mM Histidine, 55 mM Isoleucine, 55 mM Lysine, 55 mM Leucine, 55 mM Methionine, 55 mM Asparagine, 55 mM Pyrolysine, 55 mM Proline, 55 mM Glutamine, 55 mM Arginine, 55 mM Serine, 55 mM Threonine, 55 mM Selenocysteine, 55 mM Valine, 55 mM Tryptophan, 55 mM Tyrosine, 40% PEG 8000, 2000 U/mL Pyruvate kinase, 4.2 M Ammonium acetate, and 8.4 M Potassium acetate.

The sporulation medium, NEF, consisted of: 5 g glucose, 1 g yeast extract, 1 g casamino acids, 0.5 g beef extract, 20 g agar, and water to 1 L, pH 8.0 (1 M KOH).

The broth for liquid cultures, YEME, consisted of 3 g yeast extract, 5 g bacto-peptone, 3 g malt extract, 10 g glucose, 340 g sucrose, 5 g PEG 6000, and water to 1 L; 5 mM (final) $MgCl_2.6H_2O$ after autoclaving.

TSB, tryptone soya broth (Oxoid) was also used.

S30 Preparation Protocol

Cells were grown in Tryptic Soy Broth with stainless steel springs—The original protocol asks for YEME supplemented with 5 g/L of PEG 6000. Yet, S. venezuelae was incapable of growing in this medium. Growing the cells in YEME without PEG 6000, and with stainless steel springs to prevent clumping was attempted. Nonetheless, no growth was observed. Next, growing the cells in TSB with springs was attempted. This medium had been previously used to grow S. venezuelae carrying the 4-color shufflon system.

The incubation of 1 L of medium was performed in 3 L baffled Fernbach flasks, but no growth was observed. It was hypothesized that the lack of growth could be due to over-oxygenation of the culture. The protocol for this system called for "vigorous shaking" but also stated said to grow the cells in "1 L in 2 L [regular] flasks", which meant a lower air-to-surface ratio. It was thus decided to grow the spores in smaller flasks with less shaking: 4×500 mL in 4×1L flasks, at 170 rpm vs 250 rpm. This finally resulted in the sought-after mycelia.

The mycelium was harvested by centrifugation (7,000 rpm, 10 min, 4° C.), washed twice with half a volume of washing buffer and once with half a volume of S30 buffer. The pellets were resuspended in S30 buffer and filtered through Whatman no. 1 paper, in a Buchner funnel. Upon dryness of the filter, it was placed in a 50 mL falcon tube to which S30 buffer with 10% glycerol was added. The tube was rotated to resuspend the mycelium from the filter.

A French-press located in a 4° C. room was washed thoroughly with cold 30% ethanol, followed by cold sterile water and cold S30 buffer. After this, the sample was loaded and pressed at 12×103 psi into centrifuge tubes.

The A260 of the resulting extract—S30—was measured and nuclease treatment was performed: 200 μL of S30 (40-60 A260 units) were mixed with 4.1 μL of $CaCl_2$ 50 mM and 2 μL of nuclease (150 units). After 30 minutes of incubation, the nuclease was inactivated by adding 2.6 μl of 25 mM EGTA-KOH pH7.0.

The activity of the S30 fraction obtained was tested using gusA, a ß-glucuronidase gene that converts 5-bromo-4-chloro-3-indolyl glucuronide (X-Gluc) to a blue pigment (see Example 1): 40 μl S30 (2-3 A260 units), 32 μl S30 buffer, 8 μl 0.1 M magnesium, acetate (12 mM final), 32 μl Synthesis mix, and 8 μl Plasmid DNA (8 μg) or water blank.

References for Example 4

1. Sun, J., Kelemen, G. H., Fernández-Abalos, J. M. & Bibb, M. J. Green fluorescent protein as a reporter for spatial and temporal gene expression in *Streptomyces coelicolor* A3(2). Microbiology 145 (Pt 9, 2221-7 (1999).
2. Vrancken, K. et al. pspA overexpression in *Streptomyces lividans* improves both Sec- and Tat-dependent protein secretion. Appl. Microbiol. Biotechnol. 73, 1150-7 (2007).
3. Kuščer, E. et al. Roles of rapH and rapG in positive regulation of rapamycin biosynthesis in *Streptomyces hygroscopicus*. J. Bacteriol. 189, 4756-4763 (2007).

Example 5

Production and Analysis of the Small Molecules Secreted to the Growth Medium

The PKS pathway integrated into the chromosome of *S. coelicolor* is made up of 4 genes, surrounded by sites (short DNA sequences) that are recognized by the recombinase Rci and flipped.

The strain carrying the pathway as well as Rci was grown on ISP2 medium, for recombination events to occur, and colonies displaying different phenotypes were picked and streaked on Supplemented Minimal Medium (SMMS)[1], for production of natural products. Strains carrying only Rci, only the pathway or neither, were also streaked on SMMS.

The plates were incubated at 30 C for 5 days and the molecules were extracted by mixing the content of the plates (agar and cells) with 100% ethyl acetate. The mixture was left overnight at room temperature, with gentle shaking, to allow the molecules to transition from the agar to the organic solvent.

The next day the samples were centrifuged and the supernatants (organic solvent) collected. Aliquots were submitted for Matrix-Assisted Laser Desorption/Ionization Time-of-Flight (MALDI-ToF) analysis. The matrix used was alpha-cyano, having 1 μL been spotted and analyzed under positive ionization (performed at the Biopolymers and Proteomics Core Facility at the Koch Institute, MIT).

Figure 1:
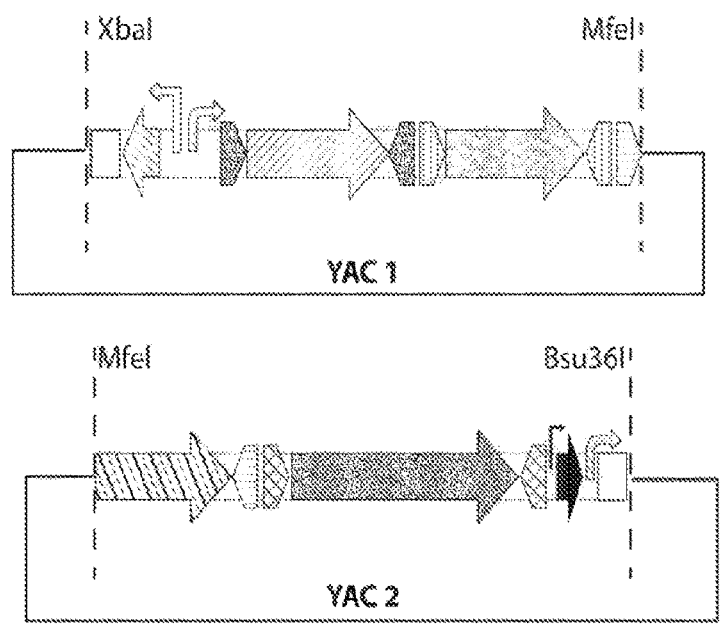
FIG. 1 shows a schematic of a two-YAC (yeast artificial chromosome) assembly of parts and restriction sites permitting their release from the YAC backbone.

The molecules with mass values ranging between 150 and 800 Da detected by MALDI-ToF were analyzed using the software mMass[2] (FIG. 1). The unique peaks detected in each test sample and not present in the control samples are listed on Table 1.

Given that all strains were grown in the same conditions and that multiple negative control strains were used, it can be stated that the mass values listed on Table 1 correspond to molecules produced by the pathway integrated, or in conjunction or as a consequence of the expression of such pathway. The random flipping of genes, mediated by Rci, leads to different sets of genes being expressed at a given time. With this, a larger diversity of molecules is expected to be assembled by the enzymes encoded in the pathway. Such diversity is reflected in the diversity of new masses found in each of the samples. The change in phenotype (production of pigmented antibiotics) is assumed to be associated with the production of new molecules, as a result of the gene shuffling. Thus, it was used for the selection of a few producer strains, which were analyzed by MALDI-ToF.

TABLE 31

List of unique mass values for each of the test samples. Values common to any of the 3 control samples were not included.

Unique mass values (Da)/strain

| 1 | 2 | 3 | 4 | 5 |
|---|---|---|---|---|
| 224.0837 | 146.05 | 164.05 | 190.0624 | 212.1232 |
| 391.5259 | 155.1352 | 212.0677 | 191.091 | 331.45 |
| 392.55 | 173.05 | 379.4 | 212.1118 | 379.4 |
| 393.55 | 178.15 | 391.5874 | 229.1461 | 391.6 |
| 394.5847 | 179.0574 | 392.6 | 234.1499 | 392.6 |
| 442.55 | 189.9411 | 393.6 | 331.4636 | 393.6 |
| 474.45 | 205.15 | 394.6104 | 341.5563 | 394.6405 |
| 490.4678 | 207.15 | 407.6 | 379.4 | 406.6 |
| 496.4855 | 209.1937 | 408.6 | 381.6272 | 407.6 |
| 506.7 | 210.1552 | 409.6 | 391.6 | 408.6 |
| 507.65 | 212.0565 | 744.701 | 392.6 | 632.9 |
| 509.8539 | 218.15 | 753.9 | 393.6 | 633.8485 |
| 513.4 | 219.2096 | 766.65 | 394.65 | |
| 546.85 | 220.1934 | 791.8308 | 407.6016 | |
| 548.5405 | 221.25 | | 408.6148 | |
| 564.05 | 223.15 | | 409.65 | |
| 578.8 | 226.15 | | | |
| 599.2736 | 228.0627 | | | |
| 603.9796 | 231.0799 | | | |
| 606.45 | 234.1 | | | |
| 609.8783 | 246.1735 | | | |
| 612.2779 | 247.2 | | | |
| 623.7656 | 250.1 | | | |
| 626.2384 | 268.25 | | | |
| 638.2 | 270.2188 | | | |
| 681.8 | 288.3295 | | | |
| | 333.3926 | | | |
| | 334.4 | | | |
| | 335.332 | | | |
| | 338.5507 | | | |
| | 341.55 | | | |
| | 358.6 | | | |
| | 379.4 | | | |
| | 381.6 | | | |
| | 383.6 | | | |
| | 648.3 | | | |

References for Example 5

1. Kieser, T., Bibb, M. J., Buttner, M. J., Chater, K. F. & Hopwood, D. A. Practical *streptomyces* genetics. (John Innes Foundation, 2000).
2. Martin Strohalm. mMass—Open Source Mass Spectrometry Tool. (2013). at <www.mmass.org>

Sequences

| Name | Sequence | SEQ ID NO: |
|---|---|---|
| RBS + tylG | CCGGCCGGCGGAGCACACCCGGCCGTCTCCGGCCCGGCCGCGGCCGGGCCGGAAGCCAT<br>CCGCCGCCCACCCGGTACCGACCCCTCAAGCCCTTCAAGCCCTTCGACCCGTCCGATCAGT<br>CAGTCCGGCGGTCCTCCACGACCGGTCCGGAATCGCCCCCACACGAGTCAGGAAGCACAC<br>CATGGCCATGTCCGCCGAGAGGCTGACGGAGGCGCTGCGGACCTCGCTCAAGGAGGCCG<br>AGCGGCTCCGGCGGCAGAACCGCGAACTGAGGGCCGCGCGGGACCGGCGCGGGAGCCG<br>ATCGCCGTCGTCGGCATGGCCTGCCGCTACCCGGGCGGTGTCACCGGCCCCGAGGAGCTG<br>TGGGAGCTGGTGGCCGGAGGCCGGGACGCGATCGGGCCGTTCCCCGTGGACCGGGGCTG<br>GGACGTGGCGTCGGTGTACGACCCGGATCCCGAGTCGAAGGGCACCACGTACTGCCGGG<br>AGGGCGGGTTCCTGGAAGGCGCCGGTGACTTCGACGCCGCCTTCTTCGGCATCTCGCCGC<br>GCGAGGCCCTGGTGATGGACCCGCAGCAGCGGCTGCTGCTGGAGGTGTCCTGGGAGGCGC<br>TGGAACGCGCGGGCATCGACCCGTCCTCGCTGCGCGGCAGCCGCGGTGGTGTCTACGTGG<br>GCGCCGCGCACGGCTCGTACGCCTCCGATCCCCGGCTGGTGCCCGAGGGCTCGGAGGGCT<br>ATCTGCTGACCGGCAGCGCCGACGCGGTGATGTCCGGCCGCATCTCCTACGCGCTCGGTC<br>TCGAAGGACCGTCCATGACGGTGGAGACGGCCTGCTCCTCCTCGCTGGTGGCGCTGCATC<br>TGGCGGTACGGGCGCTGCGGCACGGCGAGTGCGGGCTCGCGCTGGCGGGCGGGGTGGCG<br>GTGATGGCCGATCCGGCGGCGTTCGTGGAGTTCTCCCGGCAGAAGGGGCTGGCCGCCGAC<br>GGCCGCTGCAAGGCGTTCTCGGCCGCCGCCGACGGCACCGGCTGGGCCGAGGGCGTCGGC<br>GTGCTCGTCCTGGAGCGGCTGTCGGACGCGCGCCGCGCGGGGCACACGGTCCTCGGCCTG<br>GTCACCGGCACCGCGGTCAACCAGGACGGTGCCTCCAACGGGCTGACCGCGCCCAACGGC<br>CCAGCCCAGCAACGCGTCATCGCCGAGGCGCTCGCCGACGCCGGGCTGTCCCCGGAGGAC<br>GTGGACGCGGTCGAGGCGCACGGCACCGGCACCCGGCTCGGCGACCCCATCGAGGCCGG<br>GGCGCTGCTCGCCGCCTCCGGACGGAACCGTTCCGGCGACCACCCGCTGTGGCTCGGCTC<br>GCTGAAGTCCAACATCGGGCATGCCCAGGCCGCCGCCGGTGTCGGCGGCGTCATCAAGAT<br>GCTCCAGGCGCTGCGGCACGGCTTGCTGCCCCGCACCCTCCACGCCGACGAGCCGACCCC<br>GCATGCCGACTGGAGCTCCGGCCGGGTACGGCTGCTCACCTCCGAGGTGCCGTGGCAGCG<br>GACCGGCCGGCCCCGGCGGACCGGGGTGTCCGCCTTCGGCGTCGGCGGCACCAATGCCCA<br>TGTCGTCCTCGAAGAGGCACCCGCCCCGCCCGCGCCGGAACCGGCCGGGAGGCCCCCGG<br>CGGCTCCCGCGCCGCAGAAGGGGCGGAAGGGCCCCTGGCCTGGGTGGTCTCCGGACGCG<br>ACGAGCCGGCCCTGCGGTCCCAGGCCCGGCGGCTCCGCGACCACCTCTCCCGCACCCCCG<br>GGGCCCGCCCGCGTGACATCGCCTTCTCCCTCGCCGCCACGCGCGCAGCCTTTGACCACCG<br>CGCCGTGCTGATCGGCTCGGACGGGGCCGAACTCGCCGCCGCCCTGGACGCGTTGGCCGA<br>AGGACGCGACGGTCCGGCGGTGGTGCGCGGAGTCCGCGACCGGGACGGCAGGATGGCCT<br>TCCTCTTCACCGGGCAGGGCAGCCAGCGCGCCGGGATGGCCCACGACCTGCATGCCGCCC<br>ATACCTTCTTCGCGTCCGCCCTCGACGAGGTGACGGACCGTCTCGACCCGCTGCTCGGCCG<br>GCCGCTCGGCGCGCTGCTGGACGCCCGACCCGGCTCGCCCGAAGCGGCACTCCTGGACCG<br>GACCGAGTACACCCAGCCGGCGCTCTTCGCCGTCGAGGTGGCGCTCCACCGGCTGCTGGA<br>GCACTGGGGGATGCGCCCCGACCTGCTGCTGGGGCACTCGGTGGGCGAACTGCCGGCCGC<br>CCACGTCGCGGGTGTGCTCGATCTCGACGACGCCTGCGCGCTGGTGGCCGCCCGCGGCAG<br>GCTGATGCAGCGCCTGCCGCCCGGCGGCGCGATGGTCTCCGTGCGGGCCGGCGAGGACGA<br>GGTCCGCGCACTGCTGGCCGGCCGCGAGGACGCCGTCTGCGTCGCCGCGGTGAACGGCCC<br>CCGGTCGGTGGTGATCTCCGGCGCGGAGGAAGCGGTGGCCGAGGCGGCGGCGCAGCTCG<br>CCGGACGAGGCCGCCGCACCAGGCGGCTCCGCGTCGCGCACGCCTTCCACTCACCCCTGA<br>TGGACGGCATGCTCGCCGGATTCCGGGAGGTCGCCGCCGGCCTGCGCTACCGGGAACCGG<br>AGCTGACGGTCGTCTCCACGGTCACGGGGCGGCCCGCCCGCCCCGGTGAACTCACCGGCC<br>CCGACTACTGGGTGGCCCAGGTCCGTGAGCCCGTGCGCTTCGCGGACGCGGTCCGCACGG<br>CACACCGCCTCGGAGCCCGCACCTTCCTGGAGACCGGCCCGGACGGCGTGCTGTGCGGCA<br>TGGCAGAGGAGTGCCTGGAGGACGACACCGTGGCCCTGCTGCCGGCGATCCACAAGCCC<br>GGCACCGCGCCGCACGGTCCGGCGGCTCCCGGCGCGCTGCGGGCGGCCGCCGCCGCGTAC<br>GGCCGGGCGCCCGGGTGGACTGGGCCGGGATGCACGCCGACGGCCCCGAGGGGCCGGC<br>CCGCCGCGTCGAACTGCCCGTCCACGCCTTCCGGCACCGCCGCTACTGGCTCGCCCCGGG<br>CCGCGCGGCGGACACCGACGACTGGATGTACCGGATCGGCTGGGACCGGCTGCCGGCTGT<br>GACCGGCGGGGCCCGGACCGCCGGCCGCTGGCTGGTGATCCACCCCGACAGCCCGCGCTG<br>CCGGGAGCTGTCCGGCCACGCCGAACGCGCGCTGCGCGCCGCGGGCGCGAGCCCCGTACC<br>GCTGCCCGTGGACGCTCCGGCCGCCGACCGGGCGTCCTTCGCGGCCACTGCTGCGCTCCGC<br>CACCGGACCTGACACACGAGGTGACACAGCCGCGCCCGTGGCCGGTGTGCTGTCGCTGCT<br>GTCCGAGGAGGATCGGCCCATCGCCAGCACGCCCCGGTACCCGCCGGGGTCCTGGCGAC<br>GCTGTCCCTGATGCAGGCTATGGAGGAGGAGGCGGTGGAGGCTCGCGTGTGGTGCGTCTC<br>CCGCGCCGCGGTCGCCGCCGCCGACCGGGAACGGCCCGTCGGCGCGGGCGCCGCCCTGTG<br>GGGGCTGGGGCGGGTGGCCGCCCTGGAACGCCCCACCCGGTGGGGCGGTCTCGTGGACCT<br>GCCCGCCTCGCCGGTGCGGCGCACTGGGCGGCCGCCGTGGAACGGCTCGCCGGTCCCGA<br>GGACCAGATCGCCGTGCGCGCGTCCGGCAGTTGGGGCCGGCGCCTCACCAGGCTGCCGCG<br>CGACGGCGGCGGCCGGACGGCCGCACCCGCGTACCGGCCGCGCAGCCGGTGCTCGTCA<br>CCGGTGGCACCGGCGCGCTCGGCGGGCATCTCGCCCGCTGGCTCGCCGCGGCGGGCGCCG<br>AACACCTGGCGCTCACCCAGCCGCCGGGGCCCGGACGCGCCCGGCGCCGCCGGACTCGAG<br>GCCGAACTCCTCCTCCTGGGCGCCAAGGTGACGTTCGCCGCCTGCGACACCGCCGACCGC<br>GACGGCCTCGCCCGGGTCCTGCGGGCGATACCGGAGGACACCCCGCTCACCGCGGTGTTC<br>CACGCCGCGGGCGTACCGCAGGTCACGCCGCTGTCCCGTACCTCGCCCGAGCACTTCGCC | 31 |

| Name | Sequence | SEQ ID NO: |
|---|---|---|
| | GACGTGTACGCGGGCAAGGCGGCGGGCGCCGCGCACCTGGACGAACTGACCCGCGAACT<br>CGGCGCCGGACTCGACGCGTTCGTCCTCTACTCCTCCGGCGCCGGCGTCTGGGGCAGCGC<br>CGGCCAGGGTGCCTACGCCGCCGCCAACGCCGCCCTGGACGCGCTCGCCCGGCGCCGTGC<br>GGCGGACGGACTCCCCGCCACCTCCATCGCCTGGGGCGTGTGGGGCGGCGGCGGTATGGG<br>GGCCGACGAGGCGGGCGCGGAGTATCTGGGCCGGCGCGGTATGCGCCCCATGGCACCGG<br>TCTCCGCGCTCCGGGCGATGGCCACCGCCATCGCCTCCGGGGAACCCTGCCCCACCGTCA<br>CCCACACCGACTGGGAGCGCTTCGGCGAGGGCTTCACCGCCTTCCGGCCCAGCCCTCTGA<br>TCGCGGGGCTCGGCACGCCGGGCGGCGGCCGGGCGGCGGAGACCCCCGAGGAGGGGAAC<br>GCCACCGCTGCGGCGGACCTCACCGCCCTGCCGCCCGCCGAACTCCGCACCGCGCTGCGC<br>GAGCTGGTGCGAGCCCGGACCGCCGCGGCGCTCGGCCTCGACGACCCGGCCGAGGTCGCC<br>GAGGGCGAACGGTTCCCCGCCATGGGCTTCGACTCCCTGGCCACCGTACGGCTGCGCCGC<br>GGACTCGCCTCGGCCACGGGCCTCGACCTGCCCCCCGATCTGCTCTTCGACCGGGACACC<br>CCGGCCGCGCTCGCCGCCCACCTGGCCGAACTGCTCGCCACCGCACGGGACCACGGACCC<br>GGCGGCCCCGGGACCGGTGCCGCGCCGGCCGATGCCGGAAGCGGCCTGCCGGCCCTCTAC<br>CGGGAGGCCGTCCGCACCGGCCGGGCCGCGGAAATGGCCGAACTGCTCGCCGCCGCTTCC<br>CGGTTCCGCCCCGCCTTCGGGACGGCGGACCGGCAGCCGGTGGCCCTCGTGCCGCTGGCC<br>GACGGCGCGGAGGACACCGGGCTCCCGCTGCTCGTGGGCTGCGCCGGGACGGCGGTGGC<br>CTCCGGCCCGGTGGAGTTCACCGCCTTCGCCGGAGCGCTGGCGGACCTCCCGGCGGCGGC<br>CCCGATGGCCGCGCTGCCGCAGCCCGGCTTTCTGCCGGGAGAACGAGTCCCGGCCACCCC<br>GGAGGCATTGTTCGAGGCCCAGGCGGAAGCGCTGCTGCGCTACGCGGCCGGCCGGCCCTT<br>CGTGCTGCTGGGGCACTCCGCCGGCGCCAACATGGCCCACGCCCTGACCCGTCATCTGGA<br>GGCGAACGGTGGCGGCCCCGCAGGGCTGGTGCTCATGGACATCTACACCCCCGCCGACCC<br>CGGCGCGATGGGCGTCTGGCGGAACGACATGTTCCAGTGGGTCTGGCGGCGCTCGGACAT<br>CCCCCCGGACGACCACCGCCTCACGGCCATGGGCGCCTACCACCGGCTGCTTCTCGACTG<br>GTCGCCCACCCCCGTCCGCGCCCCGTACTGCATCTGCGCGCCGCGGAACCCATGGGCGA<br>CTGGCCACCCGGGGACACCGGCTGGCAGTCCCACTGGGACGGCGCGCACACCACCGCCG<br>GCATCCCCGGAAACCACTTCACGATGATGACCGAACACGCCTCCGCCGCCGCCCGGCTCG<br>TGCACGGCTGGCTCGCGGAACGGACCCCGTCCGGGCAGGGCGGGTCACCGTCCCGCGCGG<br>CGGGGAGAGAGGAGAGGCCGTGA | |
| RBS + momAVI | TCAGGAGTGGGAAGACATGCCGGGTACGAACGACATGCCGGGTACCGAGGACAAGCTC<br>CGCCACTACCTGAAGCGAGTGACCGCGGATCTCGGACAGACCCGTCAGCGCCTGCGCGAC<br>GTGGAGGAGCGCCAGCGGGAACCGATCGCCATCGTCGCGATGGCCTGCCGCTACCCGGGC<br>GGGGTGGCCTCCCCCGAGCAGCTGTGGGACCTGGTCGCCTCACGCGGCGACGCCATCGAG<br>GAGTTCCCCGCCGACCGCGGCTGGACGTGGCGGGCCTCTACCACCCCGACCCGGACCAC<br>CCCGGCACGACCTATGTACGAGAGGCCGGATTCCTGCGGGACGCCGCCCGCTTCGACGCC<br>GACTTCTTCGGCATCAACCCGCGCGAGGCGCTCGCCGCCGACCCGCAGCAACGGGTGCTC<br>CTCGAAGTGTCGTGGGAACTGTTCGAGCGGGCGGGCATCGACCCCCGCCACGCTCAAGGAC<br>ACCCTCACCGGCGTGTACGCGGGGGTGTCCAGCCAGGACCACATGTCCGGGAGCCGGGTC<br>CCGCCGGAGGTCGAGGGCTACGCCACCACGGGAACCCTCTCCAGCGTCATCTCCGGCCGC<br>ATCGCCTACACCTTCGGCCTGGAGGGCCCGGCGGTGACGCTCGACACGGCGTGCTCGGCA<br>TCGCTGGTCGCGATCCACCTCGCCTGCCAGGCCCTGCGCCAGGGCGACTGCGGCCTGGCG<br>GTGGCGGGAGGCGTGACCGTACTGTCCACGCCGACGGCGTTCGTGGAGTTCTCACGCCAG<br>CGCGGACTCGCACCGGACGGCCGCTGCAAGCCGTTCGCCGAGGCCGCCGACGGCACCGG<br>ATTCTCCGAGGGCGTCGGCCTGATCCTCCTGGAACGCCTCTCCGACGCCCGCCGCAACGG<br>ACATCAAGTACTCGGCGTCGTACGCGGATCGGCCGTCAACCAGGACGGCGCGAGCAACG<br>GCCTGACCGCCCCGAACGACGTCGCCCAGGAACGCGTGATCCGCCAGGCCCTGACCAACG<br>CCCGCGTCACCCCGGACGCCGTCGACGCCGTGGAGGCACACGGCACCGGCACCACGCTCG<br>GCGACCCGATCGAGGGGAACGCACTCCTCGCCGACGTACGGAAAGGACCGCCCCGCCGAC<br>CGGCCGCTGTGGCTCGGCTCTGTGAAGTCGAACATCGGCCACACGCAGGCGGCTGCGGGC<br>GTCGCAGGCGTCATCAAGATGGTGATGGCGATGCGCCACGGCGAGCTGCCCGCCTCCCTG<br>CACATCGACCGGCCCACGCCCCACGTGGACTGGGAGGGCGGGGAGTGCGGTTGCTCACC<br>GATCCCGTGCCGTGGCCACGGGCCGACCGCCCCGCCGCGCGGGGTCTCCTCCTTCGGC<br>ATCAGCGGCACCAACGCCCACCTGATCGTGGAACAGGCCCCCGCCCCGCCCGACACGGCC<br>GACGACGCCCCGGAAGGCGCCGCAACCCCGGCGCTTCCGACGGCCTCGTGGTGCCGTGG<br>GTGGTGTCGGCCCGTAGTCCGCAGGCCCTGCGTGATCAGGCCCTGCGTCTGCGCGACTTTG<br>CCGGTGACGCGTCCCGAGCGCCGCTCACCGACGTGGGCTGGTCTTTGCTGCGGTCGCGTG<br>CGCTGTTCGAGCAGCGGGCGGTGGTGGCGGGGCGTGAGAGGGCTGAACTGCTGGCGGGG<br>CTGGCTGCGTTGGCCGCTGGTGAGGAGCACCCGGCTGTGACGCGGTCCCGTGAGGAAGCG<br>GCGGTTGCTGCGAGCGGTGATGTGGTGTGGCTGTTCAGTGGTCAGGGCAGTCAGTTGGTC<br>GGTATGGGTGCTGGTTTGTATGAGCGGTTCCCGGTGTTTGCGGCTGCGTTTGATGAGGTGT<br>GCGGCTTGCTGGAGGGGAGCTGGGGGTTGGTTCGGGTGGGTTGCGGGAGGTGGTGTTCT<br>GGGGCCCGCGGGAGCGGTTGGATCACACGGTGTGGGCGCAGGCGGGGTTGTTTGCGTTGC<br>AGGTGGGGTTGGCCCGGTTGTGGGAGTCGGTCGGGGTGCGGCCGGATGTGGTGCTCGGGC<br>ATTCGATCGGTGAGATCGCGGCCGCGCATGTGGCGGGGGTCTTTGATCTGGCGGATGCGT<br>GTCGGGTGGTGGGGGCGCGGGCGCGTTTGATGGGTGGGTTGCCTGAGGGTGGGGCGATGT<br>GTGCGGTGCAGGCCACGCCCGCCGAGCTGGCCGCGGATGTGGATGGCTCGTCCGTGAGTG<br>TGGCGGCGGTCAACACACCTGACTCGACGGTGATTTCAGGTCCGTCGGGTGAGGTGGATC<br>GGATTGCTGGGGTGTGGCGGGAGCGTGGGCGTAAGAGAAGGCGCTGAGCGTGAGTCAT<br>GCTTTCCATTCGGCGTTGATGGAGCCGATGCTCGGGGAGTTCACGGAAGCGGATACGAGGG<br>GTCAAGTTCAGGCAGCCGTCGATCCCGCTCATGAGCAATGTCTCCGGAGAGCGGGCCGGC<br>GAGGAGATCACATCCCCGGAGTACTGGGCGAGGCATGTACGCCAGACAGTGCTCTTCCAG<br>CCCGGCGTCGCCCAAGTGGCCGCTGAGGCACGCGCGTTCGTCGAACTCGGCCCCGGCCCC<br>GTACTGACCGCCGCCGCCCAGCACACCCTCGACCACATCACCGAGCCGGAAGGCCCCGAG | 32 |

| Name | Sequence | SEQ ID NO: |
|------|----------|------------|
| | CCGGTCGTCACCGCGTCCCTCCACCCCGACCGGCCGGACGACGTGGCCTTCGCGCACGCC<br>ATGGCCGACCTCCACGTCGCCGGTATCAGCGTGGACTGGTCGGCGTACTTCCCTGACGAC<br>CCCGCCCCCGCACCGTCGACCTGCCCACCTACGCCTTCCAGGGGCGGCGCTTCTGGCTGG<br>CGGACATCGCGGCGCCCGAGGCCGTGTCCTCGACGGACGGTGAGGAGGCCGGGTTCTGG<br>GCCGCCGTCGAAGGTGCGGACTTCCAGGCGCTCTGCGACACCCTGCACCTCAAGGACGAC<br>GAGCACCGCGCGGCTCTGGAGACGGTGTTCCCCGCGCTGTCCGCGTGGCGGCGCGAACGA<br>CGTGAGCGGTCGATCGTCGATGCCTGGCGGTACCGGGTCGACTGGCGGCGCGTCGAGCTG<br>CCGACACCCGTTCCGGGCGCCGGTACCGGTCCCGACGCCGACACGGGCCTCGGGGCGTGG<br>CTGATCGTGGCTCCCACGCACGGGTCGGGTACTTGGCCGCAAGCCTGTGCCCGGGCGTTG<br>GAGGAGGCGGGCGCGCCGGTACGTATCGTCGAGGCCGGCCCGCACGCCGACCGGGCGGA<br>CATGGCGGACCTGGTCCAGGCATGGCGGGCAAGCTGTGCGGACGACACCACCCAGCTCG<br>GAGGAGTGCTCTCCCTGCTGGCTCTCGCCGAGGCACCGGCCACCAGTTCCGACACCACTT<br>CCCACACCAGTACCAGTTGCGGTACCGGCTCTCTCGCGTCCCACGGCCTCACCGGCACCTT<br>GACGCTGCTGCACGGTCTGCTGGATGCGGGCGTCGAAGCGCCTCTCTGGTGTGCCACGCG<br>CGGCGCCGTGTCGTGCGGCGACGCCGATCCGCTCGTCTCCCCGTCGCAGGCCCCGGTCTG<br>GGGACTCGGACGCGTGGCCGCCCTGGAGCATCCGGAGTTGTGGGGCGGCCTGGTCGACCT<br>GCCCGCCGACCCGGAGTCGCTCGACGCGAGCGCGTTGTATGCGGTTCTGCGCGGAGACGG<br>CGGCGAGGATCAGGTCGCGCTGCGCCGGGGCGCGGTCCTCGGCCGTCGCCTGGTGCCCGA<br>CGCAACCCCGGACGTGGCCCCCGGCTCGTCCCCGGACGTGTCCGGAGGCGCAGCCCATGC<br>CGACGCGACCTCCGGGGAGTGGCAGCCGCATGGTGCCGTCCTCGTCACCGGAGGCGTCGG<br>CCACCTGGCCGATCAGGTCGTACGGTGGCTCGCCGCGTCCGGCGCGCAACACGTCGTACT<br>CCTGGACACGGGCCCCGCCAACAGCCGTGGTCCCGGCCGGAACGACGACCTCGCCGCGG<br>AAGCCGCCGAACACGGCACCGAGCTGACGGTCCTGCGGTCCCTGAGCGAGCTGACAGAC<br>GTATCCGTACGTCCCATACGGACCGTCATCCACACATCGCTGCCCGGCGAGCTCGCGCCG<br>CTGGCCGAGGTCACCCCCGACGCGCTCGGCGCGGCCGTGTCCGCCGCCGCGCGGCTGAGC<br>GAACTCCCCGGCATCGGGTCAGTGGAGACCGTGCTGTTTCTTCCTCCGTGACGGCTTCGC<br>TCGGCAGTAGGGAGCACGGCGCGTACGCCGCCGCCAACGCCTACCTCGACGCCCTGGCGC<br>AACGGGCCGGTGCCGATGCTGCGAGCCCCCGGACGGTCTCGGTCGGGTGGGGCATCTGGG<br>ATCTGCCGGACGACGGTGACGTGGCACGCGGCGCCGCCGGGCGTGTCCGGAGGCAGGGA<br>CTCCCGCCGCTGGAACCGCAGTTGGCGCTCGGCGCCCTGCGCGCGGCGCTCGACGGGGGC<br>AAGGGGCACACGCTGGTCGCCGACATCGAGTGGGAGCGGTTCGCGCCGCTGTTCACGCTG<br>GCCAGGCCCACCCGGCTGCTCGACGGGATCCCCGCGCCCAGCGGGTCCTCGACGCCTCC<br>TCGGAGAGCGCCGAGGCCTCGGAGAACGCCTCGGCCCTCCGTCGCGAACTGACGGCCCTG<br>CCCGTGCGGGAGCGGACCGGGGCACTTCTCGACCTGGTCCGCAAACAGGTGGCCGCCGTC<br>CTGCGCTACGAGCCGGGCCAAGACGTGGCGCCCGAGAAGGCCTTCAAGGACCTGGGCTTC<br>GACTCGCTCGTGGTCGTGGAGCTGCGCAACCGGCTGCGCGCCGCCACCGGGCTCCGGCTG<br>CCCGCCACCCTGGTCTACGACTACCCCACACCCCGCACCCTCGCCGCACACCTGCTGGAC<br>AGGGTGCTGCCCGACGGCGGCGGCAGAGCTCCCCGTGGCCGCCCACCTGGACGACCTG<br>GAGGCGGCCCTCACCGACCTGCCGGCCGACGACCCCGGCGCAAGGGCCTGGTCCGGCGT<br>CTACAGACGCTGCTGTGGAAGCAGCCCGACGCCATGGGGGCGGCGGGCCCCGCCGACGA<br>GGAGGAGCAAGCCGCGCCCGAGGACCTGTCGACCGCGAGCGCCGACGACATGTTCGCCC<br>TGATCGACCGGGAGTGGGGCACGCGGTGA | |
| RBS + amphK | TGACCCGGGCCCACCCCAACTACGTGCGAAACATCTGAGGAAGGTTCAACGGACGATGCC<br>GGACGAAAGTAAGCTCGTCGATTACCTGAAGTGGGTCACGGCGGATCTCCACCAGACCCG<br>CAGGCGCCTCCAGGAAGCCGAGTCGGGCCGCCACGAGCCCGTGGCGATCGTCGGCATGG<br>CGTGCCGCTTCCCCGGCGGTGTGCGTTCCCCGGAGGACCTCTGGGAGATGCTCGCCGACG<br>GCCGCGACGCCATCTCCGGGTTCCCCGCCGACCGCGGCTGGGACCTGGAGACGCTGGCCG<br>GCGACGGAGCGGGCGGCAGCAGCACGCAGGAGGGAGGTTTCCTGCACGACGTGGCCGAC<br>TTCGACCCGGGGTTCTTCGACATCTCGCCCCGCGAGGCGCTGGCCATGGACCCGCAGCAG<br>CGGCTGCTCCTGGAGACCGCCTGGGAGGCCGTGGAGCGTGCCGGGATCGCCCCCGGCAGC<br>CTCCGCGGCAGCCGCACCGGCGTGTTCGTCGGCACCAACTCGCAGGACTACGCCCACCTC<br>GTCCTCGCCTCCGACGACGACATGGGCGGCTACGCGGGCAACGGCCTGGCCGCCAGCGTG<br>ATGTCCGGCCGGCTGTCCTTTGCGCTCGGCTTCGAAGGACCCGCCGTCACCCTCGACACCG<br>CGTGCTCCTCGGCCCTGGTCGCCCTGCACCTGGCCGCCCAGTCGGTGCGCTCCGGCGAGG<br>CCGACCTCGCGCTGGCCGGCGGTGTCACCGTCATGACCACCTCGTCCAGCTTCGTGGGCTT<br>CAGCCTCCAGGGCGGCCTCGCCACGGACGGCCGCTGCAAGGCGTTCGCCGACTTCGCCGA<br>CGGCACCGGCTGGTCCGAGGGCGTCGGCATGATCCTCGTCGAACGGCTCTCCGAGGCCCG<br>GCGCAAGGGCCACCCGGTGCTCGCCGTGCTGCGCGGCTCCGCCGTGAACCAGGACGGCGC<br>CTCCAACGGCCTCAGCGCCCCAACGGGCCCGCCCAGCAGCGCGTCATCCGCGACGCGCT<br>GGCCTCCGCCGGGCTCTCGCCCGCCGACGTCGACGCCGTCGAGGCGCACGGCACCGGCAC<br>CACCCTCGGCGACCCCATCGAGGCGCAGGCCCTGCTCGCCACCTACGGCCAGGACCGCGA<br>CGCGAGCCGTCCGCTGCCCTCGGCACGGTGGAAGTCCAACATCGGCCACACCCAGGCCGC<br>CGCCGGCGCCGCGGGCGTCATCAAGATGGTCCTGGCCCTGCGCCACGGGCTGCTGCCCCG<br>CACCCTGCACATCGACGCGCCGTCCACACACGTCGACTGGGACGCAGGACACGTCAGCCT<br>GCTCACCGAGGCCACCCCCTGGCCCGAGGGCGAGCAGACGCGCCGGGCCGGTGTGTCGTC<br>CTTCGGCATCAGCGGCACCAACGCCCATGTCATCCTCGAAGAGGCCCCCGCGGCCGAGGA<br>GGACACCGACGCGAGCAGCGGCCCGAGCCGGTCGTCCCGGGCGCCGTGCCGTGGCCCGT<br>GTCGGCCCGTACCGCCGACGCCCTCGACGCCCAGCTGGAGAAGGTGCGGCCGCTCGCCGC<br>GTCCGGCGCCGACCCCGTCGCCGTCGGCCACGCCCTGGCCGTCACCCGCACCCCCTTCGA<br>ACACCGGGCGCTGCTGGTCGCCGCGGACGGCAATCTCACCGAGGCCGCACGCGGCACCGT<br>CCCCTCCGGCGACCGCCCCGGGCTGGCCGTGCTGTTCTCGGGCAGGGCGCCCAGCGCCT<br>CGGCATGGGCCGTGAACTCCACGCCCGCTTCCCGGTGTTCGCCGCCGCCCTGGACGAGAC<br>CCTCGCCCTCCTCGACGAGCGCCTCGGCCACTCGCTGCGCGACGTCATCTGGGGCGAGGA | 33 |

-continued

| Name | Sequence | SEQ ID NO: |
|---|---|---|
| | CCCCGTGGCCCTCGACGACACCGGCCACACCCAGCCCGCGCTGTTCGCCGTGGAGGTCGC<br>CCTCTACCGCCTGTTCGCCTCCTGGGGTCTGCGCCCCGACCACCTCGCCGGACACTCCGTC<br>GGGGAGATCGCCGCCGTGCATGTGGCCGGCGCACTGTCCCTGGAGGACGCCTGCACCCTG<br>GTTGCCGCCCGCGCCGGCCTGATGCGGGACCTGCCGGCCGGCGGAGCCATGGTCGCGCTG<br>CGCGCCACCGAGGCCGAGGTGCGGCCGCTGCTCGACGAGCGGGTCTCGCTCGCCTCGGTC<br>AACGGCCCCGATTCCGTGGTGGTCTCCGGCGCCGAGGACGCCGTCCTCGCCGTCGCCGAG<br>CACTTCCGGAAGCAGGACCGGCGCACCACGCGGCTCTCCGTGAGCCACGCCTTCCACTCC<br>CCGCTCGTCGACCCGATGCTCGACGCCTTCCGGGACGTCGTCGCGAAGCTCACCTTCGGC<br>GAGCCGTCGGTACCCGTCGTCTCCACCCTCACCGGCGACGTCGTCGCCGCCGAGGAACTG<br>GCCACGCCGCACTACTGGGTGTGCCACGCCCGGCAGGCCGTCCGCTTCGCCGACGCCGTG<br>CGCACCCTCGTCGACGAGGGCGCCCGGACCTTCCTGGAGGTCGGCCCGGGCGGCGTGCTG<br>TCCGCGCTCGTCGGTGAGAACACCCAGGAGGCCGGGGTCTCTGCCGTGCCCGCGCTGCGC<br>AAGGACCAGCCGGAGGAGGCCTCCGTGCTCGCGCCCTCGGCACCCTGTGGACCCGGGGC<br>ACCGCGGCCGACTGGGACGCCGTGTTCGAGGGCACCCTGCCCGGCCGCCCGGAGTCCGTG<br>GACCTGCCGACCTACGCCTTCCAGCGCGGCCGGTACTGGCCCACCGTGCGCGCCCGCTCC<br>GGCGACCCCGCCGGACTGGGCCTCGGCGCCGCCGGGCACCCGCTGCTCAGCGCCACCGTC<br>ACCCTCGCCGAGGCCGACGAGTCCGTCCTCACCGGACGGCTCTCGCCGCTGACCCACCCC<br>TGGCTCACCGAGCACCGCGTCGACGGCCGGATCACCGTCCCCGGCACGGCCCTCGTGGAG<br>ATCGCGGTCCGTGCGGGCGACGAGAACGGCACCCCCGCCTGGACCGGCTCGACCTGCTC<br>GCCCCGCTGACCCTCGGCGACCGCGACGCGGTGCTGCTCCAGGTGCGCGTCGGCCCCGAG<br>GACGCCTCCGGCCGGCGGACGCTCTCCGTGCACGCCCGCCCGGCGACCGCGGACGACGCC<br>CCCTGGACCACGTACGCCCGTGGTGTCCTCGCCCCCGACGAGGGCGCCGAGGACACCGCC<br>GCGGACCTTGTGGAGTGGCCGCCCGCCGACGCCCGTCAGGTCCCGCTCACGGAGCTGGAG<br>TCCGAAGGACGCGCCCTCGGCCCGCTCTTCAGCGGCCTCACCGGGGTGTGGCGGCACGAG<br>GGCGAGGTGTTCGCCGAGGCCGAGCTGCCCGCAGGACCCGACAGCGGCTTCGGACTGCAC<br>CCCGCGCTGCTGTCCACCGCCCTGCGCGCCGCCGCCGTCCTCGACGGCACCACGGCCGGC<br>GAGCCCGCCGCCTTCGAGGGGCTCACCCTGCACGCCACCGGCGCCACCGCGCTGCGCGTA<br>CGGCTGAGCACCACCGGGCCCGACACCGTCGACCTCACCGCCGTCGACCCCGCGGGCAAC<br>CTCGTCCTGACCGCCGAGACCGTGCGTCTCGGCACCCCGGACGGCACCGCCGACACCCCG<br>GCCGCCACCGGCCGGGGCGACCTGTTCGGGCTGAAGTGGGTGCCCGTCAAGGCCTCGGAG<br>CGCGCCACCGGCACCCGCTGGGCCGTCGTCGGCTCCGACGAACTCGACCTCGGCTACGCC<br>ATGCACCGCGCCGACGAGACCGTCACCGCCTACGCGGAGTCCCTCGGCGGCGCCATCGGC<br>GACAGCGGGGTCGCCCCCGATGTGTTCCTGATCCCGCTCGCAGGCGAGAAGGACGCCGGA<br>GCGGAGGGCGTGCACGCCCTCACCACCCGGGTCCTCGGCTACCTCCAGGAGTGGCTGTCC<br>GAGCCCCGGCTCTCCGGCACCCGCCTGGTCTTCGTCACCCGCCGCGCCGTCGCCCTCGACG<br>ACGAGGACGTCCTGGACCCGGCCGGCGCGGCCGTCTGGGGCCTGGTGCGCTCCGCGCAGA<br>CCGAGAACCCCGGCAGCCTGCTGCTCGTCGACCTCGACGACACCTTCCTGTCCGCCGGAG<br>TACTGCCCGACGTGCTGACGCTCGACGAGCAGCAGCTCGCGGTCCGCGACTACCAGGTCC<br>GCGCCGCCCGGCTCGCCCGGCTGCCGCGCCCGGCCGACGACGCCCCGCCGCCGACTGGA<br>ACCCCGACGGCACCGTCCTGATCACCGGCGGCACCGGCGGCCTCGGCGCCGCGCTCGCCC<br>GGCACCTGGTCACCAGCCGGGGCGCCCGTCACCTGCTGCTGGCGAGCCGCCGCGGCCCGG<br>ACGCGCCCGGCACGTCCGAACTGGTCGCCGAGCTGACCGGCCTGGGAGCCCAGGTGACCG<br>TCTCCGCCTGCGACGTCGGCGACCGCGACGCGGTCGACACGCTCGTCGCGTCGGTGCCCG<br>CCGAGCACCCGCTGACCGCCGTCGTGCACACCGCGGGTGTCCTGGACGACGCCCTGACCG<br>GCTCGCTCACCCCGGAACAACTGGCTGGTGTGCTGCGCCCCAAGGCCGACGCGGCCCTGC<br>ACCTGCACGAGGCGACCCTCGGCCAGGACCTCGCCGCGTTCGTGCTGTACTCCTCGATCTC<br>CGGCGTCATCGGCGGCCCCGGCCAGGCCAACTACGCCGCCGCCAACGCCTCCCTGGACGC<br>GCTCGCCCACCGGCGCAGGGCGGCCGGTCTGCCCGGTCTGTCCCTCGCCTGGGGGCCCTG<br>GGGCCGCGGCAGCGGCATGACCAGCCAGGTCAGCGACACCGACCTGGGGCGGATGGACC<br>GCGGCGGCACCCCGCCGATGAGCCTCGAGGACGGCCTCGCCCTGTTCGACGCGCCCTGG<br>CCCGCACCGAGCCGATGGTCGTGCCCACCCGGATCAATGTCACCGGACTCCAGGTCCAGC<br>AGACGCTGCCCGCGCTCTGGCGCGACCTGGTGCCGCGCCCCGGCGCACCGCCGCCGCGG<br>ACCGCTCGCCCAAGACCGTGCTCGACGGGCTGCGCACGCTCGACACCGCGGGCCGGGAG<br>AAGCTGCTCACCGAGCTGGTCGTCGGCTTCACCGCGGGCCTGCTCGGCCACGCCGACCCC<br>GCCGCCGTCGACCCCGAGCGCGGCTTCCTGGAGCTGGGCTTCGACTCGCTGGTCTCGGTC<br>AGCCTGCGCAACCAGCTCGGCGAACTCCTCGGGCTGCGCCTGCCGACGTCGGTGGTCTTC<br>GACAGCAAGACGCCGGTGAAGCTGGCCCGCCACCTCAACGAGGAACTGGGCGACCTGTC<br>CGCCTCCGGCCCCGCGTCCGGCACCGCCGTCGCCGGCACCACGGTGCATCCCGACGACAC<br>CCTGGTCGGCCTGTTCCACAACGCGGTGCGCGGCGGCAAGCTCGTCGAGGCGATGCGGAT<br>GCTGAAGGCGGTCGCCAACACCCGGCCCACCTTCGAGACGCCCGGGACCTGGAGGAGCT<br>GTCCGAGGCCGTCACCCTGGCCACGGGGCCCGGCTCCCCGCGCGTGATCTTCGTCAGCGC<br>GCCCGGCGCCACCGGCGGTGTCCACCAGTACGCGCGCATCGCCGCCCACTTCCGCGGCAA<br>GCGCCATGTGTCGGCGATACCGCTGATGGGCTTCGCCCCCGGCGAGCTGCTGCCCGCCAC<br>CAGTGAGGCGCGGCCCGGATCGTCGCCGAGAGCGTCCTGATGGCGAGCGACGGCGAAC<br>CGTTCGTGATGGTGGGCCACTCCACCGGCGGTTCCCTCGCCTACCTCGCGGCCGGGGTGCT<br>GGAGGACACCTGGGGCGTGAAGCCGGAGGCGGTCGTCCTGCTCGACACGGCGTCCATCCG<br>GTACAACCCCTCGGAGGGCAACAACCTCGACCAGACGACCCGCTTCTACCTCGCCGACAT<br>CGACTCGCCGTCCGTGACGCTCAACAGCGCCCGGATGTCCGCGATGGCGCACTGGTTCAT<br>GGCGATGACGGACATCGACGCGCCCGCCACGACCGCCCCCACCCTGCTCCTGCGCGCCAC<br>ACAGGCCAACAACGGCTTCATGCTGGACACCTCCGCGGTGCCGGCGGACGTGGTGCGTGA<br>CATCGAGGCCGACCATCTGTCCCTGGCCATGGAGCACTCGGATCTGACCGCCGAGGCCAT<br>AGAGAACTGGCTCGCCGAACTTCCGGCCGGCGAGGCCTGA | |

| Name | Sequence | SEQ ID NO: |
|---|---|---|
| RBS + momAVIII | GCAGCGATCAGTCCTGAGCGCGATGAGCCCCGGCCACACCGGCCCCCTTGCCCTCCCCCA<br>ACCTCATACGCCCCGATCACCACGTAGCGCCAAGGAGCCTGGGTCAGATGTCGAACGAGG<br>AGAAGCTTCTCGATCACCTCAAGTGGGTCACCGCGGAGCTGCGCCAGGCCCGGCAACGGC<br>TCCACGACAAGGAATCGACCGAGCCGGTCGCCATCGTCGGCATGGCCTGCCGCTACCCGG<br>GCGGCGCCCGGTCGGCGGAGGACCTCTGGGAACTCGTGCGCGACGGGGGTGACGCGGTC<br>GCGGGGTTCCCCGACGACCGGGGCTGGGACCTGGAGTCGCTGTATCACCCGGATCCGGAG<br>CATCCGGCCACCAGCTATGTGCGGGACGGCGCCTTCCTGTACGACGCCGGCCATTTCGAC<br>GCCGAGTTCTTCGGCATCAGCCCGCGCGAGGCCACGGCGATGGATCCGCAGCAGCGGCTG<br>CTCCTGGAGACCGCGTGGGAGGCGATCGAGCACGCGGGCATGAACCCGCACGCGCTGAA<br>GGGCAGCGACACCGGCGTCTTCACCGGAGTGAGCGCCCACGACTACCTGACGCTGATCAG<br>CCAGACGGCCAGCGACGTCGAGGGGTACATCGGCACCGGCAACCTCGGCAGTGTGGTGTC<br>GGGCCGGATCTCCTACACGGTGGGGCTCGAAGGTCCCGCGGTCACCGTCGACACGGCGTG<br>CTCGTCGTCCCTGGTGGCGATCCATCTGGCAAGTCAGGCGCTGCGGCAGGGCGAGTGCTC<br>GCTCGCGCTGGCGGGCGGTTCGACGGTGATGGCGACGCCGGGTTCGTTCACCGAGTTCTC<br>CCGGCAGCGGGGCTCGCGCCCGACGGGCGGTGCAAGCCGTTCGCGGCCGCCGCCGACG<br>GCACCGGCTGGGGCGAGGGCGCCGGGTGGTGGCGCTGGAGCTGCTCTCCGAAGCGCGG<br>CGCCGCGGCCACAAGGTCCTTGCGGTGATACGGGGTTCGGCCACCCAACCAGGACGGTACG<br>AGCAACGGGCTCGCCGCCCCCAACGGCCCCTCCCAGGAACGCGTCATCCGCGCCGCCCTC<br>GCCAACGCCCGCCTCTCCGCCGAGGACATCGACGCCGTAGAGGCGCACGGCACCGGCACC<br>ACGCTCGGCGACCCCATCGAGGCGCAGGCCCTGATCGCCACGTACGGCCAGGGGCGCCCG<br>GAGGACCGTCCGCTCTGGCTCGGCTCGGTGAAATCCAACATCGGCCACACGCAGGCCGCC<br>GCCGGTGTCGCGGGCGTCATCAAGATGGTCATGGCGATGCGCAACGGTCTCCTCCCGACC<br>TCCCTGCACATCGACGCCCGTCACCGCACGTCCAGTGGGAACAGGGCAGCGTACGACTG<br>CTCTCCGAGCCGTGGACTGGCCGGCGGAGCGCACGCGGCGGGCAGGCATCTCGGCGTTC<br>GGGATCTCCGGGACGAACGCGCACCTGATTCTGGAGGAGGCGCCGCCGGAAGAGGACGC<br>GCCGGGCCCCGTGGCGGCTGAGCCGGGTGGGGTCGTGCCGTGGGTGGTGTCGGGCGGAC<br>GCCGGACGCGTTGCGTGAACAGGCGCGGCGGCTGGGCGAGTTCGCGGCCGGGCTGGCGG<br>ATGCGTCGGTCTCCGAGGTGGGCTGGTCGCTGGCCACGACACGCGCGTTGTTCGATCAGC<br>GGGCCGTGGTCGTGGGGCGGGACTTGGCTCAGGCTGGTGCCAGCCTGGAGGCATTGGCCG<br>CGGGTGAGGCGTCGGCGGATGTGGTGGCCGGGGTGGCCGGTGATGTGGGTCCTGGGCCG<br>GTGTTGGTGTTTCCGGGGCAGGGGTCGCAGTGGGTGGGCATGGGCGCCCAGCTCCTTGAC<br>GAGTCGCCCGTCTTCGCGGCGCGGATCGCGGAGTGTGAGCAGGCGCTGTCGGCGCATGTG<br>GACTGGTCGCTGAGTGATGTCTTGCGCGGGGACGGGAGCGAGCTGTCCCGGGTCGAGGTC<br>GTGCAGCCCGTGCTGTGGGCGGTGATGGTCTCGCTGGCTGCGGTGTGGGCCGATTACGGC<br>ATCACCCCGGCTGCCGTCATCGGGCACTCGCAGGGCGAGATGGCTGCCGCGTGTGTGGCG<br>GGGGCACTGTCACTGGAGGATGCGGCACGGATCGTAGCCGTACGCAGCGACGCGCTTCGT<br>CAGCTGCAAGGGCACGGCGACATGGCCTCGCTCAGCACCGGTGCCGAGCAGGCCGCAGA<br>GCTGATCGGCGACCGGCCGGGCGTAGTCGTCGCGGCCGTCAACGGACCGTCGTCGACCGT<br>GATTTCGGGCCGCCGGAGCATGTGGCAGCCGTCGTCGCCGATGCGGAGGCGCAGGGACT<br>CAGGGCCCGCGTCATCGACGTCAGGTACGCCTCCCACGGTCCCCAGATCGACCAGCTCCA<br>CGACCTCCTCACCGACCGGCTCGCCGACATCAGCCGACCACCACCGACGTGGCGTTCTA<br>CTCGACGGTCACCGCAGAGCGCCTCGACGACACCACCGCCCTAGACACCGCCTACTGGGT<br>CACCAACCTCCGCCAGCCCGTCCGCTTCGCCGACACCATCGAAGCGCTGCTGGCCGACGG<br>CTACCGCCTGTTCATCGAGGCCAGCCCCCACCCCGTCCTCAACCTCGGCATCCAGGAGAC<br>CATCGAGCAGCAGGCCGGTGCTGCGGGGACGGCCGTCACCATCCCCACCCTGCGTCGCGA<br>CCACGGTGACACCACCCAGCTCACCCGCGCGGCCGCCCACGCCTTCACCGCCGGCGCCCC<br>CGTCGACTGGCGGCGCTGGTTCCCGGCCGACCCCACCCCCGTACCGTCGACCTCCCCACC<br>TACGCCTTCCAGCACAAGCACTACTGGGTGGAGCCGCCCGCGGCGGTCGCAGCCGTGGGT<br>GGTGGGCACGATCCGGTCGAGGCCCGGGTGTGGCAGGCGATCGAGGACCTGGACATCGA<br>CGCCCTCGCCGGCAGTCTGGAGATCGAGGGGCAGGCGGAGAGCGTCGGAGCGCTGGAGT<br>CCGCGCTGCCCGTCCTCTCGGCCTGGCGGCGTCGGCACCGCGAGCAGTCCACCGTCGACT<br>CCTGGCGTTATCAGGTCACTTGGAAGCATCTGCCCGACGTGCCGGCGCCGGAGCTCAGCG<br>GGGCCTGGCTGCTGCTCGTGCCCGCCGCACGCCGACCACCCGGCCGTCCTCGCGACCG<br>CGCAGACGCTGACCGCCCATGGTGGCGAGGTGCGACGCCACGTGGTCGACGCACGTGCCA<br>TGGAGCGTACGGAGTTGGCGCAGGAGCTGCGTGTCCTGATGACGGGGCGCGTTTGCCG<br>GAGTCGTCAATCTGCTGGCCCTGGACGAGGAGCCGCATCCCGAGCACTCGGCCGTGCCCG<br>CCGGACTCGCCGCGACGACCGCTCTCGTCCAGGCCCTCGCGGACAACGGCGCCGACATCG<br>CCGTACGCACTCTCACGCAGGGGGCTGTTTCCACGAGCGCCGGCGACGCCCTCACCCACC<br>CGGTGCAGGCTCAGGTGTGGGGCTGGGCGCGTCGCTGCGCTGGAGTATCCGCGGCTGT<br>GGGGCGGGCTGGTCGATCTGCCCGCTCGTATCGACCATCAGACGCTGGCCCGGCTGGCCG<br>CCGCGCTGGTTCCGCAGGACGAGGACCAGATCTCCATCCGGCCGTCCGGCGTCCATGCCC<br>GTCGCCTTGCACACGCGCCCGCCAACACGGTCGGCAGCGGGCTTGGTTGGCGGCCCGACG<br>GCACCACTCTCATCACCGGCGGGACCGGCGGCATCGGCGCCGTTCCTCGCGCGGTGGCTCG<br>CCCGTGCGGCGCCCCGCACCTCCTCCTGACCAGCCGCCGCGGCCCCGACGCCCGGGAG<br>CACAGGAACTCGCCGCGGAACTGACGGAGTTGGGGGCCGCCGTCACCGTCACCGCCTGCG<br>ACGTCGGCGACCGCGAGCAGGTGCGACGCCTCATCGACGATGTCCCCGCCGAGCACCCGC<br>TGACCGCCGTCATCCACGCGGCCGGCGTGCCGAACTACATCGGTCTCGGCGACGTGTCGG<br>GTGCCGAGCTGGACGAGGTGCTGCGTCCGAAGGCGCTCGCCGCTCACCATCTGCATGAAC<br>TGACCCGGGAGTTGCCGCTCTCGGCGTTCGTGATGTTCTCGTCGGGCGCAGGCGTGTGGG<br>GCAGTGGCCAGCAGGGCGCCTATGGTGCGGCCAACCACTTCCTGACGCCCTCGCCGAGC<br>ACCGCCGCGCCGAGGGCCTGCCCGCCACCTCCATCGCCTGGGGGCCCTGGGCCGAGGCGG<br>GCATGGCGGCGACCAGGCCGCGTTGACGTTCTTCAGCCGCTTCGGCCTGCACCCGCTCA<br>GCCCGGAGCTGTGCGTCAAGGCGCTGCAGCAGGCCCTGGACGCGGGTGAGACGACGCTG | 34 |

| Name | Sequence | SEQ ID NO: |
|---|---|---|
| | ACCGTGGCGAACTTCGACTGGGCGCAGTTCACGTCGACGTTCACCGCGCAGCGGCCCAGC | |
| | CCGCTCCTCGCCGATCTGCCCGAGAACCGGCGGGCCAGCGCACCCGCGGCACAGCAGGA | |
| | AGACGCCACGGAGGCATCGTCGCTCCAGCAGGAGCTGACGGAGGCGAAGCCGGCGCAGC | |
| | AGCGGCAGTTGCTGCTGCAGCACGTGCGCTCCCAGGCGGCGGCCCACGCTGGGGCACTCGG | |
| | ACGTCGACGCGGTGCCCGCCACCAAGCCGTTCCAGGAGCTGGGCTTCGACTCGCTGACCG | |
| | CGGTGGAGCTGCGCAACAGGCTGAACAAGAGCACCGGCCTGACACTGCCGACCACGGTC | |
| | GTCTTCGACCACCCCACCCCCGACGCGCTCACCGACGTCCTGCGGGCCGAGCTGTCCGGT | |
| | GACGCGGCGGCCTCCGCCGACCCGGTGCGGGCGGCCGGGGCCTCCAGGGGCGCCGCCGA | |
| | CGACGAGCCGATCGCGATCGTCGGCATGGCCTGCCGCTATCGGGCGACGTCCGCTCCGC | |
| | CGAGGAGCTGTGGGATCTGGTCGCGGCCGGCAAGGACGCCATGGGGGCCTTCCCCGACG | |
| | ACCGGGCTGGGACCTGGAGACGCTGTACGACCCGGACCCGGAGAGCCGCGGCACCAGC | |
| | TATGTGCGCGAAGGCGGGTTCCTCTACGACGCGGGCGACTTCGACGCCGGATTCTTCGGC | |
| | ATCAGCCCCCGCGAGGCCGTCGCGATGGACCCGCAGCAGCGGCTGCTCCTGGAGACCGCG | |
| | TGGGAGGCGATCGAACGCGCGGGCCTCGACCGGGAGACCCTCAAGGGCAGCGACGCCGG | |
| | GGTGTTCACGGGCCTGACCATCTTCGACTACCTCGCGCTCGTCGGTGAACAGCCCACCGA | |
| | GGTCGAGGGCTACATCGGCACCGGCAACCTCGGCTGTGTCGCCTCCGGCAGGGTGTCGTA | |
| | CGTACTCGGCCTAGAAGGCCCCGCCATGACGATCGACACCGGCTGCTCTTCGTCCCTGGT | |
| | GGCGATCCACCAGGCGGCGCACGCGCTGCGCAGGGCGAGTGCTCGCTCGCTCTCGCGGG | |
| | CGGCGCGACGGTGATGGCCACGCGGGCTCGTTCGTCGAGTTCTCGCTGCAGCGCGGGCT | |
| | CGCCAAGGACGGCCGGTGCAAGCCGTTCGCGGCCGCCGCCGACGGCACCGGCTGGGCCG | |
| | AGGGAGTCGGCCTGGTCGTACTCGAACGGCTCTCGGAGGCCCGGCGCAACGGCCACAAC | |
| | GTCCTGGCGGTGATCCGGGGTTCGGCCATCAACCAGGACGGGCACGAGCAACGGGCTCACG | |
| | GCACCCAACGGGCAGGCGCAGCAGCGGGTGATCCGGCAGGCACTCGCCAACGCGCGGCT | |
| | CTCCGCCGAGGACGTCGACGCGGTGGAGGCGCACGGCACCGGCACCATGCTGGGCGACC | |
| | CCATCGAAGCCAGCGCGCTCGTCGCCACCTACGGCAAGGAGCGGCCCGCGGACCGGCCG | |
| | CTGTGGCTCGGCTCGATCAAGTCGAACATCGGGCACGCGCAGGCGTCGGCCGGTGTCGCC | |
| | GGTGTGATCAAGATGGTCATGGCGCTGCGCAACGAACAGCTGCCCGCCTCCCTGCACATC | |
| | GACGCGCCCACGCCGCACGTGGACTGGGACGGCAGTGGCGTCCGCCTGCTGTCCGAACCG | |
| | GTCTCCTGGCCGCGCGGCGAACGCCCGCCGCGCCGGGGTGTCCGCCTTCGGCATCTCC | |
| | GGCACCAACGCGCACCTCATCCTGGAACAGGCCCCGGACGCGCCGGAGCCCGTGACCGCT | |
| | CCGGCGGAGGACGCCGCGGCGCCGGCCGGAGTGGTGCCCTGGGTGGTGTCGGCGCGCGG | |
| | CGAGGAGGCGCTGCGGGCCCAGGCCCGCCTGCTGGCCGACCGCGCCACCGCCGACCCGC | |
| | GGCTCGCGTCGCGCGCTGGACGTGGGCTGGTCCCTGGTCAAGACCCGGTCGGTGTTCGAGA | |
| | ACCGAGCCGTCGTCGTGGGCAAGGACCGCCAGACTCTCCTCGCCGGGCTACGGTCCCTGG | |
| | CGGCGGGCGAGCCGTCACCGGACGTCGTCGAGGGCGCCGTACAGGGCGCCTCCGGCGCG | |
| | GGTCCGGTGTTGGTGTTTCCGGGGCAGGGGTCGCAGTGGGTGGGCATGGGTGCCCAGCTC | |
| | CTTGACGAGTCCCCCGTCTTCGCGGCGCGGATCGCGGAGTGTGAGCGGGCCCTGTCGGCG | |
| | CATGTGGACTGGTCGCTGAGTGCGGTGTTGCGCGGGGACGGGAGTGAGCTGTCCCGGGTC | |
| | GAGGTCGTGCAGCCCGTGTTGTGGGCGGTGATGGTCTCGCTGGCTTCGGTGTGGGCCGAT | |
| | TACGGCATCACCCCGGCTGCCGTCATCGGGCACTCGCAGGGCGAGATGGCCGCCGCGTGT | |
| | GTGGCGGGGCACTGTCACTGGAGGATGCGGCGCGGATCGTGGCCGTACGCAGTGACGC | |
| | GCTCCGTCAGCTCATGGGGCAGGGCGACATGGCGTCGTTGGGGGCCGGCTCGGAGCAGGT | |
| | TGCTGAGCTCATCGGCGACCGGCCCGGCGTGTGTGTCGCTGCCGTCAACGGGCCCTCCTCT | |
| | ACGGTCATTTCAGGGCGCCGGAGCATGTGGCAGCCGTGGTCGCGGATGCGGAGGCGCG | |
| | AGGCCTGCGCGCCCGCGTCATCGACGTCGGATACGCCTCCCACGCCCCCAGATCGACCA | |
| | GCTCCACGACCTCCTCACCGAGCGCCTGGCCGACATCCGGCCCACGACCACGGACGTCGC | |
| | CTTCTACTCCACGGTCACCGCCGAACGCCTCGACGACACCACCACCCTCGACACGGATTA | |
| | CTGGGTCACCAACCTCCGCCAGCCCGTCCGCTTCGCCGACACCATCGAAGCGCTGCTGGC | |
| | CGACGGCTACCGCCTGTTCATCGAGGCCAGCCCCCACCCCGTCCTCAACCTCGGCATGGA | |
| | GGAGACCATCGAGCGGGCCGACATGCCCGCCACCGTCGTGCCCACCCTGCCGCCGCGACCA | |
| | CGGCGACGCCGCGCAGCTCACCCGCGCGGCCGCCCAGGCCTTCGGCGCGGGGGCGGAGG | |
| | TCGACTGGACGGGCTGGTTCCCGGCCGTGCCGCTGCCTCGGGTGGTGGATCTGCCGACGT | |
| | ACGCCTTCCAGCGGGAGCGGTTCTGGCTGGAGGGGCGCAGGGGGCTCGCCGGGGACCCG | |
| | GCGGGGCTCGGGCTCGCGTCCGCGGGGCATCGCTGCTGCGGAGCCGCCGTGGAACTCGCG | |
| | GACGGCGGCAGTCACCTGCTGACCGGCCGGATCTCTCCGCGGGACCAGGCGTGGCTGGCC | |
| | GAGCACCGGGTCATGGACACGGTGCTGCTGCCCGGTTCGGCGTTCGTGGAGCTCGCGCTG | |
| | CAGGCCGCGGTGCGGGCCGGCTGCGCGGAGTTGGCGGAGCTGACGCTGCACACTCCGCTC | |
| | GCCTTCGGGGACGAGGGTGCGGGCGCGGTCGACGTGCAGGTGGTGCGGTTCCGTGGCC | |
| | GAGGACGGGCGGCGTCCCGTGACCGTCCATTCGCGGCCCACGGGTGAGGGCGAGGAGGC | |
| | CGTGTGGACCCGGCATGCCGCGGGCGTGGTCGCTCCCCCGGGGCCCGACGCCGGGGACGC | |
| | CTCGTTCGGCGGGACGTGGCCGCCCCGGGCGCCACACCGGTCGGCGAGCAGGATCCGTA | |
| | CGGGGAACTCGCTTCGTACGGCTATGACTTCGGGCCCGGCTCACAGGGACTGGTGAGCGC | |
| | GTGGCGGCTCGGGGACGACCTTTTCGCCGAGGTGGCGCTGCCCGAGGCGGAGAGCGGCA | |
| | GGGCCGACCGCTACCAGGTGCACCCGGTGTTGCTCGACGCCACGCTGCACGCGCTGATCC | |
| | TGGACGCGGTCACGTCGTCCGCCGACACCGACCAAGTGCTGCTGCCGTTCTCCTGGAGCG | |
| | GGTTGCGGGTGCACGCGCCGGGCGCTGAGAAGTTGCGGGTACGTATCGCACGCACCGCGC | |
| | CCGACCAGCTGGCCCTCACGGCCGTGGACGGGGCGGAGGCGGGGAGCCGGTTCTCACG | |
| | CTGGAGTCGCTCACGGTACGGCCGGTGGCCGCCCACCAGATCGCGGGCGCCCGTGCGGCG | |
| | GACCGTGACGCGCTGTTCCGGCTCGTGTGGATGGAGGTCGCCGCGCGGGCCGAGGAGACG | |
| | GGCGGCGGCGCCCCGCGTGCCGCGGTCCTCGCGCCGGTCGAGAGTGGCCCGATGGGCGGT | |
| | ACGTCGCCGGTGCGCTGGCCGACGCCTTGTCCGATGCGCTGGCCGCCGGCCCCGTGTGG | |
| | GACACGTTCGGTGCGCTCCGGGACGGAGTGGCGGCTGGGGGCGAAGCGCCCGATGTCGT | |
| | GCTCGCCGTGTGCGCCGCGCCCGGCGCAGGTGCCGGGGCCGTTGCGGATGCCGATGGCAG | |
| | GGGCGGCGACCCGGCCGGGTACGCGCGCGGCTGGCCACCGTGTCCCTTCTGTCGCTGCTCAA | |

| Name | Sequence | SEQ ID NO: |
|---|---|---|
| | GGAGTGGGTGGACGACCCGGCGTTCGCGGCGACCCGTCTCGTCGTCGTCACCCGAGGCGC<br>GGTCGCCGCGCGGCCGGGTGAGACCGCCGGTGATCTGGCGGGCGCGTCGCTGTGGGGTCT<br>GGTGCGCAGCGCGCAGGCCGAGAATCCCGGTCGCCTCACGCTGCTCGACGTGGACGGACT<br>GGAGTCTTCTCCGGCCACGCTGACCGGCGTACTGGCCTCCGGCGAACCGGAATTGGCGCT<br>GCGTGACGGGCGCGCCTACGTGCCACGGCTCGTGCGCGACGACGCGTCGGTGCGGCTGGT<br>GCCGCCGGTCGGATCGCTCACGTGGCGGCTGGCTCGGTGCCAAGAGGCGGGCGGCGGAC<br>AGCAGTTGTCCCTTGTCGACGCTCCCGAGGCCGGACGGGCGCTGGAGCCGCACGAGGTGC<br>GGGTGGCGGTGCGGGCCGCGGCGCCGGGGCCGCTCACGGCGGGCCAGGTCGAGGGTGCC<br>GGTGTGGTGACGGAAGTCGGCGGCGAGGTCGGTTCGGTGGCCGTGGGCGACCGGGTGAT<br>GGGGTTGTTCGACGCGGTGGGCCCGGTGGCCGTCACCGATGCCGCGCTGCTTATGCCGGT<br>TCCGGCGGGCTGGAGTTGGGCGCAGGCGGCCGGGTCCTTGGGGGCCTATGTGTCCGCGTA<br>TCACGTGCTGGCGGATGTCGTGGCGCCGCGCGGCGGCGAGACTCTGCTCGTCGGGGAGGA<br>AACCGGTTCCGTCGGCCGTGCCGTGCTGCGTCTTGCTCTTGCCGGGCGGTGGCGGGTCGA<br>GGCCGTGGACGGTGCGTCGACGGCGGATGATTCGGGCGCCGAGCGCGCGGCCGACGTCA<br>CCCTCCGCCACGAGGGGGCCCTGGTGGTCCACCGTGCGGGCGGTCGTCCGGACGAGGGAC<br>AGGCTGTCGTGCCGCCCGAGCCCGGGCGCGTACGGGAAATCCTCGCGGAGCTGACCGAGC<br>TGACCGAGCTTGCCGAGATCACGGAGTCGGCGGAGCCCGGGCTGCCCGCGGAACGGGGT<br>GACAGCCGTGCTCTGACGCCGCTCGACATCACCGTGTGGGACATCCGGCAGGCGCCCGCC<br>GCGATGGCGGCCCCGCCCTCGGCGGGCACGACCGTGTTCTCGCTGCCTCCCGCCTTCGACC<br>CCGAGGGCACCGTGCTGGTCACCGGCGGCACCGGAGCACTCGGCTCGCTGACGGCCCGTC<br>ACCTGGTGGAACGGTACGGAGCCAGGCACCTGTTGCTGTCCAGCAGGCGGGAGCCGAC<br>GCGCCGGGCGCACTCGAACTGGCCGCCGACCTCTCCGCGCTCGGCGCGCGAGTCACCTTC<br>GCCGCGTGCGACCCGGGCGACCGGGACGAAGCCGCCGCCCTCCTCGCGGCGGTGCCCTCG<br>GACCACCCGCTGACCGCCGTCTTCCACTGCGCGGGCACCGTGAACGACGCCGTGGTGCAG<br>AACCTCACGGCCGAGCAGGTCGAGGAGGTGATGCGCGTGAAGGCGGACGCCGCGTGGCA<br>CCTGCACGAGCTGACGCGGGACGCGGACCTGTCCGCGTTCGTCCTGTACTCCTCGGTCGCC<br>GGGCTGCTCGGCGGCCCCGGCCAGGGCAGCTACACGCCGCCAACGCCTTCTTGGACGCG<br>CTGGCCCGGCACCGGCACGACGGCGGTGCGGCGGCGACCTCCCTGGCGTGGGGCTACTGG<br>GAGCTGGCGAGCGGCATGTCGGGACGGCTCACCGACGCCGACCGGGCGCGCCATGCCCG<br>CGCCGGCGTGGTCGGGCTCGGCGCCGACGAGGGACTCGCCCTCCTCGACGCGGCGTGGGC<br>CGGCGGACTGCCCCTGTACGCGCCGGTCCGTCTGGACCTGGCCCGGATGCGCCGGCAGGC<br>CCAGAGCCACCCCGCACCGGCGCTGCTGCGCGACCTGGTGCGCGGGGGGAGCAAGAGCG<br>GCGGCGGTGCCGTGTCGGCGGGGGCGGCCGCGCTGCTCAAGTCGCTCGGCGCGATGTCCG<br>ACCCCGAGCGGGAGGAGGCGCTGCTCGACCTGGTGTGCACCCATATCGCGGCCGTCCTCG<br>GCTACGACGCGGCCACGCCCGTCAACGCGACGCAGGGCTGCGGGAACTCGGCTTCGACT<br>CCCTGACCGCGGTGGAGCTGCGCAACCGGCTCTCGGCCGCGACGGGGCTGAAGCTGCCCG<br>CCACGTTCGTCTTCGACCATCCCAACCCGGCGGAGCTCGCCGCGCAGCTGCGGCAGGAGC<br>TGGCCCCGCGCGCGGATCCGCTCGCCGACGTCCTGGCGGAGTTCGAGCGCATCGAGG<br>ACTCGCTGCTCTCGGTCTCCTCGAAGGACGGCTCGGCGCGGGCCGAACTGGCGGGGCGGC<br>TGCGCGCGACGCTGGCCAGGCTCGACGCGCCGCAGGACACGGCCGGCGAGGTCGCGGTG<br>GCCACTCGTACACGTATCCAGGACGCGTCGGCGGACGAGATCTTCGCGTTCATCGACCGG<br>GACCTCGGCAGGGACGGCGCGAGCGGACAGGGCAACGGACAGCCCACCGGGCAGGGCA<br>ACGGACACGGCAACGGCAACGGCAACGGCAACGGACACGGTCAGGCAGTGGA<br>GGGGCAGCGATGA | |
| rci_<br>NC_019104.1 | ATGCCGTCTCCACGCATCCGTAAAATGTCCCTGTCACGCGCACTGGATAAGTACCTGAAA<br>ACAGTTTCTGTTCACAAGAAAGGGCATCAACAGGAGTTTTACCGGAGCAATGTTATCAAG<br>CGATATCCCATTGCCCTTCGGAATATGGACGAAATAACAACCGTTGATATTGCTACATAC<br>AGAGACGTTCGTTTAGCAGAAATCAACCCCCCGAACGGGTAAACCCATTACAGGTAATACT<br>GTACGTCTTGAACTCGCCCTTCTGTCATCTCTGTTCAATATTGCTCGTGTTGAATGGGGAA<br>CCTGTCGTACTAACCCGGTTGAACTGGTTCGCAAGCCGAAAGTATCCTCCGGACGAGATC<br>GCCGGCTAACGTCTTCAGAAGAACGTCGCCTTTCTCGCTATTTCCGCGAAAAAAATCTGAT<br>GTTGTATGTCATTTTCCATCTTGCCCTTGAGACAGCCATGCGGCAGGGCGAAATACTGGCC<br>TTACGTTGGGAGCACATTGATTTGCGCCACGGTGTGGCTCATTTACCTGAAACCAAAAAC<br>GGTCACTCACGGGATGTTCCTCTGTCCAGACGTGCCCGTAACTTTCTTCAGATGATGCCCG<br>TTAATCTCCACGGCAATGTTTTTGATTACACCGCATCCGGCTTTAAAAATGCTGGAGAAT<br>AGCCACACAACGACTTCGCATCGAGGACCTGCATTTTCACGATCTACGGCATGAAGCAAT<br>AAGCCGCTTCTTCGAACTGGGGTAGCCTGAATGTAATGGAGATTGCTGCAATATCAGGACA<br>TCGTTCCATGAATATGCTGAAACGGTATACTCATCTTCGTGCATGGCAACTGGTCAGTAAA<br>CTTGATGCCCGCCGGCGGCAGACACAAAAAGTGGCAGCATGTTTTGTGCCGTATCCTGCC<br>CATATCACGACCATCAATGAAGAAAATGGGCAGAAAGCGCATCGTATTGAGATCGGTGAT<br>TTTGATAACCTTCACGTCACTGCCACAACGAAAGAGGAAGCAGTTCACCGCGCCAGTGAG<br>GTTTTGTTGCGTACACTGGCCATTGCAGCACAGAAAGGCGAACGTGTCCCATCTCCCGGA<br>GCGTTACCTGTTAACGACCCTGACTACATTATGATTTGCCCTCTGAACCCGGGCAGCACCC<br>CGCTGTAA | 35 |
| optimized_rci | ATGCCGTCCCCCCGCATCCGCAAGATGAGCCTCTCCCGCGCCCTCGACAAGTACCTGAAG<br>ACCGTGAGCGTCCACAAGAAGGGCCACCAGCAGGAGTTCTACCGGTCCAACGTCATCAAG<br>CGCTACCCCGATCGCCCTGCGGAACATGGACGAGATCACCACCGTCGACATCGCCACCTAC<br>CGGGACGTGCGCCTGGCGGAGATCAACCCGCGCACCGGCAAGCCCATCACCGGCAACAC<br>CGTCCGGCTGGAGCTCGCCCTGCTCTCCTCGCTGTTCAACATCGCGCGCGTGGAGTGGGC<br>ACCTGCCGGACCAACCCGGTCGAGCTGGTGCGCAAGCCCAAGGTCAGCTCCGGCCGGGAC<br>CGCCGGCTCACCTCGTCCGAGGAGCGCCGGCTGTCCCGGTACTTCCGCGAGAAGAACCTG<br>ATGCTCTACGTGATCTTCCACCTGGCCCTGGAGACCGCGATGCGCCAGGGCGAGATCCTG | 36 |

-continued

| Name | Sequence | SEQ ID NO: |
|---|---|---|
| | GCCCTCCGCTGGGAGCACATCGACCTGCGCCACGGCGTCGCGCACCTGCCGGAGACCAAG<br>AACGGCCACAGCCGCGACGTGCCCCTGTCCCGCCGGGCCCGGAACTTCCTCCAGATGATG<br>CCCGTCAACCTGCACGGCAACGTGTTCGACTACACCGCCAGCGGCTTCAAGAACGCCTGG<br>CGCATCGCGACCCAGCGGCTGCGCATCGAGGACCTGCACTTCCACGACCTGCGCCACGAG<br>GCCATCTCGCGGTTCTTCGAGCTGGGCAGCCTCAACGTCATGGAGATCGCCGCGATCTCC<br>GGCCACCGCTCGATGAACATGCTCAAGCGGTACACCCACCTGCGCGCCTGGCAGCTGGTG<br>TCGAAGCTCGACGCGCGTCGCCGCCAGACCCAGAAGGTCGCCGCGTGGTTCGTGCCGTAC<br>CCCGCCCACATCACCACCATCGACGAGGAGAACGGCCAGAAGGCGCACCGCATCGAGAT<br>CGGCGACTTCGACAACCTGCACGTCACCGCCACCACCAAGGAAGAGGCCGTGCACCGCGC<br>GTCCGAGGTGCTGCTCCGGACCCTCGCCATCGCCGCGCAGAAGGGCGAGCGGGTCCCGTC<br>GCCCGGCGCGCTGCCGGTCAACGACCCCGACTACATCATGATCTGCCCCCTGAACCCCGG<br>CTCCACCCCGCTGTGA | |
| tipAp(RBS) | CCCGGGCTGAGGGAGCCGACGGCACGCGGCGGCTCACGGCGTGGCACGCGGAACGTCCG<br>GGCTTGCACCTCACGTCACGTGAGGAGGCAGCGTGGACGGCGTCAGAGAAGGGAGCGGA<br>A | 37 |
| upstream_<br>homology | CGAAGAGAAGTACCTCGACTACCTGCGTCGTGCCACGGCGGACCTCCACGAGGCCCGTGG<br>CCGCCTCCGCGAGCTGGAGGCGAAGGCGGGCGAGCCGGTGGCGATCGTCGGCATGGCCT<br>GCCGCCTGCCCGGCGGCGTCGCCTCGCCCGAGGACCTGTGGCGGCTGGTGGCCGGCGGCG<br>AGGACGCGATCTCGGAGTTCCCCCAGGACCTGGGACGTGGAGGGCCTGTACGACC<br>CGAACCCGGAGGCCACGGGCAAGAGTTACGCCCGCGAGGCCGGATTCCTGTACGAGGCG<br>GGCGAGTTCGACGCCGACTTCTTCGGGATCTCGCCGCGCGAGGCCCTCGCCATGGACCCG<br>CAGCAGCGTCTCCTCCTGGAGGCCTCCTGGGAGGCGTTCGAGCACGCCGGGATCCCGGCG<br>GCCACCGCGCGCGGCACCTCGGTCGGCGTCTTCACCGGCGTGATGTACCACGACTACGCC<br>ACCCGTCT | 38 |
| downstream_<br>homology | CTGCTCAGCGGGCTCACCCGCGGATCGCGGGTCGGCGGCGCGCCGGTCAACCAGCGCAGG<br>GCAGCCGCCGGAGGCGCGGGCGAGGCGGACACGGACCTCGGCGGGCGGCTCGCCGCAT<br>GACACCGGACGACCGGGTCGCGCACCTGCGGGACCTCGTCCGTACGCACGTGGCCGACCGT<br>CCTGGGACACGGCACCCCGAGCCGGGTGGACCTGGAGCGGGCCTTCCGCGACACCGGTTT<br>CGACTCGCTCACCGCCGTCGAACTCCGCAACCGTCTCAACGCCGCGACCGGGCTGCGGCT<br>GCCGGCCACGCTGGTCTTCGACCACCCCACCCCGGGGGAGCTCGCCGGGCACCTGCTCGA<br>CGAACTCGCCACGGCCGCGGGCGGGTCCTGGGCGGAAGGCACCGGGTCCGGAGACACGG<br>CCTCGGCGACCGATCGGCAGACCACGGCGGCCCTCGCCGAACTCGACCGGCTGGAAGGC<br>GTGCTCGCCTCCCTCGCG | 39 |
| pYES-1L | CCTCGCCGCAGTTAATTAAAGTCAGTGAGCGAGGAAGCGCGTAACTATAACGGTCCTAAG<br>GTAGCGAATCCTGATGCGGTATTTTCTCCTTACGCATCTGTGCGGTATTTCACACCGCATA<br>GATCGGCAAGTGCACAAACAATACTTAAATAAATACTACTCAGTAATAACCTATTTCTTA<br>GCATTTTTGACGAAATTTGCTATTTTGTTAGAGTCTTTTACACCATTTGTCTCCACACCTCC<br>GCTTACATCAACACCAATAACGCCATTTAATCTAAGCGCATCACCAACATTTTCTGGCGTC<br>AGTCCACCAGCTAACATAAAATGTAAGCTTTCGGGGCTCTCTTGCCTTCCAACCCAGTCAG<br>AAATCGAGTTCCAATCCAAAAGTTCACCTGTCCCACCTGCTTCTGAATCAAACAAGGGAA<br>TAAACGAATGAGGTTTCTGTGAAGCTGCACTGAGTAGTATGTTGCAGTCTTTTGGAAATAC<br>GAGTCTTTTAATAACTGGCAAACCGAGGAACTCTTGGTATTCTTGCCACGACTCATCTCCA<br>TGCAGTTGGACGATATCAATGCCGTAATCATTGACCAGAGCCAAAACATCCTCCTTAAGT<br>TGATTACGAAACACGCCAACCAAGTATTTCGGAGTGCCTGAACTATTTTTATATGCTTTTA<br>CAAGACTTGAAATTTTCCTTGCAATAACCGGGTCAATTGTTCTCTTTCTATTGGGCACACA<br>TATAATACCCAGCAAGTCAGCATCGGAATCTAGAGCACATTCTGCGGCCTCTGTGCTCTGC<br>AAGCCGCAAACTTTCACCAATGGACCAGAACTACCTGTGAAATTAATAACAGACATACTC<br>CAAGCTGCCTTTGTGTGCTTAATCACGTATACTCACGTGCTCAATAGTCACCAATGCCCTC<br>CCTCTTGGCCCTCTCCTTTTCTTTTTTCGACCGAATTAATTCTTAATCGGCAAAAAAAGAA<br>AAGCTCCGGATCAAGATTGTACGTAAGGTGACAAGCTATTTTTCAATAAAGAATATCTTC<br>CACTACTGCCATCTGGCGTCATAACTGCAAAGTACACATATATTACGATGCTGTTCTATTA<br>AATGCTTCCTATATTATATATATAGTAATGTCGTGATCTATGGTGCACTCTCAGTACAATC<br>TGCTCTGATGCCGCATAGTTAAGCCAGCCCCGACACCCGCCAACACCCGCTGACGCGCCC<br>TGACGGGCTTGTCTGCTCCCGGCATCCGCTTACAGACAAGCTGTGACCGTCTCCGGGAGCT<br>GCATGTGTCAGAGGTTTTCACCGTCATCACCGAAACGCGCGAGACGAAAGGGCCTCGTGA<br>TACGCCTATTTTTATAGGTTAATGTCATGATAATAATGGTTTCTTAGACGGATCGCTTGCC<br>TGTAACTTACACGCGCCTCGTATCTTTTAATGATGGAATAATTTGGGAATTTACTCTGTGT<br>TTATTTATTTTTATGTTTTGTATTTGGATTTTAGAAAGTAAATAAAGAAGGTAGAAGAGTT<br>ACGGAATGAAGAAAAAAAATAAACAAAGGTTTAAAAAATTTCAACAAAAAGCGTACTT<br>TACATATATATTTATTAGACAAGAAAAGCAGATTAAATAGATATACATTCGATTAACGAT<br>AAGTAAAATGTAAAATCACAGGATTTTCGTGTGTGGTCTTCTACACAGACAAGGTGAAAC<br>AATTCGGCATTAATACCTGAGAGCAGGAAGAGCAAGATAAAAGGTAGTATTTGTTGGCGA<br>TCCCCCTAGAGTCTTTTACATCTTCGGAAAACAAAAACTATTTTTCTTTAATTTCTTTTTT<br>TACTTTCTATnTTAATTTATATATTTATATTAAAAAATTTAAATTAATTATTTTATAG<br>CACGTGATGAAAAGGACCCAGGTGGCACTTTTCGGGGAAATGTGCGCGGAACCCCTATTT<br>GTTTATTTTTCTAAATACATTCAAATATGTATCCGCTCATGAGACAATAACCCTGATAAAT<br>GCTTCAATAATATTGAAAAGGAAGAGTATGAGTATTCAACATTTCCGTGTCGCCCTTATT<br>CCCTTTTTTGCGGCATTTTGCCTTCCTGTTTTTGCTCACCCAGAAACGCTGGTGAAAGTAA<br>AAGATGCTGAAGATCAGTTGGGACGCGTAGTCTAGACCAGCCAGGACAGAAATGCCTCG<br>ACTTCGCTGCTACCCAAGGTTGCCGGGTGACGCACACCGTGGAAACGGATGAAGGCACGA | 40 |

-continued

| Name | Sequence | SEQ ID NO: |
|------|----------|------------|
| | ACCCAGTGGACATAAGCCTGTTCGGTTCGTAAGCTGTAATGCAAGTAGCGTATGCGCTCA | |
| | CGCAACTGGTCCAGAACCTTGACCGAACGCAGCGGTGGTAACGGCGCAGTGGCGGTTTTC | |
| | ATGGCTTGTTATGACTGTTTTTTTGGGGTACAGTCTATGCCTCGGGCATCCAAGCAGCAAG | |
| | CGCGTTACGCCGTGGGTCGATGTTTGATGTTATGGAGCAGCAACGATGTTACGCAGCAGG | |
| | GCAGTCGCCCTAAAACAAAGTTAAACATTATGAGGGAAGCGGTGATCGCCGAAGTATCG | |
| | ACTCAACTATCAGAGGTAGTTGGCGCCATCGAGCGCCATCTCGAACCGACGTTGCTGGCC | |
| | GTACATTTGTACGGCTCCGCAGTGGATGGCGGCCTGAAGCCACACAGTGATATTGATTTG | |
| | CTGGTTACGGTGACCGTAAGGCTTGATGAAACAACGCGGCGAGCTTTGATCAACGACCTT | |
| | TTGGAAACTTCGGCTTCCCCTGGAGAGAGCGAGATTCTCCGCGCTGTAGAAGTCACCATT | |
| | GTTGTGCACGACGACATCATTCCGTGGCGTTATCCAGCTAAGCGCGAACTGCAATTTGGA | |
| | GAATGGCAGCGCAATGACATTCTTGCAGGTATCTTCGAGCCAGCCACGATCGACATTGAT | |
| | CTGGCTATCTTGCTGACAAAAGCAAGAGAACATAGCGTTGCCTTGGTAGGTCCAGCGGCG | |
| | GAGGAACTCTTTGATCCGGTTCCTGAACAGGATCTATTTGAGGCGCTAAATGAAACCTTA | |
| | ACGCTATGGAACTCGCCGCCCGACTGGGCTGGCGATGAGCGAAATGTAGTGCTTACGTTG | |
| | TCCCGCATTTGGTACAGCGCAGTAACCGGCAAAATCGCGCCGAAGGATGTCGCTGCCGGC | |
| | TGGGCAATGGAGCGCCTGCCGGCCCAGTATCAGCCCGTCATACTTGAAGCTAGACAGGCT | |
| | TATCTTGGACAAGAAGAAGATCGCTTGGCCTCGCGCAGATCAGTTGGAAGAATTTGTC | |
| | CACTACGTGAAAGGCGAGATCACCAAGGTAGTCGGCAAATAACCCTCGAGCATTCAAGG | |
| | CGCCTTGATTATTTGACGTGGTTTGATGGCCTCCACGCACGTTGTGATATGTAGATGATAA | |
| | TCATTATCACTTTACGGGTCCTTTCCGGTGATCCGACAGGTTACGGGGCGGCGACCTCGCG | |
| | GGTTTTCGCTATTTATGAAAATTTTCCGGTTTAAGGCGTTTCCGTTCTTCTTCGTCATAACT | |
| | TAATGTTTTTATTTAAAATACCTCGCGAGTGGCAACACTGAAAATACCCATGGAGCGGCG | |
| | TAACCGTCGCACAGGAAGGACAGAGAAAGCGCGGATCTGGGAAGTGACGGACAGAACGG | |
| | TCAGGACCTGGATTGGGGAGGCGGTTGCCGCCGCTGCTGCTGACGGTGTGACGTTCTCTG | |
| | TTCCGGTCACACCACATACGTTCGCCATTCCTATGCGATGCACATGCTGTATGCCGGTAT | |
| | ACCGCTGAAAGTTCTGCAAAGCCTGATGGGACATAAGTCCATCAGTTCAACGGAGGTCTA | |
| | CACGAAGGTTTTTGCGCTGGATGTGGCTGCCCGGCACCGGGTGCAGTTTGCGATGCCGGA | |
| | GTCTGATGCGGTTGCGATGCTGAAACAATTATCCTGAGAATAAATGCCTTGGCCTTTATAT | |
| | GGAAATGTGGAACTGAGTGGATATGCTGTTTTTGTCTGTTAAACAGAGAAGCTGGCTGTT | |
| | ATCCACTGAGAAGCGAACGAAACAGTCGGGAAAATCTCCCATTATCGTAGAGATCCGCAT | |
| | TATTAATCTCAGGAGCCTGTGTAGCGTTTATAGGAAGTAGTGTTCTGTCATGATGCCTGCA | |
| | AGCGGTAACGAAAACGATTTGAATATGCCTTCAGGAACAATAGAAATCTTCGTGCGGTGT | |
| | TACGTTGAAGTGGAGCGGATTATGTCAGCAATGGACAGAACAACCTAATGAACACAGAA | |
| | CCATGATGTGGTCTGTCCTTTTACAGCCAGTAGTGCTCGCCGCAGTCGAGCGACAGGGCG | |
| | AAGCCCTCGAGTGAGCGAGGAAGCACCAGGGAACAGCACTTATATATTCTGCTTACACAC | |
| | GATGCCTGAAAAAACTTCCCTTGGGGTTATCCACTTATCCACGGGGATATTTTTATAATTA | |
| | TTTTTTTTATAGTTTTTAGATCTTCTTTTTTAGAGCGCCTTGTAGGCCTTTATCCATGCTGGT | |
| | TCTAGAAGGGTGTTGTGACAAATTGCCCTTTCAGTGTGACAAATCACCCTCAAATGACA | |
| | GTCCTGTCTGTGACAAATTGCCCTTAACCCTGTGACAAATTGCCCTCAGAAGAAGCTGTTT | |
| | TTTCACAAAGTTATCCCTGCTTATTGACTCTTTTTTATTTAGTGTGACAATCTAAAAACTTG | |
| | GCACACTTCACATGGATCTGTCATGGCGGAAACAGCGGTTATCAATCACAAGAAACGTAA | |
| | AAATAGCCCGCGAATCGTCCAGTCAAACGACCTCACTGAGGCGGCATATAGTCTCTCCG | |
| | GGATCAAAAACGTATGCTGTATCTGTTCGTTGACCAGATCAGAAAATCTGATGGCACCCT | |
| | ACAGGAACATGACGGTATCTGCGAGATCCATGTTGCTAAATATGCTGAAATATTCGGATT | |
| | GACCTCTGCGGAAGCCAGTAAGGATATACGGCAGGCATTGAAGAGTTTCGCGGGGAAGG | |
| | AAGTGGTTnTATCGCCCTGAAGAGGATGCCGGCGATGAAAAAGGCTATGAATCTTTTTC | |
| | CTTGGTTTATCAAACGTGCGCACAGTCCATCCAGAGGGCTTTACAGTGTACATATCAACCC | |
| | ATATCTCATTCCCTTCTTTATCGGGTTACAGAACCGGTTTACGCAGTTTCGGCTTAGTGAA | |
| | ACAAAAGAAATCACCAATCCGTATGCCATGCGTTTATACGAATCCCTGTGTCAGTATCGT | |
| | AAGCCGGATGGCTCAGGCATCGTCTCTCTGAAAATCGACTGGATCATAGAGCGTTACCAG | |
| | CTGCCTCAAAGTTACCAGCGTATGCCTGACTTCCGCCGCCGCTTCCTGCAGGTCTGTGTTA | |
| | ATGAGATCAACAGCAGAACTCCAATGCGCCTCTCATACATTGAGAAAAAGAAAGGCCGC | |
| | CAGACGACTCATATCGTATTTTCCTTCCGCGATATCACTTCCATGACGACAGGATAGTCTG | |
| | AGGGTTATCTGTCACAGATTTGGGGGTGGTTCGTCACATTTGTCTGACCTACTGAGGGTA | |
| | AnTGTCACAGTnTGCTGTTTCCTTCAGCCTGCATGGATTTTCTCATACTTTTTGAACTGT | |
| | AATTTTTAAGGAAGCCAAATTTGAGGGCAGTTTGTCACAGTTGATTTCCTTCTCTTTCCCTT | |
| | CGTCATGTGACCTGATATCGGGGGTTAGTTTGTCATCATTGATGAGGGTTGATTATCACAG | |
| | TTTATTACTCTGAATTGGCTATCCGCGTGTGTACCTCTACCTGGAGTTTTTCCCACGGTGGA | |
| | TATTTCTTCTTGCGCTGAGCGTAAGAGCTATCTGACAGAACAGTTCTTCTTTGCTTCCTCGC | |
| | CAGTTCGCTCGCTATGCTCGGTTACACGGCTGCGGCGAGCGCTAGTGATAATAAGTGACT | |
| | GAGGTATGTGCTCTTCTTATCTCCTTTTGTAGTGTTGCTCTTATTTTAAACAACTTTGCGGT | |
| | TTTTTGATGACTTTGCGATTTTGTTGTTGCTTTGCAGTAAATTGCAAGATTTAATAAAAA | |
| | ACGCAAAGCAATGATTAAAGGATGTTCAGAATGAAACTCATGGAAACACTTAACCAGTGC | |
| | ATAAACGCTGGTCATGAAATGACGAAGGCTATCGCCATTGCACAGTTTAATGATGACAGO | |
| | CCGGAGGCGAGGAAAATAACCCGGCGCTGGAGAATAGGTGAAGCAGCGGATTTAGTTGG | |
| | GGTTTCTTCTCAGGCTATCAGAGATGCCGAGAAAGCAGGGCGACTACCGCACCCGGATAT | |
| | GGAAATTCGAGGACGGGTTGAGCAACGTGTTGGTTATACAATTGAACAAATTAATCATAT | |
| | GCGTGATGTGTTTGGTACGCGATTGCGACGTGCTGAAGACGTATTTCACCGGTGATCGG | |
| | GGTTGCTGCCCATAAAGGTGGCGTTTACAAAACCTCAGTTTCTGTTCATCTTGCTCAGGAT | |
| | CTGGCTCTGAAGGGCTACGTGTTTGCTCGTGAAGGTAACGACCCCCAGGGAACAGCC | |
| | TCAATGTATCACGGATGGGTACCAGATCTTCATATTCATGCAGAAGACACTCTCCTGCCTT | |
| | TCTATCTTGGGGAAAGGACGATGTCACTTATGCAATAAAGCCCACTTGCTGGCCGGGGC | |
| | TTGACATTATTCCTTCCTGTCTGGCTCTGCACCGTATTGAAACTGAGTTAATGGGCAAATT | |
| | TGATGAAGGTAAACTGCCCACCGATCCACACCTGATGCTCCGACTGGCCATTGAAACTGT | |

| Name | Sequence | SEQ ID NO: |
|---|---|---|
| | TGCTCATGACTATGATGTCATAGTTATTGACAGCGCGCCTAACCTGGGTATCGGCACGATT<br>AATGTCGTATGTGCTGCTGATGTGCTGATTGTTCCCACGCCTGCTGAGTTGTTTGACTACA<br>CCTCCGCACTGCAGTTTTTCGATATGCTTCGTGATCTGCTCAAGAACGTTGATCTTAAAGG<br>GTTCGAGCCTGATGTACGTATTTTGCTTACCAAATACAGCAATAGTAATGGCTCTCAGTCC<br>CCGTGGATGGAGGAGCAAATTCGGGATGCCTGGGGAAGCATGGTTCTAAAAAATGTTGTA<br>CGTGAAACGGATGAAGTTGGTAAAGGTCAGATCCGGATGAGAACTGTTTTTGAACAGGCC<br>ATTGATCAACGCTCCTCAACTGGTGCCTGGAGAAATGCTCTTTCTATTTGGGAACCTGTCT<br>GCAATGAAATTTTCGATCGCCTGATTAAACCACGCTGGGAGATTAGATAATGAAGCGTGC<br>GCCTGTTATTCCAAAACATACGCTCAATACTCAACCGGTTGAAGATACTTCGTTATCGACA<br>CCAGCTGCCCCGATGGTGGATTCGTTAATTGCGCGCGTAGGAGTAATGGCTCGCGGTAAT<br>GCCATTACTTTGCCTGTATGTGGTCGGGATGTGAAGTTTACTCTTGAAGTGCTCCGGGGTG<br>ATAGTGTTGAGAAGACCTCTCGGGTATGGCCAGGTAATGAACGTGACCAGGAGCTGCTTA<br>CTGAGGACGCACTGGATGATCTCATCCCTTCTTTTCTACTGACTGGTCAACAGACACCGGC<br>GTTCGGTCGAAGAGTATCTGGTGTCATAGAAATTGCCGATGGGAGTCGCCGTCGTAAAGC<br>TGCTGCACTTACCGAAAGTGATTATCGTGTTCTGGTTGGCGAGCTGGATGATGAGCAGAT<br>GGCTGCATTATCCAGATTGGGTAACGATTATCGCCCAACAAGTGCTTATGAACGTGGTCA<br>GCGTTATGCAAGCCGATTGCAGAATGAATTTGCTGGAAATATTTCTGCGCTGGCTGATGC<br>GGAAAATATTFCACGTAAGATTATTACCCGCTGTATCAACACCGCCAAATTGCCTAAATC<br>AGTTGTTGCTCTTTTTTCTCACCCCGGTGAACTATCTGCCCGGTCAGGTGATGCACTTCAA<br>AAAGCCTTTACAGATAAAGAGGAATTACTTAAGCAGCAGGCATCTAACCTTCATGAGCAG<br>AAAAAAGCTGGGGTGATATTTGAAGCTGAAGAAGTTATCACTCTTTTAACTTCTGTGCTTA<br>AAACGTCATCTGCATCAAGAACTAGTTTAAGCTCACGACATCAGTTTGCTCCTGGAGCGA<br>CAGTATTGTATAAGGGCGATAAAATGGTGCTTAACCTGGACAGGTCTCGTGTTCCAACTG<br>AGTGTATAGAGAAAATTGAGGCCATTCTTAAGGAACTTGAAAAGCCAGCACCCTGATGCG<br>ACCACGTTTTAGTCTACGTTTATCTGTCTTTACTTAATGTCCTTTGCTACAGGCCAGAAAGC<br>ATAACTGGCCTGAATATTCTCTCTGGGCCCACTGTTCCACTTGTATCGTCGGACTGATAAT<br>CAGACTGGGACCACGGTCCCACTCGTATCGTCGGTCTGATTATTAGTCTGGGACCACGGTC<br>CCACTCGTATCGTCGGTCTGATTATTAGTCTGGGACCACGGTCCCACTCGTATCGTCGGTC<br>TGATAATCAGACTGGGACCACGGTCCCACTCGTATCGTCGGTCTGATTATTAGTCTGGGAC<br>CATGGTCCCACTCGTATCGTCGGTCTGATTATTAGTCTGGGACCACGGTCCCACTCGTATC<br>GTCGGTCTGATTATTAGTCTGGAACCACGGTCCCACTCGTATCGTCAGTCTGATTATTAGT<br>CTGGGACCACGGTCCCACTCGTATCGTCGGTCTGATTATTAGTCTGGGACCACGATCCCAC<br>TCGTGTTGTCGGTCTGATTATCGGTCTGGGACCACGGTCCCACTTGTATTGTCGATCAGAC<br>TATCAGCGTGAGACTACGATTCCATCAATGCCTGTCAAGGGCAAGTATTGACATGTCGTC<br>GTAACCTGTAGAACGGAGTAACCTCGGTGTGCGGTTGTATGCCTGCTGTGGATTGCTGCTG<br>TGTCCTGCTTATCCACAACATTTTGCGCACGGTTATGTGGACAAAATACCTGGTTACCCAG<br>GCCGTGCCGGCACGTTAACCGGGCTGCATCCGATGCAAGTGTGTCGCTGTCGACGGCCTC<br>CTCACCCGGTCACGTGAGCTCATTTAACCCACTCCACAAAAAGGCTCAACAGGTTGGTGG<br>TTCTCACCACCAAAAGCACCACACCCCACGCAAAAACAAGTTTTTGCTGATTTTTCTTTAT<br>AAATAGAGTGTTATGAAAAATTAGTTTCTCTTACTCTCTTTTATGATATTTAAAAAAGCGGT<br>GTCGGCGCGGCTACAACAACGCGCCGACACCGTTTTGTAGGGGTGGTACTGACTATTTTT<br>ATAAAAAACATTATTTTATATTAGGGGTGCTGCTAGCGGCGCGGTGTGTTTTTTTATAGGA<br>TACCGCTAGGGGCGCTGCTAGCGGTGCGTCCCTGTTTGCATTATGAATTAGTTACGCTAGG<br>GATAACAGGGTAATATAGAACCCGAACGACCGAGCGCAGCGGCGGCCGCGCTGATACCG<br>CCGC | |
| tsr_operon | CGGCCACGACACCCCCATCGGCATCGCGTGGCGGGCCCGATTCGCGTCCGCCCCGGGGAG<br>GAGACGGGCGTCCGCGTCGAGGGCGAGGCGGGCTTCCACCCGTAGGCGATCGGCGAGC<br>ACGACACCCGCAGATTGGCTCGACGCAGCCCAGAAATGTATGATCAAGGCGAATACTTCA<br>TATGCGGGGATCGACCGCGCGGGTCCCGGACGGGAAGAGCGGGGAGCTTTGCCAGAGA<br>GCGACGACTTCCCCTTGCGTTGGTGATTGCCGGTCAGGGCAGCCATCCGCCATCGTCGCGT<br>AGGGTGTCACACCCCAGGAATCGCGTCACTGAACACAGCAGCCGGTAGGACGACCATGA<br>CTGAGTTGGACACCATCGCAAATCCGTCCGATCCCGCGGTGCAGCGGATCATCGATGTCA<br>CCAAGCCGTCGCGATCCAACATAAAGACAACGTTGATCGAGGACGTCGAGCCCCTCATGC<br>ACAGCATCGCGGCCGGGGTGGAGTTCATCGAGGTCTACGGCAGCGACAGCAGTCCTTTTC<br>CATCTGAGTTGCTGGATCTGTGCGGGCGGCAGAACATACCGGTCCGCCTCATCGACTCCTC<br>GATCGTCAACCAGTTGTTCAAGGGGGAGCGGAAGGCCAAGACATTCGGCATCGCCCGCGT<br>CCCTCGCCCGGCCAGGTTCGGCGATATCGCGAGCCGGCGTGGGGACGTCGTCGTTCTCGA<br>CGGGGTGAAGATCGTCGGGAACATCGGCGCGATAGTACGCACGTCGCTCGCGCTCGGAGC<br>GTCGGGGATCATCCTGGTCGACAGTGACATCACCAGCATCGCGGACCGGCGTCTCCAAAG<br>GGCCAGCCGAGGTTACGTCTTCTCCCTTCCCGTCGTTCTCTCCGGTCGCGAGGAGGCCATC<br>GCCTTCATTCGGGACAGCGGTATGCAGCTGATGACGCTCAAGGCGGATGGCGACATTTCC<br>GTGAAGGAACTCGGGACAATCCGGATCGGCTGGCCTTGCTGTTCGGCAGCGAAAAGGGT<br>GGGCCTTCCGACCTGTTCGAGGAGGCGTCTTCCGCCTCGGTTTCCATCCCCATGATGAGCC<br>AGACCGAGTCTCTCAACGTTTCCGTTTCCCTCGGAATCGCGCTGCACGAGAGGATCGACA<br>GGAATCTCGCGGCCAACCGATAAGCGCCTCTGTTCCTCGGACGCTCGGTTCCTCGACCTCG<br>ATTCGTCAGTGATGATCACCTCACACGGCAGCGATCACCACTGACATATCGAGGTCAACG<br>GTCGTGGTCCGGGCGGGCACTCCTCGAAGGCGCGGCCGACGCCCTTGAACGACTCGATGG<br>CGCTGACGCCTTCCGCGATCGCCTCGACTGTGAAAACGCTCGTGGACGTCGGCGGGTAGC<br>CGATGAGTTCCATCGCCTTGCGCATCCCCTTGAGCATGGAGAACGCGTCCACCGGGTAGT<br>CACGAAGGTACTTGCGAAGGCTTCGCGCCGTCCGAGACCGTGAGCCGGCGCAAGCCGGTG<br>TGGCGCCGGTCCCGGATCC | 41 |

-continued

| Name | Sequence | SEQ ID NO: |
|---|---|---|
| gBlock_1 | ACCCCGTCCGGGCAGGGCGGGTCACCGTCCCGCGCGGCGGGGAGAGAGGAGAGGCCGTG ACCAGGTACCGGATTGGCACTTATCCGGTGCCAATCCGGTCGGTGGTCAGGAGTGGAGAA GACATGCCGGGTACGAACGACATGCCGGGTACCGAGGACAAGCTCCGCCACTACCTGAA GCGA | 42 |
| gBlock_2 | CCGACGAGGAGGAGCAAGCCGCGCCCGAGGACCTGTCGACCGCGAGCGCCGACGACATG TTCGCCCTGATCGACCGGGAGTGGGGCACGCGGTGACCACCGACCGGATTGGCACGTAGG CCAGTGCCAATCCGGTACTTGGCAATTGCCTCGCCGCAGTTAATTAAAGTCAGTGAGCGA GGAAGCGC | 43 |
| gBlock_3 | GCTTCATGCTGGACACCTCCGCGGTGCCGGCGGACGTGGTGCGTGACATCGAGGCCGACC ATCTGTCCCTGGCCATGGAGCACTCGGATCTGACCGCCGAGGCCATAGAGAACTGGCTCG CCGAACTTCCGGCCGGCGAGGCCTGACCAAGTACCGGATTGGCACTGGCCTACGTGCCAA TCCGGTACGTGGGCAGCGATCAGTCCTGAGCGCGATGAGCCCCGGCCACACCGGCCCCCT TGCCCTCCCCCAACCTCATACGCCCCGATCACCACGTAGCGCCAAGGAGCCTGGGTCAGA TGTCGAACGAGGAGAAGCTTCTCGATCACCTCAAGTGGGTCACCGCGGAGCTGCGCCAGG CCCGGCAACGGCTCCACGACAAGGAATCGACCGAGCCGGTC | 44 |
| gusA-NC_000913.3 | ATGTTACGTCCTGTAGAAACCCCAACCCGTGAAATCAAAAAACTCGACGGCCTGTGGGCA TTCAGTCTGGATCGCGAAAACTGTGGAATTGATCAGCGTTGGTGGGAAAGCGCGTTACAA GAAAGCCGGGCAATTGCTGTGCCAGGCAGTTTTAACGATCAGTTCGCCGATGCAGATATT CGTAATTATGCGGGCAACGTCTGGTATCAGCGCGAAGTCTTTATACCGAAAGGTTGGGCA GGCCAGCGTATCGTGCTGCGTTTCGATGCGGTCACTCATTACGGCAAAGTGTGGGTCAAT AATCAGGAAGTGATGGAGCATCAGGGCGGCTATACGCCATTTGAAGCCGATGTCACGCCG TATGTTATTGCCGGGAAAAGTGTACGTATCACCGTTTGTGTGAACAACGAACTGAACTGG CAGACTATCCCGCCGGGAATGGTGATTACCGACGAAAACGGCAAGAAAAAGCAGTCTTA CTTCCATGATTTCTTTAACTATGCCGGGATCCATCGCAGCGTAATGCTCTACACCACGCCG AACACCTGGGTGGACGATATCACCGTGGTGACGCATGTCGCGCAAGACTGTAACCACGCG TCTGTTGACTGGCAGGTGGTGGCCAATGGTGATGTCAGCGTTGAACTGCGTGATGCGGAT CAACAGGTGGTTGCAACTGGACAAGGCACTAGCGGGACTTTGCAAGTGGTGAATCCGCAC CTCTGGCAACCGGGTGAAGGTTATCTCTATGAACTGTGCGTCACAGCCAAAAGCCAGACA GAGTGTGATATCTACCCGCTTCGCGTCGGCATCCGGTCAGTGGCAGTGAAGGGCGAACAG TTCCTGATTAACCACAAACCGTTCTACTTTACTGGCTTTGGTCGTCATGAAGATGCGGACT TGCGTGGCAAAGGATTCGATAACGTGCTGATGGTGCACGACCACGCATTAATGGACTGGA TTGGGGCCAACTCCTACCGTACCTCGCATTACCCTTACGCTGAAGAGATGCTCGACTGGGC AGATGAACATGGCATCGTGGTGATTGATGAAACTGCTGCTGTCGGCTTTAACCTCTCTTTA GGCATTGGTTTCGAAGCGGGCAACAAGCCGAAAGAACTGTACAGCGAAGAGGCAGTCAA CGGGGAAACTCAGCAAGCGCACTTACAGGCGATTAAAGAGCTGATAGCGCGTGACAAAA ACCACCCAAGCGTGGTGATGTGGAGTATTGCCAACGAACCGGATACCCGTCCGCAAGGTG CACGGGAATATTTCGCGCCACTGGCGGAAGCAACGCGTAAACTCGACCCGACGCGTCCGA TCACCTGCGTCAATGTAATGTTCTGCGACGCTCACACCGATACCATCAGCGATCTCTTTGA TGTGCTGTGCCTGAACCGTTATTACGGATGGTATGTCCAAAGCGGCGATTTGGAAACGGC AGAGAAGGTACTGGAAAAAGAACTTCTGGCCTGGCAGGAGAAACTGCATCAGCCGATTA TCATCACCGAATACGGCGTGGATACGTTAGCCGGGCTGCACTCAATGTACACCGACATGT GGAGTGAAGAGTATCAGTGTGCATGGCTGGATATGTATCACCGCGTCTTTGATCGCGTCA GCGCCGTCGTCGGTGAACAGGTATGGAATTTCGCCGATTTTGCGACCTCGCAAGGCATAT TGCGCGTTGGCGGTAACAAGAAAGGGATCTTCACTCGCGACCGCAAACCGAAGTCGGCG GCTTTTCTGCTGCAAAAACGCTGGACTGGCATGAACTTCGGTGAAAAACCGCAGCAGGGA GGCAAACAATGA | 45 |
| gusA-optimized | ATGCTGCGCCCGGTGGAAACCCCGACCCGCGAAATCAAGAAGCTCGACGGCCTGTGGGC GTTCAGCCTCGACCGCGAAAACTGCGGCATCGACCAGCGGTGGTGGGAGAGCGCGCTGC AGGAATCGCGCGCGATCGCCGTCCCGGGCTCGTTCAACGACCAGTTCGCGGACGCCGACA TCCGGAACTACGCCGGCAACGTCTGGTACCAGCGCGAGGTGTTCATCCCGAAGGGCTGGG CGGGCCAGCGGATCGTCCTGCGCTTCGACGCCGTGACCCACTACGGCAAGGTCTGGGTGA ACAACCAGGAAGTCATGGAACACCAGGGCGGCTACACCCCGTTCGAGGCGGACGTCACG CCGTACGTGATCGCCGGCAAGTCCGTCCGGATCACCGTCTGCGTGAACAACGAGCTGAAC TGGCAGACCATCCCGCCGGGCATGGTGATCACGGACGAGAACGGCAAGAAGAAGCAGTC CTACTTCCACGACTTCTTCAACTACGCGGGCATCCACCGCAGCGTCATGCTGTACACCACG CCGAACACCTGGGTCGACGACATCACCGTCGTGACGCACGTGGCGCAGGACTGCAACCAC GCCAGCGTCGACTGGCAGGTCGTGGCCAACGGCGACGTCTCGGTGGAGCTGCGGGACGC GGACCAGCAGGTCGTGGCCACCGGCCAGGGCACCTCGGGCACGCTGCAGGTCGTGAACC GCACCCTCTGGCAGCCGGGCGAGGGCTACCTGTACGAACTCTGCGTCACCGCGAAGTCGC AGACGGAGTGCGACATCTACCCGCTGCGGGTGGGCATCCGCTCCGTCGCCGTGAAGGGCG AGCAGTTCCTCATCAACCACAAGCCGTTCTACTTCACCGGCTTCGGCCGGCACGAGGACG CGGACCTGCGCGGCAAGGGCTTCGACAACGTCCTGATGGTGCACGACCACGCGCTCATGG ACTGGATCGGCGCCAACTCGTACCGGGACCTCGCACTACCCGTACGCTGAGGAGATGCTGG ACTGGGCCGACGAGCACGGCATCGTCGTGATCGACGAAACGGCGGCGTCGGCTTCAACC TGAGCCTCGGCATCGGCTTCGAGGCGGGCAACAAGCCGAAGGAACTCTACTCGGAGGAA GCCGTGAACGGCGAGACCCAGCAGGCGCACCTGCAGGCCATCAAGGAACTCATCGCGCG GGACAAGAACCACCCCGTCCGTCGTGATGTGGAGCATCGCCAACGAGCCGGACACCCGGC CGCAGGGCGCGCGCGAGTACTTCGCCCCGCTGGCGGAAGCCACGCGGAAGCTCGACCCG ACCCGCCCGATCACGTGCGTCAACGTGATGTTCTGCGACGCGCACACCGACACGATCTCG | 46 |

| Name | Sequence | SEQ ID NO: |
|---|---|---|
| | GACCTGTTCGACGTGCTGTGCCTCAACCGGTACTACGGCTGGTACGTGCAGTCCGGCGAC<br>CTGGAGACCGCGGAAAAGGTGCTCGAGAAGGAACTGCTCGCCTGGCAGGAGAAGCTGCA<br>CCAGCCGATCATCATCACCGAATACGGCGTGGACACGCTGGCCGGCCTCCACTCGATGTA<br>CACGGACATGTGGTCCGAGGAATACCAGTGCGCGTGGCTGGACATGTACCACCGGGTCTT<br>CGACCGCGTGTCCGCCGTCGTGGGCGAGCAGGTCTGGAACTTCGCGGACTTCGCCACCAG<br>CCAGGGCATCCTCCGGGTGGGCGGCAACAAGAAGGGCATCTTCACGCGGGACCGCAAGC<br>CGAAGAGCGCGGCCTTCCTGCTCCAGAAGCGCTGGACCGGCATGAACTTCGGCGAGAAGC<br>CGCAGCAGGGCGGCAAGCAGTGA | |
| insert_1 | GAACGACCGAGCGCAGCGGCGGCCGCGCTGATACCGCCGCTctagaCGAAGAGAAGTACCTC<br>GACTACCTGCGTCGTGCCACGGCGGACCTCCACGAGGCCCGTGGCCGCCTCCGCGAGCTG<br>GAGGCGAAGGCGGGCGAGCCGGTGGCGATCGTCGGCATGGCCTGCCGCCTGCCCGGCGG<br>CGTCGCCTCGCCCGAGGACCTGTGGCGGCTGGTGGCCGGCGGCGAGGACGCGATCTCGGA<br>GTTCCCCCAGGACCGCGGCTGGGACGTGGAGGGCCTGTACGACCCGAACCCGGAGGCCA<br>CGGGCAAGAGTTACGCCCGCGAGGCCGGATTCCTGTACGAGGCGGGCGAGTTCGACGCC<br>GACTTCTTCGGGATCTCGCCGCGCGAGGCCCTCGCCATGGACCCGCAGCAGCGTCTCCTCC<br>TGGAGGCCTCCTGGGAGGCGTTCGAGCACGCGGGATCCCGGCGGCCACCGCGCGCGGC<br>ACCTCGGTCGGCGTCTTCACCGGCGTGATGTACCACGACTACGCCACCCGTCTTCACAGCG<br>GGGTGGAGCCGGGGTTCAGGGGGCAGATCATGATGTAGTCGGGGTCGTTGACCGGCAGC<br>GCGCCGGGCGACGGGACCCGCTCGCCCTTCTGCGCGGCGATGGCGAGGGTCCGGAGCAG<br>CACCTCGGACGCGCGGTGCACGGCCTCTTCCTTGGTGGTGGCGGTGACGTGCAGGTTGTC<br>GAAGTCGCCGATCTCGATGCGGTGCGCCTTCTGGCCGTTCTCCTCGTCGATGGTGGTGATG<br>TGGGCGGGGTACGGCACGAACCACGCGGCGACCTTCGGGTCTGGCGGCGACGCGCGTCG<br>AGCTTCGACACCAGCTGCCAGGCGCGCAGGTGGGTGTACCGCTTGAGCATGTTCATCGAG<br>CGGTGGCCGGAGATCGCGGCGATCTCCATGACGTTGAGGCTGCCCAGCTCGAAGAACCGC<br>GAGATGGCCTCGTGGCGCAGGTCGTGGAAGTGCAGGTCCTCGATGCGCAGCCGCTGGGTC<br>GCGATGCGCCAGGCGTTCTTGAAGCGCTGGCCGGTGTAGTCGAACACGTTGCCGTGCAGG<br>TTGACGGGCATCATCTGGAGGAAGTTCCGGGCCCGGCGGGACAGGGGCACGTCGCGGCT<br>GTGGCCGTTCTTGGTCTCCGGCAGGTGCGCGACGCCGTGGCCAGGTCGATGTGCTCCCA<br>GCGGAGGGCCAGGATCTCGCCCTGGCGCATCGCGGTCTCCAGGGCCAGGTGGAAGATCAC<br>GTAGAGCATCAGGTTCTTCTCGCGGAAGTACCGGGACAGCCGGCGCTCCTCGGACGAGGT<br>GAGCCGGCGGTCCCGGCCGGAGCTGACCTTGGGCTTGCGCACCAGCTCGACCGGGTTGGT<br>CCGGCAGGTGCCCCACTCCACGCGCGCGATGTTGAACAGCGAGGAGAGCAGGGCGAGCT<br>CCAGCCGGACGGTGTTGCCGGTGATGGGCTTGCCGGTGCGCGGGTTGATCTCCGCCAGGC<br>GCACGTCCCGGTAGGTGGCGATGTCGACGGTGGTGATCTCGTCCATGTTCCGCAGGGCGA<br>TCGGGTAGCGCTTGATGACGTTGGACCGGTAGAACTCCTGCTGGTGGCCCTTCTTGTGGAC<br>GCTCACGGTCTTCAGGTACTTGTCGAGGGCGCGGGAGAGGCTCATCTTGCGGATGCGGGG<br>GGACGGCATttccgctcccttctctgacgccgtccacgctgcctcctcacgtgacgtgaggtg<br>caagcccggacgttccgcgtgccacgcgtgagccgccgcgtgccgtcggctccctcagcccg<br>ggttatccgactgttacggtagcgtgcatcctgttagccaatctgtcagtcagagtcaggtcat<br>taatgttatgtcattgacaatgatcatgttGATGCTGTTGTGGGCACAATCGTGCCGGTTGGTA<br>GGATCCAGCGtggcctacGTGCCAATCCGGTACCTGGCCGGCCGGCGGAGCACACCGGCCGTC<br>TCCGGCCCGGCCGCGGCCGGGCCGGAAGCCATCCGCCGCCCACCCGGTACCGACCCCTCAAGCC<br>CTTCAAGCCCTTCGACCCGTCCGATCAGTCAGTCCGGCGGTCCTCCACGACCGGTCCGGAATC<br>GCCCCCACACGAGTCAGGAAGCACACCATGGCCATGTCCGCCGAGAGGCTGACGGAGGC<br>GCTGCGGACCTCGCTCAAGGAGGCCGAGCGGCTCCGGCGGCAGAACCGCGAACTGAGGG<br>CCGCGCGGGACGCGGCGCGGGAGCCGATCGCCGTCGTCGGCATGGCCTGCCGCTACCCGG<br>GCGGTGTCACCGGCCCCGAGGAGCTGTGGGAGCTGGTGGCCGGAGGCCGGGACGCGATC<br>GGGCCGTTCCCCGTGGACCGGGGCTGGGACGTGGCGTCGGTGTACGACCCGGATCCCGAG<br>TCGAAGGGCACCACGTACTGCCGGGAGGGCGGGTTCCTGGAAGGCGCCGGTGACTTCGAC<br>GCCGCCTTCTTCGGCATCTCGCCGCGCGAGGCCCTGGTGATGGACCCGCAGCAGCGGCTG<br>CTGCTGGAGGTGTCCTGGGAGGCGCTGGAACGCGCGGGCATCGACCCGTCCTCGCTGCGC<br>GGCAGCCGCGGTGGTGTCTACGTGGGCGCCGCGCACGGCTCGTACGCCTCCGATCCCCGG<br>CTGGTGCCCGAGGGCTCGGAGGGCTATCTGCTGACCGGCAGCGCCGACGCGGTGATGTCC<br>GGCCGCATCTCCTACGCGCTCGGTCTCGAAGGACCGTCCATGACGGTGGAGACGGCCTGC<br>TCCTCCTCGCTGGTGGCGCTGCATCTGGCGGTACGGGCGCTGCGGCACGGCGAGTGCGGG<br>CTCGCGCTGGCGGGCGGGGTGGCGGTGATGGCCGATCCGGCGGCGTTCGTGGAGTTCTCC<br>CGGCAGAAGGGGCTGGCCGCCGACGGCCGCTGCAAGGCGTTCTCGGCCGCCGCCGACGG<br>CACCGGCTGGGCCGAGGGCGTCGGCGTGCTCGTCCTGGAGCGGCTGTCGGACGCGCGCCG<br>CGCGGGGCACACGGTCCTCGGCCTGGTCACCGGCACCGCGGTCAACCAGGACGGTGCCTC<br>CAACGGGCTGACCGCGCCCAACGGCCCAGCCCAGCAACGCGTCATCGCCGAGGCGCTCGC<br>CGACGCCGGGCTGTCCCCGGAGGACGTGGACGCGGTCGAGGCGCACGGCACCGGCACCC<br>GGCTCGGCGACCCCATCGAGGCCGGGGCGCTGCTCGCCGCCTCCGGACGGAACCGTTCCG<br>GCGACCACCCGCTGTGGCTCGGCTCGCTGAAGTCCAACATCGGGCATGCCCAGGCCGCCG<br>CCGGTGTCGGCGGCGTCATCAAGATGCTCCAGGCGCTGCGGCACGGCTTGCTGCCCCGCA<br>CCCTCCACGCCGACGAGCCGACCCCGCATGCCGACTGGAGCTCCGGCCGGGTACGGCTGC<br>TCACCTCCGAGGTGCCGTGGCAGCGGACCGGCCGGCCCCGGCGGACCGGGGTGTCCGCCT<br>TCGGCGTCGGCGGCACCAATGCCCATGTCGTCCTCGAAGAGGCACCCGCCCCGCCCGCGC<br>CGGAACCGGCCGGGGAGGCCCCCGGCGGCTCCCGCGCCGCAGAAGGGGCGGAAGGGCCC<br>CTGGCCTGGGTGGTCTCCGGACGCGACGAGCCGGCCCTGCGGTCCCAGGCCCGGCGGCTC<br>CGCGACCACCTCTCCCGCACCCCCGGGGCCCGCCCGCGTGACATCGCCTTCTCCCTCGCCG<br>CCACGCGCGCAGCCTTTGACCACCGCGCCGTGCTGATCGGCTCGGACGGGGCCGAACTCG<br>CCGCCGCCCTGGACGCGTTGGCCGAAGGACGCGACGGTCCGCGGTGGTGCGCGGAGTCC<br>GCGACCGGGACGGCAGGATGGCCTTCCTCTTCACCGGGCAGGGCAGCCAGCGCGCCGGG | 47 |

| Name | Sequence | SEQ ID NO: |
|---|---|---|
| | ATGGCCCACGACCTGCATGCCGCCCATACCTTCTTCGCGTCCGCCCTCGACGAGGTGACG | |
| | GACCGTCTCGACCCGCTGCTCGGCCGGCCGCTCGGCGCGCTGCTGGACGCCCGACCCGGC | |
| | TCGCCCGAAGCGGCACTCCTGGACCGGACCGAGTACACCCAGCCGGCGCTCTTCGCCGTC | |
| | GAGGTGGCGCTCCACCGGCTGCTGGAGCACTGGGGGATGCGCCCCGACCTGCTGCTGGGG | |
| | CACTCGGTGGGCGAACTGGCGGCCGCCCACGTCGCGGGTGTGCTCGATCTCGACGACGCC | |
| | TGCGCGCTGGTGGCCGCCCGCGGCAGGCTGATGCAGCGCTGCCGCCCGGCGGCGCGATG | |
| | GTCTCCGTGCGGGCCGGCGAGGACGAGGTCCGCGCACTGCTGGCCGGCCGCGAGGACGC | |
| | CGTCTGCGTCGCCGCGGTGAACGGCCCCCGGTCGGTGGTGATCTCCGGCGCGGAGGAAGC | |
| | GGTGGCCGAGGCGGCGGCGCAGCTCGCCGGACGAGGCCGCCGCACCAGGCGGCTCCGCG | |
| | TCGCGCACGCCTTCCACTCACCCCTGATGGACGGCATGCTCGCCGGATTCCGGGAGGTCG | |
| | CCGCCGGCCTGCGCTACCGGGAACCGGAGCTGACGGTCGTCTCCACGGTCACGGGGCGGC | |
| | CCGCCCGCCCCGGTGAACTCACCGGCCCCGACTACTGGGTGGCCCAGGTCCGTGAGCCCG | |
| | TGCGCTTCGCGGACGCGGTCCGCACGGCACACCGCCTCGGAGCCCGCACCTTCCTGGAGA | |
| | CCGGCCCGGACGGCGTGCTGTGCGGCATGGCAGAGGAGTGCCTGGAGGACGACACCGTG | |
| | GCCCTGCTGCCGGCGATCCACAAGCCCGGCACCGCGCCGCACGGTCCGGCGGCTCCCGGC | |
| | GCGCTGCGGGCGGCCGCCGCCGCGTACGGCCGGGGCGCCCGGGTGGACTGGGCCGGGAT | |
| | GCACGCCGACGGCCCCGAGGGGCCGGCCGCCGCGTCGAACTGCCCGTCCACGCCTTCCG | |
| | GCACCGCCGCTACTGGCTCGCCCCGGGCCGCGCGGCGGACACCGACGACTGGATGTACCG | |
| | GATCGGCTGGGACCGGCTGCCGGCTGTGACCGGCGGGCCCGGACCGCCGGCCGCTGGCT | |
| | GGTGATCCACCCCGACAGCCCGCGCTGCCGGGAGCTGTCCGGCCACGCCGAACGCGCGCT | |
| | GCGCGCCGCGGGCGCGAGCCCCGTACCGCTGCCCGTGGACGCTCCGGCCGCCGACCGGGC | |
| | GTCCTTCGCGGCACTGCTGCGCTCCGCCACCGGACCTGACACACGAGGTGACACAGCCGC | |
| | GCCCGTGGCCGGTGTGCTGTCGCTGCTGTCCGAGGAGGATCGGCCCCATCGCCAGCACGC | |
| | CCCGGTACCCGCCGGGGTCCTGGCGACGCTGTCCCTGATGCAGGCTATGGAGGAGGAGGC | |
| | GGTGGAGGCTCGCGTGTGGTCGTCTCCCGCGCCGGTCGCCGCCGCCGACCGGGAACG | |
| | GCCCGTCGGCGCGGGCGCCGCCCTGTGGGGGCTGGGGCGGGTGGCCGCCCTGGAACGCCC | |
| | CACCCGGTGGGGCGGTCTCGTGGACCTGCCCGCCTCGCCCGGTGCGGCGCACTGGGCGGC | |
| | CGCCGTGGAACGGCTCGCCGGTCCCGAGGACCAGATCGCCGTGCGCGCGTCCGGCAGTTG | |
| | GGGCCGGCGCCTCACCAGGCTGCCGCGCGACGGCGGCGGCCGGACGGCCGCCACCCGCGT | |
| | ACCGGCCGCGCGGCACGGTGCTCGTCACCGGTGGCACCGGCGCGCTCGGCGGGCATCTCG | |
| | CCCGCTGGCTCGCCGCGGCGGGCGCCGAACACCTGGCGCTCACCAGCCGCCGGGGCCCGG | |
| | ACGCGCCCGGCGCCGCCGGACTCGAGGCCGAACTCCTCCTCCTGGGCGCCAAGGTGACGT | |
| | TCGCCGCCTGCGACACCGCCGACCGCGACGGCCTCGCCCGGGTCCTGCGGGCGATACCGG | |
| | AGGACACCCCGCTCACCGGTGTTCCACGCGCGGGCGTACCGCAGGTCACGCCGCTGT | |
| | CCCGTACCTCGCCCGAGCACTTCGCCGACGTGTACGGGCAAGGCGGCGGGCGCCGCGC | |
| | ACCTGGACGAACTGACCCGCGAACTCGGCGCCGGACTCGACGCGTTCGTCCTCTACTCCT | |
| | CCGGCGCCGGCGTCTGGGGCAGCGCCGGCCAGGGTGCCTACGCCGCCGCCAACGCGCCC | |
| | TGGACGCGCTCGCCCGGCGCCGTGCGGCGGACGGACTCCCCGCCACCTCCATCGCCTGGG | |
| | GCGTGTGGGGCGGCGGCGGTATGGGGCCGACGAGGCGGGCGCGGAGTATCTGGGCCGG | |
| | CGCGGTATGCGCCCCATGGCACCGGTCTCCGCGCTCCGGGCGATGGCCACCGCCATCGCC | |
| | TCCGGGGAACCCTGCCCCACCGTCACCCACACCGACTGGGAGCGCTTCGGCGAGGGCTTC | |
| | ACCGCCTTCCGGCCCAGCCCTCTGATCGCGGGGCTCGGCACGCCGGGCGGCGGCCGGGCG | |
| | GCGGAGACCCCCGAGGAGGGGAACGCCACCGCTGCGGCGGACCTCACCGCCCTGCCGCC | |
| | CGCCGAACTCCGCACCGCGCTGCGCGAGCTGGTGCGAGCCCGGACCGCCGCGGCGCTCGG | |
| | CCTCGACGACCCGGCCGAGGTCGCCGAGGGCGAACGGTTCCCCGCCATGGGCTTCGACTC | |
| | CCTGGCCACCGTACGGCTGCGCCGCGGACTCGCCTCGGCCACGGGCCTCGACCTGCCCCG | |
| | CGATCTGCTCTTCGACCGGGACACCCCGGCCGCGCTCGCCGCCCACCTGGCCGAACTGCT | |
| | CGCCACCGCACGGGACCACGGACCCGGCGGCCCCGGGACCGGTGCCGCGCCGGCCGATG | |
| | CCGGAAGCGGCCTGCCGGCCCTCTACCGGGAGGCCGTCCGCACCGGCCGGGCCGCGGAA | |
| | ATGGCCGAACTGCTCGCCGCCGCTTCCCGGTTCCGCCCCGCCTTCGGGACGGCGGACCGG | |
| | CAGCCGGTGGCCCTCGTGCCGCTGGCCGACGGCGCGGAGGACACCGGGCTCCCGCTGCTC | |
| | GTGGGCTGCGCCGGGACGGCGGTGGCCTCCGGCCCGGTGGAGTTCACCGCCTTCGCCGGA | |
| | GCGCTGGCGGACCTCCCGGCGGCGGCCCCGATGGCCGCGCTGCCGCAGCCCGGCTTTCTG | |
| | CCGGGAGAACGAGTCCCGGCCACCCCGGAGGCATTGTTCGAGGCCCAGGCGGAAGCGCT | |
| | GCTGCGCTACGCGGCCGGCCGGCCCTTCGTGCTGCTGGGGCACTCCGCCGGCGCCAACAT | |
| | GGCCCACGCCCTGACCCGTCATCTGGAGGCGAACGGTGCGGCCCCGCAGGGCTGGTGCT | |
| | CATGGACATCTACACCCCCGCCGACCCCGGCGCGATGGGCGTCTGGCGGAACGACATGTT | |
| | CCAGTGGGTCTGGCGGCGCTCGGACATCCCCCGGACGACCACCGCCTCACGGCCATGGG | |
| | CGCCTACCACCGGCTGCTTCTCGACTGGTCGCCCACCCCCGTCCGCGCCCCCGTACTGCAT | |
| | CTGCGCGCCGCGGAACCCATGGGCGACTGGCACCCGGGGACACCGGCTGGCAGTCCCAC | |
| | TGGGACGGCGCGCACACCACCGCCGGCATCCCCGGAAACCACTTCACGATGATGACCGAA | |
| | CACGCCTCCGCCGCCGCCCGGCTCGTGCACGGCTGGCTCGCGGAACGGACCCCGTCCGGG | |
| | CAGGGCGGGTCACCGTCCCGCGCGGCGGGGAGAGAGGGAGGGCCGTGACCAGGTACCGG | |
| | ATTGGCACttatccgGTGCCAATCCGGTCGGTGGTCAGGAGTGGAGAAGACATGCCGGGTACG | |
| | AACGACATGCCGGGTACCGAGGACAAGCTCCGCCACTACCTGAAGCGAGTGACCGCGGA | |
| | TCTCGGACAGACCCGTCAGCGCCTGCGCGACGTGGAGGAGCGCCAGCGGGAACCGATCG | |
| | CCATCGTCGCGATGGCCTGCCGCTACCCGGGCGGGTGGCCTCCCCGAGCAGCTGTGGG | |
| | ACCTGGTCGCCTCACGCGGCGACGCCATCGAGGAGTTCCCCGACCGCGGCTGGGACG | |
| | TGGCGGGCCTCTACCACCCCGACCCGGACCACCCCGGCACGACCTATGTACGAGAGGCCG | |
| | GATTCCTGCGGGACGCCGCCCGCTTCGACGCCGACTTCTTCGGCATCAACCCGCGCGAGG | |
| | CGCTCGCCGCCGACCCGCAGCAACGGGTGCTCCTCGAAGTGTCGTGGGAACTGTTCGAGC | |
| | GGGCGGGCATCGACCCCGCCACGCTCAAGGACACCCTCACCGGCGTGTACGCGGGGGTGT | |
| | CCAGCCAGGACCACATGTCCGGGAGCGGGTCCCGCCGGAGGTCGAGGGCTACGCCACC | |
| | ACGGGAACCCTCTCCAGCGTCATCTCCGGCCGCATCGCCTACACCTTCGGCCTGGAGGGC | |

| Name | Sequence | SEQ ID NO: |
|------|----------|------------|
| | CCGGCGGTGACGCTCGACACGGCGTGCTCGGCATCGCTGGTCGCGATCCACCTCGCCTGC<br>CAGGCCCTGCGCCAGGGCGACTGCGGCCTGGCGGTGGCGGGAGGCGTGACCGTACTGTCC<br>ACGCCGACGGCGTTCGTGGAGTTCTCACGCCAGCGCGGACTCGCACCGGACGGCCGCTGC<br>AAGCCGTTCGCCGAGGCCGCCGACGGCACCGGATTCTCCGAGGGCGTCGGCCTGATCCTC<br>CTGGAACGCCTCTCCGACGCCCGCCGAACGGACATCAAGTACTCGGCGTCGTACGCGGA<br>TCGGCCGTCAACCAGGACGGCGCGAGCAACGGCCTGACCGCCCCGAACGACGTCGCCCA<br>GGAACGCGTGATCCGCCAGGCCCTGACCAACGCCCGCGTCACCCCGGACGCCGTCGACGC<br>CGTGGAGGCACACGGCACCGGCACCACGCTCGGCGACCCGATCGAGGGGAACGCACTCC<br>TCGCGACGTACGGAAAGGACCGCCCCGCCGACCGGCCGCTGTGGCTCGGCTCTGTGAAGT<br>CGAACATCGGCCACACGCAGGCGGCTGCGGGCGTCGCAGGCGTCATCAAGATGGTGATG<br>GCGATGCGCCACGGCGAGCTGCCCGCCTCCCTGCACATCGACCGGCCCACGCCCCACGTG<br>GACTGGGAGGGCGGGGAGTGCGGTTGCTCACCGATCCCGTGCCGTGGCCACGGGCCGA<br>CCGCCCCGCCGCGCGGGGGTCTCCTCCTTCGGCATCAGCGGCACCAACGCCCACCTGAT<br>CGTGGAACAGGCCCCCGCCCCGCCCGACACGGCCGACGACGCCCGGAAGGCGCCGCAA<br>CCCCCGGCGCTTCCGACGGCCTCGTGGTGCCGTGGGTGGTGTCGGCCCGTAGTCCGCAGG<br>CCCTGCGTGATCAGGCCCTGCGTCTGCGCGACTTTGCCGGTGACGCGTCCCGAGCGCCGCT<br>CACCGACGTGGGCTGGTCTTTGCTGCGGTCGCGTGCGCTGTTCGAGCAGCGGGCGGTGGT<br>GGCGGGGCGTGAGAGGGCTGAACTGCTGGCGGGGCTGGCTGCGTTGGCCGCTGGTGAGG<br>AGCACCCGGCTGTGACGCGGTCCCGTGAGGAAGCGGCGGTTGCTGCGAGCGGTGATGTGG<br>TGTGGCTGTTCAGTGGTCAGGGCAGTCAGTTGGTCGGTATGGGTGCTGGTTTGTATGAGCG<br>GTTCCCGGTGTTTGCGGCTGCGTTTGATGAGGTGTGCGGCTTGCTGGAGGGGGAGCTGGG<br>GGTTGGTTCGGGTGGGTTGCGGGAGGTGGTGTTCTGGGGCCCGCGGGAGCGGTTGGATCA<br>CACGGTGTGGGCGCAGGCGGGGTTGTTTGCGTTGCAGGTGGGGTTGGCCCGGTTGTGGGA<br>GTCGGTCGGGGTGCGGCCGGATGTGGTGCTCGGGCATTCGATCGGTGAGATCGCGGCCGC<br>GCATGTGGCGGGGGTCTTTGATCTGGCGGATGCGTGTCGGGTGGTGGGGGCGCGGGCGCG<br>TTTGATGGGTGGGTTGCCTGAGGGTGGGGCGATGTGTGCGGTCAGGCCACGCCCGCCGA<br>GCTGGCCGCGGATGTGGATGGCTCGTCCGTGAGTGTGGCGGCGGTCAACACACCTGACTC<br>GACGGTGATTTCAGGTCCGTCGGGTGAGGTGGATCGGATTGCTGGGGTGTGGCGGGAGCG<br>TGGGCGTAAGACGAAGGCGCTGAGCGTGAGTCATGCTTTCCATTCGGCGTTGATGGAGCC<br>GATGCTCGGGGAGTTCACGGAAGCGATACGAGGGGTCAAGTTCAGGCAGCCGTCGATCCC<br>GCTCATGAGCAATGTCTCCGGAGAGCGGGCCGGCGAGGAGATCACATCCCCGGAGTACTG<br>GGCGAGGCATGTACGCCAGACAGTGCTCTTCCAGCCCGGCGTCGCCCAAGTGGCCGCTGA<br>GGCACGCGCGTTCGTCGAACTCGGCCCCCGGCCCCGTACTGACCGCCGCCGCCCAGCACAC<br>CCTCGACCACATCACCGAGCCGGAAGGCCCCGAGCCGGTCGTCACCGCGTCCCTCCACCC<br>CGACCGGCCGGACGACGTGGCCTTCGCGCACGCCATGGCCGACTCCACGTCGCCGGTAT<br>CAGCGTGGACTGGTCGGCGTACTTCCCTGACGACCCCGCCCCCGCACCGTCGACCTGCC<br>CACCTACGCCTTCCAGGGGCGGCGCTTCTGGCTGGCGGACATCGCGGCGCCCGAGGCCGT<br>GTCCTCGACGGACGGTGAGGAGGCCGGGTTCTGGGCGCCGTCGAAGGTGCGGACTTCCA<br>GGCGCTCTGCGACACCCTGCACCTCAAGGACGACGAGCACCGCGCGGCTCTGGAGACGGT<br>GTTCCCCGCGCTGTCCGCGTGGCGGCGCGAACGACGTGAGCGGTCGATCGTCGATGCCTG<br>GCGGTACCGGGTCGACTGGCGGCGCGTCGAGCTGCCGACACCCGTTCCGGGCGCCGGTAC<br>CGGTCCCGACGCCGACACGGGCCTCGGGGCGTGGCTGATCGTGGCTCCCACGCACGGGTC<br>GGGTACTTGGCCGCAAGCCTGTGCCCGGGCGTTGGAGGAGGCGGGCGCGCCGGTACGTAT<br>CGTCGAGGCCGGCCCGCACGCCGACCGGCGGACATGGCGGACCTGGTCAGGCATGGC<br>GGGCAAGCTGTGCGGACGACACCACCCAGCTCGGAGGAGTGCTCTCCCTGCTGGCTCTCG<br>CCGAGGCACCGGCCACCAGTTCCGACACCACTTCCCACACCAGTTGCGGTACCG<br>GCTCTCTCGCGTCCCACGCCTCACCGGCACCTTGACGCTGCTGCACGGTCTGCTGGATGC<br>GGGCGTCGAAGCGCCTCTCTGGTGTGCCACGCGCGGCGCCGTGTCGTGCGGCGACGCCGA<br>TCCGCTCGTCTCCCCGTCGCAGGCCCCGGTCTGGGGACTCGGACGCGTGGCCGCCCTGGA<br>GCATCCGGAGTTGTGGGGCGGCTGGTCGACCTGCCCGCCGACCCGGAGTCGCTCGACGC<br>GAGCGCGTTGTATGCGGTTCTGCGCGGAGACGGCGGCGAGGATCAGGTCGCGCTGCGCCG<br>GGGCGCGGTCCTCGGCCGTCGCCTGGTGCCCGACGCAACCCCGGACGTGGCCCCCGGCTC<br>GTCCCCGGACGTGTCCGGAGGCGCAGCCCATGCCGACGCGACCTCCGGGGAGTGGCAGCC<br>GCATGGTGCCGTCCTCGTCACCGGAGGCGTCGGCCACCTGGCCGATCAGGTCGTACGGTG<br>GCTCGCCGCGTCCGGCGCCGAACACGTCGTACTCCTGGACACGGGCCCCGCCAACAGCCG<br>TGGTCCCGGCCGGAACGACGACCTCGCCGCGGAAGCCGCCGAACACGGCACCGAGCTGA<br>CGGTCCTGCGGTCCCTGAGCGAGCTGACAGACGTATCCGTACGTCCCATACGGACCCGTCA<br>TCCACACATCGCTGCCCGGCGAGCTCGCGCCGCTGGCCGAGGTCACCCCCGACGCGCTCG<br>GCGCGGCCGTGTCCGCCGCCGCGGCTGAGCGAACTCCCCGGCATCGGGTCAGTGGAGA<br>CCGTGCTGTTCTTCCTCCGTGACGGCTTCGCTCGGCAGTAGGGAGCACGGCGCGTACGC<br>CGCCGCCAACGCCTACCTCGACGCCCTGGCGCAACGGGCCGGTGCCGATGCTGCGAGCCC<br>CCGGACGGTCTCGGTCGGGTGGGCATCTGGGATCTGCCGGACGACGGTGACGTGGCACG<br>CGGCGCCGCCGGGCTGTCCCGGAGGCAGGGACTCCCGCCGCTGGAACCGCAGTTGGCGCT<br>CGGCGCCCTGCGCGCGGCGCTCGACGGGGGCAAGGGGCACACGCTGGTCGCCGACATCG<br>AGTGGGAGCGGTTCGCGCCGCTGTTCACGCTGGCCAGGCCCACCCGGCTGCTCGACGGGA<br>TCCCCGCGGCCCAGCGGGTCCTCGACGCCTCCTCGGAGAGCGCCGAGGCCTCGGAGAACG<br>CCTCGGCCCTCCGTCGCGAACTGACGCCCCTGCCCGTGCGGGAGCGGACCGGGGCACTTC<br>TCGACCTGGTCCGCAAACAGGTGGCCGCGTCCTGCGCTACGGACCGGCCAAGACGTGG<br>CGCCCGAGAAGGCCTTCAAGGACCTGGGCTTCGACTCGCTCGTGGTCGTGGAGCTGCGCA<br>ACCGGCTGCGCGCCGCCACCGGGCTCCGGCTGCCGCCACCCTGGTCTACGACTACCCCA<br>CACCCCGCACCCTCGCCGCACACCTGCTGGACAGGGTGCTGCCCGACGGCGGCGCGCAG<br>AGCTCCCCGTGGCCGCCCACCTGGACGACCTGGAGGCGGCCCTCACCGACCTGCCGGCCG<br>ACGACCCCCGGCGCAAGGGCCTGGTCCGGCGTCTACAGACGCTGCTGTGGAAGCAGCCCG<br>ACGCCATGGGGGCGGCGGGCCCCGCCGACGAGGAGGAGCAAGCCGCGCCCGAGGACCTG | |

| Name | Sequence | SEQ ID NO: |
|---|---|---|
| | TCGACCGCGAGCGCCGACGACATGTTCGCCCTGATCGACCGGGAGTGGGGCACGCGGTGA CCACCGACCGGATTGGCACgtaggccaGTGCCAATCCGGTACTTGGcaattgCCTCGCCGCA GTTAATTAAAGTCAGTGAGCGAGGAAGCGC | |
| insert_2 | GAACGACCGAGCGCAGCGGCGGCCGCGCTGATACCGCCGCcaattgTGACCCGGGCCCACCC CAACTACGTGCGAAACATCTGAGGAAGGTTCAACGGACGATGCCGGACGAAAGTAAGCT CGTCGATTACCTGAAGTGGGTCACGGCGGATCTCCACCAGACCCGCAGGCGCCTCCAGGA AGCCGAGTCGGGCCGCCACGAGCCCGTGGCGATCGTCGGCATGGCGTGCCGCTTCCCCGG CGGTGTGCGTTCCCCGGAGGACCTCTGGGAGATGCTCGCCGACGGCCGCGACGCCATCTC CGGGTTCCCCGCCGACCGCGGCTGGGACCTGGAGACGCTGGCCGGCGACGGAGCGGGCG GCAGCAGCACGCAGGAGGGAGGTTTCCTGCACGACGTGGCCGACTTCGACCCGGGGTTCT TCGACATCTCGCCCCGCGAGGCGCTGGCCATGGACCCCGCAGCAGCGGCTGCTCCTGGAGA CCGGCTGGGAGGCCGTGGAGCGTGCCGGGATCGCCCCCGGCAGCCTCCGCGGCAGCCGCA CCGGCGTGTTCGTCGGCACCAACTCGCAGGACTACGCCCACCTCGTCCTCGCCTCCGACG ACGACATGGGCGGCTACGCGGGCAACGGCCTGGCCGCCAGCGTGATGTCCGGCCGGCTGT CCTTTGCGCTCGGCTTCGAAGGACCCGCCGTCACCCTCGACACCGCGTGCTCCTCGGCCCT GGTCGCCCTGCACCTGGCCGCCCAGTCGGTGCGCTCCGGCGAGGCCGACCTCGCGCTGGC CGGCGGTGTCACCGTCATGACCACCTCGTCCAGCTTCGTGGGCTTCAGCCTCCAGGGCGG CCTCGCCACGGACGGCCGCTGCAAGGCGTTCGCCGACTCCGCCGACGGCACCGGCTGGTC CGAGGGCGTCGGCATGATCCTCGTCGAACGGCTCTCCGAGGCCCGGCGCAAGGGCCACCC GGTGCTCGCCGTGCTGCGCGGCTCCGCCGTGAACCAGGACGGCCGCTCCAACGGCCTCAG CGCCCCCAACGGGCCCGCCCAGCAGCGCGTCATCCGCGACGCGCTGGCCTCCGCCGGGCT CTCGCCCGCCGACGTCGACGCCGTCGAGGCGCACGGCACCGGCACCACCCTCGGCGACCC CATCGAGGCGCAGGCCCTGCTCGCCACCTACGGCCAGGACCGCGACGCGAGCCGTCCGCT GCGCCTCGGCACGGTGAAGTCCAACATCGGCCACACCCAGGCCGCGCCGGCGCCGCGG GCGTCATCAAGATGGTCCTGGCCCTGCGCCACGGGCTGCTGCCCCGCACCCTGCACATCG ACGCGCCGTCCACACACGTCGACTGGGACGCAGGACACGTCAGCCTGCTCACCGAGGCCA CCCCCTGGCCCGAGGGCGAGCAGACGCGCCGGGCCGGTGTGTCGTCCTTCGGCATCAGCG GCACCAACGCCCATGTCATCCTCGAAGAGGCCCCGGCCGAGGAGGACACCGACGCC GAGCAGCGGCCCGAGCCGGTCGTCCCGGGCGCCGTGCCGTGGCCCGTGTCGGCCCGTACC GCCGACGCCCTCGACGCCCAGCTGGAGAAGGTGCGGCCGCTCGCCGCGTCCGGCGCCGAC CCCGTCGCCGTCGGCCACGCCCTGGCCGTCACCCGCACCCCCTTCGAACACCGGGCGCTG CTGGTCGCCGCGGACGGCAATCTCACCGAGGCCGCACGCGGCACCGTCCCCTCCGGCGAC CGCCCCGGGCTGGCCGTGCTGTTCTCCGGGCAGGGCGCCCAGCGCCTCGGCATGGGCCGT GAACTCCACGCCCGCTTCCCGGTGTTCGCCGCCGCCCTGGACGAGACCCTCGCCCTCCTCG ACGAGCGCCTCGGCCACTCGCTGCGCGACGTCATCTGGGGCGAGGACCCCGTGGCCCTCG ACGACACCGGCCACACCCAGCCCGCGCTGTTCGCCGTGGAGGTCGCCCTCTACCGCTGT TCGCCCTCCTGGGGTCTGCGCCCCGACCACCTCGCCGGACACTCCGTCGGGGAGATCGCC CCGTGCATGTGGCCGGCGCACTGTCCCTGGAGGACGCCTGCACCCTGGTTGCCGCCCGCG CCCGGCCTGATGCGGGACCTGCCGGCCGGCGGAGCCATGGTCGCGCTGCGCGCCACCGAGG CCGAGGTGCGGCCGCTGCTCGACGAGCGGGTCTCGCTCGCCTCGGTCAACGGCCCCGATT CCGTGGTGGTCTCCGGCGCCGAGGACGCCGTCCTCGCCGTCGCCGAGCACTTCCGGAAGC AGGACCGGCGCACCACGCGGCTCTCCGTGAGCCACGCCTTCCACTCCCCGCTCGTCGACC CGATGCTCGACGCCTTCCGGGACGTCGTCGCGAAGCTCACCTTCGGCGAGCCGTCGGTAC CCGTCGTCTCCACCCTCACCGGCGACGTCGTCGCCGCCGAGGAACTGGCCACGCCGCACT ACTGGGTGTGCCACGCCCGGCAGGCCGTCCGCTTCGCCGACGCCGTGCGCACCCTCGTCG ACGAGGGCGCCCGGACCTTCCTGGAGGTCGGCCCGGGCGGCGTGCTGTCCGCGCTCGTCG GTGAGAACACCCAGGAGGCCGGGGTCTCTGCCGTGCCCGCGCTGCGCAAGGACCAGCCG GAGGAGGCCTCCGTGCTCGCCGCCCTCGGCACCCTGTGGACCCGGGGCACCGCGGCCGAC TGGGACGCCGTGTTCGAGGGCACCCTGCCCGGCCGCCCGGAGTCCGTGGACCTGCCGACC TACGCCTTCCAGCGCGGCCGGTACTGGCCACCGTGCGCGCCCGCTCCGGCGACCCCGCC GGACTGGGCCTCGGCGCCGCCGGGCACCCGCTGCTCAGCGCCACCGTCACCCTCGCGAG GCCGACGAGTCCGTCCTCACCGGACGGCTCTCGCCGCTGACCCACCCCTGGCTCACCGAG CACCGCGTCGACGGCCGGATCACCGTCCCCGGCACGGCCCTCGTGGAGATCGCGGTCGT GCGGGCGACGAGAACGGCACCCCCGCCTGGACCGGCTCGACCTGCTCGCCCCGCTGACC CTCGGCGACCGCGACGCGGTGCTGCTCCAGGTGCGCGTCGGCCCCGAGGACGCCTCCGGC CGGCGGACGCTCTCCGTGCACGCCCGCCCGGCGACCGCGACGACGCCCCTGGACCACG TACGCCCGTGGTGTCCTCGCCCCCGACGAGGGCGCCGAGGACACCGCCGGGGACCTTGTG GAGTGGCCGCCCGCCGACGCCCGTCAGGTCCCGCTCACGGAGCTGGAGTCCGAAGGACGC GCCCTCGGCCCGCTCTTCAGCGGCCTCACCGGGGTGTGGCGGCACGAGGGCGAGGTGTTC GCCGAGGCCGAGCTGCCCGCAGGACCCGACAGCGGCTTCGGACTGCACCCCGCGCTGCTG TCCACCGCCCTGCGCGCCGCCGCCGTCCTCGACGGCACCACGGCCGGCGAGCCCGCCGCC TTCGAGGGGCTCACCCTGCACGCCACCGGCGCCACCGCGCTGCGCGGCTACGGCTGAGCACC ACCGGGCCCGACACCGTCGACCTCACCGCCGTCGACCCCGCGGGCAACCTCGTCCTGACC GCCGAGACCGTGCGTCTCGGCACCCCGGACGGCACCGCCGACACCCCGGCCGCCACCGGC CGGGGCGACCTGTTCGGGCTGAAGTGGGTGCCCGTCAAGGCCTCGGAGCGCGCCACCGGC ACCCGCTGGGCCGTCGTCGGCTCCGACGAACTCGACCTCGGCTACGCCATGCACCGCGCC GACGAGACCGTCACCGCCTACGCGGAGTCCCTCGGCGGCCGCCATCGGCGACAGCGGGGTC GCCCCGATGTGTTCCTGATCCCGCTCGCAGGCGGAGAAGGACGCCGGAGCGGAGGGCGTG CACGCCCTCACCACCCGGGTCCTCGGCTACCTCCAGGAGTGGCTGTCCGAGCCCGGCTCT CCGGCACCCGCCTGGTCTTCGTCACCCGCCGCCGTCGCCCTCGACGACGAGGACGTCC TGGACCCGGCCGGCGCGGCCGTCTGGGGCCTGGTGCGCTCCGCGCAGACCGAGAACCCCG GCAGCCTGCTGCTCGTCGACCTCGACGACACCTTCCTGTCCGCCGGAGTACTGCCCGACGT GCTGACGCTCGACGAGCAGCAGCTCGCGGTCCGCGACTACCAGGTCCGCGCCGCCCGGCT | 48 |

-continued

| Name | Sequence | SEQ ID NO: |
|---|---|---|
| | CGCCCGGCTGCCGCGCCCGGCCGACGACGCCCCGCCGCCGACTGGAACCCCGACGGCAC | |
| | CGTCCTGATCACCGGCGGCACCGGCGGCCTCGGCGCCGCGCTCGCCCGGCACCTGGTCAC | |
| | CAGCCGGGGCGCCCGTCACCTGCTGCTGGCGAGCCGCCGCGGCCCGGACGCGCCCGGCAC | |
| | GTCCGAACTGGTCGCCGAGCTGACCGGCCTGGGAGCCCAGGTGACCGTCTCCGCCTGCGA | |
| | CGTCGGCGACCGCGACGCGGTCGACACGCTCGTCGCGTCGGTGCCCGCCGAGCACCCGCT | |
| | GACCGCCGTCGTGCACACCGCGGGTGTCCTGGACGACGCCCTGACCGGCTCGCTCACCCC | |
| | GGAACAACTGGCTGGTGTGCTGCGCCCCAAGGCCGACGCGGCCCTGCACCTGCACGAGGC | |
| | GACCCTCGGCCAGGACCTCGCCGCGTTCGTGCTGTACTCCTCGATCTCCGGCGTCATCGGC | |
| | GGCCCCGGCCAGGCCAACTACGCCGCCGCCAACGCCTCCCTGGACGCGCTCGCCCACCGG | |
| | CGCAGGGCGGCCGGTCTGCCCGGTCTGTCCCTCGCCTGGGGGCCCTGGGGCCGCGGCAGC | |
| | GGCATGACCAGCCAGGTCAGCGACACCGACCTGGGGCGGATGGACCGCGGCGGCACCCC | |
| | GCCGATGAGCCTCGAGGACGGCCTCGCCCTGTTCGACGCCGCCCTGGCCCGCACCGAGCC | |
| | GATGGTCGTGCCCACCCGGATCAATGTCACCGGACTCCAGGTCCAGCAGACGCTGCCCGC | |
| | GCTCTGGCGCGACCTGGTGCCGCGCCCCGGCGCACCGCCGCCGCGGACCGCTCGCCCAA | |
| | GACCGTGCTCGACGGGCTGCGCACGCTCGACACCGCGGGCCGGGAGAAGCTGCTCACCG | |
| | AGCTGGTCGTCGGCTTCACCGCGGGCCTGCTCGGCCACGCCGACCCCGCCGCCGTCGACC | |
| | CCGAGCGCGGCTTCCTGGAGCTGGGCTTCGACTCGCTGGTCTCGGTCAGCCTGCGCAACC | |
| | AGCTCGGCGAACTCCTCGGGCTGCGCCTGCCGACGTCGGTGGTCTTCGACAGCAAGACGC | |
| | CGGTGAAGCTGGCCCGCCACCTCAACGAGGAACTGGGCGACCTGTCCGCCTCCGGCCCCG | |
| | CGTCCGGCACCGCCGTCGCCGGCACCACGGTGCATCCCGACGACACCCTGGTCGGCCTGT | |
| | TCCACAACGCGGTGCGCGGCGGCAAGCTCGTCGAGGCGATGCGGATGCTGAAGGCGGTC | |
| | GCCAACACCCGGCCCACCTTCGAGACGCCCGGGACCTGGAGGAGCTGTCCGAGGCCGTC | |
| | ACCCTGCCACGGGGCCCGGCTCCCCGCGGCTGATCTTCGTCAGCGCGCCCGGCGCCACC | |
| | GGCGGTGTCCACCAGTACGCGCGCATCGCCGCCCACTTCCGCGGCAAGCGCCATGTGTCG | |
| | GCGATACCGCTGATGGGCTTCGCCCCCGGCGAGCTGCTGCCCGCCACCAGTGAGGCGGCG | |
| | GCCCGGATCGTCGCCGAGAGCGTCCTGATGGCGAGCGACGGCGAACCGTTCGTGATGGTG | |
| | GGCCACTCCACCGGCGGTTCCCTCGCCTACCTCGCGGCCGGGGTGCTGGAGGACACCTGG | |
| | GGCGTGAAGCCGGAGGCGGTCGTCCTGCTCGACACGCGTCCATCCGGTACAACCCCTCG | |
| | GAGGGCAACAACCTCGACCAGACGACCCGCTTCTACCTCGCCGACATCGACTCGCCGTCC | |
| | GTGACGCTCAACAGCGCCCGGATGTCCGCGATGGCGCACTGGTTCATGGCGATGACGGAC | |
| | ATCGACGCGCCCGCCACGACCGCCCCACCCTGCTCCTGCGCGCCACACAGGCCAACAAC | |
| | GGCTTCATGCTGGACACCTCCGCGGTGCCGGCGGACGTGGTGCGTGACATCGAGGCCGAC | |
| | CATCTGTCCCTGGCCATGGAGCACTCGGATCTGACCGCCGAGGCCATAGAGAACTGGCTC | |
| | GCCGAACTTCCGGCCGGCGAGGCCTGACCAAGTACCGGATTGGCACtggcctacGTGCCAATC | |
| | CGGTACGTGGGCAGCGATCAGTCCTGAGCGCGATGAGCCCCGGCCACACCGGCCCCCTTG | |
| | CCCTCCCCCAACCTCATACGCCCCGATCACCACGTAGCGCCAAGGAGCCTGGGTCAGATG | |
| | TCGAACGAGGAGAAGCTTCTCGATCACCTCAAGTGGGTCACCGCCGGAGCTGCGCCAGGCC | |
| | CGGCAACGGCTCCACGACAAGGAATCGACCGAGCCGGTCGCCATCGTCGGCATGGCCTGC | |
| | CGCTACCCGGGCGGCGCCCGGTCGGCGGAGGACCTCTGGGAACTCGTGCGCGACGGGG | |
| | TGACGCGGTCGCGGGGTTCCCCGACGACCGGGCTGGGACCTGGAGTCGCTGTATCACCC | |
| | GGATCCGGAGCATCCGGCCACCAGCTATGTGCGGGACGGCGCCTTCCTGTACGACGCCGG | |
| | CCATTTCGACGCCGAGTTCTTCGGCATCAGCCCGCGCGAGGCCACGGCGATGGATCCGCA | |
| | GCAGCGGCTGCTCCTGGAGACCGCGTGGGAGGCGATCGAGCACGCGGGCATGAACCCGC | |
| | ACGCGCTGAAGGGCAGCGACACCGGCGTCTTCACCGGAGTGAGCGCCCACGACTACCTGA | |
| | CGCTGATCAGCCAGACGGCCAGCGACGTCGAGGGGTACATCGGCACCGGCAACCTCGGC | |
| | AGTGTGGTGTCGGGCCGGATCTCCTACACGGTGGGGCTCGAAGGTCCCGCGGTCACCGTC | |
| | GACACGGCGTGCTCGTCGTCCCTGGTGGCGATCCATCTGGCAAGTCAGGCGCTGCGGCAG | |
| | GGCGAGTGCTCGCTCGCGCTGGCGGGCGGTTCGACGGTGATGGCGACGCCGGGTTCGTTC | |
| | ACCGAGTTCTCTCCCGGCAGCGGGGGCTCGCGCCCGACGGGCGGTGCAAGCCGTTCGCGGCC | |
| | GCCGCCGACGGCACCGGCTGGGGCGAGGGCGCCGGGGTGGTGGCGCTGGAGCTGCTCTC | |
| | CGAAGCGCGGCGCCGCGGCCACAAGGTCCTTGCGGTGATACGGGGTTCGGCCACCAACCA | |
| | GGACGGTACGAGCAACGGGCTCGCCGCCCCCAACGGCCCCTCCCAGGAACGCGTCATCCG | |
| | CGCCGCCCTCGCCAACGCCCGCCTCTCCGCCGAGGACATCGACGCCGTAGAGGCGCACGG | |
| | CACCGGCACCACGCTCGGCGACCCCATCGAGGCGCAGGCCCTGATCGCCACGTACGGCCA | |
| | GGGGCGCCCGGAGGACCGTCCGCTCTGGCTCGGCTCGGTGAAATCCAACATCGGCCACAC | |
| | GCAGGCCGCCGCCGGTGTCGCGGGCGTCATCAAGATGGTCATGGCGATGCGCAACGGTCT | |
| | CCTCCCGACCTCCCTGCACATCGACGCCCCGTCACCGCACGTCCAGTGGGAACAGGGCAG | |
| | CGTACGACTGCTCTCCGAGCCCGTGGACTGGCCGGCGGAGCGCACGCGGCGGGCAGGCAT | |
| | CTCGGCGTTCGGGATCTCCGGGACGAACGCGCACCTGATTCTGGAGGAGGCGCCGCCGGA | |
| | AGAGGACGCGCCGGGCCCCGTGGCGGCTGAGCCGGGTGGGTCGTGCCGTGGGTGGTGT | |
| | CCGGGCGGACGCCGGACGCGTTGCGTGAACAGGCGCGGCGGCTGGGCGAGTTCGCGCC | |
| | GGGCTGGCGGATGCGTCGGTCTCCGAGGTGGGCTGGTCGCTGGCCACGACACGCGCGTTG | |
| | TTCGATCAGCGGGCCGTGGTCGTGGGGCGGGACTTGGCTCGACGTGGTGCCAGCCTGGAG | |
| | GCATTGGCCGCGGGTGAGGCGTCGGCGGATGTGGTGGCCGGGGTGGCCGGTGATGTGGGT | |
| | CCTGGGCCGGTGTTGGTGTTTCCGGGGCAGGGGTCGCAGTGGGTGGGCATGGGCGCCCAG | |
| | CTCCTTGACGAGTCGCCCGTCTTCGCGGCGCGGATCGCGGAGTGTGAGCAGGCGCTGTCG | |
| | GCGCATGTGGACTGGTCGCTGAGTGATGTCTTGCGCGGGGACGGGAGCGAGCTGTCCCGG | |
| | GTCGAGGTCGTGCAGCCCGTGCTGTGGGCGGTGATGGTCTCGCTGGCTCGGTGTGGGCC | |
| | GATTACGGCATCACCCCGGCTGCCGTCATCGGGCACTCGCAGGGCGAGATGGCTGCCGCG | |
| | TGTGTGGCGGGGGCACTGTCACTGGAGGATGCGGCACGGATCGTAGCCGTACGCAGCGAC | |
| | GCGCTTCGTCAGCTGCAAGGGCACGGCGACATGGCCTCGCTCAGCACCGGTGCCGAGCAG | |
| | GCCGCAGAGCTGATCGGCGACCGGCCGGGCGTAGTCGTCGCGGCCGTCAACGGACCGTCG | |
| | TCGACCGTGATTTCGGGCCCGCCGAGCATGTGGCAGCCGTCGTCGCCGATGCGGAGGCG | |
| | CAGGGACTCAGGGCCCGCGTCATCGACGTCAGGTACGCCTCCCACGGTCCCCAGATCGAC | |

-continued

| Name | Sequence | SEQ ID NO: |
|---|---|---|
| | CAGCTCCACGACCTCCTCACCGACCGGCTCGCCGACATCCAGCCGACCACCACCGACGTG | |
| | GCGTTCTACTCGACGGTCACCGCAGAGCGCCTCGACGACACCACCGCCCTAGACACCGCC | |
| | TACTGGGTCACCAACCTCCGCCAGCCCGTCCGCTTCGCCGACACCATCGAAGCGCTGCTG | |
| | GCCGACGGCTACCGCCTGTTCATCGAGGCCAGCCCCCACCCCGTCCTCAACCTCGGCATCC | |
| | AGGAGACCATCGAGCAGCAGGCCGGTGCTGCGGGGACGGCCGTCACCATCCCCACCCTGC | |
| | GTCGCGACCACGGTGACACCACCCAGCTCACCCGCGCGGCCGCCCACGCCTTCACCGCCG | |
| | GCGCCCCGTCGACTGGCGGCGCTGGTTCCCGGCCGACCCCACCCCCCGTACCGTCGACC | |
| | TCCCCACCTACGCCTTCCAGCACAAGCACTACTGGGTGGAGCCGCCCGCGGCGGTCGCAG | |
| | CCGTGGGTGGTGGGCACGATCCGGTCGAGGCCCGGGTGTGGCAGGCGGATCGAGGACCTG | |
| | GACATCGACGCCCTCGCCGGCAGTCTGGAGATCGAGGGGCAGGCGGAGAGCGTCGGAGC | |
| | GCTGGAGTCCGCGCTGCCCGTCCTCTCGGCCTGGCGGCGTCGGCACCGCGAGCAGTCCAC | |
| | CGTCGACTCCTGGCGTTATCAGGTCACTTGGAAGCATCTGCCCGACGTGCCGGCGCCGGA | |
| | GCTCAGCGGGGCCTGGCTGCTGCTCGTGCCCGCCGCGCACCGCGACCACCCGGCCGTCCT | |
| | CGCGACCGCGCAGACGCTGACCGCCCATGGTGGCGAGGTGCGACGCCACGTGGTCGACG | |
| | CACGTGCCATGGAGCGTACGGAGTTGGCGCAGGAGCTGCGTGTCCTGATGGACGGGGCCG | |
| | CGTTTGCCGGAGTCGTCAATCTGCTGGCCCTGGACGAGGAGCCGCATCCCGAGCACTCGG | |
| | CCGTGCCCGCCGGACTCGCCGCGACGACCGCTCTCGTCCAGGCCCTCGCGGACAACGGCG | |
| | CCGACATCGCCGTACGCACTCTCACGCAGGGGGCTGTTTCCACGAGCGCCGGCGACGCCC | |
| | TCACCCACCCGGTGCAGGCTCAGGTGTGGGGCTGGGCGCGTCGCTGCGCTGGAGTATC | |
| | CGCGGCTGTGGGCGGGCTGGTCGATCTGCCCGCTCGTATCGACCATCAGACGCTGGCCC | |
| | GGCTGGCCGCCGCGCTGGTTCCGCAGGACGAGGACCAGATCTCCATCCGGCCGTCCGGCG | |
| | TCCATGCCCGTCGCCTTGCACACGCGCCCGCCAACACGGTCGGCAGCGGGCTTGGTTGGC | |
| | GGCCCGACGGCACCACTCTCATCACCGGCGGGACCGGCGGCATCGGCGCCGTCCTCGCGC | |
| | GGTGGCTCGCCCGTGCGGGCGCCCCGCACCTCCTCCTGACCAGCCGCCGCGGCCCCGACG | |
| | CCCCGGGAGCACAGGAACTCGCCGCGGAACTGACGGAGTTGGGGGCCGCCGTCACCGTC | |
| | ACCGCCTGCGACGTCGGCGACCGCGAGCAGGTGCGACGCCTCATCGACGATGTCCCCGCC | |
| | GAGCACCCGCTGACCGCCGTCATCCACGCGGCCGGCGTGCCGAACTACATCGGTCTCGGC | |
| | GACGTGTCGGGTGCCGAGCTGGACGAGGTGCTGCGTCCGAAGGCGCTCGCCGCTCACCAT | |
| | CTGCATGAACTGACCCGGGAGTTGCCGCTCTCGGCGTTCGTGATGTTCTCGTCGGGCGCAG | |
| | GCGTGTGGGGCAGTGGCCAGCAGGGCGCCTATGGTGCGGCCAACCACTTCCTCGACGCCC | |
| | TCGCCGAGCACCGCCGCGCCGAGGGCCTGCCCGCCACCTCCATCGCCTGGGGGCCCTGGG | |
| | CCGAGGCGGGCATGGCGGCGGACCAGGCCGCGTTGACGTTCTTCAGCCGCTTCGGCCTGC | |
| | ACCCGCTCAGCCCGGAGCTGTGCGTCAAGGCGCTGCAGCAGGCCCTGGACGCGGGTGAG | |
| | ACGACGCTGACCGTGGCGAACTTCGACTGGGCGCAGTTCACGTCGACGTTCACCGCGCAG | |
| | CGGCCCAGCCCGCTCCTCGCCGATCTGCCCGAGAACCGGCGGGCCAGCGCACCCGCGGCA | |
| | CAGCAGGAAGACGCCACGGAGGCATCGTCGCTCCAGCAGGAGCTGACGGAGGCGAAGCC | |
| | GGCGCAGCAGCGGCAGTTGCTGCTGCAGCACGTGCGCTCCCAGGCGGCGGCCCACGCTGGG | |
| | GCACTCGGACGTCGACGCGGTGCCCGCCACCAAGCGCGTTCCAGGAGCTGGGCTTCGACTC | |
| | GCTGACCGCGGTGGAGCTGCGCAACAGGCTGAACAAGAGCACCGGCTGACACTGCCGA | |
| | CCACGGTCGTCTTCGACCACCCCACCCCCGACGCGCTCACCGACGTCCTGCGGGCCGAGC | |
| | TGTCCGGTGACGCGGCGGCCTCCGCCGACCGGTGCGGGCGGCCGGGGCCTCCAGGGGCG | |
| | CCGCCGACGACGAGCCGATCGCGATCGTCGGCATGGCCTGCCGCTATCCGGGCGACGTCC | |
| | GCTCCGCCGAGGAGCTGTGGGATCTGGTCGCGGCCGGCAAGGACGCCATGGGGGCCTTCC | |
| | CCGACGACCGGGCTGGGACCTGGAGACGCTGTACGACCCGGACCCGGAGAGCCGCGGC | |
| | ACCAGCTATGTGCGCGAAGGCGGGTTCCTCTACGACGCGGGCGACTTCGACGCCGGATTC | |
| | TTCGGCATCAGCCCCCGCGAGGCCGTCGCGATGGACCCGCAGCAGCGGCTGCTCCTGGAG | |
| | ACCGCGTGGGAGGCGATCGAACGCGCGGGCCTCGACCGGGAGACCCTCAAGGGCAGCGA | |
| | CGCCGGGGTGTTCACGGGCCTGACCATCTTCGACTACCTCGCGCTCGTCGGTGAACAGCC | |
| | CACCGAGGTCGAGGGCTACATCGGCACCGGCAACCTCGGCTGTGTCGCCTCCGGCAGGGT | |
| | GTCGTACGTACTCGGCCTAGAAGGCCCCGCCATGACGATCGACACCGCCTGCTCTTCGTC | |
| | CCTGGTGGCGATCCACCAGGCGGCGCACGCGCTGCGCCAGGGCGAGTGCTCGCTCGCTCT | |
| | CGCGGGCGGCGCGACGGTGATGGCCACGCCGGGCTCGTTCGTCGAGTTCTCGCTGCAGCG | |
| | CGGGCTCGCCAAGGACGGCCGGTGCAAGCCGTTCGCGGCCGCCGCCGACGGCACCGGCT | |
| | GGGCCGAGGGAGTCGGCCTGGTCGTACTCGAACGGCTCTCGGAGGCCCGGCGCAACCGC | |
| | CACAACGTCCTGGCGGTGATCCGGGGTTCGGCCATCAACCAGGACGGCACGAGCAACGG | |
| | GCTCACGGCACCCAACGGGCAGGCGCAGCAGCGGGTGATCCGGCAGGCACTCGCCAACG | |
| | CGCGGCTCTCCGCCGAGGACGTCGACGCGGTGGAGGCGCACGGCACCGGCACCATGCTG | |
| | GGCGACCCCATCGAAGCCAGCGCGCTCGTCGCCACCTACGGCAAGGAGCGGCCCGCGGA | |
| | CCGGCCGCTGTGGCTCGGCTCGATCAAGTCGAACATCGGGCACGCGCAGGCGTCGGCCGG | |
| | TGTCGCCGGTGTGATCAAGATGGTCATGGCGCTGCGCAACGAACAGCTGCCCGCCTCCCT | |
| | GCACATCGACGCGCCCACGCCGCACGTGGACTGGGACGGCAGTGGCGTCCGCCTGCTGTC | |
| | CGAACCGGTCTCCTGGCCGCGCGGCGAACGCCCGCGCCGCGCCGGGGTGTCCGCCTTCGG | |
| | CATCTCCGGCACCAACGCGCACCTCATCCTGGAACAGGCCCCGGACGCGCCGGAGCCCGT | |
| | GACCGCTCCGGCGGAGGACGCCGCGGCGCCGGCCGGAGTGGTGCCCTGGGTGGTGTCGG | |
| | CGCGCGGCGAGGAGGCGCTGCGGGCCCAGGCCCGCCTGCTGGCCGACCGCGCCACCGCC | |
| | GACCCGCGGCTCGCGTCGCCGCTGGACGTGGGCTGGTCCCTGGTCAAGACCCGGTCGGTG | |
| | TTCGAGAACCGAGCCGTCGTCGTGGGCAAGGACCGCCAGACTCTCCTCGCCGGGCTACGG | |
| | TCCCTGGCGGCGGGCGAGCCGTCACCGGACGTCGTCGAGGGCCGGTACAGGGCGCCTCC | |
| | GGCGCGGGTCCGGTGTTGGTGTTTCCGGGGCAGGGGTCGCATGGGTGGGCATGGGTGCC | |
| | CAGCTCCTTGACGAGTCCCCCGTCTTCGCGGCGCGGATCGCGGAGTGTGAGCGGGCCCTG | |
| | TCGGCGCATGTGGACTGGTCGCTGAGTGCGGTGTTGCGCGGGGACGGGAGTGAGCTGTCC | |
| | CGGGTCGAGGTCGTGCAGCCCGTGTTGTGGGCGGTGATGGTCTCGCTGGCTTCGGTGTGG | |
| | GCCGATTACGGCATCACCCCGGCTGCCGTCATCGGGCACTCGCAGGGCGAGATGGCCGCC | |
| | GCGTGTGTGGCGGGGGCACTGTCACTGGAGGATGCGGCGCGGATCGTGGCCGTACGCAGT | |

-continued

| Name | Sequence | SEQ ID NO: |
|------|----------|------------|
| | GACGCGCTCCGTCAGCTCATGGGGCAGGGCGACATGGCGTCGTTGGGGGCCGGCTCGGAG | |
| | CAGGTTGCTGAGCTCATCGGCGACCGGCCCGGCGTGTGTGTCGCTGCCGTCAACGGGCCC | |
| | TCCTCTACGGTCATTTCAGGGCCGCCGGAGCATGTGGCAGCCGTGGTCGCGGATGCGGAG | |
| | GCGCGAGGCCTGCGCGCCCGCGTCATCGACGTCGGATACGCCTCCCACGGCCCCCAGATC | |
| | GACCAGCTCCACGACCTCCTCACCGAGCGCCTGGCCGACATCCGGCCCACGACCACGGAC | |
| | GTCGCCTTCTACTCCACGGTCACCGCCGAACGCCTCGACGACACCACCACCCTCGACACG | |
| | GATTACTGGGTCACCAACCTCCGCCAGCCCGTCCGCTTCGCCGACACCATCGAAGCGCTG | |
| | CTGGCCGACGGCTACCGCCTGTTCATCGAGGCCAGCCCCCACCCCGTCCTCAACCTCGGC | |
| | ATGGAGGAGACCATCGAGCGGGCCGACATGCCCGCCACCGTCGTGCCCACCCTGCGCCGC | |
| | GACCACGGCGACGCCGCGCAGCTCACCCGCGCGGCCGCCCAGGCCTTCGGCGCGGGGGC | |
| | GGAGGTCGACTGGACGGGCTGGTTCCCGGCCGTGCCGCTGCCTCGGGTGGTGGATCTGCC | |
| | GACGTACGCCTTCCAGCGGGAGCGGTTCTGGCTGGAGGGGCGCAGGGGGCTCGCCGGGG | |
| | ACCCGGCGGGGCTCGGGCTCGCGTCCGCGGGGCATCCGCTGCTCGGAGCCGCCGTGGAAC | |
| | TCGCGGACGGCGGCAGTCACCTGCTGACCGGCCGGATCTCTCCGCGGGACCAGGCGTGGC | |
| | TGGCCGAGCACCGGGTCATGGACACGGTGCTGCTGCCCGGTTCGGCGTTCGTGGAGCTCG | |
| | CGCTGCAGGCCGCGGTGCGGGCCGGCTGCGCGGAGTTGGCGGAGCTGACGCTGCACACTC | |
| | CGCTCGCCTTCGGGGACGAGGGTGCGGGCGCGGTCGACGTGCAGGTGGTGGTCGGTTCCG | |
| | TGGCCGAGGACGGGCGGCGTCCCGTGACCGTCCATTCGCGGCCCACGGGTGAGGGCGAG | |
| | GAGGCCGTGTGGACCCGGCATGCCGCGGGCGTGGTCGCTCCCCCGGGGCCCGACGCCGGG | |
| | GACGCCTCGTTCGGCGGGACGTGGCCGCCCCGGGCGCCACACCGGTCGGCGAGCAGGAT | |
| | CCGTACGGGGAACTCGCTTCGTACGGCTATGACTTCGGGCCCGGCTCACAGGGACTGGTG | |
| | AGCGCGTGGCGGCTCGGGGACGACCTTTTCGCCGAGGTGGCGCTGCCCGAGGCGGAGAG | |
| | CGGCAGGGCCGACCGCTACCAGGTGCACCCGGTGTTGCTCGACGCCACGCTGCACGCGCT | |
| | GATCCTGGACGCGGTCACGTCGTCCGCCGACACCGACCAAGTGCTGCTGCCGTTCTCCTG | |
| | GAGCGGGTTGCGGGTGCACGCGCCGGGCGCTGAGAAGTTGCGGGTACGTATCGCACGCA | |
| | CCGCGCCCGACCAGCTGGCCCTCACGGCCGTGGACGGGGGCGGAGGCGGGGAGCCGGTT | |
| | CTCACGCTGGAGTCGCTCACGGTACGGCCGGTGGCCGCCCACCAGATCGCGGGCGCCCGT | |
| | GCGGCGGACCGTGACGCGCTGTTCCGGCTCGTGTGGATGGAGGTCGCCGCGCGGGCCGAG | |
| | GAGACGGGCGGCGGCGCCCCGCGTGCCGCGGTCCTCGCGCCGGTCGAGAGTGGCCCGAT | |
| | GGGCGGTACGTCGGCCGGTGCGCTGGCCGACGCCTTGTCCGATGCGCTGGCCGCCGGCCC | |
| | CGTGTGGGACACGTTCGGTGCGCTCCGGGACGGAGTGGCGGCTGGGGGCGAAGCGCCCG | |
| | ATGTCGTGCTCGCCGTGTGCGCCGCGCCCGGCGCAGGTGCCGGGGCCGTTGCGGATGCCG | |
| | ATGGCAGGGCGGCGACCCGGCCGGGTACGCGCGGCTGGCCACCGTGTCCCTTCTGTCGC | |
| | TGCTCAAGGAGTGGGTGGACGACCCGGCGTTCGCGGCGACCCGTCTCGTCGTCGTCACCC | |
| | GAGGCGCGGTCGCCGCGCGGCCGGGTGAGACCGCCGGTGATCTGGCGGGCGCGTCGCTGT | |
| | GGGGTCTGGTGCGCAGCGCGCAGGCCGAGAATCCCGGTCGCCTCACGCTGCTCGACGTGG | |
| | ACGGACTGGAGTCTTCTCCGGCCACGCTGACCGGCGTACTGGCCTCCGGCGAACCGGAAT | |
| | TGGCGCTGCGTGACGGGCGCGCCTACGTGCCACGGCTCGTGCGCGACGACGCGTCGGTGC | |
| | GGCTGGTGCCGCCGGTCGGATCGCTCACGTGGCGGCTGGCTCGGTGCCAAGAGGCGGGCG | |
| | GCGGACAGCAGTTGTCCCTTGTCGACGCTCCCGAGGCCGGACGGGCGCTGGAGCCGCACG | |
| | AGGTGCGGGTGGCGGTGCGGGCCGCGGCGCCGGGGCCGCTCACGGCGGGCCAGGTCGAG | |
| | GGTGCCGGTGTGGTGACGAAGTCGGCGGCGAGGTCGGTTCGGTGGCCGTGGGCGACCG | |
| | GGTGATGGGGTTGTTCGACGCGGTGGGCCCGGTGGCCGTCACCGATGCCGCGCTGCTTAT | |
| | GCCGGTTCCGGCGGGCTGGAGTTGGGCGCAGGCGGCCGGGTCCTTGGGGGCCTATGTGTC | |
| | CGCGTATCACGTGCTGGCGGATGTCGTGGCGCCGCGCGGCGGCGAGACTCTGCTCGTCGG | |
| | GGAGGAAACCGGTTCCGTCGGCCGTGCCGTGCTGCGTCTTGCTCTTGCCGGGCGGTGGCG | |
| | GGTCGAGGCCGTGGACGGTGCGTCGACGGCGGATGATTCGGGCGCCGAGCGCGCGGCCG | |
| | ACGTCACCCTCCGCCACGAGGGGGCCCTGGTGGTCCACCGTGCGGGCGGTCGTCCGGACG | |
| | AGGGACAGGCTGTCGTGCCGCCCGAGCCCGGGCGCGTACGGGAAATCCTCGCGGAGCTG | |
| | ACCGAGCTGACCGAGCTTGCCGAGATCACGGAGTCGGCGGAGCCCCGGGCTGCCCGCGGA | |
| | ACGGGGTGACAGCCGTGCTCTGACGCCGCTCGACATCACCGTGTGGGACATCCGGCAGGC | |
| | GCCCGCCGCGATGGCGGCCCCGCCCTCGGCGGGCACGACCGTGTTCTCGCTGCCTCCCGC | |
| | CTTCGACCCCGAGGGCACCGTGCTGGTCACCGGCGGCACCGGAGCACTCGGCTCGCTGAC | |
| | GGCCCGTCACCTGGTGAACGGTACGGAGCCAGGCACCTGTTGCTGTCCAGCAGGCGGGG | |
| | AGCCGACGCGCCGGGCGCACTCGAACTGGCCGCCGACCTCTCCGCGCTCGGCGCGCGAGT | |
| | CACCTTCGCCGCGTGCGACCCGGGCGACCGGGACGAAGCCGCCGCCTCCTCGCGGCGGT | |
| | GCCCTCGGACCACCCGCTGACCGCCGTCTTCCACTGCGCGGGCACCGTGAACGACGCCGT | |
| | GGTGCAGAACCTCACGGCCGAGCAGGTCGAGGAGGTGATGCGCGTGAAGGCGGACGCCG | |
| | CGTGGCACCTGCACGAGCTGACGGGGACGCGGACCTGTCCGCGTTCGTCCTGTACTCCT | |
| | CGGTCGCCGGGCTGCTCGGCGCCCCGGCCAGGGCAGCTACACGGCCGCCAACGCCTTCT | |
| | TGGACGCGCTGGCCCGGCACCGGCACGACGGCGGTGCGGCGGCGACCTCCCTGGCGTGG | |
| | GGCTACTGGGAGCTGGCGAGCGGCATGTCGGGACGGCTCACCGACGCCGACCGGGCGCG | |
| | CCATGCCCGCGCCGGCGTGGTCGGGCTCGGCGCCGACGAGGACTCGCCCTCCTCGACGG | |
| | GGCGTGGGCCGGCGGACTGCCCCTGTACGCGCCGGTCCGTCTGGACCTGGCCCGGATGCG | |
| | CCGGCAGGCCCAGAGCCACCCCGCACCGGCGCTGCTGCGCGACCTGGTGCGCGGGGGA | |
| | GCAAGAGCGGCGGCGGTGCCGTGTCGGCGGGGCGGCCGCGCTGCTCAAGTCGCTCGGC | |
| | GCGATGTCCGACCCCGAGCGGGAGGAGGCGCTGCTCGACCTGGTGTGCACCCATATCGCG | |
| | GCCGTCCTCGGCTACGACGCGGCCACGCCCGTCAACGCGACGCAGGGGCTGCGGGAACTC | |
| | GGCTTCGACTCCCTGACCGCGGTGGAGCTGCGCAACCGGCTCTCGGCCGCGACGGGCCTG | |
| | AAGCTGCCCGCCACGTTCGTCTTCGACCATCCCAACCCGGCGGAGCTCGCCGCGCAGCTG | |
| | CGGCAGGAGCTGGCCCGCGCGCGGCGGATCGCTCGCCGACGTCCTGGCGGAGTTCGAG | |
| | CGCATCGAGGACTCGCTGCTCTCGGTCTCCTCGAAGGACGGCTCGGCGCGGGCCGAACTG | |
| | GCGGGGCGGCTGCGCGCGACGCTGGCCAGGCTCGACGCGCCGCAGGACACGGCCGGCGA | |
| | GGTCGCGGTGGCCACTCGTACACGTATCCAGGACGCGTCGGCGGACGAGATCTTCGCGTT | |

| Name | Sequence | SEQ ID NO: |
|---|---|---|
| | CATCGACCGGGACCTCGGCAGGGACGGCGCGAGCGGACAGGGCAACGGACAGCCCACCG<br>GGCAGGGCAACGGACACGGCAACGGCAACGGCAACGGCAACGGCAACGGACACGGTCA<br>GGCAGTGGAGGGGCAGCGATGACCACGTACCGGATTGGCACgtaggccaggacagcaacg<br>ccacgacaccccatcggcatcgcgtggcgggcccgattcgcgtccgcccggggagga<br>gacgggcgtccgcgtcgagggcgaggcgggcttccacccgtaggcgatccggcgagcacg<br>acacccgcagattggctcgacgcagcccagaaatgtatgatcaaggcgaatacttcatat<br>gcggggatcgaccgcgcgggtcccggacggggaagagcgggagctttgccagagagcga<br>cgacttcccccttgcgttggtgattgccggtcagggcagccatccgccatcgtcgcgtagg<br>gtgtcacaccccaggaatcgcgtcactgaacacagcagccggtaggacgaccatgactga<br>gttggacaccatcgcaaatccgtcgcatcgcggccggggtggagttcatcgaggtctacg<br>gcagcgacagcagtcctttccatctgagttgctggatctgtgcgggcggcagaacatac<br>cggtccgcctcatcgactcctcgatcgtcaaccagttgttcaaggggagcggaaggcca<br>agacattcggcatcgcccgcgtccctcgcccggccaggttcggcgatatcgcgagccggc<br>gtggggacgtcgtcgttctcgacggggtgaagatcgtcgggaacatcggcgcgatagtac<br>gcacgtcgctcgcgctcggagcgtcggggatcatcctggtcgacagtgacatcaccagca<br>tcgcggaccggcgtctccaaagggccagccgaggttacgtcttctccatcccgtcgttct<br>ctccggtcgcgaggaggccatcgccttcattcgggacagcggtatgcagctgatgacgct<br>caaggcggatggcgacatttccgtgaaggaactcggggacaatccggatcggctggcctt<br>gctgttcggcagcgaaaagggtgggccttccgacctgttcgaggaggcgtcttccgcctc<br>ggtttccatccccatgatgagccagaccgagtctctcaacgtttccgtttccctcggaat<br>cgcgctgcacgagaggatcgacaggaatctcgcggccaaccgataagcgcctctgttcct<br>cggacgctcggttcctcgacctcgattcgtcagtgatgatcacctcacacggcagcgatc<br>accactgacatatcgaggtcaacggtcgtggtccgggcgggcactcctcgaaggcgcggc<br>cgacgcccttgaacgactcgatggcgctgacgccttccgcgatcgcctcgactgtgaaaa<br>cgctcgtggacgtcggcgggtagccgatgagttccatcgccttgcgcatcccctttgagca<br>tggagaacgcgtccaccgggtagtcacgaaggtacttgcgaaggcttcgcgccgtccg<br>agaccgtgagccggcgcaagccggtgtggcgccggtcccggatccacatgctggtGA<br>TGCTGTTGTGGGCACAATCGTGCCGGTTGGTAGGATCCAGCGCTGCTCAGCGGGCTCACC<br>CGCGGATCGCGGGTCGGCGGCGCGCCGGTCAACCAGCGCAGGGCAGCCGCCGGAGGCGC<br>GGGCGAGGCGGACACGGACCTCGGCGGGCGGCTCGCCGCGATGACACCGGACGACCGGG<br>TCGCGCACCTGCGGGACCTCGTCCGTACGCACGTGGCGACCGTCCTGGGACACGGCACCC<br>CGAGCCGGGTGGACCTGGAGCGGGCCTTCCGCGACACCGGTTTCGACTCGCTCACCGCCG<br>TCGAACTCCGCAACCGTCTCAACGCCGCGACCGGGCTGCGGCTGCCGGCCACGCTGGTCT<br>TCGACCACCCCACCCCGGGGGAGCTCGCCGGGCACCTGCTCGACGAACTCGCCACGGCCG<br>CGGGCGGTCCTGGGCGGAAGGCACCGGGTCCGGAGACACGGCCTCGGCGACCGATCGG<br>CAGACCACGGCGGCCCTCGCCGAACTCGACCGGCTGGAAGGCGTGCTCGCCTCCCTCGCG<br>gatatcCCTCGCCGCAGTTAATTAAAGTCAGTGAGCGAGGAAGCGCGTAACTATAACGGTCC<br>TAAGGTAGCG | |
| pSETSC3 | atctacgtctgtcgagaagtttctgatcgaaaagttcgacagcgtctccgacctgatgca<br>gctctcgcagggcgaagaatctcgtgattcagcttcgatgtaggagggcgtggatatgtc<br>ctgagggtaaatagctgcgccgatggtttctacaaagatcgttatgttgatcggcactit<br>gcatcggccgcgctcccgattccggaagtgcttgacattggggaatttatgcggtgtgaa<br>ataccgcacagatgcgtaaggagaaaataccgcatcaggcgccattcgccattcaggctg<br>cgcaactgttgggaagggcgatcggtgcgggcctcttcgctattacgccagctggcgaaa<br>ggggatgtgctgcaaggcgattaagttgggtaacgccagggtttcccagtcacgacgt<br>tgtaaaacgacggccagtgccaagatgggctgcaggtcgactctagaggatccgcggccg<br>cgcgcgatatcgaattcgtaatcatgtcatagctgtttcctgtgtgaaattgttatccgc<br>tcacaattccacacaacatacgagccggaagcataaagtgtaaagcctggggtgcctaat<br>gagtgagctaactcacattaattgcgttgcgctcactgcccgctttccagtcgggaaacct<br>gtcgtgccagctgcattaatgaatcggccaacgcgcggggagaggcggtttgcgtattgg<br>gcgctatccgcttcctcgctcactgactcgctgcgctcggtcgttcggctgcggcgagcg<br>gtatcagctcactcaaaggcggtaatacggttatccacagaatcaggggataacgcagga<br>aagaacatgtgagcaaaaggccagcaaaaggccaggaaccgtaaaaaggccgcgttgctg<br>gcgtttttccataggctccgcccccctgacgagcatcacaaaaatcgacgctcaagtcag<br>aggtggcgaaacccgacaggactataaagataccaggcgtttccccctggaagctccctc<br>gtgcgctctcctgttccgaccctgccgcttaccggatacctgtccgcctttctcccttcg<br>ggaagcgtggcgctttctcatagctcacgctgtaggtatctcagttcggtgtaggtcgtt<br>cgctccaagctgggctgtgtgcacgaaccccccgttcagcccgaccgctgcgccttatcc<br>ggtaactatcgtcttgagtccaacccggtaagacacgacttatcgccactggcagcagcc<br>actggtaacaggattagcagagcgaggtatgtaggcggtgctacagagttcttgaagtgg<br>tggcctaactacggctacactagaagaacagtatttggtatctgcgctctgctgaagcca<br>gttaccttcggaaaaagagttggtagctcttgatccggcaaacaaaccaccgctggtagc<br>ggtggtttttttgtttgcaagcagcagattacgcgcagaaaaaaaggatctcaagaagat<br>cctttgatcttttctacggggtctgacgctcagtggaacgaaaactcacgttaagggatt<br>ttggtcatgagattatcaaaaaggatcttcacctagatcctttggttcatgtgcagctc<br>catcagcaaagggatgataagtttatcaccaccgactatttgcaacagtgccgttgat<br>cgtgctatgatcgactgatgtcatcagcggtggagtgcaatgtcgtgcaatacgaatggc<br>gaaaagccgagctcatcggtcagatctcaaccttgggggttaccccccgggtgtgctgct<br>ggtcacacagctcctccgtagcgtccggcccctcgaagatgggccacttggactgatcga<br>ggccctgcgtgctgcgctgggtccgggaggacgctcgtcatgccctcgtggtcaggtct<br>ggacgacgagccgttcgatcctgccacgtcgcccgttacaccggaccttggagttgtctc<br>tgacacattctggcgcctgccaaatgtaaagcgcagcgcccatccatttgcctttgcggc<br>agcggggccacaggcagagcagatcatctctgatccattgcccctgccacctcactcgcc | 49 |

| Name | Sequence | SEQ ID NO: |
|---|---|---|
| | tgcaagcccggtcgcccgtgtccatgaactcgatgggcaggtacttctcctcggcgtggg | |
| | acacgatgccaacacgacgctgcatcttgccgagttgatggcaaaggttccctatgggt | |
| | gccgagacactgcaccattatcaggatggcaagttggtacgcgtcgattatctcgagaat | |
| | gaccactgctgtgagcgctttgccttggcggacaggtggctcaaggagaagagccttcag | |
| | aaggaaggtccagtcggtcatgcctttgctcggttgatccgctcccgcgacattgtggcg | |
| | acagccctgggtcaactgggccgagatccgttgatcttcctgcatccgccagaggcggga | |
| | tgcgaagaatgcgatgccgctcgccagtcgattggctgagctcatgagcggagaacgaga | |
| | tgacgttggaggggcaaggtcgcgctgattgctggggcaacacgtggagcggatcgggga | |
| | ttgtattcttcagctcgctgatgatatgctgacgctcaatgccgtttggcctccgactaa | |
| | cgaaaatcccgcatttggacggctgatccgattggcacggcggacggcgaatggcggagc | |
| | agacgctcgtccgggggcaatgagatatgaaaaagcctgaactcaccgcgacgtatcggg | |
| | ccctggccagctagctagagtcgacctgcaggtccccggggatcggtcttgccttgctcg | |
| | tcggtgatgtacttcaccagctccgcgaagtcgctcttcttgatggagcgcatgggacg | |
| | tgcttggcaatcacgcgcacccccggccgttttagcggctaaaaaagtcatggctctgc | |
| | cctcgggcgaccacgccatcatgaccttgccaagctcgtcctgcttctcttcgatcttt | |
| | cgccagcagggcgaggatcgtggcatcaccgaaccgcgccgtgcgcgggtcgtcggtgag | |
| | ccagagtttcagcaggccgcccaggcggcccaggtcgccattgatgcgggcgcagctcgcg | |
| | gacgtgctcatagtccacgacgcccgtgattttgtagccctggccgacggccagcaggta | |
| | ggccgacaggctcatgccggccgccgccgcctttcctcaatcgctcttcgttcgtctgg | |
| | aaggcagtacaccttgataggtgggctgccttcctggttggcttggtttcatcagccat | |
| | ccgcttgccctcatctgttacgccggcggtagccggccagcctcgcagagcaggattccc | |
| | gttgagcaccgccaggtgcgaataagggacagtgaagaaggaacaccgctcgcgggtgg | |
| | gcctacttcacctatcctgcccggctgacgccgttggatacaccaaggaaagtctacacg | |
| | aaccattggcaaaatcctgtatatcgtgcgaaaaaggatggatataccgaaaaaatcgct | |
| | ataatgaccccgaagcagggttatgcagcggaaaagatccgtcgacctgcaggcatgcaa | |
| | gctctagcgattccagacgtcccgaaggcgtggcgcggctttccccgtgccggagcaatcg | |
| | ccctgggtgggttacacgacgcccctctatggccgtactgacggacacaccgaagccccg | |
| | gcggcaaccctcagcggatgccccggggcttcacgttttcccaggtcagaagcggttttcg | |
| | gTATCGTCCATTCCGACAGCATCGCCAGTCACTATGGCGTGCTGCTAGCGCTATATGCGTT | |
| | GATGCAATTTCTATGCGCACCCGTTCTCGGAGCACTGTCCGACCGCTTTGGCCGCCGCCCA | |
| | GTCCTGCTCGCTTCGCTACTTGGAGCCACTATCGACTACGCGATCATGGCGACCACACCCG | |
| | TCCTGTGGATCTGCCTCGCTGGCCTGCCGCAGTTCTTCAACCTCCCGGCGCAGCTTTTCGTT | |
| | CTCAATTTCAGCATCCCTTTCGGCATACCATTTTTATGACGGCGGCAGAGTCATAAAGCACC | |
| | TCATTACCCTTGCCACCGCCTCGCAGAACGGGCATTCCCTGTTCCTGCCAGTTCTGAATGG | |
| | TACGGATACTCGCACCGAAAATGTCAGCCAGCTGCTTTTTGTTGACTTCCATTGTTCATTC | |
| | CACGGACAAAAACAGAGAAAGGAAACGACAGAGGCCAAAAAGCTCGCTTTCAGCACCTG | |
| | TCGTTTCCTTTCTTTTCAGAGGGTATTTTAAATAAAAACATTAAGTTATGACGAAGAAGAA | |
| | CGGAAACGCCTTAAACCGGAAAATTTTCATAAATAGCGAAAACCCGCGAGGTCGCCGCC | |
| | CGTAACAAGGCGGATCGCCGGAAAGGACCCGCAAATGATAATAATTATCAATTGCATACT | |
| | ATCGACGGCACTGCTGCCAGATAACACCACCGGGGAAACATTCCATCATGATGGCCGTGC | |
| | GGACATAGGAAGCCAGTTCATCCATCGCTTTCTTGTCTGCTGCCATTTGCTTTGTGACATC | |
| | CAGCGCCGCACATTCAGCAGCGTTTTTCAGCGCGTTTTCGATCAACGTTTTCAATGTTGGTA | |
| | TCAACACCAGGTTTAACTTTGAACTTATCGGCACTGACGGTTACCTTGTTCTGCGCTGGCT | |
| | CATCACGCTGGATACCAAGGCTGATGTTGTAGATATTGGTCACCGGCTGAGGTGTTTCGAT | |
| | TGCCGCTGCGTGGATAGCACCATTccatggGATGCTGTTGTGGGCACAATCGTGCCGGTTGGT | |
| | AGGATCCAGCGagaagggagcggaaATGCTGCGCCCGGTGGAAACCCCGACCCGCGAAATCAAG | |
| | AAGCTCGACGGCCTGTGGGCGTTCAGCCTCGACCGCGAAACTGCGGCATCGACCAGCGG | |
| | TGGTGGGAGAGCGCGCTGCAGGAATCGCGCGCGATCGCCGTCCCGGGCTCGTTCAACGAC | |
| | CAGTTCGCGGACGCCGACATCCGGAACTACGCCGGCAACGTCTGGTACCAGCGCGAGGTG | |
| | TTCATCCCGAAGGGCTGGGCGGGCCAGCGGATCGTCCTGCGCTTCGACGCCGTGACCCAC | |
| | TACGGCAAGGTCTGGGTGAACAACCAGGAAGTCATGGAACACCAGGGCGGCTACACCCC | |
| | GTTCGAGGCGGACGTCACGCCGTACGTGATCGCCGGCAAGTCCGTCCGGATCACCGTCTG | |
| | CGTGAACAACGAGCTGAACTGGCAGACCATCCCGCCGGGCATGGTGATCACGGACGAGA | |
| | ACGGCAAGAAGAAGCAGTCCTACTTCCACGACTTCTTCAACTACGCGGGCATCCACCGCA | |
| | GCGTCATGCTGTACACCACGCCGAACACCTGGGTCGACGACATCACCGTCGTGACGCACG | |
| | TGGCGCAGGACTGCAACCACGCCAGCGTCGACTGGCAGGTCGTGGCCAACGGCGACGTCT | |
| | CGGTGGAGCTGCGGGACGCGGACCAGCAGGTCGTGGCCACCGGCCAGGGCACCTCGGGC | |
| | ACGCTGCAGGTCGTGAACCCGCACCTCTGGCAGCCGGGCGAGGGCTACCTGTACGAACTC | |
| | TGCGTCACCGCGAAGTCGCAGACGGAGTGCGACATCTACCCGCTGCGGGTGGGCATCCGC | |
| | TCCGTCGCCGTGAAGGGCGAGCAGTTCCTCATCAACCACAAGCCGTTCTACTTCACCGGCT | |
| | TCGGCCGGCACGAGGACGCGGACCTGCGCGGCAAGGGCTTCGACAACGTCCTGATGGTGC | |
| | ACGACCACGCGCTCATGGACTGGATCGGCGCCAACTCGTACCGGACCTCGCACTACCCGT | |
| | ACGCGGAGGAAATGCTGGACTGGGCCGACGAGCACGGCATCGTCGTGATCGACGAAACG | |
| | GCGGCCGTCGGCTTCAACCTGAGCCTCGGCATCGGCTTCGAGGCGGGCAACAAGCCGAAG | |
| | GAACTCTACTCGGAGGAAGCCGTGAACGGCGAGACCCAGCAGGCGCACCTGCAGGCCAT | |
| | CAAGGAACTCATCGCGCGGGACAAGAACCACCCGTCCGTCGTGATGTGGAGCATCGCCAA | |
| | CGAGCCGGACACCCGGCCGCAGGGCGCGCGCGAGTACTTCGCCCCGCTGGCGGAAGCCA | |
| | CGCGGAAGCTCGACCCGACCCGCCCGATCACGTGCGTCAACGTGATGTTCTGCGACGCGC | |
| | ACACCGACACGATCTCGGACCTGTTCGACGTGCTGTGCCTCAACCGGTACTACGGCTGGT | |
| | ACGTGCAGTCCGGCGACCTGGAGACCGCGGAAAAGGTGCTCGAGAAGGAACTGCTCGCC | |
| | TGGCAGGAGAAGCTGCACCAGCCGATCATCATCACCGAATACGGCGTGGACACGCTGGCC | |
| | GGCCTCCACTCGATGTACACGGACATGTGGTCCGAGGAATACCAGTGCGCGTGGCTGGAC | |
| | ATGTACCACCGGGTCTTCGACCGCGTGTCCGCCGTCGTGGGCGAGCAGGTCTGGAACTTC | |
| | GCGGACTTCGCCACCAGCCAGGGCATCCTCCGGGTGGCGGCAACAAGAAGGGCATCTTC | |

| Name | Sequence | SEQ ID NO: |
|---|---|---|
| | ACGCGGGACCGCAAGCCGAAGAGCGCGGCCTTCCTGCTCCAGAAGCGCTGGACCGGCAT GAACTTCGGCGAGAAGCCGCAGCAGGGCGGCAAGCAGTGATTGGGGACCCTAGAGGTCC CCTTTTTTATTTTTTGGGGACCCTAGAGGTCCCCTTTTTTATTTTccatggcgagacacc cgggaagcctg | |
| pSET152-gusA | atctacgtctgtcgagaagtttctgatcgaaaagttcgacagcgtctccgacctgatgca gctctcgcagggcgaagaatctcgtgattcagcttcgatgtaggagggcgtggatatgtc ctgcgggtaaatagctgcgccgatggatctacaaagatcgttatgttgatcggcactagc atcggccgcgctcccgattccggaagtgcttgaatttatgcggtgtgaaat accgcacagatgcgtaaggagaaaataccgcatcaggcgccattcgccattcaggctgcg caactgttgggaagggcgatcggtgcgggcctcttcgctattacgccagctggcgaaagg gggatgtgctgcaaggcgattaagttgggtaacgccagggattcccagtcacgacgttgt aaaacgacggccagtgccaagcagggctgcaggtcgactctagaGATGCTGTTGTGGGCA CAATCGTGCCGGTTGGTAGGATCCAGCGagaagggagcggaaATGCTGCGCCCGGTGGAA ACCCCGACCCGCGAAATCAAGAAGCTCGACGGCCTGTGGGCGTTCAGCCTCGACCGCGAA AACTGCGGCATCGACCAGCGGTGGTGGGAGAGCGCGCTGCAGGAATCGCGCGCGATCGC CGTCCCGGGCTCGTTCAACGACCAGTTCGCGGACGCCGACATCCGGAACTACGCCGGCAA CGTCTGGTACCAGCGCGAGGTGTTCATCCCGAAGGGCTGGGCGGGCCAGCGGATCGTCCT GCGCTTCGACGCCGTGACCCACTACGGCAAGGTCTGGGTGAACAACCAGGAAGTCATGGA ACACCAGGGCGGCTACACCCCGTTCGAGGCGGACGTCACGCCGTACGTGATCGCCGGCAA GTCCGTCCGGATCACCGTCTGCGTGAACAACGAGCTGAACTGGCAGACCATCCCGCCGGG CATGGTGATCACGGACGAGAACGGCAAGAAGAAGCAGTCCTACTTCCACGACTTCTTCAA CTACGCGGGCATCCACCGCAGCGTCATGCTGTACACCACGCCGAACACCTGGGTCGACGA CATCACCGTCGTGACGCACGTGGCGCAGGACTGCAACCACGCCAGCGTCGACTGGCAGGT CGTGGCCAACGGCGACGTCTCGGTGGAGCTGCGGGACGCGGACCAGCAGGTCGTGGCCA CCGGCCAGGGCACCTCGGGCACGCTGCAGGTCGTGAACCCGCACCTCTGGCAGCCGGGCG AGGGCTACCTGTACGAACTCTGCGTCACCGCGAAGTCGCAGACGGAGTGCGACATCTACC CGCTGCGGGTGGGCATCCGCTCCGTCGCCGTGAAGGGCGAGCAGTTCCTCATCAACCACA AGCCGTTCTACTTCACCGGCTTCGGCCGGCACGAGGACGCGGACCTGCGCGGCAAGGGCT TCGACAACGTCCTGATGGTGCACGACCACGCGCTCATGGACTGGATCGGCGCCAACTCGT ACCGGACCTCGCACTACCCGTACGCGGAGGAAATGCTGGACTGGGCCGACGAGCACGGC ATCGTCGTGATCGACGAAACGGCGGCCGTCGGCTTCAACCTGAGCCTCGGCATCGGCTTC GAGGCGGGCAACAAGCCGAAGGAACTCTACTCGGAGGAAGCCGTGAACGGCGAGACCCA GCAGGCGCACCTGCAGGCCATCAAGGAACTCATCGCGCGGGACAAGAACCACCCGTCCG TCGTGATGTGGAGCATCGCCAACGAGCCGGACACCCGGCCGCAGGGCGCGCGCGAGTAC TTCGCCCCGCTGGCGGAAGCCACGCGGAAGCTCGACCCGACCCGCCCGATCACGTGCGTC AACGTGATGTTCTGCGACGCGCACACCGACACGATCTCGGACCTGTGTTCGACGTGCTGTGC CTCAACCGGTACTACGGCTGGTACGTGCAGTCCGGCGACCTGGAGACCGCGGAAAAGGTG CTCGAGAAGGAACTGCTCGCCTGGCAGGAGAAGCTGCACCAGCCGATCATCATCACCGAA TACGGCGTGGACACGCTGGCCGGCCTCCACTCGATGTACACGGACATGTGGTCCGAGGAA TACCAGTGCGCGTGGCTGGACATGTACCACCGGGTCTTCGACCGCGTGTCCGCCGTCGTG GGCGAGCAGGTCTGGAACTTCGCGGACTTCGCCACCAGCCAGGGCATCCTCCGGGTGGGC GGCAACAAGAAGGGCATCTTCACGCGGGACCGCAAGCCGAAGAGCGCGGCCTTCCTGCT CCAGAAGCGCTGGACCGGCATGAACTTCGGCGAGAAGCCGCAGCAGGGCGGCAAGCAGT GAtctagaggatccgcggccgcgcgatatcgaattcgtaatcatgtcatagctgtacc tgtgtgaaattgttatccgctcacaattccacacaacatacgagccggaagcataaagtg taaagcctggggtgcctaatgagtgagctaactcacattaattgcgttgcgctcactgcc cgctttccagtcgggaaacctgtcgtgccagctgcattaatgaatcggccaacgcgcggg gagaggcggtagcgtattgggcgctcaccgcttcctcgctcactgactcgctgcgctcgg tcgttcggctgcggcgagcggtatcagctcactcaaaggcggtaatacggttatccacag aatcaggggataacgcaggaaagaacatgtgagcaaaaggccagcaaaaggccaggaacc gtaaaaaggccgcgttgctggcgtattccataggctccgcccccctgacgagcatcacaa aaatcgacgctcaagtcagaggtggcgaaacccgacaggactataaagataccaggcgat cccccctggaagctccctcgtgcgctctcctgaccgaccctgccgcttaccggatacctgt ccgcctactccatcgggaagcgtggcgattctcatagctcacgctgtaggtatctcagtt cggtgtaggtcgttcgctccaagctgggctgtgtgcacgaaccccccgttcagcccgacc gctgcgccttatccggtaactatcgtcttgagtccaacccggtaagacacgacttatcgc cactggcagcagccactggtaacaggattagcagagcgaggtatgtaggcggtgctacag agacttgaagtggtggcctaactacggctacactagaagaacagtataggtatctgcgct ctgctgaagccagttaccacgcgaaaaagagttggtagctcttgatccggcaaacaaacca ccgctggtagcggtggtattagtttgcaagcagcagattacgcgcagaaaaaaaggatct caagaagatcctttgatcttactacggggtctgacgctcagtggaacgaaaactcacgtt aagggattttggtcatgagattatcaaaaaggatcttcacctagatcctttttggttcatg tgcagctccatcagcaaaaggggatgataagtttatcaccaccgactatttgcaacagtg ccgttgatcgtgctatgatcgactgatgtcatcagcggtggagtgcaatgtcgtgcaata cgaatggcgaaaagccgagctcatcggtcagcttctcaaccttgggttaccccggcgg tgtgctgctggtccacagctccttccgtagcgtccggcccctcgaagatgggccacttgg actgatcgaggccctgcgtgctgcgctgggtccgggagggacgctcgtcatgccctcgtg gtcaggtctggacgacgagccgttcgatcctgccacgtcgccacgtacaccggaccttgg agttgtctctgacacattctggcgcctgccaaatgtaaagcgcagcgcccatccatttgc ctttgcggcagcggggccacaggcagagcagatcatctctgatccattgccctgccacc tcactcgcctgcaagcccggtcgcccgtgtccatgaactcgatgggcaggtacttctcct cggcgtgggacacgatgccaacacgacgctgcatcttgccgagttgatggcaaaggaccc tatggggtgccgagacactgcaccattatcaggatggcaagaggtacgcgtcgattatct | 50 |

-continued

| | | SEQ |
|---|---|---|
| Name | Sequence | ID NO: |
| | cgagaatgaccactgctgtgagcgctttgccaggcggacaggtggctcaaggagaagagc | |
| | cttcagaaggaaggtccagtcggtcatgcctttgctcggttgatccgctcccgcgacatt | |
| | gtggcgacagccctgggtcaactgggccgagatccgttgatcacctgcatccgccagagg | |
| | cgggatgcgaagaatgcgatgccgctcgccagtcgattggctgagctcatgagcggagaa | |
| | cgagatgacgttggaggggcaaggtcgcgctgattgctggggcaacacgtggagcggatc | |
| | ggggattgtctttcttcagctcgctgatgatatgctgacgctcaatgccgtaggcctccg | |
| | actaacgaaaatcccgcatttggacggctgatccgattggcacggcggacggcgaatggc | |
| | ggagcagacgctcgtccgggggcaatgagatatgaaaaagcctgaactcaccgcgacgta | |
| | tcgggccctggccagctagctagagtcgacctgcaggtccccggggatcggtcttgccttt | |
| | gctcgtcggtgatgtacttcaccagctccgcgaagtcgctcttcttgatggagcgcatgg | |
| | ggacgtgcttggcaatcacgcgcacccccggccgattagcggctaaaaaagtcatggct | |
| | ctgccctcgggcggaccacgccatcatgaccttgccaagctcgtcctgcttctcttcga | |
| | tcttcgccagcagggcgaggatcgtggcatcaccgaaccgcgccgtgccgcgggtcgtcgg | |
| | tgagccagagtttcagcaggccgcccaggcggcccaggtcgccattgatgcgggccagct | |
| | cgcggacgtgctcatagtccacgacgcccgtgattttgtagccctggccgacggccagca | |
| | ggtaggccgacaggctcatgccggccgccgccgccttttcctcaatcgctcttcgttcgt | |
| | ctggaaggcagtacaccttgataggtgggctgcccttcctggttggcttggtttcatcag | |
| | ccatccgcttgccctcatctgttacgccggcggtagccggccagcctcgcagagcaggat | |
| | tcccgttgagcaccgccaggtgcgaataagggacagtgaagaaggaacacccgctcgcgg | |
| | gtgggcctacttcacctatcctgcccggctgacgccgaggatacaccaaggaaagtctac | |
| | acgaacccttttggcaaaatcctgtatatcgtgcgaaaaaggatggatataccgaaaaaat | |
| | cgctataatgaccccgaagcagggttatgcagcggaaaagatccgtcgacctgcaggcat | |
| | gcaagctctagcgattccagacgtcccgaaggcgtggcgcggcaccccgtgccggagcaa | |
| | tcgccctgggtgggttacacgacgcccctctatggcccgtactgacggacacaccgaagc | |
| | cccggcggcaaccctcagcggatgccccgggggcttcacgttttcccaggtcagaagcggt | |
| | tttcgggagtagtgccccaactggggtaacctttgagttctctcagttggggggcgtaggg | |
| | tcgccgacatgacacaaggggagtgaccggggtggacacgtacgcgggtgcttacgaccg | |
| | tcagtcgcgcgagcgcgagaattcgagcgcagcaagcccagcgacacagcgtagcgccaa | |
| | cgaagacaaggcggccgaccttcagcgcgaagtcgagcgcgacggggggccggttcaggtt | |
| | cgtcgggcatttcagcgaagcgccgggcacgtcggcgttcgggacggcggagcgcccgga | |
| | gttcgaacgcatcctgaacgaatgccgcgccgggcggctcaacatgatcaagtctatgac | |
| | gtgtcgcgatctcgcgcctgaaggtcatgacgcgattccgattgtctcggaattgctcg | |
| | ccctgggcgtgacgattgtaccactcaggaaggcgtcttccggcagggaaacgtcatgga | |
| | cctgattcacctgattatgcggctcgacgcgtcgcacaaagaatcttcgctgaagtcgc | |
| | gaagattctcgacacgaagaaccttcagcgcgaattgggcgggtacgtcggcgggaaggc | |
| | gccttacggcttcgagcttgtttcggagacgaaggagatcacgcgcaacggccgaatggt | |
| | caatgtcgtcatcaacaagcttgcgcactcgaccactcccttaccggacccttcgagtt | |
| | cgagcccgacgtaatccggtggtggtggcgtgagatcaagacgcacaaacaccttcccttt | |
| | caagccgggcagtcaagccgccattcacccgggcagcatcacggggctttgtaagcgcat | |
| | ggacgctgacgccgtgccgacccggggcgagacgattgggaagaagaccgcttcaagcgc | |
| | ctgggacccggcaaccgttatgcgaatcatcgggacccgcgtattgcgggcttcgccgct | |
| | gaggtgatctacaagaagaagccggacggcacgccgaccacgaagattgaggggttaccgc | |
| | attcagcgcgacccgatcacgctccggccggtcgagcttgattgcggaccgatcatcgag | |
| | cccgctgagtggtatgagcttcaggcgtggttggacggcagggggcgcggcaaggggcta | |
| | cccggggcaagccattctgtccgccatggacaagctgtactgcgagtgtggcgccgtca | |
| | tgacttcgaagcgcggggaagaatcgatcaaggactcttaccgctgccgtcgccggaagg | |
| | tggtcgaccgtccgcacctgggcagcacgaaggcacgtcaacgtcagcatggcggcac | |
| | tcgacaagttcgttgcggaacgcatcttcaacaagatcaggcacgccgaaggcgacgaag | |
| | agacgttggcgcttctgtgggaagccgcccgacgcttcggcaagctcactgaggcgcctg | |
| | agaagagcggcgaacgggcgaaccttgttgcggagcgcgccgacgccctgaacgcccttg | |
| | aagagctgtacgaagaccgcgcggcaggcgcgtacgacggacccgttggcaggaagcact | |
| | tccggaagcaacaggcagcgctgacgctccggcagcaaggggcggaagagcggcttgccg | |
| | aacttgaagccgccgaagcccgaagcttccccttgaccaatggttccccgaagacgccg | |
| | acgctgacccgaccggccctaagtcgtggtggggcgcgcgtcagtagacgacaagcgcg | |
| | tgacgtcgggctatcgtagacaagatcgagtcacgaagtcgactacgggcagggggcagg | |
| | gaacgcccatcgagaagcgcgcttcgatcacgtgggcgaagccgccgaccgacgacgacga | |
| | agacgacgcccaggacggcacggaagacgtagcggcgtagcgagacacccgggaagcctg | |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An engineered nucleic acid, comprising:
   (a) a promoter operably linked to at least two heterologous genes of at least one biosynthetic pathway of interest;
   (b) at least two different pairs of shufflon recombinase recognition sequences (RRSs), wherein the at least two heterologous genes are located between the at least two different pairs of shufflon RRSs and wherein the RRSs comprise nucleotide sequences selected from the sequences set forth in SEQ ID NOs. 5-8; and
   (c) a promoter operably linked to a gene encoding a *Salmonella enterica* shufflon recombinase.

2. The engineered nucleic acid of claim 1, wherein the at least two heterologous genes encode proteins selected from the group consisting of: enzymes, regulatory proteins and transport proteins.

3. The engineered nucleic acid of claim 1, further comprising (d) nucleotide sequences homologous to a chromosomal locus of a host cell of interest.

4. The engineered nucleic acid of claim 1, wherein the gene encoding the shufflon recombinase is oriented in a 3' to 5' direction.

5. The engineered nucleic acid of claim 1, wherein the promoter of (a) and/or (c) is an inducible promoter.

6. The engineered nucleic acid of claim 1, wherein the engineered nucleic acid construct further comprises an antibiotic resistance gene.

7. The engineered nucleic acid of claim 1, wherein the RRSs recombine, in the presence of shufflon recombinase activity, at different rates relative to each other.

8. The engineered nucleic acid of claim 1, wherein the promoter of (a) is oriented in the 5' to 3' direction, and wherein each gene operably linked to the promoter of (a) is oriented in a 5' to 3' direction.

9. The engineered nucleic acid of claim 1, wherein the promoter of (a) is oriented in the 5' to 3' direction, and wherein each gene operably linked to the promoter of (a) is oriented in a 3' to 5' direction.

10. A cell comprising the engineered nucleic acid of claim 1.

11. The cell of claim 10, wherein the cell comprises a deletion or modification in a gene of a biosynthetic pathway of interest.

12. The cell of claim 10, wherein the engineered nucleic acid is present on an episomal vector or integrated into a chromosome of the cell.

13. A method of producing molecules, comprising:
    culturing the cells of claim 10 under conditions that result in expression of a shufflon recombinase, recombination of RSSs, expression of at least two heterologous genes, and production of molecules produced by the biosynthetic pathway of interest.

14. The method of claim 13, further comprising isolating the molecules.

* * * * *

SEQUENCE LISTING

<160> NUMBER OF SEQ ID NOS: 69

<210> SEQ ID NO 1
<211> LENGTH: 181
<212> TYPE: DNA
<213> ORGANISM: Artificial Sequence
<220> FEATURE:
<223> OTHER INFORMATION: Synthetic Polynucleotide

<400> SEQUENCE: 1
ccggccggcg gagcacaccc ggccgtctcc ggcccggccg cggccgggcc ggaagccatc    60
cgccgcccac ccggtaccga cccctcaagc ccttcaagcc cttcgacccg tccgatcagt   120
cagtccggcg gtcctccacg accggtccgg aatcgccccc acacgagtca ggaagcacac   180
c                                                                  181

<210> SEQ ID NO 2
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 2
tcaggagtgg agaagac                                                  17

<210> SEQ ID NO 3
<211> LENGTH: 107
<212> TYPE: DNA
<213> ORGANISM: Artificial Sequence
<220> FEATURE:
<223> OTHER INFORMATION: Synthetic Polynucleotide

<400> SEQUENCE: 3
gcagcgatca gtcctgagcg cgatgagccc cggccacacc ggccccccttg ccctccccca    60 acctcatacg ccccgatcac cacgtagcgc caaggagcct gggtcag                 107

<210> SEQ ID NO 4
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 4
tgacccgggc ccaccccaac tacgtgcgaa acatctgagg aaggttcaac ggacg         55

<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
gtgccaatcc ggtacgtgg                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 6
gtgccaatcc ggtacctgg                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 7
gtgccaatcc ggtcggtgg                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 8
gtgccaatcc ggtacttgg                                                19

<210> SEQ ID NO 9
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 9
ggtagcgtgc atcctgttag cc                                            22

<210> SEQ ID NO 10
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 10
gtcatggacg gtccttcgag acc                                           23

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
ccgatctgct cttcgaccgg                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
tcacggcctc tcctctctcc                                               20

<210> SEQ ID NO 13
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 13
cgtttgatga ggtgtgcggc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
gatgtccgcc agccagaagc                                              20

<210> SEQ ID NO 15
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 15
ggagaagaca tgccgggtac g                                            21

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
cgtacgtcgc gaggagtgcg                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
ggacctgggc ttcgactcgc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
gcacttgccg atctatgcgg                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
ctcgctggtc tcggtcagcc                                              20
```

<210> SEQ ID NO 20
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 20
ggcctcggcg gtcagatcc                                            19

<210> SEQ ID NO 21
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 21
gcgatcagtc ctgagcgcg                                            19

<210> SEQ ID NO 22
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 22
cgtatcaccg caaggacctt gtgg                                      24

<210> SEQ ID NO 23
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 23
gtgcgacgcc tcatcgacg                                            19

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
cgtacagcgt ctccaggtcc                                           20

<210> SEQ ID NO 25
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 25
cgacgtacgc cttccagcg                                            19

<210> SEQ ID NO 26
<211> LENGTH: 18
<212> TYPE: DNA
<213> ORGANISM: Artificial Sequence
<220> FEATURE:

<223> OTHER INFORMATION: Synthetic Polynucleotide

<400> SEQUENCE: 26
cgcaccgaac gtgtccca                                                           18

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
ggtcgaggag gtgatgcgcg                                                         20

<210> SEQ ID NO 28
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 28
cgttgccgtg tccgttgccc tgc                                                     23

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
gcacttgccg atctatgcgg                                                         20

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 30
gcacttgccg atctatgcgg                                                         20

<210> SEQ ID NO 31
<211> LENGTH: 5707
<212> TYPE: DNA
<213> ORGANISM: Artificial Sequence
<220> FEATURE:
<223> OTHER INFORMATION: Synthetic Polynucleotide

<400> SEQUENCE: 31
ccggccggcg gagcacaccc ggccgtctcc ggcccggccg cggccgggcc ggaagccatc             60
cgccgcccac ccggtaccga cccctcaagc ccttcaagcc cttcgacccg tccgatcagt            120
cagtccggcg gtcctccacg accggtccgg aatcgccccc acacgagtca ggaagcacac            180
catggccatg tccgccgaga ggctgacgga ggcgctgcgg acctcgctca aggaggccga            240
gcggctccgg cggcagaacc gcgaactgag ggccgcgcgg gacgcggcgc gggagccgat            300
cgccgtcgtc ggcatggcct gccgctacc ggcggtgtc accggccccg aggagctgtg             360
ggagctggtg gccggaggcc gggacgcgat cgggccgttc cccgtggacc ggggctggga            420
cgtggcgtcg gtgtacgacc cggatcccga gtcgaagggc accacgtact gccggagggg            480

-continued

| | |
|---|---|
| cggggttcctg gaaggcgccg gtgacttcga cgccgccttc ttcggcatct cgccgcgcga | 540 |
| ggccctggtg atggacccgc agcagcggct gctgctggag gtgtcctggg aggcgctgga | 600 |
| acgcgcgggc atcgacccgt cctcgctgcg cggcagccgc ggtggtgtct acgtgggcgc | 660 |
| cgcgcacggc tcgtacgcct ccgatccccg gctggtgccc gagggctcgg agggctatct | 720 |
| gctgaccggc agcgccgacg cggtgatgtc cggccgcatc tcctacgcgc tcggtctcga | 780 |
| aggaccgtcc atgacggtgg agacggcctg ctcctcctcg ctggtggcgc tgcatctggc | 840 |
| ggtacgggcg ctgcggcacg gcgagtgcgg gctcgcgctg cgggcgggg tggcggtgat | 900 |
| ggccgatccg gcggcgttcg tggagttctc ccggcagaag gggctggccg ccgacggccg | 960 |
| ctgcaaggcg ttctcggccg ccgccgacgg caccggctgg gccgagggcg tcggcgtgct | 1020 |
| cgtcctggag cggctgtcgg acgcgcgccg cgcggggcac acggtcctcg gcctggtcac | 1080 |
| cggcaccgcg gtcaaccagg acggtgcctc caacgggctg accgcgccca acggcccagc | 1140 |
| ccagcaacgc gtcatcgccg aggcgctcgc cgacgccggg ctgtcccgg aggacgtgga | 1200 |
| cgcggtcgag gcgcacggca ccggcacccg gctcggcgac ccatcgagg ccggggcgct | 1260 |
| gctcgccgcc tccggacgga accgttccgg cgaccaccg ctgtggctcg gctcgctgaa | 1320 |
| gtccaacatc gggcatgccc aggccgccgc cggtgtcggc ggcgtcatca agatgctcca | 1380 |
| ggcgctgcgg cacggcttgc tgccccgcac cctccacgcc gacgagccga ccccgcatgc | 1440 |
| cgactggagc tccggccggg tacggctgct cacctccgag gtgccgtggc agcggaccgg | 1500 |
| ccggccccgg cggaccgggg tgtccgcctt cggcgtcggc ggcaccaatg ccatgtcgt | 1560 |
| cctcgaagag caccccgccc cgcccgcgcc ggaaccggcc ggggaggccc ccggcggctc | 1620 |
| ccgcgccgca aaggggcgg aagggcccct ggcctgggtg gtctccggac gcgacgagcc | 1680 |
| ggccctgcgg tcccaggccc ggcggctccg cgaccacctc tcccgcaccc ccggggcccg | 1740 |
| cccgcgtgac atcgccttct ccctcgccgc cacgcgcgca gcctttgacc accgcgccgt | 1800 |
| gctgatcggc tcggacgggg ccgaactcgc cgccgccctg gacgcgttgg ccgaaggacg | 1860 |
| cgacggtccg gcggtggtgc gcggagtccg cgaccgggac ggcaggatgg ccttcctctt | 1920 |
| caccgggcag ggcagccagc gcgccgggat ggcccacgac ctgcatgccg cccataccct | 1980 |
| cttcgcgtcc gccctcgacg aggtgacgga ccgtctcgac ccgctgctcg gccggccgct | 2040 |
| cggcgcgctc ctggacgccc gacccggctc gcccgaagcg gcactcctgg accggaccga | 2100 |
| gtacacccag ccggcgctct tcgccgtcga ggtggcgctc caccggctgc tggagcactg | 2160 |
| ggggatgcgc cccgacctgc tgctggggca ctcggtgggc gaactggcgg ccgcccacgt | 2220 |
| cgcgggtgtg ctcgatctcg acgacgcctg cgcgctggtg ccgcccgcg gcaggctgat | 2280 |
| gcagcgcctg ccgccggcg gcgcgatggt tccgtgcgg gccggcgagg acgaggtccg | 2340 |
| cgcactgctg gccggccgcg aggacgccgt ctgcgtcgcc gcggtgaacg gccccggtc | 2400 |
| ggtggtgatc tccggcgcgg aggaagcggt ggccgaggcg gcggcgcagc tcgccggacg | 2460 |
| aggccgccgc accaggcggc tccgcgtcgc gcacgccttc cactcacccc tgatggacgg | 2520 |
| catgctcgcc ggattccggg aggtcgccgc cggcctgcgc taccgggaac cggagctgac | 2580 |
| ggtcgtctcc acggtcacgg gcggccccgc ccgcccggt gaactcaccg gccccgacta | 2640 |
| ctgggtggcc caggtccgtg agcccgtgcg cttcgcggac gcggtccgca cggcacaccg | 2700 |
| cctcggagcc cgcaccttcc tggagaccgg cccggacggc gtgctgtgcg gcatggcaga | 2760 |
| ggagtgcctg gaggacgaca ccgtggccct gctgccggcg atccacaagc ccggcaccgc | 2820 |

```
gccgcacggt ccggcggctc ccggcgcgct gcgggcggcc gccgccgcgt acggccgggg   2880
cgcccgggtg gactgggccg ggatgcacgc cgacggcccc gaggggccgg cccgccgcgt   2940
cgaactgccc gtccacgcct tccggcaccg ccgctactgg ctcgcccccgg gccgcgcggc   3000 ggacaccgac gactggatgt accggatcgg ctgggaccgg ctgccggctg tgaccggcgg   3060
ggcccggacc gccggccgct ggctggtgat ccaccccgac agcccgcgct gccgggagct   3120
gtccggccac gccgaacgcg cgctgcgcgc gcgggcgcg agcccgtac cgctgcccgt   3180 ggacgctccg gccgccgacc gggcgtcctt cgcggcactg ctgcgctccg ccaccggacc   3240
tgacacacga ggtgacacag ccgcgcccgt ggccggtgtg ctgtcgctgc tgtccgagga   3300
ggatcggccc catcgccagc acgccccggt accgccgggg gtcctggcga cgctgtccct   3360
gatgcaggct atggaggagg aggcggtgga ggctcgcgtg tggtgcgtct cccgcgccgc   3420
ggtcgccgcc gccgaccggg aacggcccgt cggcgcgggc gccgccctgt gggggctggg   3480
gcgggtggcc gccctggaac gccccacccg gtgggcggt ctcgtggacc tgcccgcctc   3540
gcccggtgcg gcgcactggg cggccgccgt ggaacggctc gccggtcccg aggaccagat   3600
cgccgtgcgc gcgtccggca gttggggccg gcgcctcacc aggctgccgc gcgacggcgg   3660
cggccggacg gccgcacccg cgtaccggcc gcgcggcacg gtgctcgtca ccggtggcac   3720
cggcgcgctc ggcgggcatc tcgcccgctg gctcgccgcg gcgggcgccg aacacctggc   3780
gctcaccagc cgccggggcc cggacgcgcc cggcgccgcc ggactcgagg ccgaactcct   3840
cctcctgggc gccaaggtga cgttcgccgc ctgcgacacc gccgaccgcg acggcctcgc   3900
ccgggtcctg cgggcgatac cggaggacac cccgctcacc gcggtgttcc acgccgcggg   3960
cgtaccgcag gtcacgccgc tgtcccgtac ctcgcccgag cacttcgccg acgtgtacgc   4020
gggcaaggcg gcgggcgccg cgcacctgga cgaactgacc cgcgaactcg cgccggact   4080 cgacgcgttc gtcctctact cctccggcgc cggcgtctgg ggcagcgccg ccagggtgc   4140 ctacgccgcc gccaacgcgg ccctggacgc gctcgcccgg cgccgtgcgg cggacgact   4200 ccccgccacc tccatcgcct ggggcgtgtg gggcggcggc ggtatggggg ccgacgaggc   4260
gggcgcggag tatctggggcc ggcgcggtat gcgccccatg gcaccggtct ccgcgctccg   4320
ggcgatggcc accgccatcg cctccgggga accctgcccc accgtcaccc acaccgactg   4380
ggagcgcttc ggcgagggct tcaccgcctt ccggcccagc cctctgatcg cggggctcgg   4440
cacgccgggc ggcggccggg cggcggagac ccccgaggag gggaacgcca ccgctgcggc   4500
ggacctcacc gccctgccgc ccgccgaact ccgcaccgcg ctgcgcgagc tggtgcgagc   4560
ccggaccgcc gcggcgctcg gcctcgacga cccggccgag gtcgccgagg gcgaacggtt   4620
ccccgccatg ggcttcgact ccctggccac cgtacggctg cgccgcggac tcgcctcggc   4680
cacgggcctc gacctgcccc ccgatctgct cttcgaccgg gacaccccgg ccgcgctcgc   4740
cgcccacctg gccgaactgc tcgccaccgc acgggaccac ggaccggcg gccccgggac   4800 cggtgccgcg ccggccgatg ccggaagcgg cctgccggcc ctctaccggg aggccgtccg   4860
caccggccgg gccgcggaaa tggccgaact gctcgccgcc gcttcccggt tccgccccgc   4920
cttcgggacg gcggaccggc agccggtggc cctcgtgccg ctggccgacg gcgcggagga   4980
caccgggctc ccgctgctcg tgggctgcgc cgggacggcg gtggcctccg gcccggtgga   5040
gttcaccgcc ttcgcggag cgctggcgga cctccccggcg gcggcccga tggccgcgct   5100 gccgcagccc ggctttctgc cgggagaacg agtcccggcc accccggagg cattgttcga   5160
ggcccaggcg gaagcgctgc tgcgctacgc ggccggccgg cccttcgtgc tgctggggca   5220
```

```
ctccgccggc gccaacatgg cccacgccct gacccgtcat ctggaggcga acggtggcgg    5280
ccccgcaggg ctggtgctca tggacatcta caccccgcc gaccccggcg cgatgggcgt     5340
ctggcggaac gacatgttcc agtgggtctg gcggcgctcg gacatccccc cggacgacca    5400
ccgcctcacg gccatgggcg cctaccaccg gctgcttctc gactggtcgc ccaccccgt     5460 ccgcgccccc gtactgcatc tgcgcgccgc ggaacccatg ggcgactggc acccggga     5520 caccggctgg cagtcccact gggacggcgc gcacaccacc gccggcatcc ccggaaacca   5580
cttcacgatg atgaccgaac acgcctccgc cgccgcccgg ctcgtgcacg gctggctcgc    5640
ggaacggacc ccgtccgggc agggcgggtc accgtcccgc gcggcgggga gagaggagag    5700
gccgtga                                                             5707
```

<210> SEQ ID NO 32
<211> LENGTH: 5120
<212> TYPE: DNA
<213> ORGANISM: Artificial Sequence
<220> FEATURE:
<223> OTHER INFORMATION: Synthetic Polynucleotide

<400> SEQUENCE: 32

```
tcaggagtgg agaagacatg ccgggtacga acgacatgcc gggtaccgag acaagctcc      60 gccactacct gaagcgagtg accgcggatc tcggacagac ccgtcagcgc ctgcgcgacg    120
tggaggagcg ccagcgggaa ccgatcgcca tcgtcgcgat ggcctgccgc tacccgggcg    180
gggtggcctc ccccgagcag ctgtgggacc tggtcgcctc acgcggcgac gccatcgagg    240
agttccccgc cgaccgcggc tgggacgtgg cgggcctcta ccaccccgac ccggaccacc    300
ccggcacgac ctatgtacga gaggccggat tcctgcggga cgccgcccgc ttcgacgccg    360
acttcttcgg catcaacccg cgcgaggcgc tgccgccgca cccgcagcaa cgggtgctcc    420
tcgaagtgtc gtgggaactg ttcgagcggg cgggcatcga ccccgccacg ctcaaggaca    480
ccctcaccgg cgtgtacgcg ggggtgtcca gccaggacca catgtccggg agccgggtcc    540
cgccggaggt cgagggctac gccaccacgg gaaccctctc cagcgtcatc tccgccgca    600 tcgcctacac cttcggcctg gagggcccgg cggtgacgct cgacacggcg tgctcggcat    660
cgctggtcgc gatccacctc gcctgccagg ccctgcgcca gggcgactgc ggcctggcgg    720
tggcgggagg cgtgaccgta ctgtccacgc cgacggcgtt cgtggagttc tcacgccagc    780
gcggactcgc accggacggc cgctgcaagc cgttcgccga ggccgccgac ggcaccggat    840
tctccgaggg cgtcggcctg atcctcctgg aacgcctctc cgacgccgc cgcaacggac    900 atcaagtact cggcgtcgta cgcggatcgg ccgtcaacca ggacggcgcg agcaacggcc    960
tgaccgcccc gaacgacgtc gcccaggaac gcgtgatccg ccaggccctg accaacgccc   1020
gcgtcacccc ggacgccgtc gacgccgtgg aggcacacgg caccggcacc acgctcggcg   1080
acccgatcga ggggaacgca ctcctcgcga cgtacgaaaa ggaccgcccc gccgaccggc   1140
cgctgtggct cggctctgtg aagtcgaaca tcggccacac gcaggcggct gcgggcgtcg   1200
caggcgtcat caagatggtg atggcgatgc gccacggcga gctgcccgcc tccctgcaca   1260
tcgaccggcc cacgccccac gtggactggg agggcggggg agtgcggttg ctcaccgatc   1320
ccgtgccgtg gccacgggcc gaccgccccc gccgcgcggg ggtctcctcc ttcggcatca   1380
gcggcaccaa cgcccacctg atcgtggaac aggcccccgc cccgcccgac acggccgacg   1440
acgccccgga aggcgccgca accccccgcg cttccgacgg cctcgtggtg ccgtgggtgg   1500
```

-continued

```
tgtcggcccg tagtccgcag gccctgcgtg atcaggccct gcgtctgcgc gactttgccg  1560
gtgacgcgtc ccgagcgccg ctcaccgacg tgggctggtc tttgctgcgg tcgcgtgcgc  1620
tgttcgagca gcgggcggtg gtggcggggc gtgagagggc tgaactgctg gcggggctgg  1680
ctgcgttggc cgctggtgag gagcacccgg ctgtgacgcg gtcccgtgag gaagcggcgg  1740
ttgctgcgag cggtgatgtg gtgtggctgt tcagtggtca gggcagtcag ttggtcggta  1800
tgggtgctgg tttgtatgag cggttcccgg tgtttgcggc tgcgtttgat gaggtgtgcg  1860
gcttgctgga gggggagctg ggggttggtt cgggtgggtt gcgggaggtg gtgttctggg  1920
gcccgcggga gcggttggat cacacggtgt gggcgcaggc ggggttgttt gcgttgcagg  1980
tggggttggc ccggttgtgg gagtcggtcg gggtgcggcc ggatgtggtg ctcgggcatt  2040
cgatcggtga gatcgcggcc gcgcatgtgg cggggtcttt tgatctggcg gatgcgtgtc  2100
gggtggtggg ggcgcgggcg cgtttgatgg gtgggttgcc tgagggtggg gcgatgtgtg  2160
cggtgcaggc cacgcccgcc gagctggccg cggatgtgga tggctcgtcc gtgagtgtgg  2220
cggcggtcaa cacacctgac tcgacggtga tttcaggtcc gtcgggtgag gtggatcgga  2280
ttgctggggt gtggcgggag cgtgggcgta agacgaaggc gctgagcgtg agtcatgctt  2340
tccattcggc gttgatggag ccgatgctcg gggagttcac ggaagcgata cgaggggtca  2400
agttcaggca gccgtcgatc ccgctcatga gcaatgtctc cggagagcgg gccggcgagg  2460
agatcacatc cccggagtac tgggcgaggc atgtacgcca gacagtgctc ttccagcccg  2520
gcgtcgccca agtggccgct gaggcacgcg cgttcgtcga actcggcccc ggccccgtac  2580
tgaccgccgc cgcccagcac accctcgacc acatcaccga gccggaaggc cccgagccgg  2640
tcgtcaccgc gtccctccac cccgaccggc cggacgacgt ggccttcgcg cacgccatgg  2700
ccgacctcca cgtcgccggt atcagcgtgg actggtcggc gtacttccct gacgaccccg  2760 cccccgcac cgtcgacctg cccacctacg ccttccaggg gcggcgcttc tggctggcgg  2820
acatcgcggc gcccgaggcc gtgtcctcga cggacggtga ggaggccggg ttctgggccg  2880
ccgtcgaagg tgcggacttc caggcgctct gcgacaccct gcacctcaag gacgacgagc  2940
accgcgcggc tctggagacg gtgttccccg cgctgtccgc gtggcggcgc gaacgacgtg  3000
agcggtcgat cgtcgatgcc tggcggtacc gggtcgactg gcggcgcgtc gagctgccga  3060
cacccgttcc gggcgccggt accggtcccg acgccgacac gggcctcggg gcgtggctga  3120
tcgtggctcc cacgcacggg tcgggtactt ggccgcaagc ctgtgcccgg gcgttggagg  3180
aggcgggcgc gccggtacgt atcgtcgagg ccggcccgca cgccgaccgg gcggacatgg  3240
cggacctggt ccaggcatgg cgggcaagct gtgcggacga caccacccag ctcggaggag  3300
tgctctccct gctggctctc gccgaggcac cggccaccag ttccgacacc acttcccaca  3360
ccagtaccag ttgcggtacc ggctctctcg cgtcccacgg cctcaccggc accttgacgc  3420
tgctgcacgg tctgctggat gcgggcgtcg aagcgcctct ctggtgtgcc acgcgcggcg  3480
ccgtgtcgtg cggcgacgcc gatccgctcg tctccccgtc gcaggcccg gtctggggac  3540 tcggacgcgt ggccgccctg gagcatccgg agttgtgggg cggcctggtc gacctgcccg  3600
ccgaccggga gtcgctcgac gcgagcgcgt tgtatgcggt tctgcgcgga gacgcgggcg  3660
aggatcaggt cgcgctgcgc cggggcgcgg tcctcggccg tcgcctggtg cccgacgcaa  3720
ccccggacgt ggccccggc tcgtccccgg acgtgtccgg aggcgcagcc catgccgacg  3780
cgacctccgg ggagtggcag ccgcatggtg ccgtcctcgt caccgaggc gtcggccacc  3840 tggccgatca ggtcgtacgg tggctcgccg cgtccggcgc cgaacacgtc gtactcctgg  3900
```

```
acacgggccc cgccaacagc cgtggtcccg gccggaacga cgacctcgcc gcggaagccg   3960
ccgaacacgg caccgagctg acggtcctgc ggtccctgag cgagctgaca gacgtatccg   4020
tacgtcccat acggaccgtc atccacacat cgctgcccgg cgagctgcgc ccgctggccg   4080
aggtcacccc cgacgcgctc ggcgcggcg tgtccgccgc cgcgcggctg agcgaactcc   4140
ccggcatcgg gtcagtggag accgtgctgt tcttctcctc cgtgacggct cgctcggca   4200 gtagggagca cggcgcgtac gccgccgcca acgcctacct cgacgccctg cgcaacggg   4260 ccggtgccga tgctgcgagc ccccggacgg tctcggtcgg gtgggcatc tgggatctgc   4320 cggacgacgg tgacgtggca cgcggcgccg ccgggctgtc ccggaggcag ggactcccgc   4380
cgctggaacc gcagttggcg ctcggcgccc tgcgcgcggc gctcgacggg ggcaaggggc   4440
acacgctggt cgccgacatc gagtgggagc ggttcgcgcc gctgttcacg ctggccaggc   4500
ccacccggct gctcgacggg atccccgcgg cccagcgggt cctcgacgcc tcctcggaga   4560
gcgccgaggc ctcggagaac gcctcggccc tccgtcgcga actgacggcc ctgcccgtgc   4620
gggagcggac cggggcactt ctcgacctgg tccgcaaaca ggtggccgcc gtcctgcgct   4680
acgagccggg ccaagacgtg gcgcccgaga aggccttcaa ggacctgggc ttcgactcgc   4740
tcgtggtcgt ggagctgcgc aaccggctgc gcgccgccac cgggctccgg ctgcccgcca   4800
ccctggtcta cgactacccc acaccccgca ccctcgccgc acacctgctg acagggtgc   4860 tgcccgacgg cggcgcggca gagctccccg tggccgccca cctggacgac ctggaggcgg   4920
ccctcaccga cctgccggcc gacgacccc ggcgcaaggg cctggtccgg cgtctacaga   4980
cgctgctgtg gaagcagccc gacgccatgg ggcggcggg ccccgccgac gaggaggagc   5040
aagccgcgcc cgaggacctg tcgaccgcga gcgccgacga catgttcgcc ctgatcgacc   5100
gggagtgggg cacgcggtga                                              5120

<210> SEQ ID NO 33
<211> LENGTH: 6160
<212> TYPE: DNA
<213> ORGANISM: Artificial Sequence
<220> FEATURE:
<223> OTHER INFORMATION: Synthetic Polynucleotide

<400> SEQUENCE: 33
tgacccgggc ccaccccaac tacgtgcgaa acatctgagg aaggttcaac ggacgatgcc     60
ggacgaaagt aagctcgtcg attacctgaa gtgggtcacg gcggatctcc accagacccg    120
caggcgcctc caggaagccg agtcgggcg ccacagagcc cgtggcgatcg tcggcatggc    180 gtgccgcttc cccggcggtg tgcgttcccc ggaggacctc tgggagatgc tcgccgacgg    240
ccgcgacgcc atctccgggt tccccgccga ccgcggctgg gacctggaga cgctggccgg    300
cgacggagcg ggcggcagca gcacgcagga gggaggttc ctgcacgacg tggccgactt    360
cgacccgggg ttcttcgaca tctcgcccg cgaggcgctg ccatggacc cgcagcagcg    420 gctgctcctg gagaccgcct gggaggccgt ggagcgtgcc gggatcgccc ccggcagcct    480
ccgcggcagc cgcaccggcg tgttcgtcgg caccaactcg caggactacg cccacctcgt    540
cctcgcctcc gacgacgaca tgggcggcta cgcgggcaac ggcctggccg ccagcgtgat    600
gtccggccgg ctgtccttg cgctcggctt cgaaggaccc gccgtcaccc tcgacaccgc    660
gtgctcctcg gccctggtcg ccctgcacct ggccgcccag tcggtgcgct ccggcgaggc    720
cgacctcgcg ctggccggcg gtgtcaccgt catgaccacc tcgtccagct tcgtgggctt    780
```

```
cagcctccag ggcggcctcg ccacggacgg ccgctgcaag gcgttcgccg actccgccga   840
cggcaccggc tggtccgagg gcgtcggcat gatcctcgtc gaacggctct ccgaggcccg   900
gcgcaagggc cacccggtgc tcgccgtgct gcgcggctcc gccgtgaacc aggacggcgc   960
ctccaacggc ctcagcgccc ccaacgggcc cgcccagcag cgcgtcatcc gcgacgcgct  1020
ggcctccgcc gggctctcgc ccgccgacgt cgacgccgtc gaggcgcacg gcaccggcac  1080
cacccctcggc gacccatcg aggcgcagg cctgctcgcc acctacggcc aggaccgcga  1140
cgcgagccgt ccgctgcgcc tcggcacggt gaagtccaac atcggccaca cccaggccgc  1200
cgccggcgcc gcgggcgtca tcaagatggt cctggccctg cgccacgggc tgctgccccg  1260
cacccctgcac atcgacgcgc cgtccacaca cgtcgactgg gacgcaggac acgtcagcct  1320
gctcaccgag gccacccct ggcccgaggg cgagcagacg cgccgggccg gtgtgtcgtc  1380
cttcggcatc agcggcacca acgcccatgt catcctcgaa gaggccccccg cggccgagga  1440
ggacaccgac gccgagcagc ggcccgagcc ggtcgtcccg ggcgccgtgc cgtggcccgt  1500
gtcggcccgt accgccgacg ccctcgacgc ccagctggag aaggtgcggc cgctcgccgc  1560
gtccggcgcc gaccccgtcg cgtcggcca cgccctggcc gtcacccgca ccccccttcga  1620
acaccggggcg ctgctggtcg ccgcggacgg caatctcacc gaggccgcac gcggcaccgt  1680
cccctccggc gaccgccccg ggctggccgt gctgttctcc gggcagggcg cccagcgcct  1740
cggcatgggc cgtgaactcc acgcccgctt cccggtgttc gccgccgccc tggacgagac  1800
cctcgccctc ctcgacgagc gcctcggcca tcgctgcgc gacgtcatct ggggcgagga  1860
ccccgtggcc ctcgacgaca ccggccacac ccagcccgcg ctgttcgccg tggaggtcgc  1920
cctctaccgc ctgttcgcct cctggggtct gcgccccgac cacctcgccg gacactccgt  1980
cggggagatc gccgccgtgc atgtggccgg cgcactgtcc ctggaggacg cctgcaccct  2040
ggttgccgcc cgcgccggcc tgatgcggga cctgccggcc ggcggagcca tggtcgcgct  2100
gcgcgccacc gaggccgagg tgcggccgct gctcgacgag cgggtctcgc tcgcctcggt  2160
caacggcccc gattccgtgg tggtctccgg cgccgaggac gccgtcctcg ccgtcgccga  2220
gcacttccgg aagcaggacc ggcgcaccac gcggctctcc gtgagccacg ccttccactc  2280
cccgctcgtc gacccgatgc tcgacgcctt ccgggacgtc gtcgcgaagc tcaccttcgg  2340
cgagccgtcg gtaccgtcg tctccaccct caccggcgac gtcgtcgccg ccgaggaact  2400
ggccacgccg cactactggg tgtgccacgc ccggcaggcc gtccgcttcg ccgacgccgt  2460
gcgcaccctc gtcgacgagg gcgcccgac cttcctggag gtcggccgg gcggcgtgct  2520
gtccgcgctc gtcggtgaga acacccagga ggccggggtc tctgccgtgc ccgcgctgcg  2580
caaggaccag ccggaggagg cctccgtgct cgccgcccte ggcaccctgt ggacccgggg  2640
caccgcggcc gactgggacg ccgtgttcga gggcaccctg cccggccgcc cggagtccgt  2700
ggacctgccg acctacgcct tccagcgcgg ccggtactgg cccaccgtgc gcgcccgctc  2760
cggcgacccc gccggactgg gcctcggcgc cgccgggcac ccgctgctca gcgccaccgt  2820
cacccctcgcc gaggccgacg agtccgtcct caccggacgg ctctcgccgc tgacccaccc  2880
ctggctcacc gagcaccgcg tcgacggccg gatcaccgtc cccggcacgg ccctcgtgga  2940
gatcgcggtc cgtgcgggcg acgagaacgg cacccccgc ctggaccggc tcgacctgct  3000
cgccccgctg accctcggcg accgcacgc ggtgctgctc caggtgcgcg tcggccccga  3060
ggacgcctcc ggcggcgga cgctctccgt gcacgcccgc ccggcgaccg cggacgacgc  3120
ccccctggacc acgtacgccc gtggtgtcct cgcccccgac gagggcgccg aggacaccgc  3180
```

```
cgcggacctt gtggagtggc cgcccgccga cgcccgtcag gtcccgctca cggagctgga   3240
gtccgaagga cgcgccctcg gcccgctctt cagcggcctc accggggtgt ggcggcacga   3300
gggcgaggtg ttcgccgagg ccgagctgcc cgcaggaccc gacagcggct tcggactgca   3360
ccccgcgctg ctgtccaccg ccctgcgcgc cgccgccgtc ctcgacggca ccacggccgg   3420
cgagcccgcc gccttcgagg ggctcaccct gcacgccacc ggcgccaccg cgctgcgcgt   3480
acggctgagc accaccgggc ccgacaccgt cgacctcacc gccgtcgacc ccgcgggcaa   3540
cctcgtcctg accgccgaga ccgtgcgtct cggcaccccg gacggcaccg ccgacacccc   3600
ggccgccacc ggccggggcg acctgttcgg gctgaagtgg gtgcccgtca aggcctcgga   3660
gcgcgccacc ggcacccgct gggccgtcgt cggctccgac gaactcgacc tcggctacgc   3720
catgcaccgc gccgacgaga ccgtcaccgc ctacgcggag tccctcggcg cgccatcgg   3780
cgacagcggg gtcgccccg atgtgttcct gatcccgctc gcaggcgaga aggacgccgg   3840
agcggagggc gtgcacgccc tcaccacccg ggtcctcggc tacctccagg agtggctgtc   3900
cgagccccgg ctctccggca cccgcctggt cttcgtcacc cgccgcgccg tcgccctcga   3960
cgacgaggac gtcctggacc cggccggcgc ggccgtctgg ggcctggtgc gctccgcgca   4020
gaccgagaac cccggcagcc tgctgctcgt cgacctcgac gacaccttcc tgtccgccgg   4080
agtactgccc gacgtgctga cgctcgacga gcagcagctc gcggtccgcg actaccaggt   4140
ccgcgccgcc cggctcgccc ggctgccgcg cccggccgac gacgccccg ccgccgactg   4200
gaaccccgac ggcaccgtcc tgatcaccgg cggcaccggc ggcctcggcg ccgcgctcgc   4260
ccggcacctg gtcaccagcc ggggcgcccg tcacctgctg ctggcgagcc gccgcggccc   4320
ggacgcgccc ggcacgtccg aactggtcgc cgagctgacc ggcctgggag cccaggtgac   4380
cgtctccgcc tgcgacgtcg gcgaccgcga cgcggtcgac acgctcgtcg cgtcggtgcc   4440
cgccgagcac ccgctgaccg ccgtcgtgca caccgcgggt gtcctggacg acgccctgac   4500
cggctcgctc acccccggaac aactggctgg tgtgctgcgc cccaaggccg acgcggccct   4560
gcacctgcac gaggcgaccc tcggccagga cctcgccgcg ttcgtgctgt actcctcgat   4620
ctccggcgtc atcggcggcc ccggccaggc caactacgcc gccgccaacg cctccctgga   4680
cgcgctcgcc caccggcgca gggcggccgg tctgcccggt ctgtccctcg cctgggggcc   4740
ctggggccgc ggcagcggca tgaccagcca ggtcagcgac accgacctgg ggcggatgga   4800
ccgcggcggc accccgccga tgagcctcga ggacggcctc gccctgttcg acgccgccct   4860
ggcccgcacc gagccgatgg tcgtgcccac ccggatcaat gtcaccggac tccaggtcca   4920
gcagacgctg cccgcgctct ggcgcgacct ggtgccgcgc cccggcgca ccgccgccgc   4980
ggaccgctcg cccaagaccg tgctcgacgg gctgcgcacg ctcgacaccg cgggccggga   5040
gaagctgctc accgagctgg tcgtcggctt caccgcgggc ctgctcggcc acgccgaccc   5100
cgccgccgtc gaccccgagc gcggcttcct ggagctgggc ttcgactcgc tggtctcggt   5160
cagcctgcgc aaccagctcg gcgaactcct cgggctgcgc ctgccgacgt cggtggtctt   5220
cgacagcaag acgccggtga agctggcccg ccacctcaac gaggaactgg gcgacctgtc   5280
cgcctccggc cccgcgtccg gcaccgccgt cgccggcacc acggtgcatc ccgacgacac   5340
cctggtcggc ctgttccaca acgcggtgcg cggcggcaag ctcgtcgagg cgatgcggat   5400
gctgaaggcg gtcgccaaca cccggcccac cttcgagacg cccgcggacc tggaggagct   5460
gtccgaggcc gtcacccctgg ccacggggcc cggctccccg cggctgatct tcgtcagcgc   5520
```

```
gcccggcgcc accggcggtg tccaccagta cgcgcgcatc gccgcccact tccgcggcaa    5580
gcgccatgtg tcggcgatac cgctgatggg cttcgccccc ggcgagctgc tgcccgccac    5640
cagtgaggcg gcggcccgga tcgtcgccga gagcgtcctg atggcgagcg acggcgaacc    5700
gttcgtgatg gtgggccact ccaccggcgg ttccctcgcc tacctcgcgg ccggggtgct    5760
ggaggacacc tggggcgtga agccggaggc ggtcgtcctg ctcgacacgg cgtccatccg    5820
gtacaacccc tcggagggca caacctcga ccagacgacc cgcttctacc tcgccgacat    5880
cgactcgccg tccgtgacgc tcaacagcgc ccggatgtcc gcgatggcgc actggttcat    5940
ggcgatgacg gacatcgacg cgcccgccac gaccgccccc accctgctcc tgcgcgccac    6000
acaggccaac aacggcttca tgctggacac ctccgcggtg ccggcggacg tggtgcgtga    6060
catcgaggcc gaccatctgt ccctggccat ggagcactcg gatctgaccg ccgaggccat    6120
agagaactgg ctcgccgaac ttccggccgg cgaggcctga                          6160

<210> SEQ ID NO 34
<211> LENGTH: 11369
<212> TYPE: DNA
<213> ORGANISM: Artificial Sequence
<220> FEATURE:
<223> OTHER INFORMATION: Synthetic Polynucleotide

<400> SEQUENCE: 34
gcagcgatca gtcctgagcg cgatgagccc cggccacacc ggccccttg ccctccccca      60 acctcatacg ccccgatcac cacgtagcgc caaggagcct gggtcagatg tcgaacgagg    120
agaagcttct cgatcacctc aagtgggtca ccgcggagct cgccaggcc cggcaacggc     180 tccacgacaa ggaatcgacc gagccggtcg ccatcgtcgg catggcctgc cgctacccgg    240
gcggcgcccg gtcggcggag gacctctggg aactcgtgcg cgacggggt gacgcggtcg     300 cggggttccc cgacgaccgg ggctgggacc tggagtcgct gtatcacccg gatccggagc    360
atccggccac cagctatgtg cgggacgcg ccttcctgta cgacgccggc catttcgacg     420
ccgagttctt cggcatcagc ccgcgcgagg ccacggcgat ggatccgcag cagcggctgc    480
tcctggagac cgcgtgggag gcgatcgagc acgggcat gaacccgcac gcgctgaagg      540
gcagcgacac cggcgtcttc accggagtga cgcccacga ctacctgacg ctgatcagcc    600
agacggccag cgacgtcgag gggtacatcg gcaccggcaa cctcggcagt gtggtgtcgg    660
gccggatctc ctacacggtg gggctcgaag gtcccgcggt caccgtcgac acggcgtgct    720
cgtcgtccct ggtggcgatc catctggcaa gtcaggcgct gcggcagggc gagtgctcgc    780
tcgcgctggc gggcggttcg acggtgatgg cgacgccggg ttcgttcacc gagttctccc    840
ggcagcgggg gctcgcgccc gacggcggt gcaagccgtt cgcggccgcc gccgacggca    900
ccggctgggg cgagggcgcc ggggtggtgg cgctggagct gctctccgaa gcgcggcgcc    960
gcggccacaa ggtccttgcg gtgatacggg gttcggccac caaccaggac ggtacgagca    1020
acgggctcgc cgcccccaac ggcccctccc aggaacgcgt catccgcgcc gccctcgcca    1080
acgcccgcct ctccgccgag gacatcgacg ccgtagaggc gcacggcacc ggcaccacgc    1140
tcggcgaccc catcgaggcg caggcctga tcgccacgta cggccagggg cgcccggagg     1200
accgtccgct ctggctcggc tcggtgaaat ccaacatcgg ccacacgcag gccgccgccg    1260
gtgtcgcggg cgtcatcaag atggtcatgg cgatgcgcaa cggtctcctc ccgacctccc    1320
tgcacatcga cgccccgtca ccgcacgtcc agtgggaaca gggcagcgta cgactgctct    1380
ccgagcccgt ggactggccg gcggagcgca cgcggcgggc aggcatctcg gcgttcggga    1440
```

```
tctccgggac gaacgcgcac ctgattctgg aggaggcgcc gccggaagag gacgcgccgg   1500
gccccgtggc ggctgagccg ggtggggtcg tgccgtgggt ggtgtccggg cggacgccgg   1560
acgcgttgcg tgaacaggcg cggcggctgg gcgagttcgc ggccgggctg gcggatgcgt   1620
cggtctccga ggtgggctgg tcgctggcca cgacacgcgc gttgttcgat cagcgggccg   1680
tggtcgtggg gcgggacttg gctcaggctg gtgccagcct ggaggcattg gccgcgggtg   1740
aggcgtcggc ggatgtggtg gccggggtgg ccggtgatgt gggtcctggg ccggtgttgg   1800
tgtttccggg gcaggggtcg cagtgggtgg gcatgggcgc ccagctcctt gacgagtcgc   1860
ccgtcttcgc ggcgcggatc gcggagtgtg agcaggcgct gtcggcgcat gtggactggt   1920
cgctgagtga tgtcttgcgc ggggacggga gcgagctgtc ccgggtcgag gtcgtgcagc   1980
ccgtgctgtg ggcggtgatg gtctcgctgg ctgcggtgtg ggccgattac ggcatcaccc   2040
cggctgccgt catcgggcac tcgcagggcg agatggctgc cgcgtgtgtg gcggggcac    2100 tgtcactgga ggatgcggca cggatcgtag ccgtacgcag cgacgcgctt cgtcagctgc   2160
aagggcacgg cgacatggcc tcgctcagca ccggtgccga gcaggccgca gagctgatcg   2220
gcgaccggcc gggcgtagtc gtcgcggccg tcaacggacc gtcgtcgacc gtgatttcgg   2280
gcccgccgga gcatgtggca gccgtcgtcg ccgatgcgga ggcgcaggga ctcagggccc   2340
gcgtcatcga cgtcaggtac gcctcccacg gtccccagat cgaccagctc cacgacctcc   2400
tcaccgaccg gctcgccgac atccagccga ccaccaccga cgtggcgttc tactcgacgg   2460
tcaccgcaga gcgcctcgac gacaccaccg ccctagacac cgcctactgg gtcaccaacc   2520
tccgccagcc cgtccgcttc gccgacacca tcgaagcgct gctggccgac ggctaccgcc   2580
tgttcatcga ggccagcccc cacccccgtcc tcaacctcgg catccaggag accatcgagc   2640
agcaggccgg tgctgcgggg acggccgtca ccatccccac cctgcgtcgc gaccacggtg   2700
acaccaccca gctcacccgc gcggccgccc acgccttcac cgccggcgcc ccgtcgact    2760 ggcggcgctg gttcccggcc gacccccacc cccgtaccgt cgacctcccc acctacgcct   2820
tccagcacaa gcactactgg gtggagccgc ccgcggcgt cgcagccgtg ggtggtgggc   2880
acgatccggt cgaggcccgg gtgtggcagg cgatcgagga cctggacatc gacgccctcg   2940
ccggcagtct ggagatcgag gggcaggcgg agagcgtcgg agcgctggag tccgcgctgc   3000
ccgtcctctc ggcctggcgg cgtcggcacc gcgagcagtc caccgtcgac tcctggcgtt   3060
atcaggtcac ttggaagcat ctgcccgacg tgccggcgcc ggagctcagc ggggcctggc   3120
tgctgctcgt gcccgccgcg cacgccgacc acccggccgt cctcgcgacc gcgcagacgc   3180
tgaccgccca tggtggcgag gtgcgacgcc acgtggtcga cgcacgtgcc atggagcgta   3240
cggagttggc gcaggagctg cgtgtcctga tggacggggc cgcgtttgcc ggagtcgtca   3300
atctgctggc cctggacgag gagccgcatc ccgagcactc ggccgtgccc gccggactcg   3360
ccgcgacgac cgctctcgtc caggcccctcg ggacaacgg cgccgacatc gccgtacgca   3420
ctctcacgca gggggctgtt tccacgagcg ccggcgacgc cctcacccac ccggtgcagg   3480
ctcaggtgtg ggggctgggg cgcgtcgctg cgctggagta tccgcggctg tggggcgggc   3540
tggtcgatct gcccgctcgt atcgaccatc agacgctggc ccggctggcc gccgcgctgg   3600
ttccgcagga cgaggaccag atctccatcc ggccgtccgg cgtccatgcc cgtcgccttg   3660
cacacgcgcc cgccaacacg gtcggcagcg ggcttggttg gcggcccgac ggcaccactc   3720
tcatcaccgg cgggaccggc ggcatcggcg ccgtcctcgc gcggtggctc gcccgtgcgg   3780
```

```
gcgccccgca cctcctcctg accagccgcc gcggccccga cgccccggga gcacaggaac    3840
tcgccgcgga actgacggag ttgggggccg ccgtcaccgt caccgcctgc gacgtcggcg    3900
accgcgagca ggtgcgacgc ctcatcgacg atgtccccgc cgagcacccg ctgaccgccg    3960
tcatccacgc ggccggcgtg ccgaactaca tcggtctcgg cgacgtgtcg ggtgccgagc    4020
tggacgaggt gctgcgtccg aaggcgctcg ccgctcacca tctgcatgaa ctgacccggg    4080
agttgccgct ctcggcgttc gtgatgttct cgtcgggcgc aggcgtgtgg ggcagtggcc    4140
agcagggcgc ctatggtgcg ccaaccact tcctcgacgc cctcgccgag caccgccgcg    4200
ccgagggcct gcccgccacc tccatcgcct ggggccctg gccgaggcg gcatggcgg    4260 cggaccaggc cgcgttgacg ttcttcagcc gcttcggcct gcacccgctc agcccggagc    4320
tgtgcgtcaa ggcgctgcag caggccctgg acgcgggtga gacgacgctg accgtggcga    4380
acttcgactg ggcgcagttc acgtcgacgt tcaccgcgca gcggcccagc ccgctcctcg    4440
ccgatctgcc cgagaaccgg cgggccagcc caccccgcggc acagcaggaa gacgccacgg    4500
aggcatcgtc gctccagcag gagctgacgg aggcgaagcc ggcgcagcag cggcagttgc    4560
tgctgcagca cgtgcgctcc caggcggcgg ccacgctggg gcactcggac gtcgacgcgg    4620
tgcccgccac caagccgttc caggagctgg gcttcgactc gctgaccgcg gtggagctgc    4680
gcaacaggct gaacaagagc accggcctga cactgccgac cacggtcgtc ttcgaccacc    4740 ccaccccga cgcgctcacc gacgtcctgc gggccgagct gtccggtgac gcggcggcct    4800
ccgccgaccc ggtgcgggcg ccggggcct ccaggggcgc cgccgacgac gagccgatcg    4860
cgatcgtcgg catggcctgc cgctatccgg gcgacgtccg ctccgccgag gagctgtggg    4920
atctggtcgc ggccggcaag gacgccatgg gggccttccc cgacgaccgg ggctgggacc    4980
tggagacgct gtacgacccg gacccggaga gccgcggcac cagctatgtg cgcgaaggcg    5040
ggttcctcta cgacgcgggc gacttcgacg ccggattctt cggcatcagc ccccgcgagg    5100
ccgtcgcgat ggaccgcag cagcggctgc tcctggagac cgcgtgggag gcgatcgaac    5160
gcgcgggcct cgaccgggag accctcaagg gcagcgacgc cggggtgttc acgggcctga    5220
ccatcttcga ctaccctcgcg ctcgtcggtg aacagcccac cgaggtcgag ggctacatcg    5280
gcaccggcaa cctcggctgt gtcgcctccg gcagggtgtc gtacgtactc ggcctagaag    5340
gccccgccat gacgatcgac accggctgct cttcgtccct ggtggcgatc caccaggcgg    5400
cgcacgcgct gcgccagggc gagtgctcgc tcgctctcgc gggcggcgcg acggtgatgg    5460
ccacgccggg ctcgttcgtc gagttctcgc tgcagcgcgg gctcgccaag gacggccggt    5520
gcaagccgtt cgcggccgcc gccgacggca ccggctgggc cgagggagtc ggcctggtcg    5580
tactcgaacg gctctcggag gcccggcgca acggccacaa cgtcctggcg gtgatccggg    5640
gttcggccat caaccaggac ggcacgagca acgggctcac ggcacccaac gggcaggcgc    5700
agcagcgggt gatccggcag gcactcgcca acgcgcggct ctccgccgag gacgtcgacg    5760
cggtggaggc gcacggcacc ggcaccatgc tgggcgaccc catcgaagcc agcgcgctcg    5820
tcgccaccta cggcaaggag cggcccgcgg accggccgct gtggctcggc tcgatcaagt    5880
cgaacatcgg gcacgcgcag gcgtcggccg gtgtcgccgc tgtgatcaag atggtcatgg    5940
cgctgcgcaa cgaacagctg cccgcctccc tgcacatcga cgcgcccacg ccgcacgtgg    6000
actgggacgg cagtgcgtc cgcctgctgt ccgaaccggt ctcctggccg cgcggcgaac    6060
gcccgcgccg cgccggggtg tccgccttcg gcatctccgg caccaacgcg cacctcatcc    6120
tggaacaggc cccggacgcg ccggagcccg tgaccgctcc ggcggaggac gccgcggcgc    6180
```

```
cggccggagt ggtgccctgg gtggtgtcgg cgcgcggcga ggaggcgctg cgggcccagg    6240
cccgcctgct ggccgaccgc gccaccgccg acccgcggct cgcgtcgccg ctggacgtgg    6300
gctggtccct ggtcaagacc cggtcggtgt tcgagaaccg agccgtcgtc gtgggcaagg    6360
accgccagac tctcctcgcc gggctacggt ccctggcggc gggcgagccg tcaccggacg    6420
tcgtcgaggg cgccgtacag ggcgcctccg gcgcgggtcc ggtgttggtg tttccggggc    6480
aggggtcgca gtgggtgggc atgggtgccc agctccttga cgagtccccc gtcttcgcgg    6540
cgcggatcgc ggagtgtgag cgggccctgt cggcgcatgt ggactggtcg ctgagtgcgg    6600
tgttgcgcgg ggacgggagt gagctgtccc gggtcgaggt cgtgcagccc gtgttgtggg    6660
cggtgatggt ctcgctggct tcggtgtggg ccgattacgg catcaccccg gctgccgtca    6720
tcgggcactc gcaggggcgag atggccgccg cgtgtgtggc gggggcactg tcactggagg    6780
atgcggcgcg gatcgtggcc gtacgcagtg acgcgctccg tcagctcatg gggcagggcg    6840
acatggcgtc gttgggggcc ggctcggagc aggttgctga gctcatcggc gaccggcccg    6900
gcgtgtgtgt cgctgccgtc aacgggccct cctctacggt catttcaggg ccgccggagc    6960
atgtggcagc cgtggtcgcg gatgcggagg cgcgaggcct gcgcgcccgc gtcatcgacg    7020
tcggatacgc ctcccacggc ccccagatcg accagctcca cgacctcctc accgagcgcc    7080
tggccgacat ccggcccacg accacggacg tcgccttcta ctccacggtc accgccgaac    7140
gcctcgacga caccaccacc ctcgacacgg attactgggt caccaacctc cgccagcccg    7200
tccgcttcgc cgacaccatc gaagcgctgc tggccgacgg ctaccgcctg ttcatcgagg    7260
ccagccccca ccccgtcctc aacctcggca tggaggagac catcgagcgg gccgacatgc    7320
ccgccaccgt cgtgcccacc ctgcgccgcg accacggcga cgccgcgcag ctcacccgcg    7380
cggccgccca ggccttcggc gcgggggcgg aggtcgactg gacgggctgg ttcccggccg    7440
tgccgctgcc tcgggtggtg gatctgccga cgtacgcctt ccagcgggag cggttctggc    7500
tggaggggcg caggggggctc gccggggacc cggcggggct cgggctcgcg tccgcggggc    7560
atccgctgct cggagccgcc gtggaactcg cggacggcgg cagtcacctg ctgaccggcc    7620
ggatctctcc gcgggaccag gcgtggctgg ccgagcaccg ggtcatggac acggtgctgc    7680
tgcccggttc ggcgttcgtg gagctcgcgc tgcaggccgc ggtgcgggcc ggctgcgcgg    7740
agttggcgga gctgacgctg cacactccgc tcgccttcgg ggacgagggt gcgggcgcgg    7800
tcgacgtgca ggtggtggtc ggttccgtgg ccgaggacgg gcggcgtccc gtgaccgtcc    7860
attcgcggcc cacgggtgag ggcgaggagg ccgtgtggac ccggcatgcc gcgggcgtgg    7920
tcgctccccc ggggcccgac gccggggacg cctcgttcgg cgggacgtgg ccgccccgg    7980 gcgccacacc ggtcggcgag caggatccgt acggggaact cgcttcgtac ggctatgact    8040
tcgggcccgg ctcacaggga ctggtgagcg cgtggcggct cggggacgac cttttcgccg    8100
aggtggcgct gccgaggcg gagagcggca gggccgaccg ctaccaggtg cacccggtgt    8160
tgctcgacgc cacgctgcac gcgctgatcc tggacgcggt cacgtcgtcc gccgacaccg    8220
accaagtgct gctgccgttc tcctggagcg ggttgcgggt gcacgcgccg ggcgctgaga    8280
agttgcgggt acgtatcgca cgcaccgcgc ccgaccagct ggccctcacg gccgtggacg    8340
ggggcggagg cggggagccg gttctcacgc tggagtcgct cacggtacgg ccggtggccg    8400
cccaccagat cgcgggcgcc cgtgcggcgg accgtgacgc gctgttccgg ctcgtgtgga    8460
tggaggtcgc cgcgcgggcc gaggagacgg gcggcggcgc cccgcgtgcc gcggtcctcg    8520
```

```
cgccggtcga gagtggcccg atgggcggta cgtcggccgg tgcgctggcc gacgccttgt    8580
ccgatgcgct ggccgccggc cccgtgtggg acacgttcgg tgcgctccgg gacggagtgg    8640
cggctggggg cgaagcgccc gatgtcgtgc tcgccgtgtg cgccgcgccc ggcgcaggtg    8700
ccggggccgt tgcggatgcc gatggcaggg gcggcgaccc ggccgggtac gcgcggctgg    8760
ccaccgtgtc ccttctgtcg ctgctcaagg agtgggtgga cgacccggcg ttcgcggcga    8820
cccgtctcgt cgtcgtcacc cgaggcgcgg tcgccgcgcg gccgggtgag accgccggtg    8880
atctggcggg cgcgtcgctg tggggtctgg tgcgcagcgc gcaggccgag aatcccggtc    8940
gcctcacgct gctcgacgtg gacggactgg agtcttctcc ggccacgctg accggcgtac    9000
tggcctccgg cgaaccggaa ttggcgctgc gtgacgggcg cgcctacgtg ccacggctcg    9060
tgcgcgacga cgcgtcggtg cggctggtgc cgccggtcgg atcgctcacg tggcggctgg    9120
ctcggtgcca agaggcgggc ggcggacagc agttgtccct tgtcgacgct cccgaggccg    9180
gacgggcgct ggagccgcac gaggtgcggg tggcggtgcg ggccgcggcg ccggggccgc    9240
tcacggcggg ccaggtcgag ggtgccggtg tggtgacgga agtcggcggc gaggtcggtt    9300
cggtggccgt gggcgaccgg gtgatggggt tgttcgacgc ggtgggcccg gtggccgtca    9360
ccgatgccgc gctgcttatg ccggttccgg cgggctggag ttgggcgcag gcggccgggt    9420
ccttgggggc ctatgtgtcc gcgtatcacg tgctggcgga tgtcgtggcg ccgcgcggcg    9480
gcgagactct gctcgtcggg gaggaaaccg gttccgtcgg ccgtgccgtg ctgcgtcttg    9540
ctcttgccgg gcggtggcgg gtcgaggccg tggacggtgc gtcgacggcg gatgattcgg    9600
gcgccgagcg cgcggccgac gtcaccctcc gccacgaggg ggccctggtg gtccaccgtg    9660
cgggcggtcg tccggacgag ggacaggctg tcgtgccgcc cgagcccggg cgcgtacggg    9720
aaatcctcgc ggagctgacc gagctgaccg agcttgccga gatcacggag tcggcggagc    9780
ccgggctgcc cgcggaacgg ggtgacagcc gtgctctgac gccgctcgac atcaccgtgt    9840
gggacatccg gcaggcgccc gccgcgatgg cggccccgcc ctcggcgggc acgaccgtgt    9900
tctcgctgcc tcccgccttc gaccccgagg gcaccgtgct ggtcaccggc ggcaccggag    9960
cactcggctc gctgacggcc cgtcacctgg tggaacggta cggagccagg cacctgttgc    10020
tgtccagcag gcggggagcc gacgcgccgg gcgcactcga actggccgcc gacctctccg    10080
cgctcggcgc gcgagtcacc ttcgccgcgt gcgaccgggg cgaccgggac gaagccgccg    10140
ccctcctcgc ggcggtgccc tcggaccacc cgctgaccgc cgtcttccac tgcgcgggca    10200
ccgtgaacga cgccgtggtg cagaacctca cggccgagca ggtcgaggag gtgatgcgcg    10260
tgaaggcgga cgccgcgtgg cacctgcacg agctgacgcg ggacgcggac ctgtccgcgt    10320
tcgtcctgta ctcctcggtc gccgggctgc tcggcggccc cggccagggc agctacacgg    10380
ccgccaacgc cttcttggac gcgctggccc ggcaccggca cgacggcggt gcggcggcga    10440 cctcctggc gtggggctac tgggagctgg cgagcggcat gtcgggacgg ctcaccgacg    10500
ccgaccgggc gcgccatgcc cgcgccgcg tggtcgggct cggcgccgac gagggactcg    10560
ccctcctcga cgcggcgtgg gccggcggac tgccctgta cgcgccggtc cgtctggacc    10620
tggcccggat gcgccggcag gcccagagcc accccgcacc ggcgctgctg cgcgacctgg    10680
tgcgcggggg gagcaagagc ggcggcggtg ccgtgtcggc gggggcggcc gcgctgctca    10740
agtcgctcgg cgcgatgtcc gaccccgagc gggaggaggc gctgctcgac ctggtgtgca    10800
cccatatcgc ggccgtcctc ggctacgacg cggccacgcc cgtcaacgcg acgcaggggc    10860
tgcgggaact cggcttcgac tccctgaccg cggtggagct gcgcaaccgg ctctcggccg    10920
```

```
cgacggggct gaagctgccc gccacgttcg tcttcgacca tcccaacccg gcggagctcg   10980
ccgcgcagct gcggcaggag ctggccccgc gcgcggcgga tccgctcgcc gacgtcctgg   11040
cggagttcga gcgcatcgag gactcgctgc tctcggtctc ctcgaaggac ggctcggcgc   11100
gggccgaact ggcggggcgg ctgcgcgcga cgctggccag gctcgacgcg ccgcaggaca   11160
cggccggcga ggtcgcggtg gccactcgta cacgtatcca ggacgcgtcg gcggacgaga   11220
tcttcgcgtt catcgaccgg gacctcggca gggacggcgc gagcggacag ggcaacggac   11280
agcccaccgg gcagggcaac ggacacggca acggcaacgg caacggcaac ggcaacggac   11340
acggtcaggc agtggagggg cagcgatga                                    11369

<210> SEQ ID NO 35
<211> LENGTH: 1155
<212> TYPE: DNA
<213> ORGANISM: Artificial Sequence
<220> FEATURE:
<223> OTHER INFORMATION: Synthetic Polynucleotide

<400> SEQUENCE: 35
atgccgtctc cacgcatccg taaaatgtcc ctgtcacgcg cactggataa gtacctgaaa     60
acagtttctg ttcacaagaa agggcatcaa caggagtttt accggagcaa tgttatcaag    120
cgatatccca ttgcccttcg gaatatggac gaaataacaa ccgttgatat tgctacatac    180
agagacgttc gtttagcaga atcaaccccc gaacgggta aacccattac aggtaatact    240
gtacgtcttg aactcgccct tctgtcatct ctgttcaata ttgctcgtgt tgaatgggga    300
acctgtcgta ctaacccggt tgaactggtt cgcaagccga aagtatcctc cggacgagat    360
cgccggctaa cgtcttcaga agaacgtcgc ctttctcgct atttccgcga aaaaaatctg    420
atgttgtatg tcattttcca tcttgcccct tgagacagcca tgcggcaggg cgaaatactg    480
gccttacgtt gggagcacat tgatttgcgc cacggtgtgg ctcatttacc tgaaaccaaa    540
aacggtcact cacgggatgt tcctctgtcc agacgtgccc gtaactttct tcagatgatg    600
cccgttaatc tccacggcaa tgttttgat tacaccgcat ccggctttaa aaatgcctgg    660
agaatagcca cacaacgact tcgcatcgag gacctgcatt ttcacgatct acggcatgaa    720
gcaataagcc gcttcttcga actgggtagc ctgaatgtaa tggagattgc tgcaatatca    780
ggacatcgtt ccatgaatat gctgaaacgg tatactcatc ttcgtgcatg gcaactggtc    840
agtaaacttg atgcccgccg gcggcagaca caaaaagtgg cagcatggtt tgtgccgtat    900
cctgcccata tcacgaccat caatgaagaa aatgggcaga agcgcatcg tattgagatc    960 ggtgattttg ataaccttca cgtcactgcc acaacgaaag aggaagcagt tcaccgcgcc   1020
agtgaggttt tgttgcgtac actggccatt gcagcacaga aaggcgaacg tgtcccatct   1080
cccggagcgt tacctgttaa cgaccctgac tacattatga tttgccctct gaacccgggc   1140
agcaccccgc tgtaa                                                   1155

<210> SEQ ID NO 36
<211> LENGTH: 1155
<212> TYPE: DNA
<213> ORGANISM: Artificial Sequence
<220> FEATURE:
<223> OTHER INFORMATION: Synthetic Polynucleotide

<400> SEQUENCE: 36
atgccgtccc ccgcatccg caagatgagc ctctcccgcg ccctcgacaa gtacctgaag     60
```

| | |
|---|---|
| accgtgagcg tccacaagaa gggccaccag caggagttct accggtccaa cgtcatcaag | 120 |
| cgctacccga tcgccctgcg gaacatggac gagatcacca ccgtcgacat cgccacctac | 180 |
| cgggacgtgc gcctggcgga gatcaacccg cgcaccggca agcccatcac cggcaacacc | 240 |
| gtccggctgg agctcgccct gctctcctcg ctgttcaaca tcgcgcgcgt ggagtggggc | 300 |
| acctgccgga ccaacccggt cgagctggtg cgcaagccca aggtcagctc cggccgggac | 360 |
| cgccggctca cctcgtccga ggagcgccgg ctgtcccggt acttccgcga agaacctg | 420 |
| atgctctacg tgatcttcca cctggccctg gagaccgcga tgcgccaggg cgagatcctg | 480 |
| gccctccgct gggagcacat cgacctgcgc cacggcgtcg cgcacctgcc ggagaccaag | 540 |
| aacgccaca gccgcgacgt gcccctgtcc cgccgggccc ggaacttcct ccagatgatg | 600 |
| cccgtcaacc tgcacggcaa cgtgttcgac tacaccgcca gcggcttcaa gaacgcctgg | 660 |
| cgcatcgcga cccagcggct gcgcatcgag gacctgcact ccacgacct gcgccacgag | 720 |
| gccatctcgc ggttcttcga gctgggcagc ctcaacgtca tggagatcgc cgcgatctcc | 780 |
| ggccaccgct cgatgaacat gctcaagcgg tacacccacc tgcgcgcctg gcagctggtg | 840 |
| tcgaagctcg acgcgcgtcg ccgccagacc cagaaggtcg ccgcgtggtt cgtgccgtac | 900 |
| cccgcccaca tcaccaccat cgacgaggag aacggccaga aggcgcaccg catcgagatc | 960 |
| ggcgacttcg acaacctgca cgtcaccgcc accaccaagg aagaggccgt gcaccgcgcg | 1020 |
| tccgaggtgc tgctccggac cctgccatc gccgcgcaga agggcgagcg ggtcccgtcg | 1080 |
| cccggcgcgc tgccggtcaa cgaccccgac tacatcatga tctgccccct gaaccccggc | 1140 |
| tccacccgc tgtga | 1155 |

<210> SEQ ID NO 37
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 37

| | |
|---|---|
| cccgggctga gggagccgac ggcacgcggc ggctcacggc gtggcacgcg gaacgtccgg | 60 |
| gcttgcacct cacgtcacgt gaggaggcag cgtggacggc gtcagagaag ggagcggaa | 119 |

<210> SEQ ID NO 38
<211> LENGTH: 486
<212> TYPE: DNA
<213> ORGANISM: Artificial Sequence
<220> FEATURE:
<223> OTHER INFORMATION: Synthetic Polynucleotide

<400> SEQUENCE: 38

| | |
|---|---|
| cgaagagaag tacctcgact acctgcgtcg tgccacggcg gacctccacg aggcccgtgg | 60 |
| ccgcctccgc gagctggagg cgaaggcggg cgagccggtg gcgatcgtcg gcatggcctg | 120 |
| ccgcctgccc ggcggcgtcg cctcgcccga ggacctgtgg cggctggtgg ccggcggcga | 180 |
| ggacgcgatc tcggagttcc cccaggaccg cggctgggac gtggagggcc tgtacgaccc | 240 |
| gaacccggag gccacgggca agagttacgc ccgcgaggcc ggattcctgt acgaggcggg | 300 |
| cgagttcgac gccgacttct tcgggatctc gccgcgcgag gccctcgcca tggacccgca | 360 |
| gcagcgtctc ctcctggagg cctcctggga ggcgttcgag cacgccggga tcccggcggc | 420 |
| caccgcgcgc ggcacctcgg tcggcgtctt caccggcgtg atgtaccacg actacgccac | 480 |
| ccgtct | 486 |

<210> SEQ ID NO 39
<211> LENGTH: 495
<212> TYPE: DNA
<213> ORGANISM: Artificial Sequence
<220> FEATURE:
<223> OTHER INFORMATION: Synthetic Polynucleotide

<400> SEQUENCE: 39

```
ctgctcagcg ggctcacccg cggatcgcgg gtcggcggcg cgccggtcaa ccagcgcagg      60
gcagccgccg gaggcgcggg cgaggcggac acggacctcg gcgggcggct cgccgcgatg     120
acaccggacg accgggtcgc gcacctgcgg gacctcgtcc gtacgcacgt ggcgaccgtc     180
ctgggacacg gcaccccgag ccgggtggac ctggagcggg ccttccgcga caccggtttc     240
gactcgctca ccgccgtcga actccgcaac cgtctcaacg ccgcgaccgg gctgcggctg     300
ccggccacgc tggtcttcga ccaccccacc ccgggggagc tcgccgggca cctgctcgac     360
gaactcgcca cggccgcggg cgggtcctgg gcggaaggca ccgggtccgg agacacggcc     420
tcggcgaccg atcggcagac cacggcggcc ctcgccgaac tcgaccggct ggaaggcgtg     480
ctcgcctccc tcgcg                                                     495
```

<210> SEQ ID NO 40
<211> LENGTH: 9380
<212> TYPE: DNA
<213> ORGANISM: Artificial Sequence
<220> FEATURE:
<223> OTHER INFORMATION: Synthetic Polynucleotide

<400> SEQUENCE: 40

```
cctcgccgca gttaattaaa gtcagtgagc gaggaagcgc gtaactataa cggtcctaag      60
gtagcgaatc ctgatgcggt attttctcct tacgcatctg tgcggtattt cacaccgcat     120
agatcggcaa gtgcacaaac aatacttaaa taaatactac tcagtaataa cctatttctt     180 agcattttg acgaaatttg ctattttgtt agagtctttt acaccatttg tctccacacc      240
tccgcttaca tcaacaccaa taacgccatt taatctaagc gcatcaccaa cattttctgg     300
cgtcagtcca ccagctaaca taaaatgtaa gctttcgggg ctctcttgcc ttccaaccca     360
gtcagaaatc gagttccaat ccaaaagttc acctgtccca cctgcttctg aatcaaacaa     420
gggaataaac gaatgaggtt tctgtgaagc tgcactgagt agtatgttgc agtcttttgg     480
aaatacgagt cttttaataa ctggcaaacc gaggaactct tggtattctt gccacgactc     540
atctccatgc agttggacga tatcaatgcc gtaatcattg accagagcca aaacatcctc     600
cttaagttga ttacgaaaca cgccaaccaa gtatttcgga gtgcctgaac tattttata     660 tgcttttaca agacttgaaa ttttcctgc aataaccggg tcaattgttc tctttctatt     720
gggcacacat ataatacccca gcaagtcagc atcggaatct agagcacatt ctgcggcctc     780
tgtgctctgc aagccgcaaa cttttcaccaa tggaccagaa ctacctgtga aattaataac     840
agacatactc caagctgcct ttgtgtgctt aatcacgtat actcacgtgc tcaatagtca     900
ccaatgccct ccctcttggc cctctccttt tcttttttcg accgaattaa ttcttaatcg     960
gcaaaaaaag aaaagctccg gatcaagatt gtacgtaagg tgacaagcta tttttcaata    1020
aagaatatct tccactactg ccatctggcg tcataactgc aaagtacaca tatattacga    1080
tgctgttcta ttaaatgctt cctatattat atatatagta atgtcgtgat ctatggtgca    1140
ctctcagtac aatctgctct gatgccgcat agttaagcca gccccgacac ccgccaacac    1200
```

```
ccgctgacgc gccctgacgg gcttgtctgc tcccggcatc cgcttacaga caagctgtga      1260
ccgtctccgg gagctgcatg tgtcagaggt tttcaccgtc atcaccgaaa cgcgcgagac      1320
gaaagggcct cgtgatacgc ctattttat aggttaatgt catgataata atggtttctt       1380
agacggatcg cttgcctgta acttacacgc gcctcgtatc ttttaatgat ggaataattt      1440
gggaatttac tctgtgttta tttatttta tgttttgtat ttggatttta gaaagtaaat       1500
aaagaaggta gaagagttac ggaatgaaga aaaaaaata aacaaaggtt taaaaaattt      1560
caacaaaaag cgtactttac atatatattt attagacaag aaaagcagat taaatagata     1620
tacattcgat taacgataag taaaatgtaa aatcacagga ttttcgtgtg tggtcttcta      1680
cacagacaag gtgaaacaat tcggcattaa tacctgagag caggaagagc aagataaaag     1740
gtagtatttg ttggcgatcc ccctagagtc ttttacatct tcggaaaaca aaaactattt     1800
tttctttaat ttcttttttt actttctatt tttaatttat atatttatat taaaaaattt     1860
aaattataat tatttttata gcacgtgatg aaaaggaccc aggtggcact tttcggggaa    1920
atgtgcgcgg aaccctatt tgtttatttt tctaaataca ttcaaatatg tatccgctca     1980
tgagacaata accctgataa atgcttcaat aatattgaaa aggaagagt atgagtattc     2040 aacatttccg tgtcgccctt attcccttt ttgcggcatt ttgccttcct gttttgctc      2100 acccagaaac gctggtgaaa gtaaagatg ctgaagatca gttgggacgc gtagtctaga     2160
ccagccagga cagaaatgcc tcgacttcgc tgctacccaa ggttgccggg tgacgcacac    2220
cgtggaaacg gatgaaggca cgaacccagt ggacataagc ctgttcggtt cgtaagctgt    2280
aatgcaagta gcgtatgcgc tcacgcaact ggtccagaac cttgaccgaa cgcagcggtg   2340
gtaacggcgc agtggcggtt ttcatggctt gttatgactg ttttttggg gtacagtcta    2400 tgcctcgggc atccaagcag caagcgcgtt acgccgtggg tcgatgtttg atgttatgga   2460
gcagcaacga tgttacgcag cagggcagtc gccctaaaac aaagttaaac attatgaggg   2520
aagcggtgat cgccgaagta tcgactcaac tatcagaggt agttggcgcc atcgagcgcc  2580
atctcgaacc gacgttgctg gccgtacatt tgtacggctc cgcagtggat ggcggcctga   2640
agccacacag tgatattgat ttgctggtta cggtgaccgt aaggcttgat gaaacaacgc   2700
ggcgagcttt gatcaacgac cttttggaaa cttcggcttc ccctggagag agcgagattc    2760
tccgcgctgt agaagtcacc attgttgtgc acgacgacat cattccgtgg cgttatccag    2820
ctaagcgcga actgcaattt ggagaatggc agcgcaatga cattcttgca ggtatcttcg   2880
agccagccac gatcgacatt gatctggcta tcttgctgac aaaagcaaga gaacatagcg   2940
ttgccttggt aggtccagcg gcggaggaac tctttgatcc ggttcctgaa caggatctat   3000
ttgaggcgct aaatgaaacc ttaacgctat ggaactcgcc gcccgactgg gctggcgatg   3060
agcgaaatgt agtgcttacg ttgtcccgca tttggtacag cgcagtaacc ggcaaaatcg   3120
cgccgaagga tgtcgctgcc ggctgggcaa tggagcgcct gccggcccag tatcagcccg   3180
tcatacttga agctagacag gcttatcttg acaagaaga gatcgcttg gcctcgcgcg    3240 cagatcagtt ggaagaattt gtccactacg tgaaaggcga gatcaccaag gtagtcggca   3300
aataaccctc gagcattcaa ggcgccttga ttatttgacg tggtttgatg gcctccacgc    3360
acgttgtgat atgtagatga taatcattat cactttacgg gtcctttccg gtgatccgac    3420
aggttacggg gcggcgacct cgcgggtttt cgctatttat gaaaattttc cggtttaagg   3480
cgtttccgtt cttcttcgtc ataacttaat gtttttattt aaaataccctc gcagtggca    3540 acactgaaaa tacccatgga gcggcgtaac cgtcgcacag gaaggacaga gaaagcgcgg   3600
```

```
atctgggaag tgacggacag aacggtcagg acctggattg gggaggcggt tgccgccgct   3660
gctgctgacg gtgtgacgtt ctctgttccg gtcacaccac atacgttccg ccattcctat   3720
gcgatgcaca tgctgtatgc cggtataccg ctgaaagttc tgcaaagcct gatgggacat   3780
aagtccatca gttcaacgga ggtctacacg aaggttttg cgctggatgt ggctgccgg    3840
caccgggtgc agtttgcgat gccggagtct gatgcggttg cgatgctgaa acaattatcc   3900
tgagaataaa tgccttggcc tttatatgga atgtgaac tgagtggata tgctgttttt    3960
gtctgttaaa cagagaagct ggctgttatc cactgagaag cgaacgaaac agtcgggaaa   4020
atctcccatt atcgtagaga tccgcattat taatctcagg agcctgtgta gcgtttatag   4080
gaagtagtgt tctgtcatga tgcctgcaag cggtaacgaa aacgatttga atatgccttc   4140
aggaacaata gaaatcttcg tgcggtgtta cgttgaagtg gagcggatta tgtcagcaat   4200
ggacagaaca acctaatgaa cacagaacca tgatgtggtc tgtccttta cagccagtag    4260
tgctcgccgc agtcgagcga cagggcgaag ccctcgagtg agcgaggaag caccagggaa   4320
cagcacttat atattctgct tacacacgat gcctgaaaaa acttcccttg gggttatcca   4380
cttatccacg gggatatttt tataattatt ttttttatag tttttagatc ttctttttta   4440
gagcgccttg taggcccttta tccatgctgg ttctagagaa ggtgttgtga caaattgccc   4500
tttcagtgtg acaaatcacc ctcaaatgac agtcctgtct gtgacaaatt gcccttaacc   4560
ctgtgacaaa ttgccctcag aagaagctgt tttttcacaa agttatccct gcttattgac   4620
tctttttttat ttagtgtgac aatctaaaaa cttggcacac ttcacatgga tctgtcatgg   4680
cggaaacagc ggttatcaat cacaagaaac gtaaaaatag cccgcgaatc gtccagtcaa   4740
acgacctcac tgaggcggca tatagtctct cccgggatca aaaacgtatg ctgtatctgt   4800
tcgttgacca gatcagaaaa tctgatggca ccctacagga acatgacggt atctgcgaga   4860
tccatgttgc taaatatgct gaaatattcg gattgacctc tgcggaagcc agtaaggata   4920
tacggcaggc attgaagagt ttcgcgggga aggaagtggt tttttatcgc cctgaagagg   4980
atgccggcga tgaaaaaggc tatgaatctt ttccttggtt tatcaaacgt gcgcacagtc   5040
catccagagg gctttacagt gtacatatca acccatatct cattcccttc tttatcgggt   5100
tacagaaccg gtttacgcag tttcggctta gtgaaacaaa agaaatcacc aatccgtatg   5160
ccatgcgttt atacgaatcc ctgtgtcagt atcgtaagcc ggatggctca ggcatcgtct   5220
ctctgaaaat cgactggatc atagagcgtt accagctgcc tcaaagttac cagcgtatgc   5280
ctgacttccg ccgccgcttc ctgcaggtct gtgttaatga gatcaacagc agaactccaa   5340
tgcgcctctc atacattgag aaaaagaaag ccgccagac gactcatatc gtattttcct   5400
tccgcgatat cacttccatg acgacaggat agtctgaggg ttatctgtca cagatttggg   5460
ggtggttcgt cacatttgtt ctgacctact gagggtaatt tgtcacagtt ttgctgtttc   5520
cttcagcctg catggatttt ctcatacttt ttgaactgta atttttaagg aagccaaatt   5580
tgagggcagt ttgtcacagt tgatttcctt ctctttccct tcgtcatgtg acctgatatc   5640
gggggttagt ttgtcatcat tgatgagggt tgattatcac agtttattac tctgaattgg   5700
ctatccgcgt gtgtacctct acctggagtt tttcccacgg tggatatttc ttcttgcgct   5760
gagcgtaaga gctatctgac agaacagttc ttctttgctt cctcgccagt tcgctcgcta   5820
tgctcggtta cacggctgcg gcgagcgcta gtgataataa gtgactgagg tatgtgctct   5880
tcttatctcc ttttgtagtg ttgctcttat tttaaacaac tttgcggttt tttgatgact   5940
```

-continued

```
ttgcgatttt gttgttgctt tgcagtaaat tgcaagattt aataaaaaaa cgcaaagcaa      6000
tgattaaagg atgttcagaa tgaaactcat ggaaacactt aaccagtgca taaacgctgg      6060
tcatgaaatg acgaaggcta tcgccattgc acagtttaat gatgacagcc cggaggcgag      6120
gaaaataacc cggcgctgga gaataggtga agcagcggga ttagttgggg tttcttctca      6180
ggctatcaga gatgccgaga aagcagggcg actaccgcac ccggatatgg aaattcgagg      6240
acgggttgag caacgtgttg gttatacaat tgaacaaatt aatcatatgc gtgatgtgtt      6300
tggtacgcga ttgcgacgtg ctgaagacgt atttccaccg gtgatcgggg ttgctgccca      6360
taaaggtggc gtttacaaaa cctcagtttc tgttcatctt gctcaggatc tggctctgaa      6420
ggggctacgt gttttgctcg tggaaggtaa cgaccccag ggaacagcct caatgtatca      6480
cggatgggta ccagatcttc atattcatgc agaagacact ctcctgcctt tctatcttgg      6540
ggaaaaggac gatgtcactt atgcaataaa gcccacttgc tggccggggc ttgacattat      6600
tccttcctgt ctggctctgc accgtattga aactgagtta atgggcaaat ttgatgaagg      6660
taaactgccc accgatccac acctgatgct ccgactggcc attgaaactg ttgctcatga      6720
ctatgatgtc atagttattg acagcgcgcc taacctgggt atcggcacga ttaatgtcgt      6780
atgtgctgct gatgtgctga ttgttcccac gcctgctgag ttgtttgact acacctccgc      6840
actgcagttt ttcgatatgc ttcgtgatct gctcaagaac gttgatctta aagggttcga      6900
gcctgatgta cgtattttgc ttaccaaata cagcaatagt aatggctctc agtccccgtg      6960
gatggaggag caaattcggg atgcctgggg aagcatggtt ctaaaaaatg ttgtacgtga      7020
aacggatgaa gttggtaaag gtcagatccg gatgagaact gttttgaac aggccattga      7080 tcaacgctcc tcaactggtg cctggagaaa tgctctttct atttgggaac ctgtctgcaa      7140
tgaaattttc gatcgcctga ttaaaccacg ctggggagatt agataatgaa gcgtgcgcct      7200
gttattccaa acatacgct caatactcaa ccggttgaag atacttcgtt atcgacacca      7260
gctgccccga tggtggattc gttaattgcg cgcgtaggag taatggctcg cggtaatgcc      7320
attactttgc ctgtatgtgg tcgggatgtg aagtttactc ttgaagtgct ccggggtgat      7380
agtgttgaga agacctctcg ggtatggcca ggtaatgaac gtgaccagga gctgcttact      7440
gaggacgcac tggatgatct catcccttct tttctactga ctggtcaaca gacaccggcg      7500
ttcggtcgaa gagtatctgg tgtcatagaa attgccgatg ggagtcgccg tcgtaaagct      7560
gctgcactta ccgaaagtga ttatcgtgtt ctggttggcg agctggatga tgagcagatg      7620
gctgcattat ccagattggg taacgattat cgcccaacaa gtgcttatga acgtggtcag      7680
cgttatgcaa gccgattgca gaatgaattt gctggaaata tttctgcgct ggctgatgcg      7740
gaaaatattt cacgtaagat tattacccgc tgtatcaaca ccgccaaatt gcctaaatca      7800
gttgttgctc ttttttctca ccccggtgaa ctatctgccc ggtcaggtga tgcacttcaa      7860
aaagccttta cagataaaga ggaattactt aagcagcagg catctaacct tcatgagcag      7920
aaaaaagctg gggtgatatt tgaagctgaa gaagttatca ctcttttaac ttctgtgctt      7980
aaaacgtcat ctgcatcaag aactagttta agctcacgac atcagtttgc tcctggagcg      8040
acagtattgt ataagggcga taaaatgtg cttaacctgg acaggtctcg tgttccaact      8100
gagtgtatag agaaaattga ggccattctt aaggaacttg aaaagccagc accctgatgc      8160
gaccacgttt tagtctacgt ttatctgtct ttacttaatg tcctttgcta caggccagaa      8220
agcataactg gcctgaatat tctctctggg cccactgttc cacttgtatc gtcggactga      8280
taatcagact gggaccacgg tcccactcgt atcgtcggtc tgattattag tctgggacca      8340
```

```
cggtcccact cgtatcgtcg gtctgattat tagtctggga ccacggtccc actcgtatcg    8400
tcggtctgat aatcagactg ggaccacggt cccactcgta tcgtcggtct gattattagt    8460
ctgggaccat ggtcccactc gtatcgtcgg tctgattatt agtctgggac cacggtccca    8520
ctcgtatcgt cggtctgatt attagtctgg aaccacggtc ccactcgtat cgtcagtctg    8580
attattagtc tgggaccacg gtcccactcg tatcgtcggt ctgattatta gtctgggacc    8640
acgatcccac tcgtgttgtc ggtctgatta tcggtctggg accacggtcc cacttgtatt    8700
gtcgatcaga ctatcagcgt gagactacga ttccatcaat gcctgtcaag gcaagtatt     8760 gacatgtcgt cgtaacctgt agaacggagt aacctcggtg tgcggttgta tgcctgctgt    8820
ggattgctgc tgtgtcctgc ttatccacaa cattttgcgc acggttatgt ggacaaaata    8880
cctggttacc caggccgtgc cggcacgtta accgggctgc atccgatgca agtgtgtcgc    8940
tgtcgacggc ctcctcaccc ggtcacgtga gctcatttaa cccactccac aaaaaggctc    9000
aacaggttgg tggttctcac caccaaaagc accacacccc acgcaaaaac aagttttgc    9060 tgattttct ttataaatag agtgttatga aaaattagtt tctcttactc tctttatgat     9120
atttaaaaaa gcggtgtcgg cgcggctaca acaacgcgcc gacaccgttt tgtaggggtg    9180
gtactgacta tttttataaa aaacattatt ttatattagg ggtgctgcta gcggcgcggt    9240
gtgttttttt ataggatacc gctaggggcg ctgctagcgg tgcgtccctg tttgcattat    9300
gaattagtta cgctagggat aacagggtaa tatagaaccc gaacgaccga gcgcagcggc    9360
ggccgcgctg ataccgccgc                                                9380

<210> SEQ ID NO 41
<211> LENGTH: 1521
<212> TYPE: DNA
<213> ORGANISM: Artificial Sequence
<220> FEATURE:
<223> OTHER INFORMATION: Synthetic Polynucleotide

<400> SEQUENCE: 41
cggccacgac accccatcg gcatcgcgtg gcgggcccga ttcgcgtccg ccccggggag      60
gagacgggcg tccgcgtcga gggcgaggcg ggcttccacc cgtaggcgat ccggcgagca    120
cgacacccgc agattggctc gacgcagccc agaaatgtat gatcaaggcg aatacttcat    180
atgcggggat cgaccgcgcg ggtcccggac ggggaagagc ggggagcttt gccagagagc    240
gacgacttcc ccttgcgttg gtgattgccg gtcagggcag ccatccgcca tcgtcgcgta    300
gggtgtcaca ccccaggaat cgcgtcactg aacacagcag ccggtaggac gaccatgact    360
gagttggaca ccatcgcaaa tccgtccgat cccgcggtgc agcggatcat cgatgtcacc    420
aagccgtcgc gatccaacat aaagacaacg ttgatcgagg acgtcgagcc cctcatgcac    480
agcatcgcgg ccggggtgga gttcatcgag gtctacggca gcgacagcag tccttttcca    540
tctgagttgc tggatctgtg cgggcggcag aacataccgg tccgcctcat cgactcctcg    600
atcgtcaacc agttgttcaa gggggagcgg aaggccaaga cattcggcat cgcccgcgtc    660
cctcgcccgg ccaggttcgg cgatatcgcg agcggcgtg gggacgtcgt cgttctcgac    720
ggggtgaaga tcgtcgggaa catcggcgcg atagtacgca cgtcgctcgc gctcggagcg    780
tcggggatca tcctggtcga cagtgacatc accagcatcg cggaccggcg tctccaaagg    840
gccagccgag gttacgtctt ctcccttccc gtcgttctct ccggtcgcga ggaggccatc    900
gccttcattc gggacagcgg tatgcagctg atgacgctca aggcggatgg cgacatttcc    960
```

```
gtgaaggaac tcggggacaa tccggatcgg ctggccttgc tgttcggcag cgaaaagggt    1020
gggccttccg acctgttcga ggaggcgtct tccgcctcgg tttccatccc catgatgagc    1080
cagaccgagt ctctcaacgt ttccgtttcc ctcggaatcg cgctgcacga gaggatcgac    1140
aggaatctcg cggccaaccg ataagcgcct ctgttcctcg gacgctcggt tcctcgacct    1200
cgattcgtca gtgatgatca cctcacacgg cagcgatcac cactgacata tcgaggtcaa    1260
cggtcgtggt ccgggcgggc actcctcgaa ggcgcggccg acgcccttga acgactcgat    1320
ggcgctgacg ccttccgcga tcgcctcgac tgtgaaaacg ctcgtggacg tcggcgggta    1380
gccgatgagt tccatcgcct tgcgcatccc cttgagcatg gagaacgcgt ccaccgggta    1440
gtcacgaagg tacttgcgaa ggcttcgcgc cgtccgagac cgtgagccgg cgcaagccgg    1500
tgtggcgccg gtcccggatc c                                              1521

<210> SEQ ID NO 42
<211> LENGTH: 182
<212> TYPE: DNA
<213> ORGANISM: Artificial Sequence
<220> FEATURE:
<223> OTHER INFORMATION: Synthetic Polynucleotide

<400> SEQUENCE: 42
accccgtccg ggcagggcgg gtcaccgtcc cgcgcggcgg ggagagagga gaggccgtga      60
ccaggtaccg gattggcact tatccggtgc caatccggtc ggtggtcagg agtggagaag     120
acatgccggg tacgaacgac atgccgggta ccgaggacaa gctccgccac tacctgaagc     180
ga                                                                    182

<210> SEQ ID NO 43
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 43
ccgacgagga ggagcaagcc gcgcccgagg acctgtcgac cgcgagcgcc gacgacatgt      60
tcgccctgat cgaccgggag tggggcacgc ggtgaccacc gaccggattg cacgtaggc     120 cagtgccaat ccggtacttg gcaattgcct cgccgcagtt aattaaagtc agtgagcgag     180
gaagcgc                                                               187

<210> SEQ ID NO 44
<211> LENGTH: 401
<212> TYPE: DNA
<213> ORGANISM: Artificial Sequence
<220> FEATURE:
<223> OTHER INFORMATION: Synthetic Polynucleotide

<400> SEQUENCE: 44
gcttcatgct ggacacctcc gcggtgccgg cggacgtggt gcgtgacatc gaggccgacc      60
atctgtccct ggccatggag cactcggatc tgaccgccga ggccatagag aactggctcg     120
ccgaacttcc ggccggcgag gcctgaccaa gtaccggatt ggcactggcc tacgtgccaa     180
tccggtacgt gggcagcgat cagtcctgag cgcgatgagc cccggccaca ccggccccct     240
tgccctcccc caacctcata cgccccgatc accacgtagc gccaaggagc ctgggtcaga     300
tgtcgaacga ggagaagctt ctcgatcacc tcaagtgggt caccgcgag ctgcgccagg     360 cccggcaacg gctccacgac aaggaatcga ccgagccggt c                         401
```

<210> SEQ ID NO 45
<211> LENGTH: 1812
<212> TYPE: DNA
<213> ORGANISM: Artificial Sequence
<220> FEATURE:
<223> OTHER INFORMATION: Synthetic Polynucleotide

<400> SEQUENCE: 45

```
atgttacgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat tgaagccga tgtcacgccg      360
tatgttattg ccgggaaaag tgtacgtatc accgtttgtg tgaacaacga actgaactgg     420
cagactatcc cgccgggaat ggtgattacc gacgaaaacg gcaagaaaaa gcagtcttac     480
ttccatgatt tctttaacta tgccgggatc catcgcagcg taatgctcta caccacgccg     540
aacacctggg tggacgatat caccgtggtg acgcatgtcg cgcaagactg taaccacgcg     600
tctgttgact ggcaggtggt ggccaatggt gatgtcagcg ttgaactgcg tgatgcggat     660
caacaggtgg ttgcaactgg acaaggcact agcgggactt gcaagtggt gaatccgcac      720
ctctggcaac cgggtgaagg ttatctctat gaactgtgcg tcacagccaa agccagaca      780
gagtgtgata tctacccgct tcgcgtcggc atccggtcag tggcagtgaa gggcgaacag     840
ttcctgatta ccacaaaacc gttctacttt actggctttg gtcgtcatga agatgcggac     900
ttgcgtggca aaggattcga taacgtgctg atggtgcacg accacgcatt aatggactgg     960
attgggccaa actcctaccg tacctcgcat taccttacg ctgaagagat gctcgactgg     1020
gcagatgaac atggcatcgt ggtgattgat gaaactgctg ctgtcggctt taacctctct    1080
ttaggcattg gtttcgaagc gggcaacaag ccgaaagaac tgtacagcga agaggcagtc    1140
aacgggaaa ctcagcaagc gcacttacag gcgattaaag agctgatagc gcgtgacaaa     1200
aaccacccaa gcgtggtgat gtggagtatt gccaacgaac cggatacccg tccgcaaggt    1260
gcacgggaat atttcgcgcc actggcgaa gcaacgcgta actcgaccc gacgcgtccg      1320
atcacctgcg tcaatgtaat gttctgcgac gctcacaccg ataccatcag cgatctcttt    1380
gatgtgctgt gcctgaaccg ttattacgga tggtatgtcc aaagcggcga tttggaaacg    1440
gcagagaagg tactggaaaa agaacttctg gcctggcagg agaaactgca tcagccgatt    1500
atcatcaccg aatacggcgt ggatacgtta gccgggctgc actcaatgta caccgacatg    1560
tggagtgaag agtatcagtg tgcatggctg gatatgtatc accgcgtctt tgatcgcgtc    1620
agcgccgtcg tcggtgaaca ggtatggaat ttcgccgatt ttgcgacctc gcaaggcata    1680
ttgcgcgttg gcggtaacaa gaaagggatc ttcactcgcg accgcaaacc gaagtcggcg    1740
gcttttctgc tgcaaaaacg ctggactggc atgaacttcg gtgaaaaacc gcagcaggga    1800
ggcaaacaat ga                                                       1812
```

<210> SEQ ID NO 46
<211> LENGTH: 1812
<212> TYPE: DNA
<213> ORGANISM: Artificial Sequence
<220> FEATURE:

<223> OTHER INFORMATION: Synthetic Polynucleotide

<400> SEQUENCE: 46

```
atgctgcgcc cggtggaaac cccgacccgc gaaatcaaga agctcgacgg cctgtgggcg      60
ttcagcctcg accgcgaaaa ctgcggcatc gaccagcggt ggtgggagag cgcgctgcag     120
gaatcgcgcg cgatcgccgt cccgggctcg ttcaacgacc agttcgcgga cgccgacatc     180
cggaactacg ccggcaacgt ctggtaccag cgcgaggtgt tcatcccgaa gggctgggcg     240
ggccagcgga tcgtcctgcg cttcgacgcc gtgacccact acggcaaggt ctgggtgaac     300
aaccaggaag tcatggaaca ccagggcggc tacaccccgt cgaggcgga cgtcacgccg      360
tacgtgatcg ccggcaagtc cgtccggatc accgtctgcg tgaacaacga gctgaactgg     420
cagaccatcc cgccgggcat ggtgatcacg acgagaacg gcaagaagaa gcagtcctac      480
ttccacgact tcttcaacta cgcgggcatc caccgcagcg tcatgctgta caccacgccg     540
aacacctggg tcgacgacat caccgtcgtg acgcacgtgg cgcaggactg caaccacgcc     600
agcgtcgact ggcaggtcgt ggccaacggc gacgtctcgg tggagctgcg ggacgcggac     660
cagcaggtcg tggccaccgg ccagggcacc tcgggcacgc tgcaggtcgt gaacccgcac     720
ctctggcagc cgggcgaggg ctacctgtac gaactctgcg tcaccgcgaa gtcgcagacg     780
gagtgcgaca tctacccgct gcgggtgggc atccgctccg tcgccgtgaa gggcgagcag     840
ttcctcatca accacaagcc gttctacttc accggcttcg gccggacga ggacgcggac       900
ctgcgcggca agggcttcga caacgtcctg atggtgcacg accacgcgct catggactgg     960
atcggcgcca actcgtaccg gacctcgcac tacccgtacg cggaggaaat gctggactgg    1020
gccgacgagc acggcatcgt cgtgatcgac gaaacggcgg ccgtcggctt caacctgagc    1080
ctcggcatcg gcttcgaggc gggcaacaag ccgaaggaac tctactcgga ggaagccgtg    1140
aacggcgaga cccagcaggc gcacctgcag gccatcaagg aactcatcgc gcgggacaag    1200
aaccaccgt ccgtcgtgat gtggagcatc gccaacgagc cggacacccg gccgcagggc     1260
gcgcgcgagt acttcgcccc gctggcggaa gccacgcgga agctcgaccc gacccgcccg    1320
atcacgtgcg tcaacgtgat gttctgcgac gcgcacaccg acacgatctc ggacctgttc    1380
gacgtgctgt gcctcaaccg gtactacggc tggtacgtgc agtccggcga cctggagacc    1440
gcggaaaagg tgctcgagaa ggaactgctc gcctggcagg agaagctgca ccagccgatc    1500
atcatcaccg aatacggcgt ggacacgctg gccggcctcc actcgatgta cacggacatg    1560
tggtccgagg aataccagtg cgcgtggctg gacatgtacc accgggtctt cgaccgcgtg    1620
tccgccgtcg tgggcgagca ggtctggaac ttcgcggact cgccaccag ccagggcatc      1680
ctccgggtgg gcggcaacaa gaagggcatc ttcacgcggg accgcaagcc gaagagcgcg    1740
gccttcctgc tccagaagcg ctggaccggc atgaacttcg gcgagaagcc gcagcagggc    1800
ggcaagcagt ga                                                         1812
```

<210> SEQ ID NO 47
<211> LENGTH: 12934
<212> TYPE: DNA
<213> ORGANISM: Artificial Sequence
<220> FEATURE:
<223> OTHER INFORMATION: Synthetic Polynucleotide

<400> SEQUENCE: 47

```
gaacgaccga gcgcagcggc ggccgcgctg ataccgccgc tctagacgaa gagaagtacc      60
tcgactacct gcgtcgtgcc acggcggacc tccacgaggc ccgtggccgc ctccgcgagc     120
```

```
tggaggcgaa ggcgggcgag ccggtggcga tcgtcggcat ggcctgccgc ctgcccggcg    180
gcgtcgcctc gcccgaggac ctgtggcggc tggtggccgg cggcgaggac gcgatctcgg    240
agttccccca ggaccgcggc tgggacgtgg agggcctgta cgacccgaac ccggaggcca    300
cgggcaagag ttacgcccgc gaggccggat tcctgtacga ggcgggcgag ttcgacgccg    360
acttcttcgg gatctcgccg cgcgaggccc tcgccatgga cccgcagcag cgtctcctcc    420
tggaggcctc ctgggaggcg ttcgagcacg ccgggatccc ggcggccacc gcgcgcggca    480
cctcggtcgg cgtcttcacc ggcgtgatgt accacgacta cgccacccgt cttcacagcg    540
gggtggagcc ggggttcagg gggcagatca tgatgtagtc ggggtcgttg accggcagcg    600
cgccgggcga cgggacccgc tcgcccttct gcgcggcgat ggcgagggtc cggagcagca    660
cctcggacgc gcggtgcacg gcctcttcct tggtggtggc ggtgacgtgc aggttgtcga    720
agtcgccgat ctcgatgcgg tgcgccttct ggccgttctc ctcgtcgatg gtggtgatgt    780
gggcggggta cggcacgaac cacgcggcga ccttctgggt ctggcggcga cgcgcgtcga    840
gcttcgacac cagctgccag gcgcgcaggt gggtgtaccg cttgagcatg ttcatcgagc    900
ggtgccggga gatcgcggcg atctccatga cgttgaggct gcccagctcg aagaaccgcg    960
agatggcctc gtggcgcagg tcgtggaagt gcaggtcctc gatgcgcagc cgctgggtcg   1020
cgatgcgcca ggcgttcttg aagccgctgg cggtgtagtc gaacacgttg ccgtgcaggt   1080
tgacgggcat catctggagg aagttccggg cccggcggga caggggcacg tcgcggctgt   1140
ggccgttctt ggtctccggc aggtgcgcga cgccgtggcg caggtcgatg tgctcccagc   1200
ggagggccag gatctcgccc tggcgcatcg cggtctccag ggccaggtgg aagatcacgt   1260
agagcatcag gttcttctcg cggaagtacc gggacagccg gcgctcctcg gacgaggtga   1320
gccggcggtc ccggccggag ctgaccttgg gcttgcgcac cagctcgacc gggttggtcc   1380
ggcaggtgcc ccactccacg cgcgcgatgt tgaacagcga ggagagcagg gcgagctcca   1440
gccggacggt gttgccggtg atgggcttgc cggtgcgcgg gttgatctcc gccaggcgca   1500
cgtcccggta ggtggcgatg tcgacggtgg tgatctcgtc catgttccgc agggcgatcg   1560
ggtagcgctt gatgacgttg gaccggtaga actcctgctg gtggcccttc ttgtggacgc   1620
tcacggtctt caggtacttg tcgagggcgc gggagaggct catcttgcgg atgcgggggg   1680
acggcatttc cgctcccttc tctgacgccg tccacgctgc ctcctcacgt gacgtgaggt   1740
gcaagcccgg acgttccgcg tgccacgccg tgagccgccg cgtgccgtcg gctccctcag   1800
cccgggttat ccgactgtta cggtagcgtg catcctgtta gccaatctgt cagtcagttg   1860
tcaggtcatt aatgttatgt cattgacaat gatcatgttg atgctgttgt gggcacaatc   1920
gtgccggttg gtaggatcca gcgtggccta cgtgccaatc cggtacctgg ccggccggcg   1980
gagcacaccc ggccgtctcc ggcccggccg cggccgggcc ggaagccatc gccgcccac    2040 ccggtaccga cccctcaagc ccttcaagcc cttcgacccg tccgatcagt cagtccggcg   2100
gtcctccacg accggtccgg aatcgccccc acacgagtca ggaagcacac catggccatg   2160
tccgccgaga ggctgacgga ggcgctgcgc acctcgctca aggaggccga gcggctccgg   2220
cggcagaacc gcgaactgag ggccgcgcgg gacgcggcgc gggagccgat cgccgtcgtc   2280
ggcatggcct gccgctaccc gggcggtgtc accggccccg aggagctgtg ggagctggtg   2340
gccgagggcc gggacgcgat cgggccgttc ccgtggacc ggggctggga cgtgcgtcg    2400 gtgtacgacc cggatcccga gtcgaagggc accacgtact gccggagggg cgggttcctg   2460
```

```
gaaggcgccg gtgacttcga cgccgccttc ttcggcatct cgccgcgcga ggccctggtg    2520
atggacccgc agcagcggct gctgctggag gtgtcctggg aggcgctgga acgcgcgggc    2580
atcgacccgt cctcgctgcg cggcagccgc ggtggtgtct acgtgggcgc cgcgcacggc    2640
tcgtacgcct ccgatcccg gctggtgccc gagggctcgg agggctatct gctgaccggc     2700
agcgccgacg cggtgatgtc cggccgcatc tcctacgcgc tcggtctcga aggaccgtcc    2760
atgacggtgg agacgcctg ctcctcctcg ctggtggcgc tgcatctggc ggtacgggcg     2820
ctgcggcacg gcgagtgcgg gctcgcgctg gcgggcgggg tggcggtgat ggccgatccg    2880
gcggcgttcg tggagttctc ccggcagaag gggctggccg ccgacggccg ctgcaaggcg    2940
ttctcggccg ccgccgacgg caccggctgg gccgagggcg tcggcgtgct cgtcctggag    3000
cggctgtcgg acgcgcgccg cgcggggcac acggtcctcg gcctggtcac cggcaccgcg    3060
gtcaaccagg acggtgcctc caacgggctg accgcgccca cggcccagc ccagcaacgc     3120 gtcatcgccg aggcgctcgc cgacgccggg ctgtccccgg aggacgtgga cgcggtcgag    3180
gcgcacggca ccggcacccg gctcggcgac cccatcgagg ccggggcgct gctcgccgcc    3240
tccggacgga accgttccgg cgaccacccg ctgtggctcg gctcgctgaa gtccaacatc    3300
gggcatgccc aggccgccgc cggtgtcgg ggcgtcatca agatgctcca ggcgctgcgg     3360
cacggcttgc tgccccgcac cctccacgcc gacgagccga ccccgcatgc cgactggagc    3420
tccggccggg tacggctgct cacctccgag gtgccgtggc agcggaccgg ccggccccgg    3480
cggaccgggg tgtccgcctt cggcgtcggc ggcaccaatg cccatgtcgt cctcgaagag    3540
gcacccgccc cgcccgcgcc ggaaccggcc ggggaggccc ccggcggctc ccgcgccgca    3600 gaagggcgg aagggcccct ggcctgggtg gtctccggac gcgacgagcc ggccctgcgg     3660
tcccaggccc ggcggctccg cgaccacctc tcccgcaccc ccggggcccg cccgcgtgac    3720
atcgccttct ccctcgccgc cacgcgcgca gcctttgacc accgcgccgt gctgatcggc    3780
tcggacgggg ccgaactcgc cgccgccctg gacgcgttgg ccgaaggacg cgacggtccg    3840
gcggtggtgc gcggagtccg cgaccgggac ggcaggatgg ccttcctctt caccgggcag    3900
ggcagccagc gcgccgggat ggcccacgac ctgcatgccg cccatacctt cttcgcgtcc    3960
gccctcgacg aggtgacgga ccgtctcgac ccgctgctcg gccggccgct cggcgcgctg    4020
ctggacgccc gacccggctc gcccgaagcg gcactcctgg accggaccga gtacacccag    4080
ccggcgctct tcgccgtcga ggtggcgctc caccggctgc tggagcactg ggggatgcgc    4140
cccgacctgc tgctggggca ctcggtgggc gaactggcgg ccgcccacgt cgcgggtgtg    4200
ctcgatctcg acgacgcctg cgcgctggtg gccgcccgcg gcaggctgat gcagcgcctg    4260
ccgcccggcg gcgcgatggt ctccgtgcgg ccggccgagg acgaggtccg cgcactgctg    4320
gccggccgcg aggacgccgt ctgcgtcgcc gcggtgaacg gcccccggtc ggtggtgatc    4380 tccgcgcgg aggaagcggt ggccgaggcg gcggcgcagc tcgccggacg aggccgccgc     4440
accaggcggc tccgcgtcgc gcacgccttc cactcacccc tgatggacgg catgctcgcc    4500
ggattccggg aggtcgccgc cggcctgcgc taccgggaac cggagctgac ggtcgtctcc    4560
acggtcacgg gcggccgc ccgcccggt gaactcaccg gccccgacta ctgggtggcc       4620
caggtccgtg agcccgtgcg cttcgcggac gcggtccgca cggcacaccg cctcggagcc    4680
cgcaccttcc tggagaccgg cccggacggc gtgctgtgcg gcatggcaga ggagtgcctg    4740
gaggacgaca ccgtggccct gctgccggcg atccacaagc ccggcaccgc gccgcacggt    4800
ccggcggctc ccggcgcgct gcgggcggcc gccgccgcgt acggccgggg cgcccgggtg    4860
```

-continued

```
gactgggccg ggatgcacgc cgacggcccc gaggggccgg cccgccgcgt cgaactgccc    4920
gtccacgcct tccggcaccg ccgctactgg ctcgccccgg gccgcgcggc ggacaccgac    4980
gactggatgt accggatcgg ctgggaccgg ctgccggctg tgaccggcgg ggcccggacc    5040
gccggccgct ggctggtgat ccaccccgac agcccgcgct gccgggagct gtccggccac    5100
gccgaacgcg cgctgcgcgc cgcgggcgcg agcccgtac  cgctgcccgt ggacgctccg    5160
gccgccgacc gggcgtcctt cgcggcactg ctgcgctccg ccaccggacc tgacacacga    5220
ggtgacacag ccgcgcccgt ggccggtgtg ctgtcgctgc tgtccgagga ggatcggccc    5280
catcgccagc acgccccggt acccgccggg gtcctggcga cgctgtccct gatgcaggct    5340
atggaggagg aggcggtgga ggctcgcgtg tggtgcgtct cccgcgccgc ggtcgccgcc    5400
gccgaccggg aacggcccgt cggcgcgggc gccgccctgt gggggctggg gcgggtggcc    5460
gccctggaac gccccacccg gtggggcggt ctcgtggacc tgcccgcctc gcccggtgcg    5520
gcgcactggg cggccgccgt ggaacggctc gccggtcccg aggaccagat cgccgtgcgc    5580
gcgtccggca gttggggccg gcgcctcacc aggctgccgc gcgacggcgg cggccggacg    5640
gccgcacccg cgtaccggcc gcgcggcacg gtgctcgtca ccggtggcac cggcgcgctc    5700
ggcgggcatc tcgcccgctg gctcgccgcg gcgggcgccg aacacctggc gctcaccagc    5760
cgccggggcc cggacgcgcc cggcgccgcc ggactgcagg ccgaactcct cctcctgggc    5820
gccaaggtga cgttcgccgc ctgcgacacc gccgaccgcg acggcctcgc ccgggtcctg    5880
cgggcgatac cggaggacac cccgctcacc gcggtgttcc acgccgcggg cgtaccgcag    5940
gtcacgccgc tgtcccgtac ctcgcccgag cacttcgccg acgtgtacgc gggcaaggcg    6000
gcgggcgccg cgcacctgga cgaactgacc cgcgaactcg cgccggact  cgacgcgttc    6060 gtcctctact cctccggcgc cggcgtctgg ggcagcgccg gccagggtgc ctacgccgcc    6120
gccaacgccg ccctgacgc  gctcgcccgg cgccgtgcgg cggacggact ccccgccacc    6180
tccatcgcct ggggcgtgtg gggcggcggc ggtatggggg ccgacgaggc gggcgcggag    6240
tatctgggcc ggcgcggtat gcgccccatg gcaccggtct ccgcgctccg ggcgatggcc    6300
accgccatcg cctccgggga accctgcccc accgtcaccc acaccgactg ggagcgcttc    6360
ggcgagggct tcaccgcctt ccggcccagc cctctgatcg cggggctcgg cacgccgggc    6420
ggcggccggg cggcggagac cccgaggag  gggaacgcca ccgctgcggc ggacctcacc    6480
gccctgccgc ccgccgaact ccgcaccgcg ctgcgcgagc tggtgcgagc ccggaccgcc    6540
gcggcgctcg gcctcgacga cccggccgag gtcgccgagg gcgaacggtt ccccgccatg    6600
ggcttcgact ccctggccac cgtacggctg cgccgcggac tcgcctcggc cacgggcctc    6660
gacctgcccc ccgatctgct cttcgaccgg gacacccccgg ccgcgctcgc cgcccacctg    6720
gccgaactgc tcgccaccgc acgggaccac ggacccggcg gccccgggac cggtgccgcg    6780
ccggccgatg ccggaagcgg cctgccggcc ctctaccggg aggccgtccg caccggccgg    6840
gccgcggaaa tggccgaact gctcgccgcc gcttcccggt tccgcccgc  cttcgggacg    6900 gcggaccggc agccggtggc cctcgtgccg ctggccgacg cgcggagga caccgggctc    6960 ccgctgctcg tgggctgcgc cgggacgcg  gtggcctccg gccggtgga  gttcaccgcc    7020 ttcgccggag cgctggcgga cctcccggcg gcggcccga  tggccgcgct gccgcagccc    7080
ggctttctgc cgggagaacg agtcccgcc  accccgagg  cattgttcga ggcccaggcg    7140
gaagcgctgc tgcgctacgc ggccggccgg cccttcgtgc tgctggggca ctccgccggc    7200
```

```
gccaacatgg cccacgccct gacccgtcat ctggaggcga acggtggcgg ccccgcaggg    7260
ctggtgctca tggacatcta cacccccgcc gaccccggcg cgatgggcgt ctggcggaac    7320
gacatgttcc agtgggtctg gcggcgctcg gacatccccc cggacgacca ccgcctcacg    7380
gccatgggcg cctaccaccg gctgcttctc gactggtcgc ccaccccgt ccgcgccccc     7440 gtactgcatc tgcgcgccgc ggaacccatg ggcgactggc cacccgggga caccggctgg    7500
cagtcccact gggacggcgc gcacaccacc gccggcatcc ccggaaacca cttcacgatg    7560
atgaccgaac acgcctccgc cgccgcccgg ctcgtgcacg gctggctcgc ggaacggacc    7620
ccgtccgggc agggcgggtc accgtcccgc gcggcgggga gagaggagag gccgtgacca    7680
ggtaccggat tggcacttat ccggtgccaa tccggtcggt ggtcaggagt ggagaagaca    7740
tgccgggtac gaacgacatg ccgggtaccg aggacaagct ccgccactac ctgaagcgag    7800
tgaccgcgga tctcggacag acccgtcagc gcctgcgcga cgtggaggag cgccagcggg    7860
aaccgatcgc catcgtcgcg atggcctgcc gctaccgggg cggggtggcc tcccccgagc    7920
agctgtggga cctggtcgcc tcacgcggcg acgccatcga ggagttcccc gccgaccgcg    7980
gctgggacgt ggcgggcctc taccaccccg acccggacca ccccggcacg acctatgtac    8040
gagaggccga ttcctgcgg gacgccgccc gcttcgacgc cgacttcttc ggcatcaacc      8100
cgcgcgaggc gctcgccgcc gacccgcagc aacgggtgct cctcgaagtg tcgtgggaac    8160
tgttcgagcg ggcgggcatc gaccccgcca cgctcaagga cccctcacc ggcgtgtacg      8220 cgggggtgtc cagccaggac cacatgtccg ggagccgggt cccgccggag gtcgagggct    8280
acgccaccac gggaaccctc tccagcgtca tctccggccg catcgcctac accttcggcc    8340
tggagggccc ggcggtgacg ctcgacacgg cgtgctcggc atcgctggtc gcgatccacc    8400
tcgcctgcca ggccctgcgc cagggcgact cggcctggc ggtggcggga ggcgtgaccg      8460
tactgtccac gccgacggcg ttcgtggagt tctcacgcca gcgcggactc gcaccggacg    8520
gccgctgcaa gccgttcgcc gaggccgccg acggcaccgg attctccgag ggcgtcggcc    8580
tgatcctcct ggaacgcctc tccgacgccc gccgcaacgg acatcaagta ctcggcgtcg    8640
tacgcggatc ggccgtcaac caggacggcg cgagcaacgg cctgaccgcc cgaacgacg     8700 tcgcccagga acgcgtgatc cgccaggccc tgaccaacgc ccgcgtcacc ccggacgccg    8760
tcgacgccgt ggaggcacac ggcaccggca ccacgctcgg cgaccgatc gagggggaacg    8820 cactcctcgc gacgtacgga aaggaccgcc ccgccgaccg gccgctgtgg ctcggctctg    8880
tgaagtcgaa catcggccac acgcaggcgg ctgcgggcgt cgcaggcgtc atcaagatgg    8940
tgatggcgat gcgccacggc gagctgcccg cctccctgca catcgaccgg cccacgcccc    9000
acgtggactg ggagggcggg ggagtgcggt tgctcaccga tcccgtgccg tggccacggg    9060
ccgaccgccc ccgccgcgcg ggggtctcct ccttcggcat cagcggcacc aacgcccacc    9120
tgatcgtgga acaggccccc gcccgcccg acacggccga cgacgcccg gaaggcgccg      9180 caacccccgg cgcttccgac ggcctcgtgg tgccgtgggt ggtgtcggcc cgtagtccgc    9240
aggccctgcg tgatcaggcc ctgcgtctgc gcgactttgc cggtgacgcg tcccgagcgc    9300
cgctcaccga cgtgggctgg tctttgctgc ggtcgcgtgc gctgttcgag cagcgggcgg    9360
tggtggcggg gcgtgagagg gctgaactgc tggcggggct ggctgcgttg ccgctggtg     9420 aggagcaccc ggctgtgacg cggtcccgtg aggaagcggc ggttgctgcg agcggtgatg    9480
tggtgtggct gttcagtggt cagggcagtc agttggtcgg tatgggtgct ggtttgtatg    9540
agcggttccc ggtgtttgcg gctgcgtttg atgaggtgtg cggcttgctg gagggggagc    9600
```

```
tgggggttgg ttcgggtggg ttgcgggagg tggtgttctg gggcccgcgg gagcggttgg    9660
atcacacggt gtgggcgcag gcggggttgt ttgcgttgca ggtgggggttg gcccggttgt   9720
gggagtcggt cggggtgcgg ccggatgtgg tgctcgggca ttcgatcggt gagatcgcgg    9780
ccgcgcatgt ggcgggggtc tttgatctgg cggatgcgtg tcgggtggtg ggggcgcggg   9840
cgcgtttgat gggtgggttg cctgagggtg gggcgatgtg tgcggtgcag gccacgcccg   9900
ccgagctggc cgcggatgtg gatggctcgt ccgtgagtgt ggcggcggtc aacacacctg   9960
actcgacggt gatttcaggt ccgtcgggtg aggtggatcg gattgctggg gtgtggcggg   10020
agcgtgggcg taagacgaag gcgctgagcg tgagtcatgc tttccattcg gcgttgatgg   10080
agccgatgct cggggagttc acggaagcga tacgaggggt caagttcagg cagccgtcga   10140
tcccgctcat gagcaatgtc tccggagagc gggccggcga ggagatcaca tccccggagt   10200
actgggcgag gcatgtacgc cagacagtgc tcttccagcc cggcgtcgcc caagtggccg   10260
ctgaggcacg cgcgttcgtc gaactcggcc ccggccccgt actgaccgcc gccgcccagc   10320
acaccctcga ccacatcacc gagccggaag gccccgagcc ggtcgtcacc gcgtccctcc   10380
accccgaccg gccggacgac gtggccttcg cgcacgccat ggccgacctc cacgtcgccg   10440
gtatcagcgt ggactggtcg gcgtacttcc ctgacgaccc cgccccccgc accgtcgacc   10500
tgcccaccta cgccttccag gggcggcgct tctggctggc ggacatcgcg cgcgcccgagg  10560
ccgtgtcctc gacggacggt gaggaggccg ggttctgggc cgccgtcgaa ggtgcggact   10620
tccaggcgct ctgcgacacc ctgcacctca aggacgacga gcaccgcgcg gctctggaga   10680
cggtgttccc cgcgctgtcc gcgtggcggc gcgaacgacg tgagcggtcg atcgtcgatg   10740
cctggcggta ccgggtcgac tggcggcgcg tcgagctgcc gacacccgtt ccgggcgccg   10800
gtaccggtcc cgacgccgac acgggcctcg gggcgtggct gatcgtggct cccacgcacg   10860
ggtcgggtac ttggccgcaa gcctgtgccc gggcgttgga ggaggcgggc gcgccggtac   10920
gtatcgtcga ggccggcccg cacgccgacc gggcggacat ggcggacctg tccaggcat    10980
ggcgggcaag ctgtgcggac gacaccaccc agctcggagg agtgctctcc ctgctggctc   11040
tcgccgaggc accggccacc agttccgaca ccacttccca caccagtacc agttgcggta   11100
ccggctctct cgcgtcccac ggcctcaccg gcaccttgac gctgctgcac ggtctgctgg   11160
atgcgggcgt cgaagcgcct ctctggtgtg ccacgcgcgg cgccgtgtcg tgcggcgacg   11220
ccgatccgct cgtctccccg tcgcaggccc cggtctgggg actcggacgc gtggccgccc   11280
tggagcatcc ggagttgtgg ggcggcctgg tcgacctgcc cgccgacccg gagtcgctcg   11340
acgcgagcgc gttgtatgcg gttctgcgcg gagacggcgg cgaggatcag gtcgcgctgc   11400
gccggggcgc ggtcctcggc cgtcgcctgg tgcccgacgc aacccggac gtggccccg     11460
gctcgtcccc ggacgtgtcc ggaggcgcag cccatgccga cgcgacctcc ggggagtggc   11520
agccgcatgg tgccgtcctc gtcaccggag gcgtcggcca cctggccgat caggtcgtac   11580
ggtggctcgc cgcgtccggc gccgaacacg tcgtactcct ggacacgggc cccgccaaca   11640
gccgtggtcc cggccggaac gacgacctcg ccgcggaagc cgccgaacac ggcaccgagc   11700
tgacggtcct gcggtccctg agcgagctga cagacgtatc cgtacgtccc atacggaccg   11760
tcatccacac atcgctgccc ggcgagctcg cgccgctggc cgaggtcacc cccgacgcgc   11820
tcggcgcggc cgtgtccgcc gccgcgcggc tgagcgaact ccccggcatc gggtcagtgg   11880
agaccgtgct gttcttctcc tccgtgacgg cttcgctcgg cagtagggag cacggcgcgt   11940
```

```
acgccgccgc caacgcctac ctcgacgccc tggcgcaacg ggccggtgcc gatgctgcga    12000
gcccccggac ggtctcggtc gggtggggca tctgggatct gccggacgac ggtgacgtgg    12060
cacgcggcgc cgccgggctg tcccggaggc agggactccc gccgctggaa ccgcagttgg    12120
cgctcggcgc cctgcgcgcg cgctcgacg ggggcaaggg gcacacgctg gtcgccgaca    12180
tcgagtggga gcggttcgcg ccgctgttca cgctggccag gcccacccgg ctgctcgacg    12240
ggatccccgc ggcccagcgg gtcctcgacg cctcctcgga gagcgccgag gcctcggaga    12300
acgcctcggc cctccgtcgc gaactgacgg ccctgcccgt gcgggagcgg accggggcac    12360
ttctcgacct ggtccgcaaa caggtggccg ccgtcctgcg ctacgagccg gccaagacg     12420 tggcgcccga gaaggccttc aaggacctgg gcttcgactc gctcgtggtc gtggagctgc    12480
gcaaccggct gcgcgccgcc accgggctcc ggctgcccgc caccctggtc tacgactacc    12540
ccacaccccg caccctcgcc gcacacctgc tggacagggt gctgcccgac ggcggcgcg    12600 cagagctccc cgtggccgcc cacctggacg acctggaggc ggccctcacc gacctgccgg    12660
ccgacgaccc ccggcgcaag ggcctggtcc ggcgtctaca cgcgctgctg tggaagcagc    12720
ccgacgccat gggggcggcg ggccccgccg acgaggagga gcaagccgcg cccgaggacc    12780
tgtcgaccgc gagcgccgac gacatgttcg ccctgatcga ccgggagtgg ggcacgcggt    12840
gaccaccgac cggattggca cgtaggccag tgccaatccg gtacttggca attgcctcgc    12900
cgcagttaat taaagtcagt gagcgaggaa gcgc                                12934
```

<210> SEQ ID NO 48
<211> LENGTH: 19799
<212> TYPE: DNA
<213> ORGANISM: Artificial Sequence
<220> FEATURE:
<223> OTHER INFORMATION: Synthetic Polynucleotide

<400> SEQUENCE: 48

```
gaacgaccga gcgcagcggc ggccgcgctg ataccgccgc caattgtgac ccgggcccac      60
cccaactacg tgcgaaacat ctgaggaagg ttcaacggac gatgccggac gaaagtaagc     120
tcgtcgatta cctgaagtgg gtcacggcgg atctccacca gacccgcagg cgcctccagg     180
aagccgagtc gggccgccac gagcccgtgg cgatcgtcgg catggcgtgc cgcttccccg     240
gcggtgtgcg ttccccggag gacctctggg agatgctcgc cgacgccgc gacgccatct     300 ccggggttccc cgccgaccgc ggctgggacc tggagacgct ggccggcgac ggagcgggcg     360
gcagcagcac gcaggaggga ggtttcctgc acgacgtggc cgacttcgac ccggggttct     420
tcgacatctc gccccgcgag gcgctggcca tggacccgca gcagcggctg ctcctggaga     480
ccgcctggga ggccgtggag cgtgccggga tcgccccggg cagcctccgc ggcagccgca     540
ccggcgtgtt cgtcggcacc aactcgcagg actacgccca cctcgtcctc gcctccgacg     600
acgacatggg cggctacgcg ggcaacggcc tggccgccag cgtgatgtcc ggccggctgt     660
cctttgcgct cggcttcgaa ggacccgccg tcaccctcga caccgcgtgc tcctcggccc     720
tggtcgccct gcacctggcc gcccagtcgg tgcgctccgg cgaggccgac ctcgcgctgg     780
ccggcggtgt caccgtcatg accacctcgt ccagcttcgt gggcttcagc ctccaggcg     840 gcctcgccac ggacggccgc tgcaaggcgt tcgccgactc gcgcgacggc accggctggt     900
ccgagggcgt cggcatgatc ctcgtcgaac ggctctccga ggctcggcgc aagggccacc     960
cggtgctcgc cgtgctgcgc ggctccgccg tgaaccagga cggcgcctcc aacgcctca    1020 gcgcccccaa cggccccgcc cagcagcgcg tcatccgcga cgcgctggcc tccgccgggc    1080
```

```
tctcgcccgc cgacgtcgac gccgtcgagg cgcacggcac cggcaccacc ctcggcgacc    1140
ccatcgaggc gcaggccctg ctcgccacct acggccagga ccgcgacgcg agccgtccgc    1200
tgcgcctcgg cacggtgaag tccaacatcg gccacaccca ggccgccgcc ggcgccgcgg    1260
gcgtcatcaa gatggtcctg gccctgcgcc acgggctgct gccccgcacc ctgcacatcg    1320
acgcgccgtc cacacacgtc gactgggacg caggacacgt cagcctgctc accgaggcca    1380
cccctggcc cgagggcgag cagacgcgcc gggccggtgt gtcgtccttc ggcatcagcg    1440
gcaccaacgc ccatgtcatc ctcgaagagg ccccgcggc cgaggaggac accgacgccg    1500
agcagcggcc cgagccggtc gtcccggggcg ccgtgccgtg gcccgtgtcg gcccgtaccg    1560
ccgacgccct cgacgcccag ctggagaagg tgcggccgct cgccgcgtcc ggcgccgacc    1620
ccgtcgccgt cggccacgcc ctggccgtca cccgcacccc cttcgaacac cgggcgctgc    1680
tggtcgccgc ggacggcaat ctcaccgagg ccgcacgcgg caccgtcccc tccggcgacc    1740
gccccgggct ggccgtgctg ttctccgggc agggcgccca cgcctcggc atgggccgtg    1800
aactccacgc ccgcttcccg gtgttcgccg ccgccctgga cgagaccctc gccctcctcg    1860
acgagcgcct cggccactcg ctgcgcgacg tcatctgggg cgaggacccc gtggccctcg    1920
acgacaccgg ccacacccag cccgcgctgt tcgccgtgga ggtcgccctc taccgcctgt    1980
tcgcctcctg gggtctgcgc cccgaccacc tcgccggaca ctccgtcggg gagatcgccg    2040
ccgtgcatgt ggccggcgca ctgtccctgg aggacgcctg caccctggtt gccgcccgcg    2100
ccggcctgat gcgggacctg ccggccgcg gagccatggt cgcgctgcgc gccaccgagg    2160
ccgaggtgcg gccgctgctc gacgagcggg tctcgctcgc ctcggtcaac ggccccgatt    2220
ccgtggtggt ctccggcgcc gaggacgccg tcctcgccgt cgccgagcac ttccggaagc    2280
aggaccggcg caccacgcgg ctctccgtga gccacgcctt ccactcccccg ctcgtcgacc    2340
cgatgctcga cgccttccgg gacgtcgtcg cgaagctcac cttcggcgag ccgtcggtac    2400
ccgtcgtctc caccctcacc ggcgacgtcg tcgccgccga ggaactggcc acgccgcact    2460
actgggtgtg ccacgcccgg caggccgtcc gcttcgccga cgccgtgcgc accctcgtcg    2520
acgagggcgc ccggaccttc ctggaggtcg gcccgggcgg cgtgctgtcc cgctcgtcg    2580
gtgagaacac ccaggaggcc ggggtctctg ccgtgcccgc gctgcgcaag gaccagccgg    2640
aggaggcctc cgtgctcgcc gccctcggca ccctgtggac ccggggcacc gcggccgact    2700
gggacgccgt gttcgagggc accctgcccg gccgccgga gtccgtggac ctgccgacct    2760
acgccttcca gcgcggccgg tactggccca ccgtgcgcgc ccgctccggc gaccccgccg    2820
gactgggcct cggcgccgcc gggcacccgc tgctcagcgc caccgtcacc ctcgccgagg    2880
ccgacgagtc cgtcctcacc ggacggctct cgccgctgac ccaccctgg ctcaccgagc    2940
accgcgtcga cggccggatc accgtccccg gcacggccct cgtggagatc gcggtccgtg    3000
cgggcgacga gaacggcacc ccccgcctgg accggctcga cctgctcgcc ccgctgaccc    3060
tcggcgaccg cgacgcggtg ctgctccagg tgcgcgtcgg ccccgaggac gcctccggcc    3120
ggcggacgct ctccgtgcac gcccgcccgg cgaccgcgga cgacgccccc tggaccacgt    3180
acgcccgtgg tgtcctcgcc cccgacgagg gcgccgagga caccgccgcg gaccttgtgg    3240
agtggccgcc cgccgacgcc cgtcaggtcc cgctcacgga gctggagtcc gaaggacgcg    3300
ccctcggccc gctcttcagc ggcctcaccg gggtgtggcg gcacgagggc gaggtgttcg    3360
ccgaggccga gctgccccgca ggacccgaca gcggcttcgg actgcacccc gcgctgctgt    3420
```

-continued

```
ccaccgccct gcgcgccgcc gccgtcctcg acggcaccac ggccggcgag cccgccgcct    3480
tcgaggggct caccctgcac gccaccggcg ccaccgcgct gcgcgtacgg ctgagcacca    3540
ccgggcccga caccgtcgac ctcaccgccg tcgaccccgc gggcaacctc gtcctgaccg    3600
ccgagaccgt gcgtctcggc accccggacg gcaccgccga caccccgccc gccaccggcc    3660
ggggcgacct gttcgggctg aagtgggtgc ccgtcaaggc ctcggagcgc gccaccggca    3720
cccgctgggc cgtcgtcggc tccgacgaac tcgacctcgg ctacgccatg caccgcgccg    3780
acgagaccgt caccgcctac gcggagtccc tcggcggcgc catcggcgac agcggggtcg    3840
cccccgatgt gttcctgatc ccgctcgcag gcgagaagga cgccggagcg gagggcgtgc    3900
acgccctcac caccgggtc ctcggctacc tccaggagtg gctgtccgag ccccggctct    3960
ccggcacccg cctggtcttc gtcaccgccg cgccgtcgc cctcgacgac gaggacgtcc    4020
tggacccggc cggcgcggcc gtctggggcc tggtgcgctc cgcgcagacc gagaaccccg    4080
gcagcctgct gctcgtcgac ctcgacgaca ccttcctgtc cgccggagta ctgcccgacg    4140
tgctgacgct cgacgagcag cagctcgcgg tccgcgacta ccaggtccgc gccgcccggc    4200
tcgcccggct gccgcgcccg ccgacgacg ccccgccgc cgactggaac cccgacggca    4260
ccgtcctgat caccggcggc accggcggcc tcggcgccgc gctcgcccgg cacctggtca    4320
ccagccgggg cgcccgtcac ctgctgctgg cgagccgccg cggcccggac gcgcccggca    4380
cgtccgaact ggtcgccgag ctgaccggcc tgggagccca ggtgaccgtc tccgcctgcg    4440
acgtcggcga ccgcgacgcg gtcgacacgc tcgtcgcgtc ggtgcccgcc gagcacccgc    4500
tgaccgccgt cgtgcacacc gcgggtgtcc tggacgacgc cctgaccggc tcgctcaccc    4560
cggaacaact ggctggtgtg ctgcgcccca aggccgacgc ggccctgcac ctgcacgagg    4620
cgaccctcgg ccaggacctc gccgcgttcg tgctgtactc ctcgatctcc ggcgtcatcg    4680
gcggccccgg ccaggccaac tacgccgccg ccaacgcctc cctggacgcg ctcgcccacc    4740
ggcgcagggc ggccggtctg cccggtctgt ccctcgcctg ggggccctgg ggccgcggca    4800
gcggcatgac cagccaggtc agcgacaccg acctggggcg gatggaccgc ggcggcaccc    4860
cgccgatgag cctcgaggac ggcctcgccc tgttcgacgc cgccctggcc cgcaccgagc    4920
cgatggtcgt gcccacccgg atcaatgtca ccggactcca ggtccagcag acgctgcccg    4980
cgctctggcg cgacctggtg ccgcgccccc ggcgcaccgc cgccgcggac cgctcgccca    5040
agaccgtgct cgacgggctg cgcacgctcg acaccgcggg ccgggagaag ctgctcaccg    5100
agctggtcgt cggcttcacc gcgggcctgc tcggccacgc cgaccccgcc gccgtcgacc    5160
ccgagcgcgg cttcctggag ctgggcttcg actcgctggt ctcggtcagc ctgcgcaacc    5220
agctcggcga actcctcggg ctgcgcctgc cgacgtcggt ggtcttcgac agcaagacgc    5280
cggtgaagct ggcccgccac ctcaacgagg aactgggcga cctgtccgcc tccggccccg    5340
cgtccggcac cgccgtcgcc ggcaccacgg tgcatcccga cgacccctg gtcggcctgt    5400 tccacaacgc ggtgcgcggc ggcaagctcg tcgaggcgat gcggatgctg aaggcggtcg    5460
ccaacacccg gcccaccttc gagacgcccg cggacctgga ggagctgtcc gaggccgtca    5520
ccctggccac ggggcccggc tccccgcggc tgatcttcgt cagcgcgccc ggcgccaccg    5580
gcggtgtcca ccagtacgcg cgcatcgccg cccacttccg cggcaagcgc catgtgtcgg    5640
cgataccgct gatgggcttc gccccggcg agctgctgcc cgccaccagt gaggcggcgg    5700 cccgatcgt cgccgagagc gtcctgatgg cgagcgacgg cgaaccgttc gtgatggtgg    5760
gccactccac cggcggttcc ctcgcctacc tcgcggccgg ggtgctggag gacacctggg    5820
```

```
gcgtgaagcc ggaggcggtc gtcctgctcg acacggcgtc catccggtac aaccectcgg   5880 agggcaacaa cctcgaccag acgacccgct tctacctcgc cgacatcgac tcgccgtccg   5940
tgacgctcaa cagcgcccgg atgtccgcga tggcgcactg gttcatggcg atgacggaca   6000
tcgacgcgcc cgccacgacc gcccccaccc tgctcctgcg cgccacacag ccaacaacg    6060 gcttcatgct ggacacctcc gcggtgccgg cggacgtggt gcgtgacatc gaggccgacc   6120
atctgtccct ggccatggag cactcggatc tgaccgccga ggcctagag aactggctcg    6180 ccgaacttcc ggccggcgag gcctgaccaa gtaccggatt ggcactggcc tacgtgccaa   6240
tccggtacgt gggcagcgat cagtcctgag cgcgatgagc cccggccaca ccggccccct   6300
tgccctcccc caacctcata cgccccgatc accacgtagc gccaaggagc ctgggtcaga   6360
tgtcgaacga ggagaagctt ctcgatcacc tcaagtgggt caccgcggag ctgcgccagg   6420
cccggcaacg gctccacgac aaggaatcga ccgagccggt cgccatcgtc ggcatggcct   6480
gccgctaccc gggcggcgcc cggtcggcgg aggacctctg gaactcgtg cgcgacgggg    6540 gtgacgcggt cgcggggttc cccgacgacc ggggctggga cctggagtcg ctgtatcacc   6600
cggatccgga gcatccggcc accagctatg tgcgggacgg cgccttcctg tacgacgccg   6660
gccatttcga cgccgagttc ttcggcatca gcccgcgcga ggccacggcg atggatccgc   6720
agcagcggct gctcctggag accgcgtggg aggcgatcga gcacgcgggc atgaacccgc   6780
acgcgctgaa gggcagcgac accggcgtct tcaccggagt gagcgcccac gactacctga   6840
cgctgatcag ccagacggcc agcgacgtcg aggggtacat cggcaccggc aacctcggca   6900
gtgtggtgtc gggccggatc tcctacacgg tggggctcga aggtcccgcg gtcaccgtcg   6960
acacggcgtg ctcgtcgtcc ctggtggcga tccatctggc aagtcaggcg ctgcggcagg   7020
gcgagtgctc gctcgcgctg gcgggcggtt cgacggtgat ggcgacgccg ggttcgttca   7080
ccgagttctc ccggcagcgg gggctcgcgc ccgacgggcg gtgcaagccg ttcgcggccg   7140
ccgccgacgg caccggctgg ggcgagggcg ccggggtggt ggcgctggag ctgctctccg   7200
aagcgcggcg ccgcggccac aaggtccttg cggtgatacg gggttcggcc accaaccagg   7260
acggtacgag caacgggctc gccgcccca acggccctc ccaggaacgc gtcatccgcg     7320
ccgccctcgc caacgcccgc ctctccgccg aggacatcga cgccgtagag gcgcacggca   7380
ccggcaccac gctcggcgac cccatcgagg cgcaggccct gatcgccacg tacgccagg    7440 ggcgcccgga ggaccgtccg ctctggctcg gctcggtgaa atccaacatc ggccacacgc   7500
aggccgccgc cggtgtcgcg ggcgtcatca agatggtcat ggcgatgcgc aacggtctcc   7560
tcccgacctc cctgcacatc gacgccccgt caccgcacgt ccagtgggaa cagggcagcg   7620
tacgactgct ctccgagccc gtggactggc cggcggagcg cacgcggcgg gcaggcatct   7680
cggcgttcgg gatctccggg acgaacgcgc acctgattct ggaggaggcg ccgccggaag   7740
aggacgcgcc gggcccccgtg gcggctgagc cgggtgggg cgtgccgtgg gtggtgtccg    7800
ggcggacgcc ggacgcgttg cgtgaacagg cgcggcggct gggcgagttc gcggccgggc   7860
tggcggatgc gtcggtctcc gaggtgggct ggtcgctggc cacgacacgc gcgttgttcg   7920
atcagcgggc cgtggtcgtg gggcgggact tggctcaggc tggtgccagc ctggaggcat   7980
tggccgcggg tgaggcgtcg gcggatgtgg tggccgggt ggccggtgat gtgggtcctg     8040
ggccggtgtt ggtgtttccg gggcaggggt cgcagtgggt gggcatgggc gcccagctcc   8100
ttgacgagtc gcccgtcttc gcggcgcgga tcgcggagtg tgagcaggcg ctgtcggcgc   8160
```

```
atgtggactg gtcgctgagt gatgtcttgc gcggggacgg gagcgagctg tcccgggtcg    8220
aggtcgtgca gcccgtgctg tgggcggtga tggtctcgct ggctgcggtg tgggccgatt    8280
acggcatcac cccggctgcc gtcatcgggc actcgcaggg cgagatggct gccgcgtgtg    8340
tggcgggggc actgtcactg gaggatgcgc acggatcgt agccgtacgc agcgacgcgc     8400
ttcgtcagct gcaagggcac ggcgacatgg cctcgctcag caccggtgcc gagcaggccg    8460
cagagctgat cggcgaccgg ccgggcgtag tcgtcgcggc cgtcaacgga ccgtcgtcga    8520
ccgtgatttc gggcccgccg gagcatgtgg cagccgtcgt cgccgatgcg gaggcgcagg    8580
gactcagggc ccgcgtcatc gacgtcaggt acgcctccca cggtcccag atcgaccagc     8640 tccacgacct cctcaccgac cggctcgccg acatccagcc gaccaccacc gacgtggcgt    8700
tctactcgac ggtcaccgca gagcgcctcg acgacaccac cgccctagac accgcctact    8760
gggtcaccaa cctccgccag cccgtccgct cgccgacac catcgaagcg ctgctggccg     8820
acggctaccg cctgttcatc gaggccagcc cccaccccgt cctcaacctc ggcatccagg    8880
agaccatcga gcagcaggcc ggtgctgcgg ggacggccgt caccatcccc accctgcgtc    8940
gcgaccacgg tgacaccacc cagctcaccc gcgcggccgc ccacgccttc accgccggcg    9000
cccccgtcga ctggcggcgc tggttcccgg ccgaccccac ccccgtacc gtcgacctcc     9060 ccacctacgc cttccagcac aagcactact gggtggagcc gcccgcggcg gtcgcagccg    9120
tgggtggtgg gcacgatccg gtcgaggccc gggtgtggca ggcgatcgag gacctggaca    9180
tcgacgccct cgccggcagt ctggagatcg aggggcaggc ggagagcgtc ggagcgctgg    9240
agtccgcgct gcccgtcctc tcggcctggc ggcgtcggca ccgcgagcag tccaccgtcg    9300
actcctggcg ttatcaggtc acttggaagc atctgcccga cgtgccggcg ccggagctca    9360
gcggggcctg gctgctgctc gtgcccgccg cgcacgccga ccaccggcc gtcctcgcga     9420 ccgcgcagac gctgaccgcc catggtggcg aggtgcgacg ccacgtggtc gacgcacgtg    9480
ccatggagcg tacggagttg gcgcaggagc tgcgtgtcct gatggacggg gccgcgtttg    9540
ccggagtcgt caatctgctg gccctggacg aggagccgca tcccgagcac tcggccgtgc    9600
ccgccggact cgccgcgacg accgctctcg tccaggccct cgcggacaac ggcgccgaca    9660
tcgccgtacg cactctcacg cagggggctg tttccacgag cgccggcgac gccctcaccc    9720
acccggtgca ggctcaggtg tgggggctgg ggcgcgtcgc tgcgctggag tatccgcggc    9780
tgtggggcgg gctggtcgat ctgcccgctc gtatcgacca tcagacgctg gcccggctgg    9840
ccgccgcgct ggttccgcag gacgaggacc agatctccat ccggccgtcc ggcgtccatg    9900
cccgtcgcct tgcacacgcg cccgccaaca cggtcggcag cgggcttggt tggcggcccg    9960
acggcaccac tctcatcacc ggcgggaccg gcggcatcgg cgccgtcctc gcgcggtggc    10020
tcgcccgtgc gggcgcccg cacctcctcc tgaccagccg ccgcggcccc gacgcccgg      10080 gagcacagga actcgccgcg gaactgacgg agttgggggc cgccgtcacc gtcaccgcct    10140
gcgacgtcgg cgaccgcgag caggtgcgac gcctcatcga cgatgtcccc gccgagcacc    10200
cgctgaccgc cgtcatccac gcggccggcg tgccgaacta catcggtctc ggcgacgtgt    10260
cgggtgccga gctggacgag gtgctgcgtc gaaggcgct cgccgctcac catctgcatg      10320
aactgacccg ggagttgccg ctctcggcgt tcgtgatgtt ctcgtcgggc gcaggcgtgt    10380
ggggcagtgg ccagcagggc gcctatggtg cggccaacca cttcctcgac gccctcgccg    10440
agcaccgccg cgccgagggc ctgcccgcca cctccatcgc ctgggggccc tgggccgagg    10500
cgggcatggc ggcggaccag gccgcgttga cgttcttcag ccgcttcggc ctgcacccgc    10560
```

```
tcagcccgga gctgtgcgtc aaggcgctgc agcaggccct ggacgcgggt gagacgacgc   10620
tgaccgtggc gaacttcgac tgggcgcagt tcacgtcgac gttcaccgcg cagcggccca   10680
gcccgctcct cgccgatctg cccgagaacc ggcgggccag cgcacccgcg gcacagcagg   10740
aagacgccac ggaggcatcg tcgctccagc aggagctgac ggaggcgaag ccggcgcagc   10800
agcggcagtt gctgctgcag cacgtgcgct cccaggcggc ggccacgctg gggcactcgg   10860
acgtcgacgc ggtgcccgcc accaagccgt tccaggagct gggcttcgac tcgctgaccg   10920
cggtggagct gcgcaacagg ctgaacaaga gcaccggcct gacactgccg accacggtcg   10980
tcttcgacca ccccacccce gacgcgctca ccgacgtcct gcgggccgag ctgtccggtg   11040
acgcggcggc ctccgccgac ccggtgcggg cggccggggc ctccaggggc gccgccgacg   11100
acgagccgat cgccgatcgtc ggcatggcct gccgctatcc gggcgacgtc cgctccgccg   11160
aggagctgtg ggatctggtc gcggccggca aggacgccat gggggccttc cccgacgacc   11220
ggggctggga cctggagacg ctgtacgacc cggacccgga gagccgcggc accagctatg   11280
tgcgcgaagg cgggttcctc tacgacgcgg gcgacttcga cgccggattc ttcggcatca   11340
gcccccgcga ggccgtcgcg atggaccgc agcagcggct gctcctggag accgcgtggg   11400
aggcgatcga acgcgcgggc ctcgaccggg agaccctcaa gggcagcgac gccggggtgt   11460
tcacgggcct gaccatcttc gactacctcg cgctcgtcgg tgaacagccc accgaggtcg   11520
agggctacat cggcaccggc aacctcggct gtgtcgcctc cggcagggtg tcgtacgtac   11580
tcggcctaga aggccccgcc atgacgatcg acaccggctg ctcttcgtcc ctggtggcga   11640
tccaccaggc ggcgcacgcg ctgcgccagg gcgagtgctc gctcgctctc gcgggcggcg   11700
cgacggtgat ggccacgccg ggctcgttcg tcgagttctc gctgcagcgc gggctcgcca   11760
aggacggccg gtgcaagccg ttcgcggccg ccgccgacgg caccggctgg gccgagggag   11820
tcggcctggt cgtactcgaa cggctctcgg aggcccggcg caacgccac aacgtcctgg   11880 cggtgatccg gggttcggcc atcaaccagg acggcacgag caacgggctc acggcaccca   11940 acggcaggc gcagcagcgg gtgatccggc aggcactcgc caacgcgcgg ctctccgccg   12000
aggacgtcga cgcggtggag gcgcacgcca ccggcaccat gctgggcgac cccatcgaag   12060
ccagcgcgct cgtcgccacc tacggcaagg agcggcccgc ggaccggccg ctgtggctcg   12120
gctcgatcaa gtcgaacatc gggcacgcgc aggcgtcggc cggtgtcgcc ggtgtgatca   12180
agatggtcat ggcgctgcgc aacgaacagc tgcccgcctc cctgcacatc gacgcgccca   12240
cgccgcacgt ggactgggac ggcagtggcg tccgcctgct gtccgaaccg gtctcctggc   12300
cgcgcggcga acgcccgcgc cgcgccgggg tgtccgcctt cggcatctcc ggcaccaacg   12360
cgcacctcat cctggaacag gccccggacg cgccggagcc cgtgaccgct ccggcggagg   12420
acgccgcggc gccggccgga gtggtgccct gggtggtgtc ggcgcgcggc gaggaggcgc   12480
tgcgggccca ggcccgcctg ctggccgacc gcgccaccgc cgaccgcgg ctcgcgtcgc   12540 cgctggacgt gggctggtcc ctggtcaaga cccggtcggt gttcgagaac cgagccgtcg   12600
tcgtgggcaa ggaccgccag actctcctcg ccgggctacg gtccctggcg gcgggcgagc   12660
cgtcaccgga cgtcgtcgag ggcgccgtac agggcgcctc cggcgcgggt ccggtgttgg   12720
tgtttccggg gcaggggtcg cagtgggtgg gcatgggtgc ccagctcctt gacgagtccc   12780
ccgtcttcgc ggcgcggatc gcggagtgtg agcgggccct gtcggcgcat gtggactggt   12840
cgctgagtgc ggtgttgcgc ggggacggga gtgagctgtc ccgggtcgag gtcgtgcagc   12900
```

```
ccgtgttgtg ggcggtgatg gtctcgctgg cttcggtgtg ggccgattac ggcatcaccc    12960
cggctgccgt catcgggcac tcgcagggcg agatggccgc cgcgtgtgtg gcggggggcac    13020
tgtcactgga ggatgcggcg cggatcgtgg ccgtacgcag tgacgcgctc cgtcagctca    13080
tggggcaggg cgacatggcg tcgttggggg ccggctcgga gcaggttgct gagctcatcg    13140
gcgaccggcc cggcgtgtgt gtcgctgccg tcaacgggcc ctcctctacg gtcatttcag    13200
ggccgccgga gcatgtggca gccgtggtcg cggatgcgga ggcgcgaggc ctgcgcgccc    13260
gcgtcatcga cgtcggatac gcctcccacg gcccccagat cgaccagctc cacgacctcc    13320
tcaccgagcg cctggccgac atccggccca cgaccacgga cgtcgccttc tactccacgg    13380
tcaccgccga acgcctcgac gacaccacca ccctcgacac ggattactgg gtcaccaacc    13440
tccgccagcc cgtccgcttc gccgacacca tcgaagcgct gctggccgac ggctaccgcc    13500
tgttcatcga ggccagcccc cacccgtcc tcaacctcgg catggaggag accatcgagc    13560
gggccgacat gcccgccacc gtcgtgccca ccctgcgccg cgaccacggc gacgccgcgc    13620
agctcacccg cgcggccgcc caggccttcg gcgcgggggc ggaggtcgac tggacgggct    13680
ggttccggc cgtgccgctg cctcggggtgg tggatctgcc gacgtacgcc ttccagcggg    13740
agcggttctg gctggagggg cgcagggggc tcgccgggga cccggcgggg ctcgggctcg    13800
cgtccgcggg gcatccgctg ctcggagccg ccgtggaact cgcggacggc ggcagtcacc    13860
tgctgaccgg ccggatctct ccgcgggacc aggcgtggct ggccgagcac cgggtcatgg    13920
acacggtgct gctgcccggt tcggcgttcg tggagctcgc gctgcaggcc gcggtgcggg    13980
ccggctgcgc ggagttggcg gagctgacgc tgcacactcc gctcgccttc ggggacgagg    14040
gtgcgggcgc ggtcgacgtg caggtggtgg tcggttccgt ggccgaggac gggcggcgtc    14100
ccgtgaccgt ccattcgcgg cccacgggtg agggcgagga ggccgtgtgg acccggcatg    14160
ccgcgggcgt ggtcgctccc ccggggcccg acgccgggga cgcctcgttc ggcgggacgt    14220
ggccgccccc gggcgccaca ccggtcggcg agcaggatcc gtacgggaa ctcgcttcgt    14280
acggctatga cttcgggccc ggctcacagg gactggtgag cgcgtggcgg ctcggggacg    14340
acctttcgc cgaggtggcg ctgcccgagg cggagagcgg cagggccgac cgctaccagg    14400
tgcaccggt gttgctcgac gccacgctgc acgcgctgat cctggacgcg gtcacgtcgt    14460
ccgccgacac cgaccaagtg ctgctgccgt tctcctggag cgggttgcgg gtgcacgcgc    14520
cgggcgctga gaagttgcgg gtacgtatcg cacgcaccgc gcccgaccag ctggccctca    14580
cggccgtgga cggggggcgga ggcgggggagc cggttctcac gctggagtcg ctcacggtac    14640
ggccggtggc cgcccaccag atcgcgggcg cccgtgcggc ggaccgtgac gcgctgttcc    14700
ggctcgtgtg gatggaggtc gccgcgcggg ccgaggagac gggcggcggc gcccgcgtg    14760
ccgcggtcct cgcgccggtc gagagtggcc cgatgggcgg tacgtcggcc ggtgcgctgg    14820
ccgacgcctt gtccgatgcg ctggccgccg gcccgtgtg ggacacgttc ggtgcgctcc    14880
gggacggagt ggcggctggg ggcgaagcgc ccgatgtcgt gctcgccgtg tgcgccgcgc    14940
ccggcgcagg tgccggggcc gttgcggatg ccgatggcag gggcggcgac ccggccgggt    15000
acgcgcggct ggccaccgtg tcccttctgt cgctgctcaa ggagtgggtg gacgaccgg    15060
cgttcgcggc gacccgtctc gtcgtcgtca cccgaggcgc ggtcgccgcg cggccgggtg    15120
agaccgccgt tgatctggcg ggcgcgtcgc tgtggggtct ggtgcgcagc gcgcaggccg    15180
agaatcccgg tcgcctcacg ctgctcgacg tggacggact ggagtcttct ccggccacgc    15240
tgaccggcgt actggcctcc ggcgaaccgg aattggcgct gcgtgacggg cgcgcctacg    15300
```

```
tgccacggct cgtgcgcgac gacgcgtcgg tgcggctggt gccgccggtc ggatcgctca   15360
cgtggcggct ggctcggtgc caagaggcgg gcggcggaca gcagttgtcc cttgtcgacg   15420
ctcccgaggc cggacgggcg ctggagccgc acgaggtgcg ggtggcggtg cgggccgcgg   15480
cgccggggcc gctcacggcg ggccaggtcg agggtgccgg tgtggtgacg gaagtcggcg   15540
gcgaggtcgg ttcggtggcc gtgggcgacc gggtgatggg gttgttcgac gcggtgggcc   15600
cggtggccgt caccgatgcc gcgctgctta tgccggttcc ggcgggctgg agttgggcgc   15660
aggcggccgg gtccttgggg gcctatgtgt ccgcgtatca cgtgctggcg gatgtcgtgg   15720 cgccgcgcg cggcgagact ctgctcgtcg gggaggaaac cggttccgtc ggccgtgccg   15780
tgctgcgtct tgctcttgcc gggcggtggc gggtcgaggc cgtggacggt cgtcgacgg   15840 cggatgattc gggcgccgag cgcgcggccg acgtcaccct ccgccacgag ggggccctgg   15900
tggtccaccg tgcgggcggt cgtccggacg agggacaggc tgtcgtgccg cccgagcccg   15960
ggcgcgtacg ggaaatcctc gcggagctga ccgagctgac cgagcttgcc gagatcacgg   16020
agtcggcgga gcccgggctg cccgcggaac ggggtgacag ccgtgctctg acgccgctcg   16080
acatcaccgt gtgggacatc cggcaggcgc ccgccgcgat ggcggccccg ccctcggcgg   16140
gcacgaccgt gttctcgctg cctcccgcct tcgaccccga gggcaccgtg ctggtcaccg   16200
gcggcaccga agcactcggc tcgctgacgg cccgtcacct ggtggaacgg tacgagcca   16260 ggcacctgtt gctgtccagc aggcggggag ccgacgcgcc gggcgcactc gaactggccg   16320
ccgacctctc cgcgctcggc gcgcgagtca ccttcgccgc gtgcgacccg ggcgaccggg   16380
acgaagccgc cgccctcctc gcggcggtgc cctcggacca cccgctgacc gccgtcttcc   16440
actgcgcggg caccgtgaac gacgccgtgg tgcagaacct cacggccgag caggtcgagg   16500
aggtgatgcg cgtgaaggcg gacgccgcgt ggcacctgca cgagctgacg cgggacgcgg   16560
acctgtccgc gttcgtcctg tactcctcgg tcgcccgggct gctcggcggc cccggccagg   16620
gcagctacac ggccgccaac gccttcttgg acgcgctggc ccggcaccgg cacgacggcg   16680
gtgcggcggc gacctccctg gcgtgggggct actgggagct ggcgagcggc atgtcgggac   16740
ggctcaccga cgccgaccgg gcgcgccatg cccgcgccgg cgtggtcggg ctcggcgccg   16800
acgagggact cgccctcctc gacgcggcgt gggccggcgg actgcccctg tacgcgccgg   16860
tccgtctgga cctggcccgg atgcgccggc aggcccagag ccaccccgca ccggcgctgc   16920
tgcgcgacct ggtgcgcggg gggagcaaga gcggcggcgg tgccgtgtcg gcggggggcgg   16980 ccgcgctgct caagtcgctc ggcgcgatgt ccgaccccga gcgggaggag cgctgctcg   17040 acctggtgtg cacccatatc gcggccgtcc tcggctacga cgcggccacg cccgtcaacg   17100
cgacgcaggg gctgcgggaa ctcggcttcg actccctgac cgcggtggag ctgcgcaacc   17160
ggctctcggc cgcgacgggg ctgaagctgc ccgccacgtt cgtcttcgac catcccaacc   17220
cggcggagct cgccgcgcag ctgcggcagg agctggcccc gcgcgcggcg gatccgctcg   17280
ccgacgtcct ggcggagttc gagcgcatcg aggactcgct gctctcggtc tcctcgaagg   17340
acggctcggc gcgggccgaa ctggcgggc ggctgcgcgc gacgctggcc aggtcgacg   17400 cgccgcagga cacggccggc gaggtcgcgg tggccactcg tacacgtatc caggacgcgt   17460
cggcggacga gatcttcgcg ttcatcgacc gggacctcgg cagggacggc gcgagcggac   17520
agggcaacgg acagcccacc gggcagggca acggacacgg caacggcaac ggcaacggca   17580
acggcaacgg acacggtcag gcagtggagg ggcagcgatg accacgtacc ggattggcac   17640
```

```
gtaggccagg acagcaacgg ccacgacacc cccatcggca tcgcgtggcg ggcccgattc    17700
gcgtccgccc cggggaggag acgggcgtcc gcgtcgaggg cgaggcgggc ttccacccgt    17760
aggcgatccg gcgagcacga cacccgcaga ttggctcgac gcagcccaga aatgtatgat    17820
caaggcgaat acttcatatg cggggatcga ccgcgcgggt cccggacggg gaagagcggg    17880
gagctttgcc agagagcgac gacttcccct tgcgttggtg attgccggtc agggcagcca    17940
tccgccatcg tcgcgtaggg tgtcacaccc caggaatcgc gtcactgaac acagcagccg    18000
gtaggacgac catgactgag ttggacacca tcgcaaatcc gtccgatccc gcggtgcagc    18060
ggatcatcga tgtcaccaag ccgtcgcgat ccaacataaa gacaacgttg atcgaggacg    18120
tcgagcccct catgcacagc atcgcggccg gggtggagtt catcgaggtc tacggcagcg    18180
acagcagtcc ttttccatct gagttgctgg atctgtgcgg gcggcagaac ataccggtcc    18240
gcctcatcga ctcctcgatc gtcaaccagt tgttcaaggg ggagcggaag gccaagacat    18300
tcggcatcgc ccgcgtccct cgcccggcca ggttcggcga tatcgcgagc cggcgtgggg    18360
acgtcgtcgt tctcgacggg gtgaagatcg tcgggaacat cggcgcgata gtacgcacgt    18420
cgctcgcgct cggagcgtcg gggatcatcc tggtcgacag tgacatcacc agcatcgcgg    18480
accggcgtct ccaaagggcc agccgaggtt acgtcttctc ccttcccgtc gttctctccg    18540
gtcgcgagga ggccatcgcc ttcattcggg acagcggtat gcagctgatg acgctcaagg    18600
cggatggcga catttccgtg aaggaactcg gggacaatcc ggatcggctg gccttgctgt    18660
tcggcagcga aaagggtggg ccttccgacc tgttcgagga ggcgtcttcc gcctcggttt    18720
ccatccccat gatgagccag accgagtctc tcaacgtttc cgtttccctc ggaatcgcgc    18780
tgcacgagag gatcgacagg aatctcgcgg ccaaccgata agcgcctctg ttcctcggac    18840
gctcggttcc tcgacctcga ttcgtcagtg atgatcacct cacacggcag cgatcaccac    18900
tgacatatcg aggtcaacgg tcgtggtccg ggcgggcact cctcgaaggc gcggccgacg    18960
cccttgaacg actcgatggc gctgacgcct tccgcgatcg cctcgactgt gaaaacgctc    19020
gtggacgtcg gcgggtagcc gatgagttcc atcgccttgc gcatcccctt gagcatggag    19080
aacgcgtcca ccgggtagtc acgaaggtac ttgcgaaggc ttcgcgccgt ccgagaccgt    19140
gagccggcgc aagccggtgt ggcgccggtc ccggatccac atgctggtga tgctgttgtg    19200
ggcacaatcg tgccggttgg taggatccag cgctgctcag cgggctcacc cgcggatcgc    19260
gggtcggcgg cgcgccggtc aaccagcgca gggcagccgc cggaggcgcg ggcgaggcgg    19320
acacggacct cggcgggcgg ctcgccgcga tgacaccgga cgaccgggtc gcgcacctgc    19380
gggacctcgt ccgtacgcac gtggcgaccg tcctgggaca cggcaccccg agccgggtgg    19440
acctggagcg ggccttccgc gacaccggtt tcgactcgct caccgccgtc gaactccgca    19500
accgtctcaa cgccgcgacc gggctgcggc tgccggccac gctggtcttc gaccacccca    19560
ccccggggga gctcgccggg cacctgctcg acgaactcgc cacggccgcg ggcgggtcct    19620
gggcggaagg caccgggtcc ggagacacgg cctcggcgac cgatcggcag accacggcgg    19680
ccctcgccga actcgaccgg ctggaaggcg tgctcgcctc cctcgcggat atccctcgcc    19740
gcagttaatt aaagtcagtg agcgaggaag cgcgtaacta taacggtcct aaggtagcg     19799
```

<210> SEQ ID NO 49
<211> LENGTH: 6752
<212> TYPE: DNA
<213> ORGANISM: Artificial Sequence
<220> FEATURE:
<223> OTHER INFORMATION: Synthetic Polynucleotide

<400> SEQUENCE: 49

```
atctacgtct gtcgagaagt ttctgatcga aaagttcgac agcgtctccg acctgatgca      60
gctctcgcag ggcgaagaat ctcgtgcttt cagcttcgat gtaggagggc gtggatatgt     120
cctgagggta aatagctgcg ccgatggttt ctacaaagat cgttatgttg atcggcactt     180
tgcatcggcc gcgctcccga ttccggaagt gcttgacatt ggggaattta tgcggtgtga     240
aataccgcac agatgcgtaa ggagaaaata ccgcatcagg cgccattcgc cattcaggct     300
gcgcaactgt tgggaagggc gatcggtgcg ggcctcttcg ctattacgcc agctggcgaa     360
agggggatgt gctgcaaggc gattaagttg ggtaacgcca gggttttccc agtcacgacg     420
ttgtaaaacg acggccagtg ccaagcttgg gctgcaggtc gactctagag gatccgcggc     480
cgcgcgcgat atcgaattcg taatcatgtc atagctgttt cctgtgtgaa attgttatcc     540
gctcacaatt ccacacaaca tacgagccgg aagcataaag tgtaaagcct ggggtgccta     600
atgagtgagc taactcacat taattgcgtt gcgctcactg cccgctttcc agtcgggaaa     660
cctgtcgtgc cagctgcatt aatgaatcgg ccaacgcgcg gggagaggcg gtttgcgtat     720
tgggcgctct tccgcttcct cgctcactga ctcgctgcgc tcggtcgttc ggctgcggcg     780
agcggtatca gctcactcaa aggcggtaat acggttatcc acagaatcag gggataacgc     840
aggaaagaac atgtgagcaa aaggccagca aaaggccagg aaccgtaaaa aggccgcgtt     900
gctggcgttt ttccataggc tccgcccccc tgacgagcat cacaaaaatc gacgctcaag     960
tcagaggtgg cgaaacccga caggactata aagataccag gcgtttcccc ctggaagctc    1020
cctcgtgcgc tctcctgttc cgaccctgcc gcttaccgga tacctgtccg cctttctccc    1080
ttcgggaagc gtggcgcttt ctcatagctc acgctgtagg tatctcagtt cggtgtaggt    1140
cgttcgctcc aagctgggct gtgtgcacga accccccgtt cagcccgacc gctgcgcctt    1200
atccggtaac tatcgtcttg agtccaaccc ggtaagacac gacttatcgc cactggcagc    1260
agccactggt aacaggatta gcagagcgag gtatgtaggc ggtgctacag agttcttgaa    1320
gtggtggcct aactacggct acactagaag aacagtattt ggtatctgcg ctctgctgaa    1380
gccagttacc ttcggaaaaa gagttggtag ctcttgatcc ggcaaacaaa ccaccgctgg    1440
tagcggtggt ttttttgttt gcaagcagca gattacgcgc agaaaaaaag gatctcaaga    1500
agatcctttg atcttttcta cggggtctga cgctcagtgg aacgaaaact cacgttaagg    1560
gattttggtc atgagattat caaaaaggat cttcacctag atccttttgg ttcatgtgca    1620
gctccatcag caaaagggga tgataagttt atcaccaccg actatttgca acagtgccgt    1680
tgatcgtgct atgatcgact gatgtcatca gcggtggagt gcaatgtcgt gcaatacgaa    1740
tggcgaaaag ccgagctcat cggtcagctt ctcaaccttg ggttacccc cggcggtgtg    1800
ctgctggtcc acagctcctt ccgtagcgtc cggcccctcg aagatgggcc acttggactg    1860
atcgaggccc tgcgtgctgc gctgggtccg gagggacgc tcgtcatgcc ctcgtggtca    1920
ggtctggacg acgagccgtt cgatcctgcc acgtcgcccg ttacaccgga ccttggagtt    1980
gtctctgaca cattctggcg cctgccaaat gtaaagcgca gcgcccatcc atttgccttt    2040
gcggcagcgg ggccacaggc agagcagatc atctctgatc cattgcccct gccacctcac    2100
tcgcctgcaa gcccggtcgc ccgtgtccat gaactcgatg ggcaggtact tctcctcggc    2160
gtgggacacg atgccaacac gacgctgcat cttgccgagt tgatggcaaa ggttccctat    2220
ggggtgccga gacactgcac cattcttcag gatggcaagt tggtacgcgt cgattatctc    2280
```

```
gagaatgacc actgctgtga gcgctttgcc ttggcggaca ggtggctcaa ggagaagagc    2340
cttcagaagg aaggtccagt cggtcatgcc tttgctcggt tgatccgctc ccgcgacatt    2400
gtggcgacag ccctgggtca actgggccga gatccgttga tcttcctgca tccgccagag    2460
gcgggatgcg aagaatgcga tgccgctcgc cagtcgattg gctgagctca tgagcggaga    2520
acgagatgac gttggagggg caaggtcgcg ctgattgctg gggcaacacg tggagcggat    2580
cggggattgt ctttcttcag ctcgctgatg atatgctgac gctcaatgcc gtttggcctc    2640
cgactaacga aaatcccgca tttggacggc tgatccgatt ggcacggcgg acggcgaatg    2700
gcggagcaga cgctcgtccg ggggcaatga gatatgaaaa agcctgaact caccgcgacg    2760
tatcgggccc tggccagcta gctagagtcg acctgcaggt ccccgggdat cggtcttgcc    2820
ttgctcgtcg gtgatgtact tcaccagctc cgcgaagtcg ctcttcttga tggagcgcat    2880
ggggacgtgc ttggcaatca cgcgcacccc ccggccgttt tagcggctaa aaaagtcatg    2940
gctctgccct cgggcggacc acgcccatca tgaccttgcc aagctcgtcc tgcttctctt    3000
cgatcttcgc cagcagggcg aggatcgtgg catcaccgaa ccgcgccgtg cgcgggtcgt    3060
cggtgagcca gagtttcagc aggccgccca ggcggcccag gtcgccattg atgcgggcca    3120
gctcgcggac gtgctcatag tccacgacgc ccgtgatttt gtagccctgg ccgacggcca    3180
gcaggtaggc cgacaggctc atgccggccg ccgccgcctt ttcctcaatc gctcttcgtt    3240
cgtctggaag gcagtacacc ttgataggtg ggctgccctt cctggttggc ttggtttcat    3300
cagccatccg cttgccctca tctgttacgc cggcggtagc cggccagcct cgcagagcag    3360 gattccgtt gagcaccgcc aggtgcgaat aagggacagt gaagaaggaa cacccgctcg    3420
cgggtgggcc tacttcacct atcctgcccg gctgacgccg ttggatacac caaggaaagt    3480
ctacacgaac cctttggcaa aatcctgtat atcgtgcgaa aaaggatgga tataccgaaa    3540
aaatcgctat aatgaccccg aagcagggtt atgcagcgga aaagatccgt cgacctgcag    3600
gcatgcaagc tctagcgatt ccagacgtcc cgaaggcgtg gcgcggcttc cccgtgccgg    3660
agcaatcgcc ctgggtgggt tacacgacgc ccctctatgg cccgtactga cggacacacc    3720
gaagccccgg cggcaaccct cagcggatgc cccggggctt cacgttttcc caggtcagaa    3780
gcggttttcg gtatcgtcca ttccgacagc atcgccagtc actatggcgt gctgctagcg    3840
ctatatgcgt tgatgcaatt tctatgcgca cccgttctcg gagcactgtc cgaccgcttt    3900
ggccgccgcc cagtcctgct cgcttcgcta cttggagcca ctatcgacta cgcgatcatg    3960
gcgaccacac ccgtcctgtg gatctgcctc gctggcctgc cgcagttctt caacctcccg    4020
gcgcagcttt tcgttctcaa tttcagcatc cctttcggca taccatttta tgacggcggc    4080
agagtcataa agcacctcat tacccttgcc accgctcgc agaacgggca ttccctgttc    4140
ctgccagttc tgaatggtac ggatactcgc accgaaaatg tcagccagct gcttttgtt    4200 gacttccatt gttcattcca cggacaaaaa cagagaaagg aaacgacaga ggccaaaaag    4260
ctcgctttca gcacctgtcg tttcctttct tttcagaggg tatttaaat aaaaacatta    4320 agttatgacg aagaagaacg gaaacgcctt aaaccggaaa attttcataa atagcgaaaa    4380
cccgcgaggt cgccgcccg taacaaggcg atcgccggga aaggaccgc aaatgataat    4440 aattatcaat tgcatactat cgacggcact gctgccagat aacaccaccg gggaaacatt    4500
ccatcatgat ggccgtgcgg acataggaag ccagttcatc catcgctttc ttgtctgctg    4560
ccatttgctt tgtgacatcc agcgccgcac attcagcagc gttttcagc gcgttttcga    4620 tcaacgtttc aatgttggta tcaacaccag gtttaacttt gaacttatcg gcactgacgg    4680
```

```
ttaccttgtt ctgcgctggc tcatcacgct ggataccaag gctgatgttg tagatattgg    4740
tcaccggctg aggtgtttcg attgccgctg cgtggatagc accattccat gggatgctgt    4800
tgtgggcaca atcgtgccgg ttggtaggat ccagcgagaa gggagcggaa atgctgcgcc    4860
cggtggaaac cccgacccgc gaaatcaaga agctcgacgg cctgtgggcg ttcagcctcg    4920
accgcgaaaa ctgcggcatc gaccagcggt ggtgggagag cgcgctgcag gaatcgcgcg    4980
cgatcgccgt cccgggctcg ttcaacgacc agttcgcgga cgccgacatc cggaactacg    5040
ccggcaacgt ctggtaccag cgcgaggtgt tcatcccgaa gggctgggcg gccagcgga    5100 tcgtcctgcg cttcgacgcc gtgacccact acggcaaggt ctgggtgaac aaccaggaag    5160
tcatggaaca ccagggcggc tacaccccgt tcgaggcgga cgtcacgccg tacgtgatcg    5220
ccggcaagtc cgtccggatc accgtctgcg tgaacaacga gctgaactgg cagaccatcc    5280
cgccgggcat ggtgatcacg gacgagaacg gcaagaagaa gcagtcctac ttccacgact    5340
tcttcaacta cgcgggcatc caccgcagcg tcatgctgta caccacgccg aacacctggg    5400
tcgacgacat caccgtcgtg acgcacgtgg cgcaggactg caaccacgcc agcgtcgact    5460
ggcaggtcgt ggccaacggc gacgtctcgg tggagctgcg ggacgcggac cagcaggtcg    5520
tggccaccgg ccagggcacc tcgggcacgc tgcaggtcgt gaacccgcac ctctggcagc    5580
cgggcgaggg ctacctgtac gaactctgcg tcaccgcgaa gtcgcagacg gagtgcgaca    5640
tctacccgct gcgggtgggc atccgctccg tcgccgtgaa gggcgagcag ttcctcatca    5700
accacaagcc gttctacttc accggcttcg gccggcacga ggacgcggac ctgcgcggca    5760
agggcttcga caacgtcctg atggtgcacg accacgcgct catggactgg atcggcgcca    5820
actcgtaccg gacctcgcac tacccgtacg cggaggaaat gctggactgg gccgacgagc    5880
acggcatcgt cgtgatcgac gaaacggcgg ccgtcggctt caacctgagc ctcggcatcg    5940
gcttcgaggc gggcaacaag ccgaaggaac tctactcgga ggaagccgtg aacggcgaga    6000
cccagcaggc gcacctgcag gccatcaagg aactcatcgc gcgggacaag aaccacccgt    6060
ccgtcgtgat gtggagcatc gccaacgagc cggacacccg gccgcagggc gcgcgcgagt    6120
acttcgcccc gctggcggaa gccacgcgga agctcgaccc gacccgcccg atcacgtgcg    6180
tcaacgtgat gttctgcgac gcgcacaccg acacgatctc ggacctgttc gacgtgctgt    6240
gcctcaaccg gtactacggc tggtacgtgc agtccggcga cctggagacc gcggaaaagg    6300
tgctcgagaa ggaactgctc gcctggcagg agaagctgca ccagccgatc atcatcaccg    6360
aatacggcgt ggacacgctg gccggcctcc actcgatgta cacggacatg tggtccgagg    6420
aataccagtg cgcgtggctg gacatgtacc accgggtctt cgaccgcgtg tccgccgtcg    6480
tgggcgagca ggtctggaac ttcgcggact tcgccaccag ccaggcatc ctccgggtgg    6540 gcggcaacaa gaagggcatc ttcacgcggg accgcaagcc gaagagcgcg gccttcctgc    6600
tccagaagcg ctggaccggc atgaacttcg gcgagaagcc gcagcagggc ggcaagcagt    6660
gattggggac cctagaggtc cccttttta tttttgggg acccctagagg tccccttttt    6720 tatttccat ggcgagacac ccgggaagcc tg                                   6752
```

<210> SEQ ID NO 50
<211> LENGTH: 7591
<212> TYPE: DNA
<213> ORGANISM: Artificial Sequence
<220> FEATURE:
<223> OTHER INFORMATION: Synthetic Polynucleotide

```
<400> SEQUENCE: 50
atctacgtct gtcgagaagt ttctgatcga aaagttcgac agcgtctccg acctgatgca      60
gctctcgcag ggcgaagaat ctcgtgcttt cagcttcgat gtaggagggc gtggatatgt     120
cctgcgggta aatagctgcg ccgatggttt ctacaaagat cgttatgttg atcggcactt     180
tgcatcggcc gcgctcccga ttccggaagt gcttgacatt ggggaattta tgcggtgtga     240
aataccgcac agatgcgtaa ggagaaaata ccgcatcagg cgccattcgc cattcaggct     300
gcgcaactgt tgggaagggc gatcggtgcg ggcctcttcg ctattacgcc agctggcgaa     360
agggggatgt gctgcaaggc gattaagttg gtaacgcca gggttttccc agtcacgacg     420
ttgtaaaacg acggccagtg ccaagcttgg gctgcaggtc gactctagag atgctgttgt     480
gggcacaatc gtgccggttg gtaggatcca gcgagaaggg agcggaaatg ctgcgcccgg     540
tggaaacccc gacccgcgaa atcaagaagc tcgacggcct gtgggcgttc agcctcgacc     600
gcgaaaactg cggcatcgac cagcggtggt gggagagcgc gctgcaggaa tcgcgcgcga     660
tcgccgtccc gggctcgttc aacgaccagt tcgcggacgc cgacatccgg aactacgccg     720
gcaacgtctg gtaccagcgc gaggtgttca tcccgaaggg ctgggcgggc cagcggatcg     780
tcctgcgctt cgacgccgtg acccactacg gcaaggtctg ggtgaacaac caggaagtca     840
tggaacacca gggcggctac accccgttcg aggcggacgt cacgccgtac gtgatcgccg     900
gcaagtccgt ccggatcacc gtctgcgtga caacgagct gaactggcag accatcccgc     960
cgggcatggt gatcacggac gagaacggca agaagaagca gtcctacttc cacgacttct    1020
tcaactacgc gggcatccac cgcagcgtca tgctgtacac cacgccgaac acctgggtcg    1080
acgacatcac cgtcgtgacg cacgtggcgc aggactgcaa ccacgccagc gtcgactggc    1140
aggtcgtggc caacggcgac gtctcggtgg agctgcggga gcggaccag caggtcgtgg    1200 ccaccggcca gggcacctcg ggcacgctgc aggtcgtgaa cccgcacctc tggcagccgg    1260
gcgagggcta cctgtacgaa ctctgcgtca ccgcgaagtc gcagacggag tgcgacatct    1320
acccgctgcg ggtgggcatc cgctccgtcg ccgtgaaggg cgagcagttc ctcatcaacc    1380
acaagccgtt ctacttcacc ggcttcggcc ggcacgagga gcggacctg gcggcaaggg    1440 gcttcgacaa cgtcctgatg gtgcacgacc acgcgctcat ggactggatc ggcgccaact    1500
cgtaccggac ctcgcactac ccgtacgcgg aggaaatgct ggactgggcc gacgagcacg    1560
gcatcgtcgt gatcgacgaa acggcggccg tcggcttcaa cctgagcctc ggcatcggct    1620
tcgaggcggg caacaagccg aaggaactct actcggagga agccgtgaac ggcgagaccc    1680
agcaggcgca cctgcaggcc atcaaggaac tcatcgcgcg ggacaagaac cacccgtccg    1740
tcgtgatgtg gagcatcgcc aacgagccgg acacccggcc gcagggcgcg cgcgagtact    1800
tcgccccgct ggcggaagcc acgcggaagc tcgacccgac ccgcccgatc acgtgcgtca    1860
acgtgatgtt ctgcgacgcg cacaccgaca cgatctcgga cctgttcgac gtgctgtgcc    1920
tcaaccggta ctacggctgg tacgtgcagt ccggcgacct ggagaccgcg gaaaaggtgc    1980
tcgagaagga actgctcgcc tggcaggaga agctgcacca gccgatcatc atcaccgaat    2040
acggcgtgga cacgctggcc ggcctccact cgatgtacac ggacatgtgg tccgaggaat    2100
accagtgcgc gtggctggac atgtaccacc gggtcttcga ccgcgtgtcc gccgtcgtgg    2160
gcgagcaggt ctggaacttc gcggacttcg ccaccagcca gggcatcctc cgggtgggcg    2220
gcaacaagaa gggcatcttc acgcgggacc gcaagccgaa gagcgcggcc ttcctgctcc    2280
agaagcgctg gaccggcatg aacttcggcg agaagccgca gcagggcggc aagcagtgat    2340
```

```
ctagaggatc cgcggccgcg cgcgatatcg aattcgtaat catgtcatag ctgtttcctg   2400
tgtgaaattg ttatccgctc acaattccac acaacatacg agccggaagc ataaagtgta   2460
aagcctgggg tgcctaatga gtgagctaac tcacattaat tgcgttgcgc tcactgcccg   2520
ctttccagtc gggaaacctg tcgtgccagc tgcattaatg aatcggccaa cgcgcgggga   2580
gaggcggttt gcgtattggg cgctcttccg cttcctcgct cactgactcg ctgcgctcgg   2640
tcgttcggct gcggcgagcg gtatcagctc actcaaaggc ggtaatacgg ttatccacag   2700
aatcagggga taacgcagga aagaacatgt gagcaaaagg ccagcaaaag gccaggaacc   2760
gtaaaaaggc cgcgttgctg gcgttttttcc ataggctccg ccccctgac gagcatcaca   2820 aaaatcgacg ctcaagtcag aggtggcgaa acccgacagg actataaaga taccaggcgt   2880
ttccccctgg aagctccctc gtgcgctctc ctgttccgac cctgccgctt accggatacc   2940
tgtccgcctt tctcccttcg ggaagcgtgg cgctttctca tagctcacgc tgtaggtatc   3000
tcagttcggt gtaggtcgtt cgctccaagc tgggctgtgt gcacgaaccc cccgttcagc   3060
ccgaccgctg cgccttatcc ggtaactatc gtcttgagtc aacccggta agacacgact   3120 tatcgccact ggcagcagcc actggtaaca ggattagcag agcgaggtat gtaggcggtg   3180
ctacagagtt cttgaagtgg tggcctaact acggctacac tagaagaaca gtatttggta   3240
tctgcgctct gctgaagcca gttaccttcg gaaaaagagt tggtagctct tgatccggca   3300
aacaaaccac cgctggtagc ggtggttttt ttgtttgcaa gcagcagatt acgcgcagaa   3360
aaaaaggatc tcaagaagat cctttgatct tttctacggg gtctgacgct cagtggaacg   3420
aaaactcacg ttaagggatt ttggtcatga gattatcaaa aaggatcttc acctagatcc   3480
ttttggttca tgtgcagctc catcagcaaa aggggatgat aagtttatca ccaccgacta   3540
tttgcaacag tgccgttgat cgtgctatga tcgactgatg tcatcagcgg tggagtgcaa   3600
tgtcgtgcaa tacgaatggc gaaaagccga gctcatcgt cagcttctca accttggggt   3660 taccccccggc ggtgtgctgc tggtccacag ctccttccgt agcgtccggc ccctcgaaga   3720
tgggccactt ggactgatcg aggccctgcg tgctgcgctg gtccgggag ggacgctcgt   3780 catgccctcg tggtcaggtc tggacgacga gccgttcgat cctgccacgt cgcccgttac   3840
accggacctt ggagttgtct ctgacacatt ctggcgcctg ccaaatgtaa agcgcagcgc   3900
ccatccattt gcctttgcgg cagcggggcc acaggcagag cagatcatct ctgatccatt   3960
gcccctgcca cctcactcgc ctgcaagccc ggtcgcccgt gtccatgaac tcgatgggca   4020
ggtacttctc ctcggcgtgg gacacgatgc caacacgacg ctgcatcttg ccgagttgat   4080
ggcaaaggtt ccctatgggg tgccgagaca ctgcaccatt cttcaggatg gcaagttggt   4140
acgcgtcgat tatctcgaga atgaccactg ctgtgagcgc tttgccttgg cggacaggtg   4200
gctcaaggag aagagccttc agaaggaagg tccagtcggt catgcctttg ctcggttgat   4260
ccgctcccgc gacattgtgg cgacagccct gggtcaactg gccgagatc cgttgatctt   4320 cctgcatccg ccagaggcgg gatgcgaaga atgcgatgcc gctcgccagt cgattggctg   4380
agctcatgag cggagaacga gatgacgttg gaggggcaag gtcgcgctga ttgctgggggc   4440 aacacgtgga gcggatcggg gattgtcttt cttcagctcg ctgatgatat gctgacgctc   4500
aatgccgttt ggcctccgac taacgaaaat cccgcatttg gacggctgat ccgattggca   4560
cggcggacgc cgaatggcgg agcagacgct cgtccggggg caatgagata tgaaaaagcc   4620
tgaactcacc gcgacgtatc gggccctggc cagctagcta gagtcgacct gcaggtcccc   4680
```

-continued

```
ggggatcggt cttgccttgc tcgtcggtga tgtacttcac cagctccgcg aagtcgctct   4740
tcttgatgga gcgcatgggg acgtgcttgg caatcacgcg cacccccggg ccgttttagc   4800
ggctaaaaaa gtcatggctc tgccctcggg cggaccacgc ccatcatgac cttgccaagc   4860
tcgtcctgct tctcttcgat cttcgccagc agggcgagga tcgtggcatc accgaaccgc   4920
gccgtgcgcg ggtcgtcggt gagccagagt tcagcaggc cgcccaggcg cccaggtcg    4980 ccattgatgc gggccagctc gcggacgtgc tcatagtcca cgacgcccgt gattttgtag   5040
ccctggccga cggccagcag gtaggccgac aggctcatgc cggccgccgc cgccttttcc   5100
tcaatcgctc ttcgttcgtc tggaaggcag tacaccttga taggtgggct gcccttcctg   5160
gttggcttgg tttcatcagc catccgcttg ccctcatctg ttacgccggc ggtagccggc   5220
cagcctcgca gagcaggatt cccgttgagc accgccaggt gcgaataagg gacagtgaag   5280
aaggaacacc cgctcgcggg tgggcctact tcacctatcc tgcccggctg acgccgttgg   5340
atacaccaag gaaagtctac acgaacccTT tggcaaaatc ctgtatatcg tgcgaaaaag   5400
gatggatata ccgaaaaaat cgctataatg accccgaagc agggttatgc agcggaaaag   5460
atccgtcgac ctgcaggcat gcaagctcta gcgattccag acgtcccgaa ggcgtggcgc   5520
ggcttccccg tgccggagca atcgccctgg gtgggttaca cgacgcccct ctatggcccg   5580
tactgacgga cacaccgaag ccccggcggc aaccctcagc ggatgccccg gggcttcacg   5640
ttttcccagg tcagaagcgg ttttcgggag tagtgcccca actggggtaa cctttgagtt   5700
ctctcagttg ggggcgtagg gtcgccgaca tgacacaagg ggttgtgacc ggggtggaca   5760
cgtacgcggg tgcttacgac cgtcagtcgc gcgagcgcga gaattcgagc gcagcaagcc   5820
cagcgacaca gcgtagcgcc aacgaagaca aggcggccga ccttcagcgc gaagtcgagc   5880
gcgacggggg ccggttcagg ttcgtcgggc atttcagcga agcgccgggc acgtcggcgt   5940
tcgggacggc ggagcgcccg gagttcgaac gcatcctgaa cgaatgccgc gccgggcggc   6000
tcaacatgat cattgtctat gacgtgtcgc gcttctcgcg cctgaaggtc atggacgcga   6060
ttccgattgt ctcggaattg ctcgccctgg gcgtgacgat tgtttccact caggaaggcg   6120
tcttccggca gggaaacgtc atggacctga ttcacctgat tatgcggctc gacgcgtcgc   6180
acaaagaatc ttcgctgaag tcggcgaaga ttctcgacac gaagaacctt cagcgcgaat   6240
tgggcgggta cgtcggcggg aaggcgcctt acgcttcga gcttgtttcg gagacgaagg   6300
agatcacgcg caacggccga atggtcaatg tcgtcatcaa caagcttgcg cactcgacca   6360 ctcccttac cggaccctc gagttcgagc ccgacgtaat ccggtggtgg tggcgtgaga   6420
tcaagacgca caaacacctt cccttcaagc cgggcagtca agccgccatt caccgggca   6480 gcatcacggg gctttgtaag cgcatggacg ctgacgccgt gccgaccgg ggcgagacga   6540 ttgggaagaa gaccgcttca agcgcctggg acccggcaac cgttatgcga atccttcggg   6600
acccgcgtat tgcgggcttc gccgctgagg tgatctacaa gaagaagccg gacggcacgc   6660
cgaccacgaa gattgagggt taccgcattc agcgcgaccc gatcacgctc cggccggtcg   6720
agcttgattg cggaccgatc atcgagcccg ctgagtggta tgagcttcag gcgtggttgg   6780
acggcagggg gcgcggcaag gggctttccc ggggcaagc cattctgtcc gccatggaca   6840
agctgtactg cgagtgtggc gccgtcatga cttcgaagcg cggggaagaa tcgatcaagg   6900
actcttaccg ctgccgtcgc cggaaggtgg tcgacccgtc cgcacctggg cagcacgaag   6960
gcacgtgcaa cgtcagcatg gcggcactcg acaagttcgt tgcggaacgc atcttcaaca   7020
agatcaggca cgccgaaggc gacgaagaga cgttggcgct tctgtgggaa gccgcccgac   7080
```

-continued

```
gcttcggcaa gctcactgag gcgcctgaga agagcggcga acgggcgaac cttgttgcgg    7140
agcgcgccga cgcccctgaac gcccttgaag agctgtacga agaccgcgcg gcaggcgcgt    7200
acgacggacc cgttggcagg aagcacttcc ggaagcaaca ggcagcgctg acgctccggc    7260
agcaaggggc ggaagagcgg cttgccgaac ttgaagccgc cgaagcccca aagcttcccc    7320
ttgaccaatg gttccccgaa gacgccgacg ctgacccgac cggccctaag tcgtggtggg    7380
ggcgcgcgtc agtagacgac aagcgcgtgt tcgtcgggct cttcgtagac aagatcgttg    7440
tcacgaagtc gactacgggc aggggggcagg gaacgcccat cgagaagcgc gcttcgatca    7500
cgtgggcgaa gccgccgacc gacgacgacg aagacgacgc ccaggacggc acggaagacg    7560
tagcggcgta gcgagacacc cgggaagcct g                                   7591
```

<210> SEQ ID NO 51
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 51
cctggccggc cggcggagca cacccgg                                        27

<210> SEQ ID NO 52
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 52
tcacggcctc tcctctctcc                                                20

<210> SEQ ID NO 53
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 53
ggagaagaca tgccgggtac g                                              21

<210> SEQ ID NO 54
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 54
tcaccgcgtg ccccactc                                                  18

<210> SEQ ID NO 55
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 55
cgacggtgat ttcaggtccg                                                20

<210> SEQ ID NO 56
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 56
ccgagcgcag cggcggccgc gctgataccg ccgccaattg tgacccgggc ccaccccaac    60

<210> SEQ ID NO 57
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 57
ggcctcggcg gtcagatcc                                                 19

<210> SEQ ID NO 58
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 58
ccacgtagcg ccaaggagcc                                                20

<210> SEQ ID NO 59
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 59
cgtacagcgt ctccaggtcc                                                20

<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 60
ccgacgacga gccgatcgcg                                                20

<210> SEQ ID NO 61
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 61
cgttgccgtg tccgttgccc tgc                                            23

<210> SEQ ID NO 62
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 62
gtgcgacgcc tcatcgacg                                              19

<210> SEQ ID NO 63
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 63
ccgacacgtc gccgagacc                                              19

<210> SEQ ID NO 64
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 64
gcgagcagga tccgtacgg                                              19

<210> SEQ ID NO 65
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 65
gctcaccagt ccctgtgagc                                             20

<210> SEQ ID NO 66
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 66
ccacgtaccg gattggcac                                              19

<210> SEQ ID NO 67
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 67
ccaggtaccg gattggcac                                              19

<210> SEQ ID NO 68
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 68
ccaccgaccg gattggcac                                              19

<210> SEQ ID NO 69

```
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 69
ccaagtaccg gattggcac                                              19
```